US007807465B2

(12) United States Patent
Vance et al.

(10) Patent No.: US 7,807,465 B2
(45) **Date of Patent: *Oct. 5, 2010**

(54) METHODS FOR IDENTIFYING AN INDIVIDUAL AT INCREASED RISK OF DEVELOPING CORONARY ARTERY DISEASE

(75) Inventors: Jeffery M. Vance, Chapel Hill, NC (US); Pascal J. Goldschmidt, Chapel Hill, NC (US); Simon S. Gregory, Durham, NC (US); William E. Kraus, Hillsborough, NC (US); Elizabeth R. Hauser, Durham, NC (US)

(73) Assignee: Duke University, Durham, NC (US)

( * ) Notice: Subject to any disclaimer, the term of this patent is extended or adjusted under 35 U.S.C. 154(b) by 213 days.

This patent is subject to a terminal disclaimer.

(21) Appl. No.: 11/260,842

(22) Filed: Oct. 27, 2005

(65) Prior Publication Data

US 2006/0115845 A1 Jun. 1, 2006

Related U.S. Application Data

(60) Provisional application No. 60/622,447, filed on Oct. 27, 2004.

(51) Int. Cl.
*C12Q 1/68* (2006.01)
*C07H 21/02* (2006.01)
*C07H 21/04* (2006.01)

(52) U.S. Cl. ......................... 436/6; 536/23.1; 536/23.5; 536/24.31

(58) Field of Classification Search ....................... None
See application file for complete search history.

(56) References Cited

U.S. PATENT DOCUMENTS

| | | | | |
|---|---|---|---|---|
| 5,449,604 | A | 9/1995 | Schellenberg et al. | |
| 5,508,167 | A | 4/1996 | Roses et al. | |
| 5,879,884 | A | 3/1999 | Peroutka | |
| 5,922,556 | A | 7/1999 | Mayeux et al. | |
| 5,958,684 | A | 9/1999 | Van Leeuwen et al. | |
| 6,027,896 | A | 2/2000 | Roses et al. | |
| 6,108,635 | A | 8/2000 | Herren et al. | |
| 6,165,727 | A | 12/2000 | Lalouel et al. | |
| 6,194,153 | B1 | 2/2001 | St. George-Hyslop et al. | |
| 6,342,350 | B1 | 1/2002 | Tanzi et al. | |
| 2002/0037508 | A1 | 3/2002 | Cargill et al. | |
| 2003/0083485 | A1* | 5/2003 | Milos et al. | 536/23.2 |
| 2004/0014109 | A1 | 1/2004 | Pericak-Vance et al. | |
| 2004/0053251 | A1 | 3/2004 | Pericak-Vance et al. | |
| 2004/0248092 | A1 | 12/2004 | Vance et al. | |
| 2005/0191652 | A1 | 9/2005 | Vance et al. | |
| 2006/0068428 | A1 | 3/2006 | Vance et al. | |
| 2006/0115845 | A1 | 6/2006 | Vance et al. | |
| 2007/0148661 | A1 | 6/2007 | Vance et al. | |
| 2009/0087844 | A1 | 4/2009 | Vance et al. | |
| 2009/0226420 | A1 | 9/2009 | Hauser et al. | |

FOREIGN PATENT DOCUMENTS

| | | | |
|---|---|---|---|
| WO | WO 99/57129 | A1 | 11/1999 |
| WO | WO 00/31253 | A2 | 6/2000 |
| WO | WO 01/20998 | A1 | 3/2001 |
| WO | WO 01/92576 | A1 | 12/2001 |
| WO | WO 02/02000 | A3 | 1/2002 |
| WO | WO 2004/005534 | A3 | 1/2004 |
| WO | WO 2004/007681 | A3 | 1/2004 |
| WO | WO 2007/086980 | A2 | 8/2007 |

OTHER PUBLICATIONS

NCBI Database, National Center for Biotechnology Information, National Library of Medicine, NIH (Bethesda, MD, USA), rs1875518 (ss2752812) Jan. 2, 2001.*
Hirschhorn et al. Genetics in Medicine. 2002. 4(2): 45-.*
Halushka et al. Nature. Jul. 1999. 22: 239-247.*
Brasch-Andersen et al. Journal of Medical Genetics. 2006. 43:e10.*
Wu et al. Circulation. 2001. 103: 1386-1389.*
Sanghera et al. Arteriosclerosis. 1997. 17: 1067-1073.*
Abbas et al. " A Wide Variety of Mutations in the *Parkin* Gene are Responsible for Autosomal Recessive Parkinsonism in Europe" *Hum. Mol. Genet.* 8(4):567-574 (1999).
Amos "Robust Variance-Components Approach for Assessing Genetic Linkage in Pedigrees" *Am J Human Genetics* 54:535-543 (1994).
Antonarakis et al. "Recommendations for a Nomenclature System for Human Gene Mutations" *Human Mutation* 11:1-3 (1998).
Baker "Association of an extended haplotype in the *tau* gene with progressive supranuclear palsy" *Hum. Mol. Genet.* 8(4):711-715 (1999).
Bengtsson et al. "Polymorphism in the β1-Adrenergic Receptor Gene and Hypertension" *Circulation* 104:187-190 (2001).
Bertram et al. "No Association between marker D10S1423 and Alzheimer's Disease" *Molecular Psychiatry* 8:571-573 (2003).
Bertram et al. "Evidence for Genetic Linkage of Alzheimer's Disease to Chromosome 10q" *Science* 290:2302-2305 (2000).
Blacker et al. "Results of high-resolution genome screen of 437 Alzheimer's Disease families" *Hum. Mol. Genet.* 12(1):23-32 (2003).
Blangero et al. "Multipoint Oligogenic Linkage Anaylsis of Quantitative Traits" *Genetic Epidemiology* 14:959-964 (1997).

(Continued)

*Primary Examiner*—Carla Myers
(74) *Attorney, Agent, or Firm*—Myers Bigel Sibley & Sajovec, P.A.

(57) ABSTRACT

The present invention provides methods of identifying a subject having an increased or decreased risk of developing cardiovascular disease, comprising: a) correlating the presence of one or more genetic markers in chromosome 3q13.31 with an increased or decreased risk of developing cardiovascular disease; and b) detecting the one or more genetic markers of step (a) in the subject, thereby identifying the subject as having an increased or decreased risk of developing cardiovascular disease. Also provided are methods of identifying subjects with cardiovascular disease as having a good or poor prognosis, as well as methods of identifying effective treatment regimens for cardiovascular disease, based on correlation with genetic markers in chromosome 3q13.31.

14 Claims, 8 Drawing Sheets

OTHER PUBLICATIONS

Board et al. "Identification, Characterization, and Crystal Structure of the Omega Class Glutathione Transferases" *Journal of Biological Chemistry* 275(32):24798-24806 (2000).
Bouffard et al. GenBank Accession No. G20124. Sep. 28, 1998.
Boyles et al. "Linkage Disequilibrium Inflates Type 1 Error Rates in Multipoint Linkage Analysis when Parental Genotypes Are Missing" *Hum Hered.* 59(4):220-227 (2005).
Specification for U.S. Appl. No. 10/520,695, filed Jan. 7, 2005.
Specification for U.S. Appl. No. 10/520,779, filed Jan. 7, 2005.
Corder et al. "Gene dose of Apolipoprotein E Type 4 Allele and the Risk of Alzheimer's Disease in Late Onset Families" *Science* 261(5123):921-923 (1993).
Daw et al. "Multipoint Oligogenic Analysis of Age-at-Onset Data with Applications to Alzheimer Disease Pedigrees" *Am J Human Genetics* 64:839-851 (1999).
Daw et al. "The Number of Trait Loci in Late-Onset Alzheimer Disease" *Am J Human Genetics* 66:196-204 (2000).
DeStefano et al. "Genome-Wide Scan for Parkinson's Disease: The *Gene*PD Study" *Neurology* 57:1124-1126 (2001).
Dizier et al. "Genome screen for asthma and related phenotypes in the French EGEA study" *American Journal Respiratory and Critical Care Medicine* 162:1812-1818 (2000).
Duggirala et al. "Linkage of Type 2 Diabetes Mellitus and of Age at Onset to a Genetic Location on Chromosome 10g in Mexican Americans" *Am J Human Genetics* 64:1127-1140 (1999).
Dulhunty et al. "The Glutathione Transferase Structural Family Includes a Nuclear Chloride Channel and a Ryanodine Receptor Calcium Release Channel Modulator" *Journal of Biological Chemistry* 276(5):3319-3323 (2001).
Ertekin-Taner et al. "Linkage of Plasma Aβ42 to a Quantitative Locus on Chromosome 10 in Late-Onset Alzheimer's Disease Pedigrees" *Science* 290:2303-2304 (2000).
GenBank Accession No. rs4925, Reference SNP.
Goate et al. "Segregation of a Missense Mutation in the Amyloid Precursor Protein Gene with Familial Alzheimer's Disease" *Nature* 349:704-706 (1991).
Goldgar "Mulitipoint Analysis of Human Quantitative Genetic Variation" *Am J Human Genetics* 47:957-967 (1990).
Grover et al. "Effects on splicing and protein function of three mutations in codon N296 of *tau* in vitro" *Neuroscience Letters* 323:33-36 (2002).
Hattori et al. "Point Mutations (Thr240Arg and Ala311Stop) in the *Parkin* Gene" *Biochem. Biophys. Res. Commun.* 249:754-758 (1998).
Hiltunen et al. "Linkage disequilibrium in the 13q12 region in Finnish late onset Alzheimer's disease patients" *European Journal of Human Genetics* 7:652-658 (1999).
Hiltunen et al. "Linkage disequilibrium of Late-Onset Alzheimer's Disease at 13q12 Region" *Society for Neuroscience* 24:1218m entry 478.4 (1998).
Hauser et al. "A Genomewide Scan for Early-Onset Coronary Artery Disease in 438 Families: The GENECARD study" *Am. J. Hum. Genet.* 75:436-447 (2004).
International Search Report corresponding to PCT/US03/22259 dated Mar. 5, 2004.
International Search Report corresponding to PCT/US01/16940 dated Aug. 24, 2001.
International Search Report corresponding to PCT/US03/21963 dated Sep. 9, 2004.
International Search Report corresponding to PCT/US01/41224 dated Jan. 15, 2002.
Ioannidis et al. "Replication validity of genetic association studies" *Nature Genetics* 29:306-309 (2001).
Kehoe et al. "A Full Genome Scan for Late Onset Alzheimer's Disease" *Human Molecular Genetics* 8(2):237-245 (1999).
Khan et al. "Parkinson's Disease Is Not Associated With the Combined α-Synuclein/Apolipoprotein E Susceptibility Genotype" *Annals of Neurology* 49(5):665-668 (2001).
Kitada et al. "Mutations in the *parkin* gene cause autosomal recessive juvenile parkinsonism" *Nature* 392:605-608 (1998).
Levy-Lahad et al. "Candidate Gene for the Chromosome 1 Familial Alzheimer's Disease Locus" *Science* 269:973-977 (1995).
Li et al. "Modulation of Age at Onset and Risk in Alzheimer Disease" Abstract presented at American Society of Human Genetics Meeting, San Diego, CA Oct. 2001.
Li et al. "Glutathione S-transferase omega-1 modifies age-at-onset of Alzheimer disease and Parkinson disease" *Human Molecular Genetics* 12(24):3259-3267 (2003).
Li et al. "Age at Onset in Two Common Neurodegenerative Diseases Is Genetically Controlled" *Am. J. Hum. Genet.* 70:985-993 (2002).
Li et al. "Revealing the role of glutathione S-transferase omega in age-at-onset of Alzheimer and Parkinson Disease" *Neurobiology of Aging* 27:1087-93 (Epub. Jun. 27, 2005).
Liang et al. "Covariate analysis of late-onset Alzheimer disease refines the chromosome 12 locus" *Molecular Psychiatry* 11:280-285 (2006).
Lippa et al."α-Synuclein in Familial Alzheimer Disease" *Arch Neurol.* 58:1817-1820 (2001).
Lucentini et al. "Gene Association Studies Typically Wrong," *The Scientist* 18(24):20 (2004).
Martin et al. "Association of Single-Nucleotide Polymorphisms of the *Tau* Gene with Late-Onset Parkinson Disease" *JAMA* 286(18):2245-2250 (2001).
Martin et al. "SNPing Away at Complex Diseases: Analysis of Single-Nucleotide Polymorphisms around APOE in Alzheimer Disease" *Am. J. Hum. Genet. 67*:383-394 (2000).
Morris et al. "The *tau* gene A0 polymorphism in progressive supranuclear palsy and related neurodegenerative diseases" *J. Neurol. Neurosurg. Psychiatry* 66:665-667 (1999).
Murray et al. GenBank Accession No. G08525. Feb. 5, 1997.
Murray et al. GenBank Accession No. G08539. Feb. 5, 1997.
Myers et al. "Susceptibility Locus for Alzheimer's Disease on Chromosome 10" *Science* 290:2304-2305 (2000).
Neuman et al. "Linkage Analysis of a Complex Disease: Application to Familial Alzheimer's Disease" *Genetic Epidemiology* 10:419-424 (1993).
Nussbaum et al. "Genetics of Parkinson's Disease" *Human Molecular Genetics* 6(10):1687-1691 (1997).
Oliveira et al. "Association Study of Parkin Gene Polymorphisms With Idiopathic Parkinson Disease" *Arch Neurol.* 60:975-980 (2003).
Oliveira et al. "Identification of Risk and Age-At-Onset Genes on Chromosome 1p in Parkinson Disease" *Am. J. Hum. Genet.* 77:252-264 (2005).
Oliveira et al. "Linkage disequilibrium and haplotype tagging polymorphisms in the *Tau* H1 haplotype" *Neurogenetics* 5:147-155 (2004).
Oliveira et al. "Parkin Mutations and Susceptibility Alleles in Late-Onset Parkinson's Disease" *Ann Neurol* 53:624-629 (2003).
Pastor et al. "Significant Association between the tau Gene A0/A0 Genotype and Parkinson's Disease" *Annals of Neurology* 47(2):242-245 (2000).
Perez et al. "β1-adrenergic receptor polymorphisms confer differential function and predisposition to heart failure" *Nature Medicine* 9(10):1300-1305 (2003).
Pericak-Vance et al. "Complete Genomic Screen in Late-Onset Familial Alzheimer's Disease" *Neurobiology of Aging* 19(1S):S39-S42 (1998).
Pericak-Vance et al. "Modulation of Age at Onset and Risk in Alzheimer Disease" Abstract presented at the National Institute on Aging, Neuroscience Symposium on the Genetics of Alzheimer Disease, Nov. 2001.
Pericak-Vance et al. "Identification of Novel Genes in Late-Onset Alzheimer's Disease" *Exp. Gerontol.* 35:1343-1352 (2000).
Polymeropoulos et al. "Mapping of a Gene for Parkinson's Disease to Chromosome 4q21-q23" *Science* 274(5290):1197-1199 (1996).
Results of Search for "MAPT" in SNP database in GenBank.
Rogaev et al. "Familial Alzheimer's disease in kindreds with missense mutations in a gene on chromosome 1 related to the Alzheimer's disease type 3 gene" *Nature* 376:775-778 (1995).
Scott et al. "Complete Genomic Screen in Parkinson Disease" *JAMA* 286(18):2239-2244 (2001).

Scott et al. "Fine Mapping of the Chromosome 12 Late-Onset Alzheimer Disease Locus: Potential Genetic and Phenotypic Heterogeneity" *Am. J. Hum. Genet.* 66:922-932 (2000).

Scott et al. "Ordered Subsets Linkage Analysis Detects Novel Alzheimer Disease Loci on Chromosomes 2q34 and 15q22" *Am. J. Hum. Genet.* 73:1041-1051 (2003).

Shashidharan et al. "*TorsinA accumulation in Lewy bodies in sporadic Parkinson's disease" Brain Research* 877:379-381 (2000).

Sherrington et al. "Cloning of a gene bearing missense mutations in early-onset familial Alzheimer's disease" *Nature* 375:754-760 (1995).

van der Walt et al. "Genetic polymorphisms of the N-acetyltransferase genes and risk of Parkinson's diesease" *Neurology* 60:1189-1191 (2003).

van der Walt et al. "Mitochondrial Polymorphisms Significantly Reduce the Risk of Parkinson Disease" *Am. J. Hum. Genet.* 72:804-811 (2003).

van der Walt et al. "Fibroblast Growth Factor 20 Polymorphisms and Haplotypes Strongly Influence Risk of Parkinson Disease" *Am. J. Hum. Genet.* 74:1121-1127 (2004).

Vance et al. "Methods of Genotyping" in *Approaches to Gene Mapping in Complex Human Diseases*, pp. 213-228, Eds. J. Haines and M. Pericak-Vance, John Wiley & Sons, Inc. New York.

Wacholder et al. "Assessing the Probability That a Positive Report is False: An Approach for Molecular Epidemiology Studies" *Journal of the National Cancer Institute* 96(6):434-442 (2004).

Wjst et al. "A Genome-Wide Search for Linkage to Asthma," *Genomics 58*:1-8 (1999).

Xu et al. "Genomewide Screen and Identification of Gene-Gene Interactions for Asthma-Susceptibility in three U.S. Populations: Collaborative Study on Genetics in Asthma" *American Journal of Human Genetics* 68:1437-1446 (2001).

Zakharyan et al. "Human Monomethylarsonic Acid (MMA$^V$) Reductase Is a Member of the Glutathione-S-transferase Superfamily" *Chem. Res. Toxicol.* 14:1051-1057 (2001).

Hauser et al. "A Genomewide Scan for Early-Onset Coronary Artery Disease in 438 Families: The GENECARD Study" *Am J Hum Genet* 75:436-447 (2004).

Perez et al. "$\beta_1$ -adrenergic Receptor Polymorphisms Confer Differential Function and Predisposition to Heart Failure" *Nat Med* 9(10):1300-1305 (2003).

Vance et al. "A 100 kb Region in 3q13.31 is Significantly Associated with Coronary Artery Disease: the Power of Genome-Wide Linkage Combined with Peak-Wide Association Analysis" Abstract/Session Information for Program No. 27, Meeting of the American Society of Human Genetics, Oct. 26-30, 2004, Toronto, Canada (Abstract available online Sep. 2004).

Wang et al. "Peakwide Mapping on Chromosome 3q13 Identifies the Kalirin Gene as a Novel Candidate Gene for Coronary Artery Disease" *Am J Hum Genet* 80:650-663 (2007).

Wang et al. "Polymorphisms of the Tumor Suppressor Gene *LSAMP* are Associated with Left Main Coronary Artery Disease" *Ann Hum Genet* 72(Pt 4):443-453 (2008).

* cited by examiner

Association Analysis on SNPs around rs1875518: based on Genotype in Caucasian)

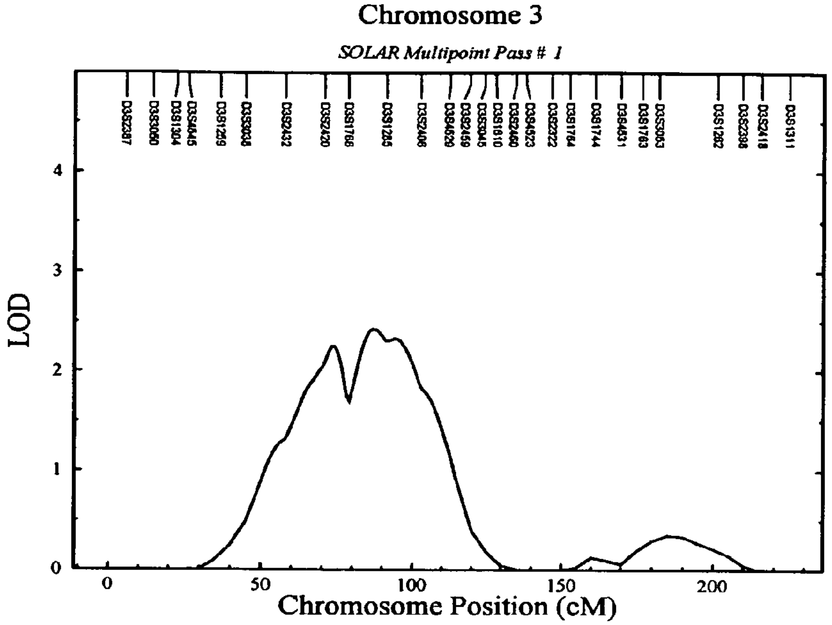
Figure 4. Quantitative trait loci (QTL) map, HDL cholesterol, chromosome 3.

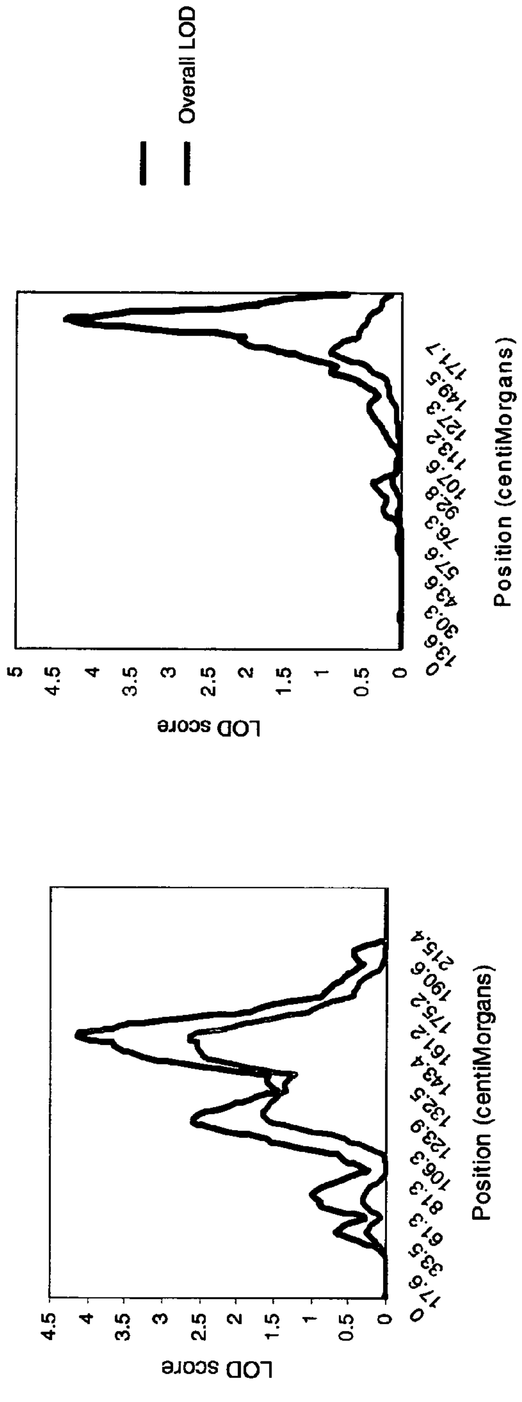
Chromosome 3, low mean family triglycerides
Chromosome 5, high mean family TC.
Figure 5. OSA results, chromosomes 3 and 5.
*Max LOD: maximum lod in subset of families with most extreme of covariate means.

Figure 6. Genotypes of affected vs. normal individuals

| Phenotype | OA | OA | OA | OA | OA | OA | OA | OA | OA | ON | ON | ON | ON | ON | ON | [illegible] |
|---|---|---|---|---|---|---|---|---|---|---|---|---|---|---|---|---|
| ID | 1 | 2 | 3 | 4 | 5 | 6 | 7 | 8 | 9 | 10 | 11 | 12 | 13 | 14 | 15 | 16 |
| A Deletion | -/- | -/- | -/- | -/- | -/- | -/- | -/- | -/- | -/- | +/+ | +/+ | +/+ | +/+ | +/+ | +/+ | +/- |
| CAA insertion | -/- | -/- | -/- | -/- | -/- | -/- | -/- | -/- | -/- | +/+ | -/- | -/- | +/- | +/+ | +/+ | -/- |
| 27 bp Duplication | -/- | -/- | -/+ | -/- | -/- | -/- | n/a | -/- | -/- | +/+ | +/+ | +/+ | +/+ | +/+ | n/a | n/a |

Figure 7. Allele frequency differences between case and control (DNA pooling)
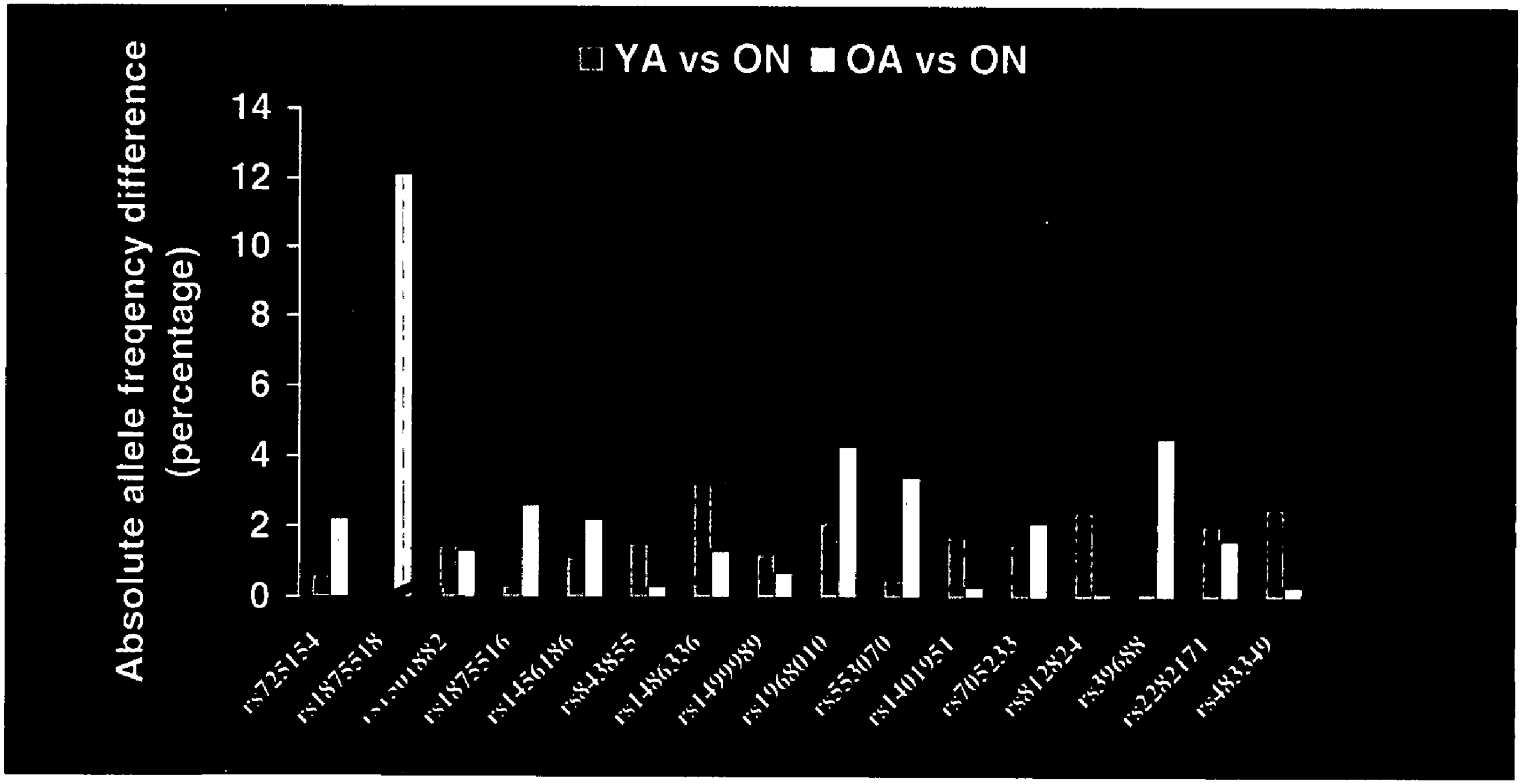

Figure 8. Identification of a significant haplotype
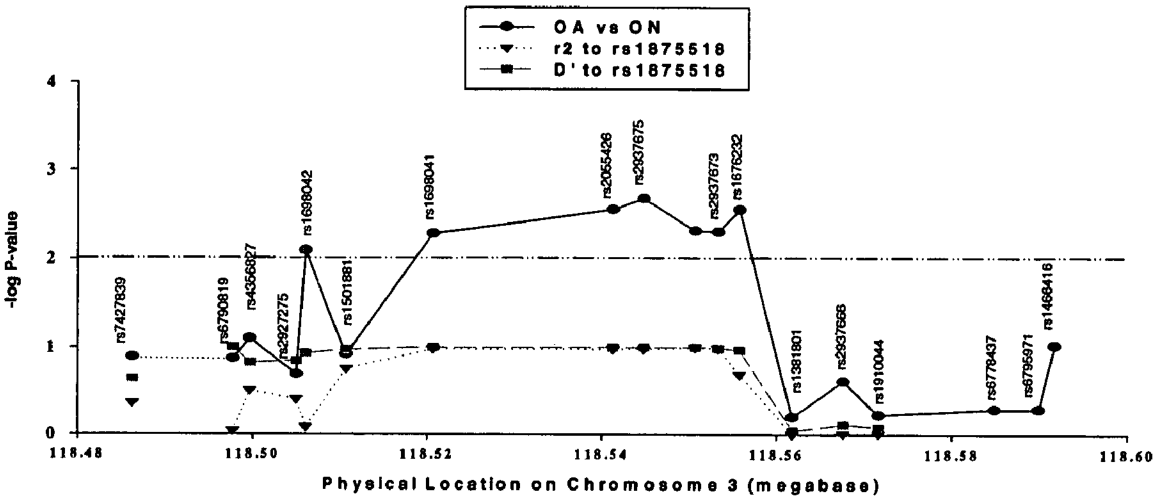
| | Frequency | | | |
|---|---|---|---|---|
| Markerse | OA | ON | OA-ON | p-value |
| rs1875518_G | 60.99% | 48.32% | 12.67% | 0.0041 |
| rs1875518_G-3M0238_245 | 4.06% | 5.99% | -1.93% | 0.6218 |
| rs1875518_G-3M0238_249 | 10.27% | 6.86% | 3.42% | 0.1915 |
| rs1875518_G-3M0238_253 | 21.39% | 11.39% | 10.00% | 0.0046 |
| rs1875518_G-3M0238_256 | 8.19% | 11.17% | -2.98% | 0.4718 |
| rs1875518_G-3M0238_249 | 8.73% | 6.85% | 1.88% | 0.5348 |
| rs1875518_G-3M0238_250 | 4.94% | 4.54% | 0.40% | 0.5944 |

Figure 9. Association analysis of SNPs with CAD
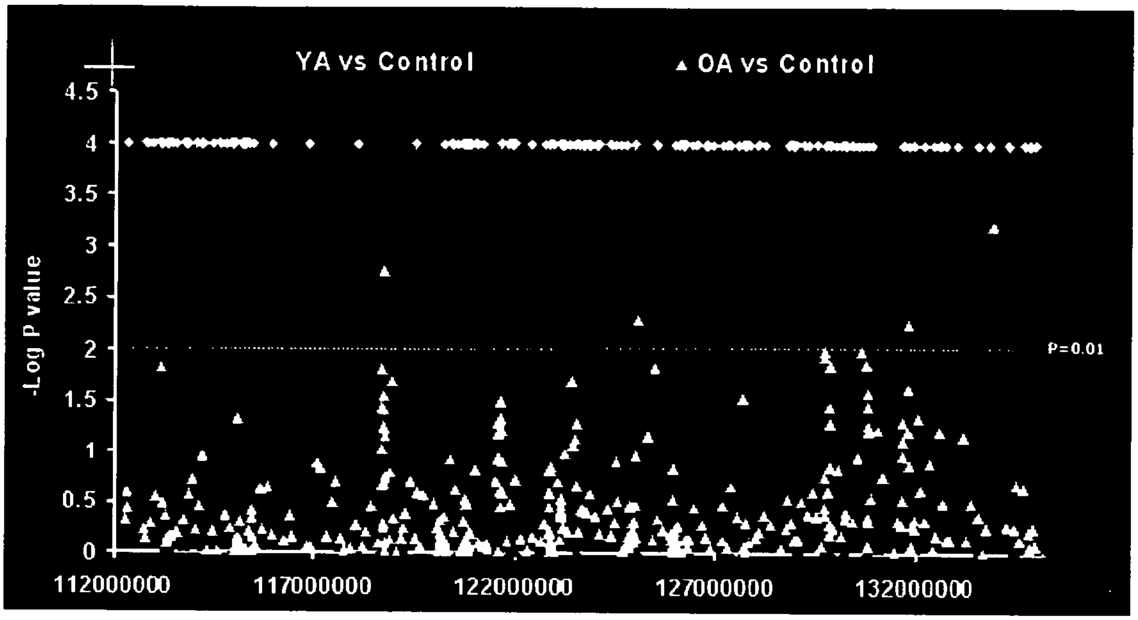

SEQUENCE LISTING

<160> NUMBER OF SEQ ID NOS: 39

<210> SEQ ID NO 1
<211> LENGTH: 261789
<212> TYPE: DNA
<213> ORGANISM: Homo sapiens

<400> SEQUENCE: 1

```
tttctaacaa tttctcttcc ttcctttctt tggagtgtta tctcactgag cagtcatcta      60

cagatattga cagtcatgtt ttatcttttt agtgttgctg tgtgttggct tccaatcaat     120

gacataaatt atgctgctat ttatgtatag ttagaatgac ttaattgccc tattaaatat     180

caacattttt atcttttcat ttttaagcta ccaatttaca agaatatttg taagtggctg     240

ccactgtctt aaattttaga ataattaaca gtgacttttc cagatctaaa tatttgatag     300

ataccttaag attccacact tcctaactta cgtggaagct aagggaaaca agtttttgag     360

cacatatgaa aagataaatt gcaacaaaat agagttcaag gagactggag atgtgtcaga     420

gtgcacaact gcagaagtca atattcagtt gttctaacta accctgaagg tctcagaacc     480

tactatcatc ctggtgttaa cataggttta tgagtatctt ccttttggtt ttctcctgat     540

ttggggaaca tttgcttcat cttcagtatc agaacgtttt cctcttctct ttttccccgc     600

cccctgtctg aagaggttcc atagtctgga ctgcaagtct cccttatatg tttctcaaat     660

ccattactcc ttatgtctgt agcccctata tttagctttg gcttgtagaa cacagataac     720

taaatcctct tcaaattcct aacactcctc tgctccaccc accttgacct cttctgtcat     780

gtaatgcata catggaacat gaaagacatt cttgccactt tatcctcttc ctcatgcctg     840

gtcatgttat aagaacaaat aatatttcaa aaataggagg aagtttcagt acatgacctt     900

gactctcctg ctctgagatt aaaacattta atttgtgata tcatcaccag ctttaaattc     960

tattcttaat ctgttgcctt gaatttattc aacattatac ctctcatcta caacaactat    1020

aatgcccatt gtagattttt atttttattt cagttaccac atactgctct atattgttac    1080

catagctcat gtatgtcaca cttgaaaatc cattaagggt agattttagt tgacactgct    1140

gcactgacag ttattaaaaa aatacttatc tcccccctct aatttcctgc tatcttaacc    1200

ttatatatgt cattttattt ttttctagag agttcataat ctactctgtc cttttttttt    1260

ctttgaagcc acttcccatt acatattaaa cctattatgc ttttattctt tttcatcaaa    1320

gtgcctatcc aacttcacat cctccaagga acctttcttg ttaaggaaga aagacaggaa    1380

ttttattacc ccagatagat acaacaaact actcttttgt gataaaacat acacataaac    1440

acaaacacac aaccccctcc ccaccagtat gaatataagt gtaaatgttt ctctttctac    1500

attcctagaa tggggagaga aacatcctct atgattcata atatgccact ctaacaacat    1560
```

-continued

```
gaacatctaa tgcacaacac ataatgtctc tgatgataat agaatagcaa gtaacttctt   1620
aaacataaaa tggtattgtc aagtcaaata ctcctaaatc taatccatat taaaaatatt   1680
tataaccctg aaatatatgg gtgtttatct aagtagaatc tccaactttc aggaaactca   1740
tttatttctt acgttttgcc tctgcagagg aggcaatttg ttaggaaagt ttctgcagct   1800
gctgaggctg ccataccatt ggtactttcc agataaagaa ctgcagcctc tagggcagtc   1860
caaatagcac cctcctccaa tgttaatctc acttcattat cccattttat aaaaggtcac   1920
aactcttttt atgtcacact ttggtttggg cacattttct tacatttaat ttgacacaat   1980
ataagaaata catgattatt cagagaactc tttcaagcct gtctcaaaca agtataattt   2040
attgtcttaa ttactgaaga atgggagaat gggtgtgcat gaaacacaca atgtttgttc   2100
acacaaagtg aactatcact ttgttctccc ggagtttctg ataggtctcc ttacatagaa   2160
cgtagagcag aaaaaagggg gccctaaata gtattagaat ttaaaagttt caaaaatatg   2220
tcagatatcc aaagaaggag gcataaccaa tgtcttatga atctatgaag cgagacgtgc   2280
taagttcaca gacatcttct gagcagctgc cacatgtgag gaacataaag aagtaaaaca   2340
tgcttgttca caaaaaagca tacagcctag ttcagaccgt gaataatcat aagaaagata   2400
acactattca acatgcagtc ttcaaaatgt tttacctgtt ttaatggatt taatcctcac   2460
agaatcctaa ttatgttggt atgtactgct cttatcccaa ttttacctgt gaggaaactg   2520
aggcaggttg agacaataat tcgctgacag tcacatgtat agatagtact gaagacaaaa   2580
ttcagaccta gagagatggg ctctggagcc aatattatta atcactacaa tgattggggt   2640
tccaaaggat gctgcactct gggtttcata gtttggactg gtatagttag cgcatgtaga   2700
acagtgtact aatgagaata tgtaaaagtc aatgttatat aagttctatt gtgtttggct   2760
cattatctca ctgttgggaa ctttgctaaa gtagagtagg catccacctt ttgggaggag   2820
ttaagcaatt ctacctttg cctgctacta ctcccatagg aagatctttt gaacccatgt   2880
ttgatatatt tccattgata gctcatttgt ttgcattaaa actagcaatc ctgtccttag   2940
gtgtttcttt ctaaaatagg tgtgttatag tactgaacta gttaacgcat atgccctctt   3000
gctcataagt gcaatagccc agaaaaggca atcattacat atttgttaaa tgaataaaaa   3060
cagaaatgcg acaagaaagt atgtatagaa tagatatcac ctctactaga ttagtaaata   3120
aatgtatgaa agagacatat ctggtttaca tttatacgct aaggaccatc atattccatc   3180
atcttacata ggtggaaatg ctgaaaaaag acgatttcac tatataaagg gacttttcct   3240
aaagaaggca aatctggaaa tggtatgatg gtgggggcat agaatactgg atgaaaaccg   3300
tagacccgca ccaaaagtat gggtgcaaga ggacagcaac agcctagagt aaaccaaagc   3360
aaagccaaag gcaaagtatt actagtaaaa gacaattcat attagtccac tgattctagg   3420
taacctctcg actccgtagt cctggatgat cttcaactgc attccagttt tacttcctgt   3480
acttgactaa ccccaatctc agtgttcccc agacagccat ctgaagaaag tacctgttat   3540
gaaccctatc gccttgaatg ccacatggga ttttgggcac tgttgcgtag atgacagaca   3600
ggatgtggat accctttgtt caactggcag acaggatgcg gatactgttt gttcaactgg   3660
ttagaccaag agacaaatca ggcataagtc ttaattacta catatatctg cgtttatttc   3720
tagggacata gattataatg ctaactgatc atttagaata catgcttgaa gcttttccta   3780
tactcaagct ggcaagttca gttatgtttg tacattattt ggccccactt catgtgtctc   3840
accttcaaat atgtgcccct gttttgctct ctgtgtagaa tcaatatggc tacttcctac   3900
attagtttca actctgtttg gagatatata atttccctct ctttagaaac tttgattagc   3960
```

-continued

```
atgacggttg tagaaggctg tacctcttta tgtaggataa ttatgatgcc acatattctc   4020
tattcctttt atcttgtacg ttagcagtct ctatagtaca tatggaaact cactttgtgt   4080
cgcagcacca gagaatgaag gcatggttgc cgagtaagtg aagaataaaa gtgtgttgtt   4140
catctgcaaa tatgtgccct accctccaat gtttaactga aatttcctgt gttcgttttg   4200
gatagtctcc cagaaagagc actgcatttg tttttcagac caatctatcg accctttcat   4260
tgtctcttct aactcatttc ccgcaactgt aacagagaca gtcagttcct ctaagaactg   4320
aggattccca accttagagt ttttcactag ccattttatt ttactgctga ataaatattg   4380
gttctggtat tttatactcc ttcactaaat tataaaaatt tatattcctc tccagggatt   4440
ataaatattc ttaataggtc tgaaggcata ggtgggtcca atgattgcat ttgttagcca   4500
aaaatcctgt atattcattg tttaaatata aaaaattaaa tatttgcaga taaataaatc   4560
actgaaaaga acagaagata gtttgtaaat taaatcagag aataccaagt atgcaacaga   4620
acctaagtta ttatgtgtaa aggtacaaaa atagccattt taggtagtgg ttctgaaatt   4680
tatttataca tcaaaatcac ctgacaggct atacaaagtt acagattctt ggatcccatc   4740
cttaggtaca ctgattctga aattcagtgg gaagtaataa gaaatctccc ttttaaaggg   4800
catgtgatgt aattctaatg cagaattgtg tttagcaatc actactctaa agaagttttg   4860
tgattctctg atttgcctgt ggaatatctg tagcagggag cataaagctt cccagataga   4920
gtggggaaga acaaaattct aagaagctac agattacctg caaagaactg gtttccaagg   4980
aaaggggagg taaagccaaa atgagagaaa agattttctc agattacatt tgggcacaaa   5040
ggaatttttc ttaaaatgca atttcctggc ttacattaag agtgtcctat aaagttaaga   5100
gacattcata aaggcttata ttccaactga agatattagt cactgactgt ggcgtattgt   5160
gctatgactg gaagagctga gtaagcaatc attgagaagg aagggctgcc atggaagatc   5220
tgctgttatc aaaatataag ccattcagca gcagaatatt gaggaaatgc tttgcaaagc   5280
cttagagtgt cacttcaaaa cataatccta aaccaggtcc ctgggatcag tcaaatcttg   5340
ttgaaatagg ctgtcaacaa gggaatattt gtttgctgtt agaatgttct cattgctaaa   5400
attctcaatt ttttacccaa agccttcatt tacattatgc aatccataat gtgtaagaaa   5460
tgaaaaaaaa taatctcaag actccaaaga tcctaaacaa gaggaagaac cattattagt   5520
tgaagagcta atcctacaca aaataacaaa tatgagcctt ctacaatcat taggaaaaaa   5580
atgggaagtc agtaacgatg tgattactca acaagtagtt gtacccagaa gcaaatatgt   5640
ttaagagaca tttcaaatgg gacaaagtta ttctgtcact aagaggagcc attcaaacct   5700
gggtatcaag ataatctgaa actataagtt tgaagaagtt actgtacagg gaagaaattt   5760
tgaaaaatca ggactttgct actctgacat tgatttatac ccttcaaata aaaaatactc   5820
cattaattac ccaatagaac acagccaaat aaaagcctca tgaaatgttg cttgaaataa   5880
tcatgaagag tagcaacaac tgagaaattt gggagaaatt tctttgcttc tttgagcatg   5940
tcaaggggag aaaaataatc atttgtttct gtacttgtca ttaagaacta tagacagtag   6000
ttaagtttta ataagtaagt agttaacatt tatgcaatga ttcatttctg ttaaaatatg   6060
catcaactgc tcctttatta cttatcattg tcttcacaac agaaaatgag gctgagtggc   6120
cagaattgcc attgtttttt aaatattact ttgattttca ctacccagat cttaaataaa   6180
caattatttt ctgcatagga aaaatcatga tgatgaatta acattggcct tgcctacttg   6240
cacactccac atgaactaag cttcaaatat cagcttctgt acttagaaaa acacagagta   6300
```

-continued

```
cagtgtgttg gttgggactg agaggatcat aataatgaaa acaaacggtc tgatcactcc   6360
agttttttt tttgccactg cctattcaca gatatttgta agatggccaa tttgtatctc   6420
ctgactttct gttttatttt caatatgacc atgctaagtt actcaaatac gttactaaaa   6480
atgaaagagg attactaaat aacattgtga aattcaggat tgtttttat ttaattttt   6540
tgaggtgtca agaaattaag gtcttcacct tttctatatt atttgcttaa ttgataggag   6600
ttcataggtt tttatttggg attgtaattt acctactgtt gctaatgcta aatatttaca   6660
tggcatgttc aagtttttta ttttacctgg ctcaataaca tagtacaata ctttgagcat   6720
catcatatta tgatgtgata tcactgggaa tttaagccaa gatctgtaga tgtgtcaaaa   6780
cgtatgtgaa ggtgttcagt gtggactgca tcctgacact gtgagccata tgcctgcctg   6840
gtagaaacaa ccctcgatta gaatccagac ggactgcatt taaagcatgg tttgtatttt   6900
acaggggatt tggacaagtc acttaacctc tctatattta agttccctca tgtgaaaaag   6960
ggagatgata atgcctacat cagagacttg ctatgaggat taagtgaaag tgttttgtaa   7020
accatcaatg gccatataaa tacaaggaat ttttatttag taaggcatta gggtaaatgt   7080
atttttagtt aattatgaaa ctccctgttt cccagataca ggtatatatt ttactacccc   7140
aacaatatct tttctgggaa aactaggtct tgggaagaaa tcagttgata gagtccctta   7200
actcaagaac tagtggcaat aacccctctt cagctcctga ggacaaatag gtccatgttt   7260
cattttcccc tctgacacaa cacagccttt tcaactctca gatgaatttc ccagaaagtg   7320
tgccagaatc ttagaacaca actgctaaag acatgaagca attaaatatg taaatcaagg   7380
aaattacact gcactgatga cattcagcac tgtgtctgcc cccaccttct cctccttttc   7440
ctctctgctt ctattcccat caggactgag gctagagtga gagctccttc ttccactctg   7500
ctccgtgcta aatgtttttt attctcaacc acctgcccca ggccttctca tcaattatta   7560
atcaagttct atgaatatgt ataaaagcct gttactgggt tttattaaat taaaaaatat   7620
atataagaac attttctgtg ccatgataga taaattatta tatggttgaa gagaaaagga   7680
agaagaaata ataagtgtgg ctttttgttt tcattccact gatgatggca caaacatatt   7740
gagaccactg attatgcagg ttttttgtt tcaagtttaa tatcaaatgt gtctctaagt   7800
tcatattttt aaaggtttac attctggaca atggactatt ctggaatctg ctttcatttg   7860
atagacagga ttctttgtga ctgagagggc ataatgttgg ctagggagtg actggacagg   7920
ttactttgat atcactctag aaataagcct tcttactttc atgtgcttct ctctcattcc   7980
aaaactgtca ccaaccgcat gatgccctga ggcaggtagg tgatggggta aattcatgag   8040
ccctggagcc ctgtctactc tgtgaggtca ttggctcaaa tcactaatga ttttcacttc   8100
ccaattttct actttaggtg aaccttcctt tccaaagaga aacaatgtct cctctcatgt   8160
actatgaaga aggatatgtc tgtgaacagt attatggctt ttatcttatc agataggcct   8220
tccctgatca ccttctctca tgtggcacac ccttaacctg ctgttcttta tatgatatta   8280
tacttaccca tcctgacata cataaggatt tgtttaatgc atcttatttc ctgtaccttc   8340
tctaccatga atgtaaggtt aataagagca ggaattttgc cttctttatc caatgccaca   8400
caaaaattgt tttaaataga taaatgaata caaactataa agataccatt aaaaaattat   8460
tctcctacta gtaacatgag cttcggggac aaacaacttc tgtgtcctag caaactaatt   8520
aactatgata ggaccagtga aattatcacc acctcaccca atgttccttt actcccactc   8580
cctgtgtcct ataagtggct ttactgtaca tggacaggtg atcctggtgc acatgagctc   8640
tcaatccata tctcaatagt taagaaatta tgtgtcctaa taaaagggta cttaaaaatg   8700
```

-continued

```
ggattttatt ttgttttgct tgttgcttat ttgttcttac ccatgtaata gtcatacatt   8760
tatataatat aaatttattt agtcaaaagt gtaggtaaaa aaaatagttg tggtttgtat   8820
tatctgtggt tttggtcatg tggcttgaat aaagatttaa gccatatgac accttcctcc   8880
cacacatctt cctgtcttcc tgcctctcat gtcttggtat ctcagccact tagcatttct   8940
aagcctcaga tattgtttcc atacataaat taaagtgtcc agattagatg aacttcaagg   9000
attaatcaac aacaaaatct aactctatgg aagcaaccca ggaagaaaac agaattttaa   9060
aattattttc ttgctcacaa ctctcagttt ttgtttgttg ttattaaagt taatgtcaaa   9120
tcaatactta catttttgt ttggaatatt ctgctttatt gcactattta ttcttcattc   9180
taaagaattt taaatttaac ctccagaata gtgtattcgc ctaatgtgtt attaaaaaat   9240
ctaattttat agagtgccat ttaaacagaa atgccaattt tcagtaataa gggtcactat   9300
aacaatgttt aatgcctcag tgacttttta tcagctaaaa tccccttttaa acatatacgc   9360
ttcctttatt tcaaattcaa gaatgaatca ttacactttg atgagcattc catcacatca   9420
gacgtagtag ttaaattttc ttgttcaaca gtctcattaa tttatcactg ctttcctggc   9480
ctcccctgat gtactcattc agtagcggcc attgtgaaaa caaacagcga tggatacaaa   9540
gctctaagtt aggtgctgtt cagtcttgga agttgtacaa cctctcatgg ggtcgacagt   9600
atagaaaaat aagtaggatc tgcagaaaaa tcactatact atgaaataga atgttccagt   9660
gccacatgag aggtgcaaag gaagtactat catagagcta ggaaagtaga aatcccttct   9720
gcccagagtg attgggaagg tatcaaagag aaggtctgag agaatgggga aagatataaa   9780
aacgtataac cataggccag gccagctgaa gcacagctgt attcatgttg tcttggatga   9840
tatgaatggg agggatgagg aaggcagatg agaaagcttc ccacacatct tcctgtcttt   9900
ctgcctctcg tatctaccat aagtggtcaa aaatgttaag agattaagaa tattgagaag   9960
gtgatggaga gagagaggaa gtgagatcat ttggataaga gagtgaagtc gtaaatattc  10020
tctcccatgg tttaaagagg gtctgaatta ggccctagag actgaatttg tcccagatct  10080
cctaggaaga gcactatagt cctccaaaga acaattccac agtctcctaa gcccaagatt  10140
aactactgca tagatcagaa agcttatgca atagaaagtt ttcttagagc aaattgcgaa  10200
tacatttaaa agaaaatctt gcttcctcta catgaccttt gactcaatcc actgttgtat  10260
gtgtgtttgg atgtgtgtat gtctgtaaaa taattctact tcacagctac acatgtatat  10320
aaacccacat ttcaggcagt agatagcttt aggtaatggg aatattttta ataaatcaaa  10380
tttatgaata aatcattgcc aattccttgg ggattactgt gtgcacatgg aactggtctg  10440
acccctgagt gtgagatttg tcatcagcag tggaaatggg cctgaaagca ggaaggcagc  10500
atagccttac agagcacaat gagaaatgag gcaaaagggc ttcgaacatg cagttgccca  10560
aagcagtcaa gagagatgat ttttcaatct gacataatgg aagtccctag agagatccat  10620
ttttcattct gacatgacta agataataag tcaaaagtta aaatacatag tataaggccc  10680
aacacaaaga aaacgatttc tattttggaa atggcaaagt acaccctgat atgtattggg  10740
ttaaatggac attctttttc tgagagaagc agcccggtga ctgtagctca aaaaaataat  10800
ttttaagagt agaagtcatc aaaaaggaac aagcaaaaaa gtgctataag aagtttgatt  10860
ctttgtggat acttggagat aatccttccc tttgtgaaat atgttcaatt aaaaaaaaag  10920
atgattgaag aaattcaaca aacaaaaatc tttgtggtga tataagaaga cctttatttt  10980
attatttatt tatttattta ttttgagatg cagtcttgct ctgtagccca tgctggagtg  11040
```

-continued

```
cagtggcatg atctccgctc actgcaaact ccactaccca agttcaagct attgtcagtc  11100
tcccccgagt agctgggatt acaggtgctc accaccaagc ctagctaatt tttgtatttt  11160
tagtagagat ggggtttcat catgttggct aggctggtct caaactcctg acctcaagtg  11220
atctgcctgt cttggcctcc caaagtgctg ggattacagc tgttcacaca gttccatgtg  11280
cacacagtaa tccccaagca atgtgcaatg attaattcat aaatttgatt tactaatcaa  11340
atttgggctg ggaagaactt tattttaagg ttaggcttta catttcatga tctttttgct  11400
agccaacaga tgagagaatt gtaagtgata tcaatttatt aaagtcatag tagaccaagt  11460
tcaggataat ttaatttttt tttttttttt tttttttga gacggagtct cgctctgtcg  11520
cccaggccgg actgcggact gcagtggcgc aatctcggct cactgcaagc tccgcttccc  11580
gggttcacgc cattctcctg cctcagcctc ccgagtagct gggactacag gcgcccgcca  11640
ccgcgcccgg ctaatttttt gtatttttag tagagacggg gtttcacctt gttagccagg  11700
atggtctcga tctcctgacc tcatgatcca cccgcctcgg cctcccaaag tgctgggatt  11760
acaggcgtga gccaccgcgc ccggccagga taatttaatt ttgatactta tgaaccaaat  11820
atagaacaaa caaaatttgg tataataaaa tgcaataata agtcatgaga aatgtaattt  11880
tatattattt attttattga gaccactata gaaataaagg tgggaattgg aagagtatta  11940
tgaatatcat gactaaaggg agattttaaa agaattcttt aaaaagctga cacagtaaag  12000
ccctggacta cattcttatc tgagatgttt ggatctgagc cagattaatg aacattattc  12060
tggatgatga cataacctgt cctactacac ataatggctt tggggttatt gggttcacct  12120
cttagctaaa ttgatcttag tgtggtaata aaataaaggt tgcctaaaat ttctataaaa  12180
aactcaaatt attataaatc tttaaattcc caattgatct gacaggaagg agtcaacata  12240
accatctatg agtagcttcc caaatcagca cctgttgcag acatttttga gtttttactt  12300
tttctctggg actcagctta gatcacagtg acaatcttat agtcccctcc tacatgtaac  12360
ttgtggaaca aagttcctcg gttgagggtt taacaagaca tcagatagat aagaacagat  12420
atttcctgtt gcatattaac ttgagaatcc tctacatata ctttgaaact ctcttcaaga  12480
acatgcataa tattcaccaa gcacatcttc cattatacta caacatgatt tctttagact  12540
atttaaaatt attaattctg actcattttt taataggatt tgtttatttc tacctctctg  12600
tttctgcatc tgcttatctg taacctttgt gggatttatt tttctccttt ctgtgacatc  12660
aggcctctct tccactcaga acacaattta agttcaggtc aacaaggaag tcttagcctg  12720
cttaactcat ctactactcc agctgttttt catttttatc ttctcaactc ttcatcattt  12780
tggtaaaaca caaatttgta tgggatttg tgtgtgctta agttattttg tgtgtgtgtg  12840
tgtattaaac accctataga tccccttctt tttgtatcat ccatgtgttc tacaagtcta  12900
tggctactca atatctaatt gaatgaagac agatagaaac accacacttc cgcttttata  12960
ccactcttta gaaacttaca gtcatctcta ttattattat atttgcctaa gaatgaaatt  13020
tctattgata ttttgttgat caattattca gtcagccctc tattgcagac ttttttttat  13080
gaacccagaa gctatagagt ttgtcccagg ctcagcatca cagaggtcat atactttccc  13140
tccattattt tactctgcta ccattagact tctagttaac acaaaaaatc tctcctgaga  13200
tccagtattg actacaatga tcttctgtat ccttagggtc tttctgagat gaaaggtcag  13260
ggagaattaa aacaggtgga tgtatccagg atcggagact ggaatgggtt agaactgagg  13320
gaagaagtgc ctccctctgc cacccatcca tacatggagg gatattctcg tgtagtcagt  13380
gatgtgaagg tgaaatcctg gcagagtttg tgtcctattt accttgacaa agggcagaaa  13440
```

-continued

```
aataaagatt cgtctctact gtgatcaaga gaaaatcccc tcttttctac cctgtgagtt  13500
actcccactt attaaaaaaa aaaaaaaaca cataataggt acccaatatg tcccagaatc  13560
tataccctac aatgtaaaca gcaaatgtcc tcattgccct caggatgaat gtaaggattg  13620
catggaaggg tgctgtgata ctctggattt cagtgtggcc tcagtcaagt gtgaatggcc  13680
atccttgcca ctattcctcc accctgcaga catgctggtg aaagatgttc attttgtaaa  13740
aagtctgcaa agcttcagaa caacactaca ggcacttaaa taatatttat tttttatttg  13800
aaattgtgac aacaaaaatg agtgataaca ttttctgata gctagcagat acttccactg  13860
ttagtggtaa aaaaaagtgt tattttctgt tggggcagtg gtaagcatgt agaccacaaa  13920
gtttgaggtc tagaaggaaa ctgaatataa atctccttat agatggaaaa atgaaggccc  13980
tgaaagacag tgatttaccc aaggtcaaaa gaatggttag tgatagagtt ctttttggcc  14040
tctgtgttgc tgctccccag cccagtgttc tttcactaaa ataaccactg tctttttgaa  14100
tatttattgc aggccagaca tactgcttta tgtatattac ctagataatt cttctcccca  14160
caaaagatag gaaaatagag accattactg ttttttaaag atgtggaaac tgagagtttg  14220
aaagatgaaa cttgcttaag gttacatatc atttaaaagc ccaaagcaga atttgatttg  14280
aggtcaacag accccaaagc cctaaattcg tgaaactagg ttacctgctc tgtatcagcc  14340
tattgagttt tggctttttg agtacaatca acaagtcttg aaagaggcat catagactga  14400
cattttaaca tagttgtcta ggaaaaaatt acaggacagt ttagctataa gaaaaatagg  14460
atgtctctaa ttcctttctc actaaaggag ctatgtggat gctaatgtta tggactttgt  14520
atattgtttc ctcacagtca tttagtatgt tttactgtgg caggtaagga gttcttaact  14580
ctctctgcat ctaaaatatt ctacatacag aagagtgaac aaaactacaa tagtgaagcc  14640
atgcacattt tctaaaatca ttcaataatc ctttgctctt aatacaattt gttgcaaatt  14700
aggctttaca acttttccct ctgagtgact ctaactcact agtgtcaggt tggcatgtaa  14760
gtattatgtg cctgtgtgtg tatgtgtcat tttgagcatg tctaaaaggt gaccttgaat  14820
ttgatattct ttaaaatata ttattttgaa gttgcttggt tttgctcttt tggtccaagt  14880
ctgcatattc tcccaataag catttaattt atgttctaga ggaataattt ttttctggca  14940
cttctcactt atccctcaag attctcacaa cccttcctga ttctacatgg ttcttcctct  15000
catacaataa aacccacaac tttgttttgc agacaccact aactcttcag atccatgagt  15060
catttttggg tcctaatccc accttggaaa atattaccat aaggctttgg ctcagagggt  15120
cattgtgtct tttaaactgt tttttttttt ttttttcaa gacagggtct cacttttgaa  15180
ctattttacc aggcagctat ttccaaagac cttgtgtgtc tgcaaatcat ttttcagatg  15240
ctctcatttg tcatagaagt cactttattc ttattgtagg cttgctttca gatactttct  15300
tatttctctg taatgtcatt ctatcgaatt ctcaaaaata cacaatgacc cactggaaaa  15360
taatagtgct aactcaaacc gctctctgcc actcaccatc tttcctatct accttaagtt  15420
gctttattta tggaatactc tgtcattagc tttcagggct tttaagatat gacaaccctt  15480
tgaaaaagat tttacattca gcaatttcta tcattctcat acaaaagtgg gaagtgactg  15540
tggagatatt gaggcagaat gggccagtga caaaacaagt agattctgga gtcagaccaa  15600
ctcctggtgc aagtacatta gccattagac tgtaaagcaa aaacaaaatt ctaagccccc  15660
caactgactg gataggcccc tactgtcagt caagggattc caaagaaacc tgaaaaacta  15720
gttcaggcca tgatgggaag aggaggttgg acatgcctta ttatactttc ctccctttgg  15780
```

-continued

```
aatttaggca caactgacta ccattaacat taaaactgag atcataagac tgacaaaaca  15840
gactctttgt agcaataaga taccaaattc taacctgact ctagtataac attacatgac  15900
agagtaggcc ctgaaagaaa taaaaagatt ttactgcaaa aaatatttat ttgacctgca  15960
aagccatctc ttgtggggaa aatttacact gtgtagacaa tccccatctc tttccaggtc  16020
tttttctaat cctgaagaga ttagcttagg gtctagcatg gtttaaaggt ctgaacagga  16080
aacatttgcc atctgttttc tctaagggtg gccacctaca agatgtcatc tacatgatag  16140
gaaccttggt ctctacaacc ccttatctta aaccagatac cctttctgtc ccatctattg  16200
cctctaaggg tggctaccta tgagacttca tctacataat aggaactttg gtctctacaa  16260
cctcttatct taatccagac actcctttcc actgattcca ggtctttaaa taataactta  16320
actctttcaa tcaattgcca atcagaaaat ctttaaatcc ccctatgact tgtaaacccc  16380
ttgctacaac tcgccccacc tttctggacc aaaccaatgt atgccttaca tgtattgatt  16440
gatatctatg tcttcctaaa acatacaaaa ccaagctgta acccaaccac ctgatacgcc  16500
tgagcacatg ttctcagggc ctcttgaggt tctgtcatgg gtcatagtcc tcacatttgg  16560
ctcagaataa atctcttcac attctttaga gtttggcttt tttcatcaat aagaccttgg  16620
accatttagc taacctctca gaatttcact atctgtaaaa tgagaagaat atcttcactt  16680
cctatagttc ttgggataat aatgtgcaca aaccaccagc agctcttgtc ccatatgaac  16740
tctcagttca tcattaatag cctgtttttc taattcagat aacatttgaa aaatgtgcaa  16800
actattgttg catgtgacta tagttcattc atattgactg ctagctatat actatagttt  16860
attcttcagc tctcaatata ataggaaact tggatgtttc tagattttta attatgatga  16920
acactcatat acacacacac acacacacac acacacacat atctgtatgt acatatgcat  16980
gaattctctt agttacttgg aggttgggtt attgagtcat caggtatgta aatgttcaat  17040
tttacaatat aaagctgact tctttttgga agtggttaca ctagttcaaa tgcccaatga  17100
caatatctaa aagatctaat agatcatatc cagtacgtga tgttatcaaa ctctcaaatg  17160
tttgccattt gaataggttt aaagtggcat atattatcat ggtcttcaat tgcatttctt  17220
caatcattaa tatttaatat atttattttc catagcattt cctcttttgt gaaatgctgt  17280
tgtgtttcat tttaacccag tttttctttt aatgatatgc cttgtgtggc agatgtctaa  17340
aaatttgact atttttggca tagcactttg aaatctggga gtttatttta tggagaaaaa  17400
ttttcaaaga agcattatga aggcattcac tgaaactgtg tttgtaataa caaaatgcag  17460
taaataggct aaatgtgaaa taaatgaaaa ttatttaaat attttatgca aataaagagg  17520
aatactgaca tataatacat tcaattataa tggtggttat atatatggag ccaaagaaag  17580
atgctcacaa tatgatccta agagaaaaaa aaaagctggt aattaatagg ttttgtctct  17640
gaataaatga atttaaagtg gcattttaaa aaatctattt ttgttatttt actaaactaa  17700
atttaattat gaagacattg aagataaatc tatactatag atttttaaag acagaaaaat  17760
cttagataat ttatctaaag gcacatagct aatgataagt agaacagcag ggtttagaac  17820
ccaaacatcc ccagagtacc ggactctaag catttatctt ttattcagtt cgctggggtc  17880
ctgcttcaag aatgttggta tctgtgtcct gatcaattgt taacctttga aatggtggta  17940
agagtggcct cttcctgctt gtcagtgata actggatgta tgggcaagaa ggaatatcat  18000
ggaatgataa taaattaggg gttagggtgg atgagaagca atctattact gtgcatatac  18060
ttaatctaaa atgaagggtt aatgtacagc caatctagga aaagggactc tttcttgcag  18120
tcctcagata ttttctgata taaagaaaga tttgatatta gcataattat aaaggtcatt  18180
```

-continued

```
gctccatatg gtatttttta gtagtctgat tagtaagact atcattaacc tagtatttgg  18240
atcacatgac tgggtgtaaa acaaccactg gaataataaa catccaggtg ctttaatttc  18300
aatgtcatta aattaaattt tactgttttt tactattttt tcgttattta ttctcatcag  18360
tctctattct tcatgtcctc ctcctttctc ttaattgtac ataaaattct aactttggtt  18420
taaaatattc ccctgataac tcctgattaa aacacaataa aggccattta agggtgagca  18480
gaatgtaaag gtgactaggt aaccaaagga gcattaatct atcctcagtt aaaactgtta  18540
agcctattga aaacaatttc tcaaacctag cagaaccttg gattacagaa tagtaagggc  18600
aagaggagtc aaagtttatt tttaagccag gacctaaata ttgtctgagt caaggtagac  18660
ccaaggagtt gaagggacat aaagggaaga cagctggaat gtcatgcaga gtgtagaatt  18720
taaataccga caactactat gagctcttcc tatggtccca attttcctat tattatttct  18780
atatcttctt agtttatctc cttaatttta gcagtggcaa tggccggaac cctcatggct  18840
tctgccactg ctgctgcata taaactaaat atttggtctt tttctaatac atacacaaca  18900
attgtctatt cataaataac tgaggacaaa gtaggatgca tccttataga ctctatttaa  18960
taaaaaatat gttaaaaaca tgtagctctt ataagccatg tagaaagtat ctagaagact  19020
tcaaaagcat tgtgttttca caggcctaaa tatttgtcga caactaattc cttactaaat  19080
tgtccttggt ttttcttgct agaattgaat gacttaagca catttgttgc ttacttttat  19140
caagatcttt taatgattaa ctaagtcttc tcctcatcac tgaaaaaccc caagcccatc  19200
tatctatctt tgcctataat tgcccatgtt tagagcaaac cctcagcaac ctgtttacta  19260
tattcatgag ctcaaaggac tgaccacttt taggtcagac taattttgtg ttttaaaatg  19320
agactgtcct gctgggatat caaaaaatgt tagtgaaggg aagaaggata gcagaaagat  19380
ggcagaaata ggaagcccca accttcgttc ttccacggac ttaacagcaa tatataaacc  19440
aaaatgcctc catgaagact ctagaagcca gttaagaagt ctcagtaccc aaatgagcac  19500
aaggccaaga acagctacat taagatgtat aagaaaaagt cattttattc tacctatgat  19560
tgcccctcct ccaaactggc acagtttggc atgattgaga aaaagtaccc aattttcagc  19620
ccctccaggt ggaaacagaa tagtagaaca tgcattcagt gttttggttt tatggggagc  19680
tgagtgaggg agtaatttct gtcttctctg actcagggtg ctgatggaaa tgccatactt  19740
tggatgcctg agtgctgctg aaaacctttg atatggaaga gtgacctctt cctgtatatc  19800
agtgataact ggatgtatgg gcaaaaaaca atcatagaat gataataaat tagggagtgg  19860
gtagatgaga agtagttttg ctgtaactgt tcatgtcctt actctaaaat gaagagttca  19920
tgtacagcta atctagggaa acctgaagaa ccgcagacag acaccagagg aagcaaaaga  19980
ttatgagctc ctgaaaaaga aaatggcaaa catctctcat tggataggag ataaagtaga  20040
tgttaagtcg gaaactgtca cagatgcaga gaagggcatt acataatgac aaaaagacca  20100
attaaccaag aagatataac aatcataaat atatatacac caacatcaac atcagacacc  20160
catatatatt gaccaaacat tcacaaaatt gaagggaaaa atagagagta acatggtaat  20220
agtaagagat ttcaatactt cactttcaat aatagataaa acaaccagta agaagaaaca  20280
taaaagaaag gaaaggaatt gagcagcact gtagaccaat tggatccaac aaacacatac  20340
agagcactcc agccaacaac agtagaatac acattttcct taagagcaca cagaacacta  20400
tcaggataga tcacattagg acaaaaacgt gtcttaagaa atgtaggatt aagttagatt  20460
aaaatcattc caactatatt ttataatcac aatggaatac aaacacaata gagtaccatt  20520
```

-continued cagccataaa aagaatgaga tccagtcatt tgcaacaaca tggatggaat tggagatcat 20580
tacattaaat gaaatgagcc aggcacagaa agacagacat cacatgttct catttatttg 20640
tgggatctaa aaatcaaaac aattgaattc atagacatag agaatagaag gatggttatc 20700
agagtctggg aagcatagtg gggagctgtg gtgggtggag tgggaatggt taatgggtac 20760
aaaaagtaga aagaatgaat aagacttact ctttgatagc acaacagggt gactgtaatc 20820
aataataact ttactgtaca tttttaaata acttagagtg taactgtaac tgaactgttt 20880
gtaactgaaa ggatacaggc ttgcagggat ggatatctca tcctccatat atatatatat 20940
atatataaaa tatatatgta tatatataca tatgtatatg tatatatata cacacatata 21000
gtagatatat atgtatctac tatgtatgca caaaaaaata gaaattaaaa ttttttaaaa 21060
aatgaatagc aaaagcaaaa ctggaaaatc cataaatatg tagaaactag acaatatgct 21120
cttgaacagt taatggatga aagacaaagt catgaagaaa attagaaaat atcttgagac 21180
taatgaaaac aaaaacataa catactaaca ctcctgggat gcagcaaaag tagtactaag 21240
agagacattt agagcagtaa acacctacct taaataggca gaaggatctc aaatcaacaa 21300
tgtaaattta cacctctaga aagtaggtaa agaaggacag actaaaccaa aagttagcaa 21360
aaggaaggaa ataataaata tgagagcaga aagcaacaaa atagagaaca gaagaataga 21420
aaacatcaat gaaattaaaa gttagtgttc ttaaatcaac aaaattgaca aacttttaat 21480
gaaactaatt ttattttatt tttgagatag agtcttgttc tgtcacccaa gccggagtgc 21540
agtagcacca tcttggctca ctgcaacttc tgcctcccgg gttctggcaa ttctcctgcc 21600
tcaacctctc aagtagctgg gactacaggt gcacgccacc acttccagct aatttttgtg 21660
tttttagtag agacagggtt ttacgatgtt ggccaggctg gtctcaaact cctgacctca 21720
agtgatccac ctgcctcagc ctcccaaaat gttggaatta caggcatgag ccactgcacc 21780
tggcttaaac taactttaaa aatatagaga gaagatgtaa caaaaatcag aaattacaaa 21840
aaaaatcaca actggtgcca aataagtaaa aaagagaaaa gagtactgtg aatatatgcc 21900
aacaatgtgg ataacctgta aataatggat aaattcctag aaacaaagtg gaaaacctga 21960
accaacctat attaagtaag gaggttgaat cagtaatcaa aatctcccaa tgagaaaatg 22020
ttcaggccca gatggcttcc ctggataact ctaccaaaca tgataaacta ttaattcatt 22080
aactcattaa ttcattccat ggatatattg ttctattcat aaggcagagt cctcatgatt 22140
ctatcacctc ttaaaggcct acgtcttgat actgccacac gggggattaa gtttcaacat 22200
gaggtttgga gaggacatcc aatctatagc agaggccaaa gatttgtacc ctgaaaacta 22260
caaaattcta aaaccaatta aataatacac aaatgaatga aaagacattt tgtgatcatg 22320
gattggaaga cttaatattg ctaaaatgtc catactactc aaggtaatct acagattcaa 22380
tgaaatttct atcaaaatct caatggcatt tttgttttgc taaaatagaa gaatacaccc 22440
taaaatttat atggaatctc aaatgaattc aagtagctaa aaataaaaat atcctaagaa 22500
agaataaagc tggaagtctc acacttgctg atatataaaa aaaagactac gaaagaagaa 22560
agatggagtt ctcacacttg ctgatatcaa aatatattac aaagcttcag taatcaaaac 22620
agtatggtac ttgcataaag acagacatac agactgatac agaatagaga accaataaat 22680
aaatccacac atttaaagtc aattgatatt ctataaaggc atcagaaaga cacaacagga 22740
aaacggtagt gtcttcaata aatggtacaa ggaaactaga tattcataag aaaaatccaa 22800
acataagacc tgaaaccaca aaacttctaa aagaaaacat aaaggaaagt tttataacgt 22860
tggataaggc aatgattttt tggatatgac accaacagca caggcaacaa aagcaaaact 22920

-continued agacaaattt taaaatatca aacttaaaac ttcctgtgca gcacagaaag aaaaatattt 22980
catgatctca cttacatgtg gaatctaaaa aaataaataa atatacaaag ataaataaca 23040
aaattttggc taccagggac agggtgggaa ggtgcaaaat gaggagaggt aatccagaga 23100
atacaaggta gcagatatgt aggatgaata attctaagat ctaatgtaca acatgaaaat 23160
ataggtaata aaattgtact gtatatgaga ttcacactaa attagtagat tttagatatt 23220
ctcgccacaa aaacagacaa aaagaaatgg ataactatgt gagatgatgg atatgttaat 23280
ttgcttcatt atggtaacct ttttactatt catatgtatc ccataacatc atgccatata 23340
ccttaaatat ccataatgag aatttttaaa aaaatacttc tatgtagcag aggatataat 23400
caacagacag aaaaggcaac ctacagattg ggagaaatta tttgtgaact atatacctca 23460
taaggggtta atatccaaat taaataaaga acaactgtaa ctgttggtaa gtatgtaaaa 23520
tggtgcagct gttatggaaa acagtatgta ggttcctgaa gatattaaag ctagaaatac 23580
catatgacct agcaattcca ctttttggta tatatcaaaa aaacctgaaa gtagaatctt 23640
gaagagatat ttgcaccttc atgtttactg cagcattact cataacagcc aagagatgga 23700
agcaacctaa ttgtccatca atgtatgaac agataaagaa aatgtgatat atacatacaa 23760
tgtaatatta ttctgcccta agaaagaagg aaatcatgtt ttctgctaca acatggatga 23820
aacttgggga cattatatta ggtgaattaa gccagtcaca aaaataacta cataattacc 23880
cttatatcag gtatctaaag tagtcaaact cacagtgaca gaaaatagaa tgtgggcact 23940
agtgggtagg ggaaaggtag caatgagtag ttatttttaa tgtctacagg gcttcagttt 24000
gcaaggtaaa aagtttctag agatctgttg cacaacaatg tgcatatagt taatattaca 24060
gtattctaca ctgaaaagtg gttaagatag taattttatg agtttttcaa cataataaaa 24120
aatgttatag gagaagaatg ttagcatagt gattatgagc aaaagttttg gattctgata 24180
aacatggctt aagtttggat acagtctcat actagccata gggcccacaa gtcacttaac 24240
ctcgtagcca ggcttcctat ttggcaaaat ggggataata actgttccta cctttactat 24300
tataattttt ttagataagt gtgaaacatt gagctcagtg ctaggcactt ggcaagcact 24360
caatcaacag cagttaaatg gtgtgatgag tattccagga agatggagta taaatgaagg 24420
actggggatg aagactggtg agttcctgac agctttgggg ttggtggaaa tgatgagtaa 24480
gtgaatattt gaagacttgt tacattcaca ttattgttga gcccagacct taggatgaac 24540
acctcaagct aacatcagat ccagagccca ggagtactgc ccaaagctat ctacatgtta 24600
ctatccatgg tgctgaatta tcttgggact atgccctctt gactttttca taaacatcac 24660
agaacctgat cattctattc caaaatgcaa tttacaaaag ttcataacct atttttagaa 24720
acaaacggaa aaatgatgct tacagaaatc ccatttttgt tcccatatat catctgtaaa 24780
atttatttct gtggaaaaac ataacccagt gcactaaagt taggagagtg aaacaataaa 24840
gatatttatc gtgatccaat taatactggt tatgagaagg taagtacatg aatagatcta 24900
ctcatatcct cataatcaat tagccttctt aataaggcag acgtgttttt cagagaaatc 24960
agaaatcaaa tcagagtttg tattggtatc ttaggaaaaa gcatttcaag aataaatctt 25020
ccaaaaggca cacactttct cagttctact gataaaacaa aaacaaggat atgtaaagag 25080
gctttgctgc tcccttacaa actctcccag tttatactcc caaaggaaat aaagtctgcc 25140
ttatttcttt gcccacctgc ggtgaacttt aatgtttgtc tatatgtatt gaagaacctt 25200
aagttcattt ccccctggga tgaattcagc atatggtctg ttcctaaggc aaacatttat 25260

-continued

```
ttaaacttta aatctaaaag gaattctttc attttatttc tagttttgtt tcctttgatc  25320
ctgaaagtaa ttaactttca ctggcagcta attataagtg aagagaaatc agagtctata  25380
tggtcgtttg tttggtgcag tcctggcaaa atgttttcta attggaaagt ctctttgctc  25440
aatgcattcc aatccatttt gcactgtatt tattatccag gattcatatt ataaccatga  25500
cctttcatct aatcacagaa tctcacacag agaaaaaata attattttaa caaagagcca  25560
ccgtggctat aaaaagtgag agaggctggg agggagtaga atatgacagg agaagaacca  25620
catccaaaat ctcttcctgc tcttcactat cacagtccca tgacaacccc cttgtactga  25680
aaaacatata ccccacattt ggattaggaa attatcttct tcaaacttat acagaaatca  25740
gctcctgaaa aataatacag aaaagaagag agccataggt aaaaataatt gaggtcagag  25800
gtgctgctta ctgttccgtg ttaatactaa tcatcagaag catggaaaaa tttgaaagtt  25860
aatgaaccgc cagtcaaatg acccttacca taactcccat ttccctgaaa atgacccttg  25920
caagaactga caaatctttt tgtcatcaat tttttccttt tcaaaagaaa aaccaggcat  25980
ttaaaaaaat atattcattg tctgtttgaa ataaatatgt tacaaggatt taaaaaaaac  26040
acactgaata caatgaggga atttaaactg tattttggaa agaggactct aaacatcttt  26100
gcctttctaa acaactcctt aaccaaccaa aaacaatcag cattacagga aagcaacact  26160
cttaaacaga gataaatctt gacctgactg ctcttcttgt atgacatctt ttcatactgc  26220
tactgttaag aactggtgtg ataaagataa tctaaggggc atattatcca ccatcttcta  26280
caaatttgca tcaaattaga gcatcagaaa acaatatgcc catacctcat tagcttgcat  26340
ccatgcagaa taacacctgt gagttatttc tatagatctg gcttaatcta gagtcaatgc  26400
atatgatggt aatctcccac atcttacaaa attattggta aaagcaataa tttccatatt  26460
tttaaataac caacataaaa atttccttcc aagtagagta catacaattt tgcttcttcg  26520
gaagaattga aataatataa acttcctgat ccattgcatt tgctttttct cttttttttt  26580
tttctttctt tttgagacag agtcttactt tgttgcccat gctggagttc agtggtgcag  26640
tctcgtctca ctgcaacctc cgcctcttgg gttcaagaga ttctcctgcc tcagcctcgc  26700
gagtagctgg gcttacaggc acccaccacc atgcctggct aattttttta tttttaatgg  26760
agacgaggtt tcgccatgtt ggccaggctg ttttgaactc ctcacctcag gtgatctgcc  26820
cgcctcagcc tctcaaaatg ctgggcttac aggtgtgagc caccagggcc ccccagccac  26880
atttgctttt attgtgctgc tgctaggaag cgcagggtaa agacattatt caatcacaat  26940
gactaagtga gcctagataa attgtatatt tacccaagct cttctagatg aatttaattt  27000
tttgagttgt attttaatag gttttgttgt gtagatttaa ttccccattt tgtgagaaac  27060
tatactgtaa aacaatcttt aatattcatt actggcttga gaatttaata aaatgaaaat  27120
gttttctact tttacttgga atttcatagg tgcatcttta aagatactga caccactcta  27180
cctccacttt taaggaattc attaaagtgc tgatcattag ctgaaagtat gataaagagg  27240
tgaaaagttt tgcacatgtt gcaagtgaga aaatgtcaca ctaatgaggc aaacatcata  27300
cattataagc ccctatgtgg gctactccat tattgagttt agatggttag cgaccttgtg  27360
aattaggcca attaatgcct aaaggttacg taagatagtc ttgatgaata agaaaacatc  27420
ctttcatact gctgggaaac taaacaaaag catatgcctt tattgggcat cgctaatact  27480
aacttcacat tccatgattt ctacttactt tcattttgtg gaagtacaag aaactgttac  27540
atagcaagtc cttatatctc tcaaaacaat ctcttccctt gaaaatgtct gcagcacttt  27600
ctcaattcca ctcagtcctc ttctatttct atctttcctt aaccatctgg agaagtcaat  27660
```

-continued

```
cctagacatc atgggatggt gttctgggat ttatattatt gcagatattt atagaaagcc  27720
taattgatga gcctctttgt tcttatcttc tgtagcctca ctcgtaataa accgttaaga  27780
aaacagaaat tgcagaccag acaagacaca gcctttccag ccttggtaag acgtattttc  27840
tagaagagtg ccgtttttct ccacaataga actttaaaag tagatccatc atttaatgtt  27900
aggaatctgt caagcatgaa tttttagcct ccatcaaaat tttcaataat taattccatg  27960
ggtttgggaa cctacatatt cccttctcaa ctatgtggaa aaaaattacc tctgaaattt  28020
gataaacatt tctatgtgca gtttattaat attaataaat tttataaagt ttaaacattt  28080
cttcatcttt atagaatgat agtatcattt taaagcttat tcttgtatga atgttaatct  28140
ggctcattta caaattccct tcagttggat ttcttgctca agagaatttg tatgaaagat  28200
ggtgctgata tccaccagat tttgttctta tttttattga ttgtttactt gttttgcata  28260
atgataggtt atgtgcagaa tagttcaggt tctttttctt aggttttttt ttttgccatg  28320
tacatgtcca gttgaaatat acatgctcac ttttatgtag tccatcctct tctatattga  28380
gctaaacgtg agttcatact gctgtcttca attctgatcc attaccacaa aggtcattat  28440
aaccccctcc tccttatttt ctcacccttt caatgagttt gtttcataca tttataaatat  28500
acttagaata tcttttcaca ttctgtattc catcctggaa ttttccaacc ttctaaagga  28560
catttttttaa aaaaccttaa aaaagaagct tcactttttg tgttgtaaaa cactgtaggt  28620
tttgataaat gcttaatgtc ttctgtccat gattacagta ttgcatagaa tagtttttac  28680
cctaaaaaat tccctgcact tcatctattc aaccctcctc tgccctacta ctccagcttc  28740
tggtatccac taatttgttt cctatagttt tgccatttcc agaatgtcat atagttgaaa  28800
tcatatagta tatagccctt tcagatagct tctttcactt aacaattttc atgtaagatt  28860
tattcatttc tctgtctctc tctctctctc tctctctctg tctgtgtgtg tgtgtgtgtg  28920
tgtgtgtgtg tgagagagag agagagagag acttgacagc tcatttattt taatcactga  28980
ataatgttgt aggtctggat ataccacagt ttttatccat tctcctttaa agaatattct  29040
ggttgctttc agtttttgga aactatgaat aaagctacta taaatactca catgcaggtt  29100
tcatatggtc ataaattttt taatcagttg ggtagtacct aggagagtga tcaggcccat  29160
gtggtatgac tctgtttagt tttttaagaa acttgtcttc caaagtggtt gtatcattgc  29220
gaatttctat cagcagtgaa tgagagttcc tgttgttcca tgtcctcaac aatatttaat  29280
attgacaaat ttttgtcttt tagccatttt aaaaggtata atatgtacct attaaattaa  29340
atatttaatt aaatatttgg tatctcattg tcattttaat ttgcaactct ctcttgacaa  29400
attatgttga gcatcgtttc acattatttt ccccctgcat atttcatttg gtgaggcatc  29460
tgttttatgg tgtatttttt tcatttttaa attgagttgt tttcttatca ttgagtgtta  29520
tttgtatatt ttgaatacaa ttccttcaac aggaatgtgt ttcacaaatg ctttctccca  29580
gtctgtgact tccattttaa attttttaac agtgtattat ttaaagcatg ttttatttta  29640
atatataacc atttaatata aaaataacaa ttctttcatg gatcattcta ttgatgtatt  29700
taaatacaca aggtgatata tattttagcc tatgtttata ataatgtttt atatttttat  29760
tactttacat tcaaatctat gatgcatttt gaagaaaaag gttcagcttt tcaccactaa  29820
gtatgatgtt agttgtaggt tttatgtaag tgttcttttt caaattgaga aagttcccct  29880
ttattcctac ttcactgaga gtttttgtca taaaagaata ttgaattttt taagtgtttt  29940
ttctgtgtct attgacataa tgatatgaac gttccttttt catctgcagt gaattatatt  30000
```

-continued gatttttcaa tgttgaacta gtattggcat atctgaaata aacctcactt ggtaattata 30060
cttggttgaa tagtgtcccc acaaaattca tgttcactta ggatctcaga atgtgtactt 30120
atttggaaat aggaactttg caaatgtaat caagttaaga taagatcata ctgaattagg 30180
gtgaccctga aatccagtga ctctccttct aaggagagaa atatttgaaa acacacacaa 30240
aaggaagaag gctatgtcac agcacaggca gcattctggc tctgttctag agtaaggcag 30300
ctgcaagcca aggaatgcca atgattgttg acaaacacca aaatctaaag aaaggcaagg 30360
aaaatttctt tcctagaggt ttcagaggga acatgtccct cgtgacatca tggcttctat 30420
tctcggaaac tgtgggagaa taaattttta ttgttttaag ccactcagta tttaataatt 30480
tttaaaggca gtcttaagaa actaatacat ttctggtgta taattccttt atacattgtt 30540
ggattcaatt tgctaatatt ttgttgagga ttttgcatct atattcatga tatatattgg 30600
cctgtagttt ttcttacttg taatgtccgt atatggtttt agtattagaa taatgctgat 30660
ctcatagaat gagctaggaa gtgttccccc ttttctattt actagaaaga gattgtggag 30720
aattggtata atttctccct taaatatttg ggaaaattca ccagtgaaac catctggtca 30780
tgatgacttc attattggaa agttattaat tattaattca attcatttaa tagataaagg 30840
acacttcaag tcatttttttc tccttgtgtg agttttagta gttcatagct ttcaaagact 30900
tggcccattt catctaaatt gccaaatttg ggggcataga gttgctcata gtatttgttt 30960
attgcctttt ctaatgccca taggatcagc aatgatgact tctttttttat tcctggtatc 31020
agtaatttgt atttttatat atatatatta tatatataac atatatatat ataatatata 31080
catatatgtg ttatatataa tatatacata tatatgttat atataacata tatataatat 31140
atacatatat atgtatatat tatatatgta tatatgttat atatacatat attatatatg 31200
tataatatgt tatatatatt atgtatatgt tatacatata tgtacatata tgtacataac 31260
atatatgtta tgtatatgtt atatatatta tatatgttat atatataata tatatgtaat 31320
atacacataa aaacacacat atatacacat aaatatatat ctttttggtt agcatggtta 31380
gaggcttatc aaatttatta agcttttaaa agaaacagct ttagatttca ctgatttttct 31440
tactgttttc ctgtttctga ttttattgat ttctgttcta atacatattg atgttctaga 31500
catattgata tcttttattc tgcttgcttt aggtttaaat tacaaatttt tccccagttt 31560
tctaaagtgg aaacttaaag tattgatttt agatctttct tgtttttttaa tacagtcatt 31620
taattctata aatatccttc ttagtgaata tcacaaactt tcataattta tattttcata 31680
taaattgaat tcaattgttt ttaaaatttc tcttgagatc acctctttag attatgtgtt 31740
atttcaaagt ttgttgttta atttccaaat gtatggggat tttcaattaa ttttagttca 31800
attccattat gatccaagaa catactttat ttgatttcta ttattttgca tttgttaagg 31860
tgtattttat cacccaaaat gtgatttatg ttggtgaatg ttccatgtga actagaggag 31920
tgtgattatt ctattgttga atgaactagt caacaaatat taatgagatc aagttgattt 31980
ttagtgttgt ttaggtcaac tatattcttt ctcactttct tcctgcttga tctattaatt 32040
actgtcaggg aatgttgaaa tcttcaactc tattcgtgga tttgtgtgtt tttcctttca 32100
gttctatcag ttttggtctt gtgtattttt atgtgttgtt tctgcctgca tacatattta 32160
ggcttgatat ttcttcttgg agaattgacc cgtttgccat tattattaat gatatactcc 32220
tttattacta gtaatttgtc tccttccaaa gtctggtttg tctgaaatta atatggctac 32280
tccagtttcc tttcaatgaa tgctagcatg gttgctttat ctatcccttt atttttaacc 32340
tattagaaac tttattttta aagtgggatt ttgtagacaa catacagttg ggtcttattt 32400

-continued

```
gtttgtctac tctgaaaata tctgtctttt aattggttta tacagaccat tgacatttca  32460
agtaattatt gatatatttg ttttctgttt tgttttgttt ttgttgctgt cgttgttgtt  32520
tttggtgggg agggacaggg tctcgctctg ttactaacct agagtgccat ggtgcaaaca  32580
tggctcactg taatcttgac ctgggctcaa gcaatccttc tgccttagcc tcccacgtag  32640
ctgggacaag agacatgtgc caccacactc agctgttttt ttttcatttt tattattatt  32700
tcattattat tatgattatt attttgtaga gacagggtcc cactttgttg cccaggctgt  32760
gcttgaaatc ctgggcataa gcgatcctcc caccttggcc tcccaaagcg ttgagattac  32820
aggcatgagg caccatggcc agccaattat tgatgcattt ggattaatat gaactattct  32880
tgtaattgtt ttcatttatt gccagataat ttttccctcg tgatacctct ggttttaatt  32940
tcagttatac ttaaaaaaaa aaaagatttt tagtggtttc cctagagttt acaacataca  33000
tttctaacta ctttaatttt accttcaaac aacattattc tgcttatagc tccagttcct  33060
ccttctcatc ttttgtgaca ctgctatcat acatttcact tatccatatg ctataatcac  33120
ccaatacatt attagtatta ttactttaag cagttatcca tatgctataa tccatacgct  33180
ataatccata tgctataatc acccaacata ttattagtat tattacttta aagttacctt  33240
ttagatcaat taaaataaga aaaaataaat aatttcattt tgtcttcatt tattccttct  33300
ctaatgttct tcttttcttt atgtctatcc aagtttctaa cctacatcct ttttgttctg  33360
cctgaagaaa atcttttagc atttcttgta aagaactggc aatgaatttt ctgtttttgt  33420
ttgtttgaaa aaataggcca ggcatggtgg cttatacctg taattccagc aactgaagcc  33480
aaggttggag gattgcttga gccaggagtt caagaccagc ctgggtaaca tagggagacc  33540
ccatctctac aaaatatttt ttttaaaagg ttagctgggc atggtggcat gtgaagattg  33600
cttgagatct gggaggtcaa ggcttcagtg agccatgact gtgccactgc attccagtgt  33660
gggcaaaaga aggagactct gtctcaaaag aaaaaaaaaa aaacaaaaaa accaaaaaaa  33720
aaaacaagga aaagtatgta ctttctttca cttttaatga atattttcac tggatataga  33780
attctaggtt gatgttcttt tctttcaata ttttagatat ttccctctgt gatcttattt  33840
gcatggtgtc tgattagaaa tgtactgtaa ttcttatgct tgttccttat aatttgtata  33900
tgttgtttta tctttctctg tattatttca atattttctc ttttctttga ttttatgaag  33960
tttaaatatg ctaggcctca gggttgattt tagaaattta ttctgcctgg ggttctctgg  34020
gcttctggat ctgtggtttg gtgtctatga taaatttttg aaagctctta gtcattatta  34080
ctttaaatat ttcttctgct tcattcatgc tttcttatcc ctccagttgt ccaattgcat  34140
gtatttttta tactgtccca tagtcttgga tgttctgttg tgttgttttg ttttatttta  34200
ttttcccatc cttttcttta catttctctt tggaaatcct caagctctct aaatctttcc  34260
tcagtcacac aagtctacta atgtgttcat caaaaatatt cttcatttct ctcccagtgt  34320
tttttatttc tagtatttcc ttttgattct ttttcagaat tgcagtctct ctgattacat  34380
tacctatatg ttcttggatt ttgcctgctt tctccattag ctaccttaac atattaatca  34440
caattattta aaactctctg cacaattatt tcaacacata tgtcatatat aactctggtt  34500
ctgaaacttg ctttgtcttg ttaggctgtg ttttttttct tgatctttgc ataccttgta  34560
atttgtttgt tgaaagccag acacattgca caatagagat tgatgtaaac aggtctctag  34620
tgtgagtatt gatgttaatc tggctaggag ttgagatttt tttaatgttt tctatagctg  34680
taggatccag aggtttcaaa ttcctctgat gaccttgttt ttgttttccc ttttgatttt  34740
```

-continued

```
gggcttacta aaattaatat tcctcctcag aaagtttgtg tctcatagct cttctggcgt  34800
aattactata actcattatt agaatgccat agcctcttgg tgtggtggtg aggtggggaa  34860
tggggcacat cccatagtct cagtctttta gaaggccgta tttctgccct atgacttaca  34920
caagtgtttc ttcctgtata gcttcttctc cactccgcct tacatatgga gaggactgta  34980
gtgagaggaa taatttcccc tcacaccttt gggataaaac tctggtagtc ttcctactct  35040
agaggaagcc atttttatgg agaaggcttc ggggtcattt ctcaaggatt actcttttcc  35100
tccccctacc agagccacaa agggggtctt tcttaactct ttattgtgag aatctggcgg  35160
tttgctgggg taaattctgt gaaagacaga gtgtcttcct aagactacag cccctaggac  35220
tttctcactg tggtagtaat gcacattcaa cctctagaaa tttgtcaaaa ttcccattta  35280
attgttccta tcagttaatg gctgcagtgg cttctgctcc acgtaaacag atctcaatta  35340
tatctctctg gattctcctg tctttccaat tgttggagtg gaaatttatc ctgcaaactc  35400
agttttctaa tccgtccaag aaaagtcatt gattttcatt ttgtccagct ttgttttgtt  35460
gttaaaataa tggaagtgac catttccaag ctccttgtac gttgaagcta taactggaat  35520
ttaagctagg atttttaaac atctaatttt actacatgct tatgtgccag tggctttgaa  35580
agggatactt gaagagatac atgtccaatt caagtctgtc tctcaggaag ttttgttact  35640
ttctagagca tattagaaat actttgcact cctaccaatt tctataaatg gatcttgaaa  35700
ctgaatgcag gaaaaatgat cccttgaaac tagagaaggg tatgggcttg tgaccaatat  35760
aagctttaaa gagagaaaac atgcgtctaa taggatttag tcttctgatt tttcctagct  35820
gcttttaatt ttatcagctg ttttatagca gttttatgtt attatattct ccctatattt  35880
tttattatct tttttcaaaa agagttgttg ctgattctcg taatttaaat gtgttatcat  35940
ttttgatgat tagaagaaac ataacacaaa acatgttttt atttatattt tcaaattttc  36000
ttatatcact agatttacga aaatacatct ttcaaaaaag ccattcattt attcattctt  36060
tatttattta ccaatcaaga atccagagta cctattatgt gcacagcttt aagtacattg  36120
gggaatgaaa agatgaatag ttttcaagca aaatctttat tgctgatata ttttaagaat  36180
tatataccta atgagaaaca taagacatgt attttttgtc ttataaggtt ttttctttta  36240
aaaaatacat tatagatcac cttaaaagga gaaaaatatt aatgcagtaa atcagtttta  36300
acgttgctag cctaatgttt acattattat tcttggtata attaaaaaat actaacaaat  36360
attaacaaag attaaacaaa aatgaactta tctagatcta aggaagtaaa tggttcttga  36420
ctatttaggg ctttcagtga agtgtgcgca gcttggcttt ttcgaagaga atgacattca  36480
aatatggtat aaaaatatct gatttcaccc aactcatctg tgagaatcta gaaatgactg  36540
ctatctaaca aggcctacat aacatcttca ggaatctgtt acagcttaat tctctttttt  36600
tttctttcat tttctttttt ttattattat tattatagtt taagttttag ggtacatgtg  36660
cacattgtgc aggttagtta catatgtata catgtgccat gctggtgctc tgcacccact  36720
aactcgtcat ctagcattag gtatatctcc caatgctatc cctccctcct ccccccaccc  36780
cacaacagtc cccagagtgt gatgttcccc ttcctgtgtc catgtgttct cattgttcaa  36840
ttcccaccta tgagtgagaa tatgcagtgt ctggtttttt gttcttgcga tagtttactg  36900
agaatgatga tttccaattt catccatgtc cctacaaagg acatgaactc atcatttttt  36960
acggctgcat agtattccat ggtgtatatg tgccacattt tcttaatcca gtctatcatt  37020
gttggacatt tgggttggtt ccaagtcttt gctattgtga ataatgccgc aataaacata  37080
cgtgtgcatg tgtctttata gcagcatgat ttatagtcct ttgggtatat acccagtaat  37140
```

-continued

```
gggatggctg ggtcaaatgg tatttctagt tccagatccc tgaggaatcg ccacactgac  37200
ttccacaatg gttgaactag tttacagtcc caccaacagt gtaaaagtgt tcctatttct  37260
ccacatcctc tccggcacct gttgtttcct gactttttaa tgattgccat tctaactggt  37320
gtgagatgat atctcattgt ggttttgata tgcatttctg tgatggccgg tgatgatgag  37380
catttttcat gtgtttttg gctgcataaa tatcttcttt tgagaagtgt ctgttcatgt  37440
ccttcgccca ctttttgatg gggttgtttg ttttttcttt gtaaatttgt ttgagttcat  37500
tgtagattct ggatattagc cctttgccag atgagtacgt tgcaaaaatt ttctcccatt  37560
ttgtaggttg cctgttcact ctgatggtag tttcttttgc tgtgcagaag ctctttagtt  37620
taattagatc ccatttgtca attttgtctt ttgttgccat tgctttattc aattcgaaaa  37680
gaggaagtca aattgtccct gtttgcagac aacatgattg tatatctaga aaaccccatt  37740
gtctcagccc aaaatctcct taagctggta agcaacttca gcaaagtctc aggatacaaa  37800
atcaatgtac aaaaatcaca agcattctta tacaccaaca acagacaaac agagagccaa  37860
atcatgagtg aactcccatt cacaattgct tcaaggagaa taaaatacct aggaatccaa  37920
cttacaaggg acgtgaagga cctcttcaag gagaactaca aaccactgct caaggaaata  37980
aaagaggata caaacaaatc gaagaacatt ccatgctcat gggtaggaag aatcaatatc  38040
gtgaaaatgg ccatactgcc caaggtaatt tatagattca atgtcatccc catcaagcta  38100
ccaatgcctt tcttcacaga attggaaaaa aactacttta aagttcatat ggaaccaaaa  38160
aagagcccgc atcgccaagt caatcctaag ccaaaagaac aaagctggag gcatcatact  38220
acctgacttc aaactatact acaaggctac agtaaccaaa acagcatggt actgctacca  38280
aaacagagat atagatcaat ggaacagaac agagccctca gaaataacgc cgcatatcta  38340
caactatctg atctttgaca aacctgagaa aaacaagcaa tggggaaagg attccctatt  38400
taataaatgg tgctgggaaa actggctagc catatgtaga aagctgaaac tggatccctt  38460
ccttacacat tacacaaaaa ccaattcaaa atggattaaa gacttaaacg ttagacctaa  38520
aaccataaaa accctagaag aaaacctagg cattaccact caggacatag gcatgggcaa  38580
ggacttcatg tctaaaacac caaaagcaat ggcaacaaaa gacaaaacag cttaattctc  38640
taagcagtgg aggtttacat tttaaaagaa acaacaaact ttgtttttcg cagtggcaac  38700
cttgaacgct tttgaattaa aacctgggga tcctgtttat tggctttgag atttttttgct  38760
acaccactcc agggggcact aagcacattt tctaatctcc ataaattaaa aaaaaattaa  38820
aataacacat ttcttttta ccttgaaaaa acaatttcca tcaacacaac aatttccatt  38880
caatttcctg gatacaaact gttaatagaa gtagggaagg aaaggaaagt gataattatt  38940
taaacatgtt aaagtgaaca attcatggtt taataattgc tgtgttttca caagaaagtt  39000
attctttgaa attggctttc acatgtgaaa taaaccacct ttagatgctc tatcttcatg  39060
cacggttttc ttacatttaa tcatttcatc tttaaaacaa aaatgacatc agaaataaaa  39120
cacagtctca gtactgttct tcagttatac ttaatgaaca tacaaaatat agacaggggc  39180
agaagagagg cataaaaatg atgataatat gatactttta tgtaccattt ctagtaataa  39240
gtttgttagc tcaggtaatt tggatctaac agaagaaata gtagcagctg ccatagcccc  39300
atctcaacgt ctcctggaag ggttgacata aaagactctt ggccatggtg gttagttatg  39360
ggacagaatg agccaagttc attaaaccat tccaaggaag ggaaagagaa tcactttcaa  39420
catacacata aatacgtgtg tatacacaca cacacacaca cactatatat attatatata  39480
```

-continued

```
tatattataa ttaacaagat gaggtagatt tttatcaatt tatttcttgg cttatcagca  39540
tctatcaccc tagttcaagt accagacgtt tgaggattct accccttttc atttttatcc  39600
ctgaatttgg gtgggctcca cttacccccct gatactagaa gtaaagcatc tatcttagac  39660
ctaagtttat tagttcattg cattctccct agagacaagt acgtgacaga aacacagcca  39720
gtgagatgca atggatcttt agctggaact accaccagag tgattctcat tttgcttttt  39780
ccagggcatt tgagaatgag tttatagaaa ctaagagacc aactcagaag ccacacattt  39840
gagaggttga gacaaagtaa ccaggtcctg atgagttatt tgagcatttg cctaaagttg  39900
tgcctgaagc caggcctatc cctagacttt ttagttacat gaccccacac atccccccttt  39960
tgcttgaacc agtttgcatc gaattttctg ttacttgaac cagaaagagg cctaaatagt  40020
actgaaaaaa tatatatata tctgaggaag agattatctt atcatggatg taagcagaca  40080
attttataag aattcaagag agctaaaaaa cagaacaaac attccagtga atttttgatt  40140
ttcctactca aagtttcatg tagagaaata tatacatcat ctggtgattt ttatttaatt  40200
gcattactgg aagctgttat aacaaaatat atgtgacttg atgacataat tacatgtaat  40260
atggatacca tggcctagca tctaaatgct aagattttaa aaactctttt taaaaaagaa  40320
ttctagctaa aagtttgtgc attgaaatct ctcttattct gtttctcatg gcctcaacca  40380
aatatccttt atgtgcttgt tattttgttt tgatgccatc aaatgaaggt tcaacctcat  40440
gagaaaatct tttgaaatgg tctcctgaaa caacacagaa tatgattcta gtatgagtat  40500
aattatgtac aacacagcag tggaaccaag gacataaaat aaaatagctg acaacactaa  40560
gaagtcataa tttcagcttg ttatacacac tctcatctta aggaagatga atcaaaattc  40620
tttgcaactt gcgtcatttc tgaatatgaa ggactgcaat atacaaagct aaatttatcc  40680
ttcctttaat ggaccatgca gctaattcca gcagatgaag actgcaatcc caatatccct  40740
ccttctgaag cactaaacaa aacaggcagg ttttgtgaac ttttgctgct tattttcact  40800
atgacttttc acatttcctt tggcagcttt ggcatggaat accttaagaa aaggttttag  40860
tatctaacat cgctggaatc atatttacct gcaaggttct aaaatgtgat gttcaaaaat  40920
gaaagctcct ttaactcccc aaaccagtca tatgccatct gtaatctgtg accggccaaa  40980
gctcaacatc tatgagaagc tgaacagctt ctctctaata cacccaccag cagactctca  41040
attctttggg gtgtcttaag aacaacactc tgaaaaccca aagtaggaaa aaatccatca  41100
atgtatcaaa caaaatttcc acctcactca tggctcatga ccaatatttt ttagtgataa  41160
tggataaagg ccaagaaatt ggccgatatg aaatccagct taaaaaaaaa aaagactttc  41220
tttgcactag gaaaataaag ccatattaca gaatgaattg acttaccatt ttaccatttt  41280
gttaaaagac attctgatga gatttagaaa gcagcaagac ttacctagaa gaaaaaagag  41340
gaaaaaaagg agaagatatt aaaacaataa ataagaaagg ataatagtga agacattttt  41400
aaatggattc taagatgaca aaaagtgagc acagaccacc tacataggag taagtcagta  41460
aaggagaaag ggggaaaata aacttcttta agttgttatt acctttatcg cacgaaagga  41520
taaaatacac aggaatcgag tgtttatgtt atataaggtg tgtaacagag cccttcatat  41580
tagcacaatt cataaggaaa ttacatgatt ttaatgttac ctcttagtcc ctgagaaatt  41640
gaaaagtgac ttcacattac atacatttta aaaatattgg tgtactgggc atcagccata  41700
aagatcatca aattgtttta aaaacccagg caatatgcag atgacaggga aagaaataat  41760
ctccctacaa gcttggagtg gtcattccag gactttttgt tttgtttgtt aatcaagtct  41820
ctgtactctc ttaccattgt aataggctag acaagtataa acctttaagt ccgctgacag  41880
```

-continued

```
ggttccctgt ttccccaaag tggatgaagg gagaaaaagg aacaaagaat tgagtttcac  41940
ctctaaagag atcatatgat gtgaggtcag tttatggaag ttttgctgct agaagcatat  42000
gtggaatttc ctagccacct agacagttgt taccagcttt gtcctatctt ttgcagggag  42060
actgaggcaa cctcatacat ttttatattt tatgtttata ttaaatttcc atgttctctt  42120
tcattccctc cacctagagg gacttatctc ttcctaaatt ccctcttcta ctgggcaaag  42180
aagtaagaga agaatcagaa atgcatacag aaaagttaca ggctactttt ttcttgtttc  42240
ttcaaactga cctaaatttc taggtgttcc ggggatatac atatgcttac ctttcacatc  42300
acttcatatt aacatagtaa ctggtgcaag tggctaaccc ctacccccat aaagaccctc  42360
tttttctgaa ctacagttga gtgagtatta aaataaggac taaatcccca aacatatttt  42420
ttaatcccag aaaacatatg tattactaat ttataatcaa agcccaggac atagcaaaat  42480
gcattgcgta aatgaatgtg ggcagggcta ggagaatacc taggactttg gatgcctaat  42540
ctagtaactg agtacacgtc gacacagtgc ttttctttta atcctgagta ttttctatat  42600
tcgtttttag gaatgtttc aaaagtattt tggcatgatt tttaaaattc actacataac  42660
atttaacaa atattctttt ttttttaac gtcgaagtcg tcacctgaca tttgttatag  42720
tcaatcagta gggcaaacct ccaagtaccc ctgccatctt ataggaactg acaacagaga  42780
tttctgcagt cttattaaac agtccttttg caattacagg tacatcactc caggttagtg  42840
actgggaggt gcggtacggc agatctattc acgtaattat ctctctatga gactgtaaac  42900
acatgacatt tcttttcagt ctaaaatact gaaagcgcat tgttttagta acaacatcat  42960
gcagtttttc tgttggttag caagggcttc acctgctgtg aaattcctag atcataagtg  43020
aaagtctaac tcagagccat cagggccatg agtagcgatt tcatttttag ttcatacagt  43080
taaattagtt atttacttac atgtctgtgt atgcctgatt cttaaaaact acggttattt  43140
gaatgttatt tagtcttgag cgacatacag taattggtac atgtatttgt tggtggggag  43200
agagataagg atcattctgt ccttccctaa ctttgaaaaa cacataatat caaaatttat  43260
ttctatactt tcagggtaaa taaatagtta tgcattttaa gccagtagga gaaggtttat  43320
tttcaagctt gtgttaagac atttggtaat aattattgga gaagtggata aatacttttt  43380
tccagatgat aattttatgg cagaaaattt ctctcagtgg ctactgctat cttgaatatt  43440
ttatatttta gtgctcaaaa ttcacgattt tggtacatca tagcgtgcaa catagtaatc  43500
atcacaaatc accaattgtt taagagtggg cactttaatt gctcattaat tccctaatta  43560
attgacacaa gccaatgtta atgttattta aagattagta tcagtcctag ggtttatttt  43620
gggcttgccc tggggaatta attaggcaga tagctcaaat tatgttttct ctccaacttt  43680
ctcaggcacc agttaggctg ctgactgaca ctttgttctc tcatccagtg tacgtcgggc  43740
aggggaagaa tctaactaac acacagagta ccccacttca gagccaccat actcttctca  43800
caccaccaac agttccttgt catccacttc atgaagtcaa atctctactc tgtggatttc  43860
aaggcctgat ctgtcttggt ctatgactct caaatacatc cttctctctt gtgtctgatc  43920
tgggtcgtct attccacaca gcttaattta cacaactatg taaccatcac ttttccacag  43980
ccaggatttt tttcttttcc tttgttttgt ttttgtgatg gagttttcac tcttgttgcc  44040
taggctggaa tgcaatagcg cgatctcacc tcactacaac ctctgcctcc taggttcaag  44100
cgattctcct gcgctttagc ctcccaagta gctgggatta taggtgccca tcaccgcgcc  44160
cagctatttt ttgtgttttt agtagagacg tgttttcacc atgttggcca ggctggtctc  44220
```

-continued

```
aaactcctga cctcaggtga tccacccacc ttggcctccc aaagtgctgg gattacaggt  44280
gtgagccact gcgcccggca ggtttttttc aagtagttct ctatagtctt ccttctccat  44340
tcggcctttc tacatccctt tcactcattg tgaatttcat tcttatcctt ctctaaagat  44400
actttgctct agccagatcc caatccacat cagctgcccc actctggcca ctcccagggc  44460
ttcagcctca tctcctgtca cttcctgcca cattctttcc tttcttccag gttcacagaa  44520
ctatttgcag ttcccaaaat ataccttgcg ctttgatgtc tatgtgtttt gcttataccc  44580
tttttgaaac tcaaaagtaa agtttattga ttttccaaag ttaatttagg catttattct  44640
ctatttttcc ttaacttttg atgccttaat tttaaccttt atagcatttt ataataaata  44700
ctagtatcta gcatctcaga ctcctagaaa attgcctgat gcatagacag cattcagtaa  44760
atgtagagag aattaaatca gacataatcc ctattagatt ttgagttcct aagaggagga  44820
gctaagtctt attcattttt ggatctttgg tatacagcac agttcttggt ccagagctgg  44880
tataagatga gtggataatc aggaaaaagg aagggattat tggaaggacg gaaggaaagt  44940
ctttcatttt tggtacactt caataaatat ctgtcatttc taaattctgt agcttttaga  45000
gattcggtcc atgcttgttt gctttctgac tgagtatgtt gacaacaaat tatttaatag  45060
gaaaataggc acatctgcca aaagaatgga aggctggata tctcaggcat tgctaaagat  45120
ttctagggta gatgtagttg ttgaaaataa agacataaat aaagttgtcc tatttgtcac  45180
tggctcctca cattgttttt gtttacagta gattgaccgt aaaaataaac taacaccttt  45240
cagagctatg cactacctta tttgctaaaa ttatctcaga gaattgagaa gatttgtttt  45300
gaatatatac attcccaaac tcttcacata actaccaaca tcttcatttc acatcataca  45360
gtaccatgca aaaaaaagca aattcttttg attcttgatg tgaagtgctt tcaaatacat  45420
ttcctcaatc taaaaattac tctagaatca aaaacaaaga aaacaactgc ttaaagaaaa  45480
ggaagtgctg caaaaatgag aaatatgttt tattatatct tgattacaat aattagcagg  45540
attcaaatag tggttttgct tttgtgtctt cttacgtttg tgtaagtcaa ccctccccac  45600
ttctttctct ctctctcctt tctctcttct aattctattt attgcaaaag tataaaatat  45660
gaggtgtaca taatgcatta gtagccacat gatgaactat ttggaactct gatttcatac  45720
tttcttggcc ttttaaacat cagtgacttt tttttccttt aaaaataact gaaagacaca  45780
atcccacaca cagtgggttt tgttatgaag aatagatcta cctccaaggt cttaatatta  45840
tagttttatc tcttttctca ccttctcatc tccctctctt actctttgcc atctcttgaa  45900
tccactctct gccctacttc tgagccagac tctatcaaac cccgacaatc ctcagaaact  45960
catcggttct tctccagctt tgctttccta tgaacacatt cttgtgccaa gcatggattg  46020
gtcttttcaa tattgtttgc tgtgtagcca aagtgcagag taacagtttt tgcaagtgta  46080
ttctacagga aaaataatga tcaaaatatt aataggtgtt ttcagaggaa aaataagttc  46140
tgtatatgtt ttagctaaat agtattattt ttgtcatatt cccaaattgg aagtcccagt  46200
acatattagc ctattacaat tctaagttat ttgcagtaaa gaatatagat gaagctggtc  46260
tcatttctat tttccaagtt tttgggggcc atagtgattt ttttttaacc tgacaacacc  46320
tcaggaaatt tatggtttac agagcacaac attgtaaatt atggcaaagt aaaaaagaaa  46380
acactgaatt tcaacttgga aaatcagaat gctgttgcta atagtattag tagcaaatat  46440
attaagtatg tcaaatatgt caaatgctgt tgtaagtgat ttacatatat tagtacattt  46500
aatctcacat aaagcaaatt aagtaatatc attagctcca ttctacagat ataaagaccg  46560
agactcaggt aaattaaggt actcacccaa atttacatag cagaactgaa attcaaactt  46620
```

-continued atgcaattag tctccagtct aagattttaa ctgcactgtt attctgtcgc tgttacctac 46680
taattgggta acctgtggca agctatttta cctctctaag tcaagctgtt tattgatcag 46740
acagattaat gttatctgat gtggctgtca taaggaatca gtatttaaca gagtcaaatg 46800
cagtgcctga aatatgcagt tggtactcat aatacttatt tattaaatga gactcaagaa 46860
ctctagattt ggttatcctc ctagctgtgt acacacagct atttgttacc tatcgttatt 46920
agaggaacag gcataaagct gtgctgagct gcttgacgga aaattcccac tctagaactt 46980
caactggatc tttagaacta atcattaatc ttggatttac ccaggttgat tgcccattgc 47040
aactcatacc acaggcattt cacgtactgt atgcattcct caaaccaggg caggggggatc 47100
aggaaatgat ttaaacccgt caactgagga gccccaggag gaccatgcac tggctgccct 47160
gacattttac caaatgtggc tgtcctgtca tgatcttttc ttaagaatcc ctacgtaatt 47220
ccaaagctaa tattaaaata tacgtaaata cctctatctt cactctgtat cccttcactt 47280
ctaggctctg gctccatcaa ccattccatc atccttttga gtttccctgt tcctttcctc 47340
tctctctccc tccctctttt tccctttcac acacacagaa cactctgctc ccaaactaca 47400
tctgtgctac aactatgctg cccacctatg ccaatgtaca cagcaaagta cgaatttgtc 47460
tttactctat cagatgattc ctgcttcttc tatatttttt cccccttaaaa ccaaactttt 47520
tcaaataatc tacttatcat atttatttct ccaccaaaca ctgtcttcaa cctctgcaac 47580
tcagctacat tctcatgatc tctaaaaacc atgtttctca aagacaacag catcttccaa 47640
ctagatgaat gcaatggact ttgctcagtc ttgattctct ttggcccctc agaaactttg 47700
ttatgcccat atcctgctgg aacctctctt cttaatcaga tttcagtcac tacagtgatc 47760
gtctttccat catttcagcc attttgcatt tatctctctc actggctttc cctctatttt 47820
gtattttaaa catggagtga cccctgtggc tctgacctcc accttctgct ctttccatat 47880
tactctttca ctaggacatt atgtactcta tggctctaac aaccatttta tgcaaacggt 47940
gtgagaagct actaaattgt aactgtgagg aaagggatta tgtcattcat ctttctaatt 48000
tccaagctgt ttagcatacc accttacata taacaagtgt gtgtgtgtac atatacatac 48060
acagaaataa aagaacaaat ttttatcaaa atattacctt caggcatgga acatttatta 48120
actgaaaatg ctgaagcaaa tgccaggaaa tttatgttct acttaaggac tgtttggttg 48180
gttcatgttg ttctctttgg gaaaatattt gtgacaaaac tttataagat taaaaataat 48240
tgtccttcat tttgtttcct ctccacatgc ccttgcatct ttcaactttt taaaataact 48300
ccaggttgtt aattccatct atgtaattgt gggtgcaatc taaatgaaac taaactctac 48360
ccaaaatgag atagttaggg ttatcaatgt tggagatgca aagaagagga atacaaatct 48420
gtggtatcat agaatggaaa ataagcttta aaagtcatcc acatgaaaaa catgaggtcc 48480
tccacaccat ggaataaaat atgtacactt ttgctattat tgtgagagaa caggaagtag 48540
cagtagttac aaaaggaaag tgggtcagag gaggggtcaa tttcattttc tttctctcat 48600
gttccaagcc tagagtatct tactttggaa tatagcgaca tctggatttg ctccacttct 48660
atccaatcag taactaagtg gcactcattg caacactctc atttaaagga cctgactgtg 48720
catttcccaa cacattcgta aagtaaaaag aaattcaaaa agttcctctt tttttttgac 48780
aaggtctcac tttgttaccc aggctggagt gcagtggcgt gattacagct cactgcagcc 48840
tcaacctcct gggctcaagt gattctccca cctcagcccc ttgagtagct ggaactacag 48900
gtgtgtgtta ccatgccagc tgctttaaaa catttttttg tagaggctgg gtctcattat 48960

-continued

```
gttgcccagg ctgctcttga actcctaggc tcaagtgatc ctccctcctt ggcctcccaa  49020
agtgctggga ttacagatgt gagccacggt gcctggccac atttcaaaaa atttatatca  49080
agaaacagtt ttaaaattta atagagtgct cgggcacagc taccatcatt tagcacttaa  49140
gcaactatta gtactagggt gggatgcact aatatttagc acagtaaaga attaaaacaa  49200
aaacctagaa cttcaggctg catgttaata agtagactat ctttatgtag aattgcttga  49260
aagttcagca agaaatttcc taatgtccca gaaaaagtgc ctcattcaca cactcattga  49320
tttgcctcat tgtcacttag tttcagagaa aaaataggca tccactaaat atttagtttc  49380
tgtctttcct ccccttcccca gaacatgaga taagagtgct tcacaaggag gccatttttg  49440
tacaccagca tggaattcct catattgacc ctatggctga tcatacggct ttataaatgg  49500
gctcataact tgtcattgcc ttgcctcata attatttcta gaactttgta gagtcagtac  49560
cattagcctc ccttgaagaa aaaggaaagt tttaggaaag ttaaacaact tgcctaaagt  49620
cacatggctg attgatttgc aagggataat catgtttata ccaaatattc cattttgggc  49680
ttcttcccca aatcctggaa ttgttctagg tttccaaagt ggcaagatcc aagataccct  49740
gggcaagcct gaatatatat gcaaacagcc tcacacgtac tgtcacactc agtgcagaaa  49800
ctcttatggt agtaatagca gacaccaata taatgtatca aaatgttcac cttagaaaat  49860
atttgtcagt gtttttcac ttatgcgcaa atgaattaaa cttagtagct atgatttata  49920
agaaaagaac aagattgcat gcccataaag aaaaggaaat atacaggaga gtgtcttaca  49980
acttaccaag atacaggtat aatcaatgta ttagaaaaat tcaaatgata tacccttgtc  50040
ttcaatacac actggtaggc acctccaact ggtacctgtt ctatcctcta agctcagggc  50100
agttggagaa ctatcactaa tggaagtgtg ggtgcatgag aagtaagtaa gacaacagct  50160
ccagtagagt ttgaagttat ctgagttttc tgattaaaca agtatttggt gagggcctac  50220
tacatgctat acattatgct aattattggt gacaaatgcc agtgaataaa ggccaaggaa  50280
cacaaccaat caaagacaga agcatattaa aaatcaatat ataaatttga tagagttgtt  50340
atgagagttg tgtatacaga aataagaggg aatgcacagg gatgagtgag ggaaagatac  50400
cacttggagt tggaagacct ggaagtgtaa tcctagagga aatgactggt ggagagaaaa  50460
gaagaagtaa atgaaataaa gataagggaa attgtaggaa gagcaaaagg agtatttggc  50520
taggagaaga ggcaggtggt agtgtttggc tagtgaagag aagggagaaa agaaagcaag  50580
tgcttacgtg tcagaggcct tgaagctcct ttgcaaatga tcacatgtcc ccatgtgtca  50640
aatgtgtcac actcagatag cattgcctgt cctcaaaaga ccactgatgc actctgaata  50700
aattcatgta attcccagaa atctgtctct ttgtcaagat atttggtcaa gctgtgacta  50760
aaaacattaa gtaatggaaa aaagaagagt ggtttagcca gcattgcaag ggagtctatt  50820
caaaaggttt attatcttat gagcagagaa gggtaaaaaa aaaatgaaaa aagacatcca  50880
aacttctgct aaatttgcac tcttaatcct ttaaactcca tttcacttat atctatatgt  50940
ggtagaaaag aggtactgag aggacagggt ggcaagacct tttatttgaa catttgctaa  51000
atcctcaatt atatttcact tctaatcctg tgtcattatg agcaaaatgg cacatttgga  51060
gaccatttag atatgaatgc ctgaagcctt cctatcagac ctgctgactc tttctttctt  51120
tctcactctc ttttagtcac tacagccaat tatgttgaga tatgattttt ggccaggcaa  51180
tctagctctg gcatcagggg tcccacaata gcctggttgg agaccttcat ggcctctaat  51240
attattattt tttgggcagg gtcattgtga caatcataac tgggaacaaa tatccttatt  51300
cagcaaaaag agaaaaacaa aacagagcaa aacaaaacaa atccctatga tctaacattt  51360
```

-continued agataagcct acaaatgtaa cacaaatcca aaaagaggaa gcttacgtaa ttaaaagtta 51420
aagttaattc ttgaaattgg tgaggataat taaagaatga aagaggccaa ctgtttgaaa 51480
ttactgagtc agatctaatc tttcactggg ctccatatac acattgcatt atgtatagtt 51540
taatgtgcaa gtcagtgata ccgttcacaa tttttactgt ggctcagctt acaatgtgcc 51600
atttggacct aggttatctt tcatctgtat ttttaagtgg aacctgtaac taacaatgag 51660
ccaagtgtcc tacattcctt gttctaagtt tgagtttctc ttgggcctat gcttctttct 51720
tcagcttcag ggatagaatt cagtgtaatg agaaacgctt tgtctacttt caaagtctga 51780
gagtccttag aaactaactt acgctggcaa ttcacagaga gctaattttc aatacatata 51840
tttgtgccca ataccagaag tcacaattaa atggtatctc tccatattct gtccccatcc 51900
tcaacacaca cagacatttg cagcagaggt tgtttagttg aatgacagaa gcagtccatt 51960
tgtatctatc tgtctagtgg tataattcat tttccgctca tactctaact aaccccaacc 52020
taacttaaga aaaaaaaaaa agaaagaaag aaaagaaagc agagcctaga tgctgttggc 52080
tagaatccag aatcctcgga ttagaaaaaa gggtgaaccg gggcacagta cagcctaata 52140
aggctggcag ccaacattat gcaaagctca ctggaaggaa gcaaagcctc cttggcaaaa 52200
cagtgataaa gaattagaat tttctgaaaa tagtaataag aactcaatac aaagacctga 52260
ccaattctag cacacatgga aggggtcaag aagaaggtgt tccatactaa ggatatgcaa 52320
aacctaaata atagaaggaa ccaagaatgg accagagggg caattaatct cttgctcatt 52380
tctgtttacg agttttaagc actgtgtata actagctgta tatataagct atctatgtga 52440
taaactgtgt gcacttctca ttacatgtat aggttgagtc tttcacaact actatatttg 52500
gtgttgtcac gaagtcctcc aataaagtat attttcagtt gggtgcagtg gctcatgcct 52560
gtaatcctag cactttggga ggctgaggca ggcggatcac cagaggtcag gagttcgaga 52620
ccagcctgag caacatggag aaaccctgtc tctactaaaa atatgaaatt agccaagcat 52680
cgtggtgcat gcctactcag gaaggctgag gcaggagaat tgcttgaacc cgggaggcag 52740
aggttgcagt gagccaagat cgcgccattg cactccagcc tcggcaacaa gaacaaaact 52800
ctgtctcagc aaaaaaaaaa aaaaaaaaaa aaagtatact ttcaggtgct gttatgggca 52860
gatacttagg ctgggtggaa ctttgtcaat agcagtaaag attctagtgc ccagagcagc 52920
aaaaccaggg ctgtaatgcc ttctacacaa cagataaagc cctaacaatt cctggctggg 52980
ttggtgtgta tgtgcttcta caaatatatg ttaaattgcc agtagaaagg aaaggtgtaa 53040
agttgaaaag aatgtcatat aatattttct gtgaacttca ctaagaaaat tggctttatt 53100
gccaagaaaa cacaccttat tattgatcga ttagaaaaca cctcttcaaa atctaaagct 53160
gatattaccc ttaggtggat aaaaagttta ggacaacatt attattttaa aaaaattgtt 53220
gtctagtatg aaaatagtta tgcccaagaa aattagatgg aaatataaag ctgtaagacc 53280
aagtgctaaa ttacgggctc acaatctatc taaaaatatt tattgattcc ttattctatg 53340
caagggacag ggcaatcctc atgtaacaca ggctttatac tctaagaaag ctggcaatat 53400
tagtgaggag atatgagaca catccaaaca taaatgaatt gaagaaggaa agagattggg 53460
aggaggaaaa aaggtaaatt tagtgtggtg ccagtgagag ccatcgaagg cttttgagca 53520
agataaggat ataatgaaat gcctttagtt agattaatat ggaaagccac ttaagagaga 53580
atcactactc tagtcaaggg agggttggtt gtatagggac tttttttttt ttctatcaac 53640
caggtagcca catttgaagt ctgcatactt aaagtggagc ctcagcccag ggctgttctc 53700

-continued

```
acacttttaa gccaaagcca atgctcttcc tcctctttct acttcagtct tcctgtgttc  53760
tccatcttaa tgtttttccc ttcctggttg acttcaaaac acaacaataa aggactgttt  53820
gtgttaaact tgaggaaagg aatggcattc cataagtgtc atggcagccc ataaaataca  53880
gattctctac cttggattaa gatctgtgga atccttagag gtagagacgg tggctctatc  53940
ttcttgttgt tctttaatct tcagattcca gaacagagtt cggaacatgg tagggctaga  54000
atatatttgt gacagtcaac tagattcatc atatatttgg aaaaccaaaa agaaatatgt  54060
tggcatggaa taattggtaa ctgatgggcc catgctgacc tcacctgttt ttataaaaac  54120
ttatttcatt tttatcagaa aattttacaa tttttgaact aagaagagcc tcagaaactt  54180
tcaggttatt tgttaaattt aattctcaaa atctacctgt agaagaaata gtatctttat  54240
tttccatatg gagaaactga gactacggaa ggttatgcaa ctcccttaag gcaagctagt  54300
aaatgataga actaggctgg aactcagcaa tccttttggt aagttttttt ttattattat  54360
atgtcatgat atttttatat gatgtgtggg acattatata attaaggctg tttgagactt  54420
tctataattt gggagactct gaaataatgt aaaagataca aaattgtctt agctggatat  54480
gtaagcattt tttaaataat gtgatatggg tctggttcta gggttatagt ttatatcagc  54540
aaaagtatag ataaaatttc catgaaacct ctatccgtcc atcttggtaa tgccttctag  54600
gaaattttta ggttatctat ggaaatatcc tatgtccaca agttctttct tttttaatat  54660
gctttgccaa ttttctatac atcctccttc atgattgcat ctcctttgaa aaattactcc  54720
tattaaacta aatttctctg tcactgcaag agacataaaa ttaaaaacta tctgtcttta  54780
atcatgccag gcttcttcct tgtctcctgg gctccattaa tcaataatta atatataaag  54840
aagactgaaa tccatttcaa tttcaaaggc ccaaacgttt cgctgattaa taaaaaattg  54900
tgctcacaaa gatggacgga tatgccatgg tgaaatgatg gaggacacag cattaccagg  54960
gaatagattt gcaggaccac atgtgctgtg tggcctacct gtacaagaaa taagccatgt  55020
ggaggaacaa ttctgcagaa tacctcccac caagcctgac atctctgcat gtaagaattc  55080
ttatccacaa ttatcatctt agtctatttg atttaccatt ctacccagag tcttataagt  55140
ggaataaaag ggttaactca tactctaaga atctactccc tgggcttaca aatatatcta  55200
gtttactgaa caattaatat tcttgttatt atatacacag aactgtagat actatacatt  55260
atgggttggt gaaaaccata gatatgaggc ttgagagaat aatatctggt ttctactaac  55320
tttctgatct acccagttta tgccgttgcc agctctctta acattctggt gccgtttgct  55380
gtcagcattg gcttctctat ttaaggagtt ttagcactaa ttgctgggaa ttcagtcact  55440
cttcaagcat cccagttcta cacaagtggg acctttccat ctgtgcaagg cctaaggtct  55500
atccttgcac agaaccatta atacagaagg ctcactctcc tattcttacg tcctacaata  55560
cctactgcag tttattccca agaactgact agagttctag tctctctgtt ttgagagatt  55620
cacttttggt ctctccgtga tgtgtagcaa tgagaagaat tcttttagcc agtatctttg  55680
atagtataaa gcagtttcaa gtaaagaaat ctaccaggga actaaagagc atacaggtaa  55740
aaatggatag atatagaact ccttcttcag aaaagtccta aaagtgagtg aactcttaac  55800
actcctcata caaattctta gaggaagagt gtttcaccta cctcactggt tttacctcat  55860
aaggcctttc tctcatctgg ctgccattgt tgagtttaat tccacatgga gtgctcaaaa  55920
tcccagtgta ctcgtgcata gatttttctt cctatttaat taatccgagg ttctttcctt  55980
tattgtttct accatagcta gaattcaaat ctattgccta ccttgtatat aagtagagaa  56040
ttgaggaaac aagatatttc aggtcaggat tatggaatga gacatacata ttcacatagg  56100
```

-continued

```
tattttatgc ttttttgac ctagcctcaa acacaaaata tcgaagattt agggaactac  56160
aagagccttc aaggagaaaa tgatagcaca ttcctattga ggctcaacag gatgaataat  56220
aatcatatct aacatttaat acaaactttc ttggtacaag cgttttcata ggcatttaat  56280
atacattatc tcatgaaatc tatgacagat ctatgagcca gtactattac tttccacttt  56340
ttatgaatga ggaaatcaag tattagagga attaaaacat tttcccatgg atcacttgct  56400
cataagtggt acatctggga cttgaactca ggcagtaggg ctccagcaca catatccttt  56460
accagtgctc tcaacatcaa gtgaaccctt tataagggta gagctacaca gagccacagg  56520
ctccagatac cacctttgcc tctaccatcc aaagtgcttc tcctgtgcat acatagatta  56580
cattctccca aattaaaatc aacaagacag acactgatgg aatccaaagt aaaaattgca  56640
gaatctatgg gacattttgg tcattgatgt agagagtaaa taaaaatgtt tgaaaccaag  56700
acagatcttc atacttatat catgtgaggt aaaatgtaac tattggctga tctgaggctt  56760
cattctactg actacatgtc ctcttgattg atataatggc actaatttta gaaatgaaaa  56820
agggtcacat agatgcagag tattcaaata taactgttca agtaaatttt aaaggctgag  56880
catatgtgac aggcctgtgt tattcttttt gccatctctt ccctcttgcc tgcactgtga  56940
agcttcaaaa acactgccaa tgcaacggca accctgctgc cgaggcccaa gacaaacaac  57000
ggcaaagatg gtagatgagc cagtgattac aagtcaataa caattttgca attatacatt  57060
ctataaccaa attagaaaca atgtcattaa gcctcaatgg caaaaaaatt aattaattta  57120
atataaaaaa atcttccttg tttgtccaaa gtaaataccc tgggaaatag cactatgtca  57180
tttggtaatt actacagaac aatataggaa tagatcatga ctggtgtcta gaaaaacagc  57240
aatcacattt tgccttctaa ttatggcagc actctcaaga aacacaggga gcagtgcacc  57300
ctgctgttac accacagcaa taacactcat taccccagta aatactatgg aaatgtgcag  57360
taacacacag gggcctccct gctgtgaggc tgtggcagaa tcactcatca ggctgggaag  57420
tatcactcga tcgtctttaa ttacttccaa aatatatgat aacctgccca cagttagaat  57480
gcggtgatat cactcgttac ttctccctcc ctgctcccct tttttttttt tttttttgta  57540
acttactaag aaaccctgca gtagccttac tatagtggtg atgtattgta acttatacca  57600
atttaatcac atagatttgt gtgcttttgg ccaacatatg ctcccaatgt gaaatgagca  57660
caagaaaaat atgctcaaat actgttatct ttctagcaag atccctttc tcacgttatt  57720
gagttgtggc aacactgttg taatcctttc tttttattct ggaaattaga gtgataatta  57780
caccgtagtc ccctggaatc cagagtactt gtaattatat ccagttacct aggaaaacag  57840
caatttcaaa cctattaccc acaggtatca tttatgttta ttgccctatt tgtgaagccg  57900
cttttactct gaattccaag tggcaggatg tttcactgag gtacttgtgc tccggaggaa  57960
gggagaaagg acagagggag gggacaatag gaagaggcct ctactccttt tcaggaggct  58020
taggtctgat ctctattaga aagggtttgt tcaggccctt ttcaaatgga taaggcagat  58080
tatgggacta tgttttcctc acacagtttg gagacagggc tcaaagtttc agggttttgt  58140
gtttgacacc tcccattgtg ctcacttgtc tcaatgtgcc acaaatgcct gcagtaaggc  58200
taaactaatt cttgattatg actcaccctg gcaggtgaat taatagcttt taggacagca  58260
gtttcaaaaa taattaaacc taggtgttgc tattttcata agaaagaaga aaataactgt  58320
tatgccacag cattcatcac tttgatttgg acaatttatt ctaaacatca gtacttactt  58380
aagagaggtt ttgcatgtag ttattcagta agccattcgt attccaaaag agggagtgat  58440
```

-continued

```
ggatgtaggt ttccttctct tgctaatttt tggagtgatt tgtaagatta taattttata  58500
aggaagacct aatcttagac ttacaaataa taatattgtg tactgaatat ttaagtcaag  58560
tactagttag ctgtaacaat aactcaacac aagaacgtta ttgaccccat gtatagataa  58620
agaaattaag cctctgagag gttaagtaat gtgctcatga ttattcagtt agaaaacagt  58680
acagccagga tttgatctca gttcattcaa gcctccgatc ttgtcctttt gctatactat  58740
cacactactc catcaggtgc tgcatctatt tctattggct tcaagttctg taatgcttct  58800
tgacatataa aaagaaaact tgctcagaat gtttaaatta tgaaaaaact tccccacaaa  58860
atgtatttcc cttatgaggg agaaagactc aggtactttt aagctgaaag tattagtagt  58920
tgtctgtctt ttcctttacc ctgtgttaac agccacttga agacatacga agccttcatt  58980
ttcaccccaa attgggcttt gggtcttatt caccatttat cacaaactat tctgaagaat  59040
gaaacagcat tggagaaaat gaaaacttgg gacttctaaa gtttaacttg ggagtctatt  59100
actgaattca agtattaaac cgggcaaagt cttcttgccc gaacgattaa ttaattaaag  59160
tcaagcattc attcattttt gtaaaataac attttatatg tatttttatt tttactgttt  59220
attttcacat accttttta tagaggtttg gtaatagctc cttttttttgc actgatagag  59280
aaataagttc aacttcagta tgatccactt agtttctcaa aacatgatat tagaagcata  59340
aatccaatgt attttaataa gaaaaaaaca acataaatgt gaacatatta cacacatttg  59400
tctgaaatct attgaggtac agtaaaaagt gtaattccag agttaaacac acagagttgt  59460
tttaaattac tttcatttaa aacacttact gcatgcacaa catgatttaa ctacagataa  59520
tagtactaaa atgatttctc taaggtatct tcagagatag agattgtgta aagatcacaa  59580
atctaggaaa gtgtctctac tttaccaaaa cagcattggt catgatatca ggtcatccac  59640
tggcaattgt gacatgggca ttttgaaagc agagcttggc attcagcagt taccagcttg  59700
ctagtcagag ggcatgtcat acagtctaag agagctgcat tcatttctgg tcaggccaca  59760
gatgcaggtt accaagcaaa tgtttcattg tcccctaggg taagcaaact gaacctccca  59820
ggaagatacg tctctattat tctgagaagg ctattattga aattagttaa gaaaaccact  59880
tatctcccta ttatttaaaa atctgtcaat gtaaagatgg atggcattac tcagaatcag  59940
aaaatttgaa ttccaacact tgattatgaa acttggtagc tgtggggggc ggggcaaaga  60000
tggctgacta gaagcagctg cattcagagg cgccaatggg aaaaaaacat aaaaagcctg  60060
tgaatcctca caggcaacca aggtatccag gttctctcat caaaattgtc tagaaggttg  60120
atgtgaccca cgaagagaag gaagagcggt gttgtgccgc agcccacctg agagcaggca  60180
aggggagctg cctcccccca gccaagggag gcggtgagtg agcacactac cagggaaact  60240
gtgctttttc cttggaactg ggcaacccat ggatcggaag atcccacttg caaacccacg  60300
ccaccgggtc ctagaatccc gaaccctgaa tgcagattct tacagcctct cagctggagt  60360
ctgcttaagc ctatccaact tccccgcagg gaggggtgac cagcatgggc tgcctgacac  60420
tgccctgtgt ctaagctgtt tgagctcctt gggggagggg cagcatccag cactgggact  60480
cacaactacc taacaccacc cacgttaagc tccctgggtg ggggaagagc ggcacccatt  60540
tctatagctc caggttgcgc ttttcccctg ctggagccag aggggctgga tggcttggtc  60600
tcaagagttg tctccacagc ccaacacact ggctgcggca gtctgtggcc agagtgcctc  60660
ttcaggccca accccgaccc atccttcttc agtgggcagg gcttccctgt aggatctcca  60720
ataactccag ccaggggctc atggacagaa tttggatctg ccagggctga gcccctagtg  60780
ggaggggtgg ccacagaatt tgtggaccag cagacttagc ctgtcctcct ggtagttctg  60840
```

-continued aggaatctgg gcagcccaga tgagtgaagt tctccccagc aaagagacaa agtgcttcat 60900
taaatgggtc cttctccccg ggccacccaa ctgggtgaga ccgtccaaca gaggttgtca 60960
gacaccccat gcagaagcaa tcctactgac atcaggctgc tgccctacaa gatcagaggt 61020
cccagaagaa ggagcaggca cccatacttt gctgctttcc atcctccttg aatgacatct 61080
ccagggcgcg aatcagatgg atagggcctg aagcgaatcc acagcaaact gcagcagccc 61140
cacagaagag ggaccgtact attgaaagaa aaacgaacaa gcagaaattg acagtaacag 61200
catcaacaac aacaacaaca agaacaaaaa ggcctccaca aaaaacccat ccaagggtca 61260
gcagcctcaa agaccgaaac tagacaaact cacaaagatg agaaagaatc aacaacaaaa 61320
aaatgctgaa aacccaaaag gccagagtgc ctcttcttct ccaagtgata gcaacatctc 61380
ttcatcaagg gtgcagaact ggatggagga tcagatggat gaattgacag aagtaggctt 61440
cagaagatgg gtaataaaaa actctgctga gctaaaggag catgttctaa cccaatgcaa 61500
agaagataag aaccttgata aaagtttaga ggaattacta actagaatga ccaattcaga 61560
gaggaacaca cgtgacctaa tggagctgaa aaatacagca caagaacttt gtgaagtata 61620
cacaagtatc aacagccaaa tcgagtaagc agaagaaagg atattagagt ttgaagacca 61680
ccttactgaa ataagatatg cagaaaagca tagagaaaaa aaaaataatg aaaaggaatg 61740
aacaaagcct ccatgaaata tggacttca taaaaagacc gaacctatga ttaattggag 61800
taccagaagg agatggggag aatggaaaca agctggaaaa cacacttcag gatattatcc 61860
aggagaactt ccccaaccta gtaagacagg ccaacatgca aattcaagaa atgcagagaa 61920
cactattaag atacgccaca agaagatcaa ctcctaaaca cataataatc agattctgca 61980
aggtcaaaat gaaagaaaaa ctattaaggg cagccagtga gaaaggccag gtcacctgaa 62040
aagggaagcc catcagacta acagcagacc tctcagcagg aactctataa gccagaagag 62100
actgggggcc aatattcaac attcttaaag aaaagaatct ttgacccaga atttcatatc 62160
cagccaaact aagcttcata agtaaaggag aaataaaatt ctttccagac aagcaaatgc 62220
tgagggattt tattaccact aggcctgccc tgcaagagct cctcaaagaa gaactaaata 62280
taaaaaggaa aaaccagtac tagccactgc aaaaacacac caaaatataa agaccaatga 62340
cactatgaag aaagtgcatc aactactgtg caaaataacc aaatagcatc atgatgacag 62400
gatcagattt acacataaca atactaacct taaatgtaaa tgcaccaaac acccctgtta 62460
aaagacacag actggcaaat tggataagga gtcaagacct atcagtgtgc tgtattcagg 62520
agacccatct tacgtgcaaa gacacacaca ggctcaaaat aaagaaatgg aggaaaattt 62580
accaagagaa tggaaagcca aaaaggcagg ggctgcaatc cagtctcaga caaaacagac 62640
tttaaaccaa caagtatcaa aaaagacaaa gaagggtatt acataatggt aaagggaaca 62700
attcaacaag aagagctaac tattctaaat atatatgcac ctgatacagg agcaccgaga 62760
ttcataaaac aagttctcag agacctacaa agagacttag tctcctacac aataatagtg 62820
ggagacttta acacttcgtt gttagtatta gacatatcaa cgagacagaa aattaacaac 62880
aatattcagg tcttgaactc agctctggat caagtggact tagtagacat ctacagaact 62940
ctctacccca gatcaacaga atatacatta ttctccgtcc cacatggcac ttattctaaa 63000
atcaaccaca taattggaag taaaacactc cccagcaaat gcaaaagaac tgaaatcata 63060
acaaacagtc tctcagacca cactgcaatc aaattagaac tcaggataaa gaagctcact 63120
caaaaccaca caatttcatg gaaattgaac aacctattcc tgaatgactc ctgggtaaat 63180

-continued

```
aatgaagtta aaacagaaat caagaagttc tttgaaacaa atgagaacaa agagacaatg  63240
tgccagaatt tctgggacat agctaaagca gtgtttagag ggaaatttgt agcactaaat  63300
gcccacatca gaaagcttga aagatctcaa atcaacatcc taatatcaca attaaaagag  63360
caagagaggc aagaacaaac taatccaaaa gacagcagaa gacaagaaat aactaagatc  63420
agagaagaaa tgaaggagat agagatacga aaaccctcc aaaaaatcaa tgaatccaga  63480
agctggcttt ttgaaaaaaa taacaaaata gatcgctagc tagatgaata aagaagatga  63540
tgaaaagaat cagatagaca caataaaaaa tgataaaggg gatgtcacca atgaccccac  63600
agaaatacaa actaccatta gagaatacta taaacagctc tacacatata aacggtaaaa  63660
tctagaagaa atggataaat tcctggatgc atacacccta ccaagactaa accaggaaga  63720
agtcgaatcc ttgaatagac caataataag ctctgaaatt gaggcagtaa ttaatagcct  63780
accaaccaaa aaaagcccag gaccagacaa attcacagct gaattctacc agaaatacaa  63840
tgaggagctg gtaccattcc ttctgaaact attccaaaca attgaaaagg aaggactcct  63900
ccctaactca aataaaaaaa aaaaagagag agaaaacttt aggccaatat ccctgatgaa  63960
catcgatgca aaaatcctga ataaaatact ggcaaagcga atccagcagc acctcaacaa  64020
agttacccat cacgatcaag tcagcttcat ccctgggatg caagtttggt tcaacatatg  64080
caaatcaata agcataatcc atcacataaa cagagtcaaa gacaaaaacc acgtcattat  64140
atcaatagat gcagaaaagg cctttgaata aattcaacat cccttcacat ttaaaaactc  64200
tcaataaact aggtattgat ggaacatatc tcaaaataac aagagctatt tattacaaac  64260
ccacagccaa tatcattttg aatggtcaaa agctggaagc attccctctg aaaaccagta  64320
cgagacaagg atgccctctc tcatcattcc tattcaacat agtattggaa gttctggcca  64380
gggcaatcag acaagagaaa gaaataatgg gtattcaaat agaaagagag gaagtcaagt  64440
tgtctctgtt tgcagatgat atgattttat atttagataa ccccatcatc tcatcccaga  64500
aacttcttga attgataagc agcttcagca aagtctcagg atacaaaatc aatatgcaaa  64560
aaatcacgag catgcattta caccaacaac agagagccaa atcatgattg aactcccatt  64620
cacaattgct acaaagagaa taaaatacct aggaatacag ctagcgagca atgtgaagga  64680
cctcttcaag aaggactatg aaacactgct caaggaaata atagaggaca caaacaaatg  64740
gaaaaacatt ccatcctcat ggatagcaag aatcaatatc atgaaaatgg ccatactgcc  64800
caaagtaatt tatagattca atgctattcc catcaaacta ccattgacat tcttcacaga  64860
attagaaaaa aaaactactt taaattgcat atggaatcaa agaagacccc atgtagccaa  64920
gacaatccta agcaaaaaga acaaagctgg aggcatcatg ttacctgacc tcaaactata  64980
ctacaaggct acagtaacca aaacagcatg gtactggtac caaaacagac atatagacca  65040
atagagcaga acagagacct cagaaataac accacacatt tacatccatc tgatcttcaa  65100
caaacctgac aaaaacaagc aatggggaaa ggatctccta ttcagtaaat ggtaccaaga  65160
aaactggcta gccgtatgca gaaaactgaa actggaacac ttccttacac cttatacaaa  65220
aattaactca agatggatta aagacttaat tgtaaaaccc aaagccataa aaaccctaga  65280
agaaaaccta ggcaatacca ttcaggacat aggcaaaggc aaagacttta tgaccaaaac  65340
accaaaagca attgcaacaa aagccaaaat tgacaaatgg gatctaatta agctaaagag  65400
cttctgcaca gcaaaggaaa ctagcatcag agtgaacaga caacttacag aatgggagaa  65460
aatttttgca atctacccat ctgacaaagg tctactatcc agaatttaca aaaaaactta  65520
aacatattta caagaaaaaa aaaaaacaac cacatcaaaa agtgaacaaa ggatagaaca  65580
```

-continued gacacttttc aaaagaagac acttttcaaa agaagacatt tacgcagcca acaaacatat 65640
gaagaaaagc tcaatgtcac tgatcatcag agaaatgcaa atcaaaacca cagtgagata 65700
ccttctcaca ccagtcagaa tggtgattat taaaaagtca ggaaacaaca gatgttggca 65760
aggctgtgga gaaataggaa cacttttaca ctgttggtgg gaatgtaaat tagttcaacc 65820
attgtggaag acagtatgac aattcctcaa ggatctagaa ccagaaatac catttaaccc 65880
agcaatctca ttactgggta tatacccaaa gggttataaa tcattctact ataaagacac 65940
atgcacactt atgtttattg aagcactact tacaatagct aagatatgga accaacccaa 66000
atgcccatca atgataggct ggataaagaa aatgtggtac atatacacga aggaatacta 66060
tgcagccata aaaaagaatt agatcgtgtc tttttcaggg acatggatga agatggaagc 66120
catcatcctc agcaaactaa tacaggaaca gaaaaccaaa caccacatgt tctcactcat 66180
aagtgagagt tggacattga gaacacatgg acacagagca ggaacaacac atactagggc 66240
ctaatggagg ttggagggtg aagggaggga acttagagga tgagtcaata ggtgcagcaa 66300
accaccatgg cacacgtata cctatgtaac aaacctgtgc attctgcacg tttcctgttt 66360
tgttttgttt tgtttttctt tagaagaaat aaagaaaaaa aaaacttggt agctgtatct 66420
ccttgacaca tgtctaggca ttgctgcttc atccttaagg tgataataat accctgaaca 66480
cctaaaatcg taaggctaaa gtagataaag gattgaggtt tagcagtttc atgtttcaaa 66540
cttttcctgg aaaaagtaca catttatctg acactaatga aatatgattt tggttcttcc 66600
ctacgctaca ccccatgaat tatatatatc aaaccacttc tgtaagttta attaatgaat 66660
tgcattatta atttattttt ttggtttgaa tgcttggtcc tctcaaagaa aagctgattt 66720
gaacccattg tactttgact cttaagtgtc aaaaataata ttcgtttgag tgttttcatt 66780
ttgactgtga gatgagagcc aatataagta tctctttcct ccacctcagt cccaccaatc 66840
ttcatttttt aagtgaggtg ctgctatagt aagtttagaa cctcaccaat atttgctaat 66900
aattttaaga tcttcagggc attttaaata ctaatagttt ggggctagat gtttagtatt 66960
tatgtccaca gggtacaaag tctttttag ctcattaaat tttgctttaa ttaatcctgc 67020
cacggcttta taaagaaggt gcactctgct tcaggttaaa gcatgctgcc taggatttat 67080
acgccctttc cttaggccat ggcatttgta cctattatcc atttcaggcc ccattttaac 67140
atagctagaa aaatgaaggg agaaaggaaa agtttagttg cttagttaca ttttatcaaa 67200
ataatacttt atttagttag ttagttagtt tgttttttg aaacagagtt tcactcttgt 67260
tgcccagggt ggagtgcaat ggcgcgattt tggctcaccg cagcctccgc ctcccgggtt 67320
caagcaattc tcctgcctca gcctcccgag tagctgggat tacaggcatg tgccaccatg 67380
ccctgctaat tttgtatcgt ttttagtaga gacagagttt ctccatgttg gtcaggctgg 67440
tctcaaactt ctgacctcag gtgatctgcc tacctcggcc tcccaaagtg ctgggattac 67500
aggtgtgagc caccgcgccc agcctaaaaa taatacttta aaacaccatc acttccagca 67560
atatcctcac taccaccaag tcaaataaag agacaaaaat ttgtatccaa tcaaaattga 67620
ctctccaaat aataggcagt tgattcaatc tctaatagtc tatattaagg aacaataata 67680
acaattaact ttttaataga tttcaccatc tcaaaggctc acagcaagtc tcaaacatta 67740
tctcaattct tatattgatc ctatgaaata ggtaacgtac actatgccca ttttaaagat 67800
gaaaaaaaat tgtggttcag aggaattaag tgacttgcct atggtttata caaagactaa 67860
ataaagagat acaatataaa tctaaatatc ccaatttcaa ctttaaatgt ctactaccta 67920

-continued

```
aaccgccccc caccccacag aaatggctgg aagtagatta atggaagtta cttgaccttc  67980
atttgattaa aaagaacata aaatactttg atagaaaggc ctaacactat tcccaaaccc  68040
aatgttccat ggtcttctaa aagaactttc tcaagtcact agcagggaat caatacttat  68100
tttctaaggt ctccaggcat tcccaagact aggttcttac atgctttcct gattgttgaa  68160
aggctatgct gtcttttgcc tcttctgcag tactttctta cataacatcc tctactttac  68220
tacatgtatg gtcaggtttt gatgcttgtt ctcctacagt gagtgcatgg agatcttgag  68280
taatgcagtc tataccacag gtggaaaact acatgtatag tacaatgatt tactttgtca  68340
ctactcaatg taatagtgtg gtttttaatg gacatctcta ttttcacttt ctgtgaaact  68400
aaatgtattt ttgtcagatt tctcaaacca aactcaagga agtaagcttt tcctgtctgt  68460
cttccatctc tccttatcag ctataatcaa acatccacta tatacaactc tggcttgttt  68520
attgatctta ttcaagtcat tacaatctct tgtaaagagc atctttcatg tgcaagggca  68580
gatgaccaag agagacatgc actagacatg ttaagagtac ccagaaagag aagatggggt  68640
gaaagactgt ttgtagaata aaagtgtgca tacagagata aaaactagag atagtcatca  68700
tagttaaagg aaagaaaaaa aatctatgac tgtagcaaat gatatttgtg taagaaaaca  68760
attataaaga aatgtgcatc actaaaggaa tttaatactt tgaaatgaaa ctgttgtcta  68820
ggaaataaag ctaggtttta acagtaacaa atggcaaata gtataaaata gaatgagtta  68880
tacattagaa aaatgtttcc tgatatgcaa tcttttaaaa agacaccagt ggaatcattt  68940
tctatggaaa aaatttaaaa gaaggcagca tttcatgaac tctgtcttga gtttttggaa  69000
atatctctta ctaattatga cctctatggt ctatatggca aatgcctctc acctggtagg  69060
gtcaaaacac tttgagggtt ccctaatctt gaaaatgatt ggaaatcctc acattttagg  69120
cctggaacac tcagcattga tgcatgcttc tgccaggcaa tggcagcaga gatactaatg  69180
aaagcagcag cttagtacgg tgctctgatt agatcctcag gttggggaaa gggcaggaaa  69240
gatgagaaga ggaaagactt tcactgaaac tctgatgaga gattctagaa gtaacacatt  69300
ttaattaagc ttcctccaaa tcagcaggga gtgaaaattc agctagtatt ttattttcca  69360
atttatttct tcagggaaca tacctaaaaa ctgttttgag ggtgggctat tatgtaactg  69420
aaggacacaa tttcattatg aacaggcaga aacttgtgaa atatcaattt ttagtataca  69480
tattttggga gcacctacca aggaccttac aaaattttac gaaacattat ctaactcaac  69540
catgagtcac ctggtatttc aagtcactgt ttctcaggga aagctaagta ttttcttaag  69600
cttataaaaa cataattctt ctcagtttct tcttgtagac atctagtcag cttctatcac  69660
cctgtacaca cacgcacaca cacacacaca cgtgcacaca cacacacaca cacacacaca  69720
cactgcagag ttagttcttt atgttccagg ctcctcatgt gtaaaatgta gataacaata  69780
actgcatgat ttcaggatga gtgctgagag gtaatgtatg tgttgagggc tccacagaag  69840
taggatggac ctcataccca aaatttggtc caaatgttga gactgatgat gctacacata  69900
ccccaatgga gtacgaaaag gtttattatt cacataagga ggcccttgga aggagtagca  69960
taggctacca agtaggtcca aaaaaatggc tagagatcag gggagggccc ctggcttggg  70020
gtgttatgtt ggttagggag tgaggctgag gaacagattg tccagcatag accagggctt  70080
gcatcgtttg aaccccctgc aggtaccaaa ggagggagcc cctggaattt cttattagct  70140
tgcccagata tggggcagaa gggtaaaggg aagtggtggg gcttgaaagt tgtcagcagt  70200
tgaacataaa aatgaactca gactctttac taacctatac aaagaattta gcacagtgta  70260
cttggtagat gtgcaataaa tggtagcttt tttattattg ctgttaacac aattattata  70320
```

-continued

```
cctatgtttg tgcctcccac tgcttggctg gcatgatgaa aacagaattt tagaacatgg  70380
atctaaaagg taatcagtat gaatagaaca gaatttgagt aattgcttat gtggtccaaa  70440
tattatacca cagtagcagc ttaaagtgtt atgtttaaca tcataggtaa agtgtactgg  70500
acttggattc acaaaaccca ggcttacatc tcagctttat tccttaagaa ctacatgatt  70560
ctcaacagtg gcttacatgc cttcaaactt atctgttcaa tacaggtaat accaccaatt  70620
ccactgggtt gttatgaaca ataactggaa gataataaac agactagcat atagcaattg  70680
cccagtactt caaagatgct cggggaacaa caattgaata tgattctgaa tataacccat  70740
taagtcactt taattctctg agactgattc cccttattta caatacaagg ataatagtta  70800
tcttacttat tatacaggat gtgataagaa tcaaaatcag cagcagacca tggatctgat  70860
ggcactttct aaagggaaat gtaaagcatt tgtaaggaaa tgtaaataat gtaagacatt  70920
attattaaat acctcactta tcacataagc attgcagagg aaacattgcg gacgtgctag  70980
aatcttgaca ccactcaagc acatatggtc ccctcatggt ctcaacttca gggaagaatt  71040
cctaaatcag gtccactttt catcgtattt gctaatcaca ttacatgttg aacattctct  71100
aaagccctga cattttcaaa cagggccaaa aaagattgat atgcctgagg aacccagata  71160
tttacttcct ctcagccaag aatccccatc tgttggtatc agttgacatt tgagataact  71220
tgcccccagt aaacatgcat tttaaatcct gacttcagaa aacagactca gaagattcat  71280
cactcaagtt ttcaacaaga gaaataattg aataagaatg aagaagaaag aattgtattg  71340
gaaagcaggg aagcaaaaat ataagtggac aaaagttaga gaagtgcttt tgggaaataa  71400
ataagaatgg tgaacaagga tgagaaacat ctaccacact gattagattc actccaagaa  71460
gtcaagatta ttagtgaaac ctcttagggg agacaaaaca cagccatttt ctctttcctt  71520
cttcttttcc cttgtcttca tgcctcccca gcacaaaaac tgtataacag agatattcat  71580
gccaagtatg gattgctttc tagagccagc actctaactt ttgtcataag aaaatgatgc  71640
acacagaagc aacctatatg ctgtgctctg ttatctactg atgcctgtgt tctcctcaac  71700
actgtggcag tcaactatct ggagggatat ggagcttagt gggaagctgc cacatcttca  71760
cttttgcttc aataaggtaa ggggatcatg ctgtatatct tcacacctct cttctgcctt  71820
gttatgccaa atggtatatt cagccaggca tctggtagtc acatgtttac cgcaccaaag  71880
aaaattttag gcgcttacag aaaataactg ctcagaatac atacagcttt attcaattgt  71940
aagataaaga tgtatctatt tatattcatt ctttcataat atttgcgaaa cccgtaagta  72000
tggcacatga tatagaaacc tagtagtaaa actcttgtca ctacacaatg tccttggctt  72060
taacccacca gtttatattt ttattcaagg ataaaccatc ttctggtatt attattattt  72120
tgagacagag tcttgttctg ttgcccaggc tggagggcag tggcatgatg tcagctcact  72180
gcaatctctc cctttcgggt taaagcgatt ctcatgtctc agcctcccga gtagctagga  72240
tgcgcaacca agtccagcta atttttgtat ttttagtaga gacggtgttt cgccatgttg  72300
gccaggctgg tcttgaactc ctggcctcaa gggatcgccc acctcagcct cccaaagtgc  72360
tgagattaca ggcatgagtc actgtgcctg gcctattcag gtattttata ttcactgttt  72420
ttcttctcat aaaacttggt taatgctgaa gatctcctta attagttgga taaattacac  72480
cttcccacat ggaaaaattc cttgggggat gcatcaacat tttcttctg tacttcctca  72540
aagcacaagt tatggtttca gtgtatacaa ggttttcaag aaatattgcc atcagattga  72600
ttaaatgact gactgcatag ctttttattt ttcttaacag ttaaatagca tttatatttc  72660
```

-continued aataaggggt ttttactctg taaatcacag attccaaatc acaatttgca atagcagagc 72720
tcacctgcca aaacaacttc aaattaaata gcaacctttg ttacagtatt ttgcagccat 72780
atctgggaaa tgcaattgac actggcatgg agtagaaata gtttccacaa ggcaagaaaa 72840
ggcatattga ctggcaggag catgctctgt tgccttgaca cacaagcaag aattcggccc 72900
caatctgttg gagtctcaag gctcacaaac ctgccagatt gccatctttg tgctgaatgc 72960
aaaataatca cagtggctaa aaatgataac ttgtggatgg ctgggatggg aagcaacata 73020
tttaatcaat ctctcctttt cactctgcag gttctaacca tgaaaactgc actccaacta 73080
gagagaataa tttccattct caaactctgg aggtaagaat atgtcattcc acgatccctg 73140
agtaatctta cttacagctt ccctagaaaa tgcacattta gatttagctt gttgatgaga 73200
ttcaaataat aggcttcatt gactcccaag agactatgaa gtatcaattt tttagctctt 73260
tgatttctta aaccctttcc agtctggtct cctcctacag accaacctat tcctggacta 73320
gttctcagag tttaggaatg ttgaaggaac agttgttatt tttgtaacaa aatttaatct 73380
acctgtgcaa ttattagttc tcaacacagc tattgtatac ctgttaccat ttttctgatg 73440
tcatctatat agaaagcacc aagtattttc atggtagatc tttcagaata tatcttctaa 73500
agagttgatt ctctttttct tttcttttct ttttttcttt ttttcttttt tttttgagac 73560
agagtctcgt tctgtcaccc aggctagagt gcagtggcgt gatttcggct cactgcaatc 73620
tctgcctccc gggctcgagg aattctcatg cctcagcctc cctggtagct gggattacag 73680
gcatgcacca ccatgcctgg caaatttttt tgtattttca gtagagatgt gggttcctcc 73740
atgttggcca ggctggtctc gaacttctgg catcaagtga tcctccagcc ttagtctccc 73800
aaagtgctgg gattacaggt gtgagccact gctcccagcc aaaagttgat tttttgtagg 73860
caattctgaa ctttaaaatt ttattttctg agtcctattt caaatattta tgttgtaatt 73920
tttttattta tcaacatata tccctattgt ctctcatgct tttatttctt taaataccat 73980
aaatgaaaat aatatcttta aaaagcataa tagtttttga ttttgaataa ggatgaatag 74040
acttcatcat gacatttcag atatttagaa ctgaaaggaa tatcaagatg tttaggtaga 74100
tactgataat gacaactgaa agtagtaggt gagtcacact agtgatgttt aaactggttg 74160
ccacagtttt cccaaatcct ggtagattgc tggtgtttct gagttgtggt cacaactcca 74220
aggtggtagt tcttgcctac ttctctaaga gcttcactac agagagaaaa aaaaatttct 74280
ccagaactgg aaacctcaag tatttaggat aaagaaaagt atcttttcct ttaatatgga 74340
gtcttgagct gaatgcagct tgcatcgtat gttgacattt ttaagttgac gatgcaaata 74400
tctctcttgg tagcctggtt gtcattataa ttacttttta tgtcaatgag gctacaggct 74460
taaaagcctt ttgtttctag aagatacaca ggacaattga tctgcacatt tttcatagca 74520
atccttttat aaagtggagg aggcattttc tagtcttctt ttcctcaggg acactattct 74580
agtttttact attctttatg atctcttttc tctactccta ttttgtttgg tttttatttt 74640
attttttatt tttatagagt tggggataca agcgcagttt ttttacgtgg agatattgta 74700
tagcggtgaa atctgagctt ttagtgtatt cattgcgcaa ataatatata gtacccatta 74760
agtaatctct cattcctcac caccctctac cttctgagta tccaatgtct attatcccac 74820
tctctgtatc tatgtgtaca tagtatttag ctcccattta taagtgagaa catgtggtat 74880
ttgactgttt ctgagttatt tctcttacgc taaaaacctc taattccatc catgttgcta 74940
ggaaatgcat catttcattc tttttcatgg ctgtttactc ctattttaaa tcatgctctt 75000
cagtatgcat tctatttttt tatacatcct tttgttttta ataatactgg agatgaaatt 75060

-continued

```
tagatacatg ttactgaata gtatagcttc atctgaatgc tttacattcc attatatact  75120
tcggtggata taaatgataa tagtcctaga ggtgagaagt tgcggttgct gttgttgtta  75180
tgtcagttta gttagtttct gacttctctc tgaaagcttc catcagttag ccaatccata  75240
tcagtactga tttagtcatg taggcatcag ttattatttt atcttatttg taaggattgt  75300
tttcacaaaa tgataaggat tattacctgt atcctaaaaa taaatctttc agtaatcaat  75360
atatgaaaaa gaaaattatc attccaagaa aatttacatt ttcttttctc cataaatgca  75420
agtaactttt tgcatttttg gcaggaagtg aaaatttcat aacaaatgca gcaaaattaa  75480
gcattgagca gagaaaggtg tcagaacatt gcacgatatt cagctgagag ttacaaagta  75540
tcatcagcca gataaggaag agagagaggt gttgtaatac taaattctcc agttttgaaa  75600
ttttccataa agaatcgatg ggtccagagt ctgggttaaa aacaaacaat atgaaatgag  75660
gcttgtttct agaactctgg ccattgtgac ccagggcctg attgtcacca tgccactgta  75720
ctcaacaata gttttcaggt ttttagatac ttctgcagac atatacaaat cagtgaaaag  75780
aagaaaggga tattgtacag ataaaaccac gtatttgtat acatattagt caatgcatag  75840
atactgagca tcttctatgt acaggggtta taccatgatg gaacacatgc atgatttgca  75900
ctcattgcag tttgtacact tgaagtcata ctccgtttgt atgcctgcct ccccattagg  75960
gtgtattctc ttttaggacc aaaaacaaat tatttcattc tgtttctcca gtcccaacta  76020
acatactaga tgactgatat actagatgac tgactgccaa ttaaatgaat ggcttaaaaa  76080
taaacaaatg catcatgaat gcatgtgtag cctatgattt tgggtggagt tttccacctc  76140
tttgtgctct gtgtcctcct ttgtgatatg tcaagcaaga tggattaaga agtatgcatg  76200
ttggccgggc atggtggctc acgcctataa tcacagcact ttgggggccc gaggcaggca  76260
gatcacttga gaccaggagt ttgagacctg cctggccaac atggtgaaac cccatctcta  76320
ctaaaaatgg aataattagc caggcgtggt ggtacatgcc tgtaatccca gctacttggg  76380
aggctgaagc aggagaatca cttgaatctg ggaggcggag gttgcagtga gctgagatcg  76440
tgccactgca ctccagcctg ggcaacagag tgagactctg tctcaaaaaa aaaagaaaga  76500
aagaaagaaa gaaagtatgc atgtttgtgt gctcaattgt gtcatgtgct tcaggattca  76560
acttggacat tgcatttcct ttagaagttt gcgatgaaat aaaaaataaa gttaagatgg  76620
tcttcaaaac agttacgatc tgaacagaaa tctactttat gtctgaatat tttttcactt  76680
tgtgcttacg gcttccatct tagctttttc acctatgctg caacactatt aaatgaggtc  76740
attttacatg agtaactttg atatctgttt gttgattcac agcttctcta acttggaggc  76800
aggaaaaaca agctaatgac aaagatattt gtataccaac tttcacctta gaaattatag  76860
tttccaaata ctcacaagta aaaataccac aaactttaat gacttaatta agccagtggt  76920
aaaacacaat atatctagga gggtgttagt tacaatagca gggaaattat atggttttca  76980
gcaaggtgga ctagaagaat caggctttgg aaccaaaaac tagactcaaa atctgattgt  77040
tccctttaat gaggcttcgc tgtagcttac tctttctgca agttaatttt ctcatgtaaa  77100
atggtgataa tatgacatat tttgagagag aattcagact ttgcaaatct tccaacacca  77160
tgctagtttc ttttctctca cctttgctaa tatgagaaag acagactgat aaaaccgtgt  77220
ggggtcaaca cccactaaaa taataaatgc tcccatatgt cactgagtca taaaaatcat  77280
aaactgagct gttcttcctg atgcatcttt aactttaggg agtattattt acttttacca  77340
tttttgagta agcaattaaa gtatgtattt tacgtaattg aaggaatcag tatctccatt  77400
```

-continued

```
gatagtaaaa tattaccagg ccaattgtta tttgtatatt ttttaaaaac cttttaaaag  77460
aatagtgcat ttgcttgcaa agcaaaagat gctgtgactt accaacaaga tctggctgcc  77520
ttttctgtgt tacttattat tgtggcaaaa gaggttgtaa gtgtgacaag aaaatataac  77580
ataagaacat gaataaacaa ataagggcag ttgttatgaa aactgattct tccagaatga  77640
ggagttaaat gagctctctc cttagtacct tcttcctgtt tcccaatttt taggctaaag  77700
aagacacaaa cacttaggca gttacaagag tcctttaaaa tcctccatgg tatttttaaa  77760
aatctctaca attctcttgt attttgagta aaagctaaat tggagctgta ttgttttatt  77820
tcctgagtct tctttttatt gaattattta cagtggacat gattgctggt gatgatcaca  77880
gccttagtct tcatattcta gggacaaatc tgtcctaaac ttctgtcatt gaactttcat  77940
ggatggagct aacagttaat gattggtgta taacaaaagg cagtatcctt ctaggtagct  78000
aatgtgggcc accaaagggt caagaaaaaa gttataggcc aggcatgatg gctaacacct  78060
gtaatcccag cacactgaga ggctgaggca ggcagatcac ttgaggtcag gagtttgaga  78120
ccagcctggc caacatggtg aaaccttgtc tctactaaaa aatacaaaac ttagctgggc  78180
atggtagtgc acgcctgtaa tcccagctac ttgggaggcc gaggcaggag aatcacatga  78240
acccgggagg cagaggttgc agtgagccga gatcgtgcca ctgcactctg gcctgggtga  78300
cagaactaga ctctgtctca aaaaaaaaaa aaaaaaaaaa aaagttatag tagaataatt  78360
aaagtatttc taaacctagg ttataagatt taaaaagaat ggtttttagt ttctagtttc  78420
ctgcagtatc taagatgtct acaaggcaac attgggaact ggagtcaaaa agttgatgct  78480
tcacagctcc ttggacacta cagatagaca gtgagaaaac agtcaattgt tgtcacatcc  78540
caagaacagc aggggattcc agttaatttt atgtagcgac attgagcctc tggattttaa  78600
ggaccttgct gaactctcaa ctggtcttct tccctatctg tatctcatgg tggcagcagc  78660
ctctctgtat taatgggaaa acagagacct gaactcagat gtgttataaa ctgaacttct  78720
gtttattgtt atcaaatatc tttacaagct ttctaccact ctggacagac gacagataga  78780
aggcaagctt gacttcttac tgtgcaaatg gagcccaacc aacctaaagg gtaagccacc  78840
taagagaggt tcctcttttg gtcctacact agctactagc acatatcagg aggggatatg  78900
ctgcattaag aatgcaaata tcactttgtc taagggtgtc ttcagatgat gccagtaatt  78960
cataagtgtt ctcccaccat ccagaaaggg catcattcag agagtcctca tctctctacc  79020
atcactttca gggtccatcg ctagtactca actctccctc ttaccttgca ggtggtaaac  79080
aaaagggaag actattaaat ttatcaccta tatatttcag aaatgtttct tttctctcaa  79140
tatcatcact tttaggttat ctgcttaaca aagctcctac ccttctcaga gtctaaggat  79200
caaatctttc tgtgattcat ttcaagaagc ttttgtcgaa gcactgttat ataatgttat  79260
gaatcaaatg gacaatcaat acatattgga tgatgatgga taaagtttaa gccacagagt  79320
aaagactgtg ttgttgagct aaaagagttc agtttttatc aagcacaata aataataatt  79380
ttattttatg tgcagatttc tgatggtcag atcattgtac agtagagcat aattgaaagc  79440
aaattccctc agaggccact gaccactggt aaatgttcaa atatataata cagttcaata  79500
cgactgtact aaacaggtaa taaaatgttg gcctttgacc tcccgtgact actagtttca  79560
gctacttcat taccccatga ggcatgtcct caggtatgtg catctctggg tgggcagcta  79620
ttctcttgca ttttccagca gtcgtttgcc atcagtaggc ctgtcagagt caatgcttca  79680
gtttcataac tgtaattgga ttgtctgact tcctattcaa ttggtacatg tttcttctta  79740
tttctgtttc ttttaaaaaa tcaataaatg gtttgtgatg cctcaaatag agagaaatca  79800
```

-continued

```
ggttttacca cattatggaa ttgacatttt caacatttat ttctcaaaga ggaccattgg  79860
gtatgtcaga ttcaacgcat aagttttgga ttaattgaat tgtttggtcc cagggatata  79920
taataacgtg aacacatttc atgatggaaa ccaaagagct ctatcatgcc ccaaacttta  79980
tgcatatgag tagaaacaat tttttctctt tttcttgtct ttctttcctc cactcataaa  80040
acccaccact cataataaag ttatagaaag cataaatagc tttatgttta aactggaggc  80100
tgatattgaa accactaaaa cattatgggt gtgaatggaa tgtgcacata tatttatatg  80160
tatatataaa gtccaaattt tatatacata tatggacttt atacatagct acatatatct  80220
acacatacat atatgacacg aagagctgaa tcagttaata tatctctgca tttaagagta  80280
aatcatattt gatgcaattc tgcaagtaca tcttggctcc ataaaactgt gatagtggat  80340
gaagttgcaa aggtgagtaa gacagagtat ccaccaccaa aagtcctgac gtagaatgaa  80400
aatcttccaa aaagaattag taagttcata tcgtttcgct tttgtttaat agcttggctc  80460
ctattaggat caggtttgca ccattgatcg tgtattgact tgaataaaaa tacatttcaa  80520
aataatgtac agtattgact aaagatggga ctacctgctt aaaatcagat tcattccaca  80580
tttcattgct atctctaagt attcattctg caggaggaag agatttttcc actgcataga  80640
gaacattatc aaatgtttcc atcttccttt gaagcattca ctattaactg ctgttagagg  80700
aaggattcta gactgagtgg gccattggtt tgttctggta ggacagttcc tgagttttaa  80760
tggatatata cagtttggaa gaaaaaagaa aaaactacca gagacaaact ttaatatttt  80820
gagtggcact tagctgatat ggtaggtaga atttaccaat tccttttaaa atttaatttc  80880
ttgttaaacg tgaaagcttg aagttcagta atatgaaaat aataacattt ttcaggtcat  80940
gaatatttgc tttttaaaat agtttacttt actctacttg caagccagat ttccctattt  81000
ttaagtgagt ttattgtggg agtgggagga gttgaattag aacaagactc tctacagggt  81060
cacaacctct tcagggcttc agtgcaagga agggatgaac agatattgac agaccaactg  81120
tcttataacc tgagattccc actcgtttgt tattctgtat ggctatattt gctttcaacc  81180
tcaataggct tcattcatct gcaaacttcc tgtggccctt gatcaaaaag gctacaaaaa  81240
ataccatgtc ctcatgtgcc aagtaaaaat ttgtgactat gcagcttaaa agtcggtcat  81300
ggagaaaatg tttcttaaca acgctttgaa ctatttaaat tagagcttta ttttagaaaa  81360
tttactagac agtggtctac ttcattttat tatactaatt atctttagtt gcaagaacaa  81420
tggccatttt gtgagttgtt agttcaacca tacgttgtta tatttgtgag acaaaaatag  81480
ccaactgtga gcaattttat atggcttgac ctaatataaa attttgtgtg ctttgaatgt  81540
ctgtgataaa cacagagatg tattcccatg gaaaccatgc cccatgcatg gtgaagcagc  81600
caatatggtg gtaaggatta cactggcatg actgtctata gtccaggaaa gtattataaa  81660
gatgttgctt ggagttctgt gcaaaagaaa agtccacgtt taatcaatgt ataggtatat  81720
taagaaggaa atcctcctat ttatgattca ccatgaccaa tgtcatagta aaggctttga  81780
aaaattctgc agcaaattac atcatttagt caaataaatt ccatagggta tgctgtgctg  81840
ggccataaaa taccttttct gatcaaatgc ctatcagcat tttataggaa agcaatgttt  81900
cataattctc tgtaattcaa tttgagaaac caacacctga ctgaaaactt gacacttgta  81960
tgttcctgta ccttcagggg ttaatgcagt gccttatcca tataaggtta accttacaaa  82020
ccaaaaaaat gacagcttta gactcacagt ttgtaatcta gctctcatat ggtgcatgct  82080
gttttaaagg aaattatatc tactctcctc atccagcaaa ctggcatttc ataagataag  82140
```

-continued

```
ctatgcactc tgagtttaaa taaattcaga tatttttctt tgaatacatt tcacagccag  82200
ggcataacat tctgaacact gtgacattat ccttccttaa aacgtgtatg tctgttttct  82260
catgttaaac ttccttttg ttctatctgt atctgtaata attgcctgtg atttctggaa  82320
tgggtctcat gagggagtcc atttttcttc ccttagcctc tctctaagca cccaatatgg  82380
aagctgcagc ccatggtgca tccatgaata ttatcggaga agatcaataa atctaagtcc  82440
acagccaaca gtaattactt tctttattct ggcagagatg gtggcattat ttagacacag  82500
ttgtagagca agtgacaaac aaggcacctt tttgcagact caaatttctg ggatacattt  82560
acaacagtgg tgaaaaatta cagagggatg gcaggtatat gtgaacaggg ctgcaactaa  82620
tttggccttg ggaggtgaga ttgtcaggca tgtcaaaagc taagcctcat tcagaatcct  82680
ccccactcca gcacttctca gatctgtttg caccacctct tttctccctc tcctctagct  82740
tcaaacttac cctctctatt ggcttcatcc tctcggaata taaatatact tgagaatctc  82800
ttctcttgaa aaagaatcca ccctcacttc caccttcctg ttttctctct ccctctcttt  82860
cgtggagaag ctacttgaat gaatacccta cattcccttc tccacttcct gacctcccat  82920
gtgtgactcc atccttcata gtaggtaaac attcttgaga agattctcat ctgttgtgaa  82980
gtcttccctt accccccact ctacttctcc cacatctcgt tttagatttg gatgttaccc  83040
tcaccatgga ctcctactgt accttgaatg cttctcgatt cagtcttacc attcaagaat  83100
gtaatgtttt ttattttgtt tctgttgata agaggtagag cttgtgtctt catcatcttt  83160
gtatccggtg tccagggtat tgcctgaggg caattatagg gacttaataa cgcccaaaca  83220
catccaacct ttttcgatca aatttgtttc taaagcgaga atacaaaaaa aaaagaaaga  83280
aagaaataga aaagctccct gtttgcaaat gtgctgtgta ttttgtgctg taagcctctg  83340
ataaatgcag tggtgttatc caattaactt tccagtactc aggagagagc cttacaggtt  83400
ctgccaactt accatcgact aatcttaatt gtcttttgac ctatgctagc tgcatggagg  83460
gtagggggat tagtagtaat gtagaacttt taaatattaa cattatgtac tatgtatatt  83520
atataaggaa atttgacctc tttcagaaaa aagtagcaca agttcatata gtatgggcag  83580
taggactttg ctatttaaat cagtaccaca aaatgttttt atatggaatg ttattctaac  83640
tttctggaca aacctgaata atatgtttaa agtttcatat tacaggatcc ttatttataa  83700
tacctaaata acattttcat ccttccatag cctgaacaat attaaatcaa tatataaaat  83760
cacagtaatc ataaaattag agtttcacta tgtacactga ggtccttcag tgattaccaa  83820
gtgctgccaa ataacacaat cctacatcag ctgtcagtcc tcagttctaa ctcctaggct  83880
ctggctactt tgagatgcta tttccaaaaa gtcctcttct ctggctactc atgtcacctt  83940
gaggggcaca gctcactcgg aaaagctact cttgtagaag cctcactatc tgagacccct  84000
aacaactcat tatcatccct cctcccaaca acttaaagaa catgtattcc acaacacagg  84060
tcttatgagg gcagggcaga atggggtggc cctctctcca aaatcaatat gtgagttgag  84120
aaaaaaatga gacattttgt tctcatcaag aaatctatag acagcagtga tcctagggtc  84180
cccaactgga accaagaata tactgaccca gagacacatg aggtaaaagt tttattcttc  84240
agatttttac aactatgcca ctaaggtatt cattcagtca tcctttttga gctggcaagg  84300
aaaattaaac caaatgtttt taaggcttac catatcatgc taaattccac caaactttta  84360
aagaagaaca aacatgaatt cttttccaac aattctaaaa aaattaaagg ggatggaatt  84420
ttccaaactc attctacaag gtctgcatta ctctgacaac aaaccagaaa aggacacaac  84480
aataaataaa gaaaactact agccaatatc actgataaac acagatgcaa aaatcctcag  84540
```

-continued

```
caatgtacta atgatatgga agaggagaag ggaagtgctg gatagaggag ggcatggtcc  84600
ctggctgggg ctccactcct gggcctgtgc ccatgtacca ggtgaggaca ggcattcatg  84660
ttttcctgcc taaatgttgc atttcccaag acaaccctgg cctgccacaa ccccatcctg  84720
tgcctataaa aaccccaaga ccctagcagg ccgacacaca ggtggctgga catcgagagg  84780
agaacatcag cagaggacac atgggccgct ggatttcgag aggaacacac caacaggcac  84840
tggcactcca gcaggtcacc aactggcaga acaactgagt gtttggccag ggcagtcaga  84900
gaagagtcgg gccaccaaga ggcccaattc ctgggagaac catctccctt ctggctccct  84960
catctgctga gagctacttc cggtcaatac aactttgcac tccttctcca agcccatgta  85020
tgatccaatt cttctggtac accaaggcaa gaatcccagg atacagaaag ccctctgtcc  85080
ttgtctaatt gagctgacca caagtcacct atggacagct aaactaaaag agcaccctgt  85140
aacacacacc cactggggct tcagctgtaa acattcaccc ccagacactg ccatggagtt  85200
ggagtcccac agcctgcctg cctgtatgct tccctagagg atagagcagt ggggcactga  85260
agaagtgagc cacaccctca ccacatcccc tgtgaggggg acaagggaaa ttttcccatt  85320
tcactaacaa accaaaacca acagcacatc aaaaagatta tatactatga ttaagcagaa  85380
tttatcctag ggatgcaagt aagtttcaac atatgtaaat caataaatgt atgctactat  85440
atcaacagaa tgaagaacaa aaccatatga tcatctcagt agatgcagaa aatagcatgt  85500
gataaaattc aacatctttt cattgtaaaa actcccaaaa aatcagataa agaagaaata  85560
cacctcaaca aaatacaggc tatatttgac aaatccatgg ctaatctcat aatgaatgag  85620
gaaaaattaa aagcttttcc tctaagaact ggaagaaaac atggatactc attctcacta  85680
ctcttactca acatagtact ggaagtccta ggaagaacaa ttaggccaga gaaagaaata  85740
aagggcatct aaattggaaa agagaaagtc agtttgtctc tgtttgcaga ttacataaac  85800
ttatttatag aaaaacatag acactccacc aaaaaattct tagaactgat aaattcagta  85860
aagttgtgag atacaaaatc aacatacaac aacagtagca catctttgta ccaggaaagg  85920
aaatcagtat gtcaaaattc taatgaatga actaagaaag aaatcaagaa aacaatctta  85980
tttataatag ttataaattt taaaaaaccc taaaaataaa tgtaaccatg gagttgaaag  86040
atttctacat tgaaagctat aaaacactga tgaaagaaac tgaagagaac acacacacag  86100
gaagataacc catgctcatg gattggaaga ataaatattg ttacaatggc cataccaccc  86160
aaagtgatct acagatttag tgcaatctct ataaaaatac caatggcatt caacacagaa  86220
atagaaaaaa caatcttagc attcatatgc aaccacaaaa gaccccagat agccaacata  86280
atcctgaaca aaaagaacaa agctgaaggc atcaatctat ctgacttcaa aatatattgc  86340
aaagatatgg taaccaaaaa agcatggtat tgccataaaa acaggcagat acaacaatgg  86400
aacagaatag ggaacccaga agtaaatcca catatttaca gccaactgat ttttgacaaa  86460
aatcctaaga acatacatag gggaaaggtc tcttcaataa atggcactgg acacactgaa  86520
tatctgcgtg cagaaggtta aatacccatc tttcacgtta tacaaaaacc aactcaaaat  86580
ggattaaaga cttacatgta aaacccaaat ctatgaaagc actagaagaa aacttagggg  86640
aagcacttag ggatattggt atgggaaaat attatgaata agattttaaa agcacaggca  86700
aataaaacaa aactagacaa aagggattaa gtcaaactaa aaagattctg cacagcaaag  86760
gaaaaaaaaa atcaatggaa tgaagagaca acctacagaa tgggcaaaaa tataaattat  86820
ttatttaaca aagcttaata tctagaatat acaaggaatt caacagcaaa ataaataaat  86880
```

-continued

```
aatttgattt ttaaaataga caaatgatct agatagatag ttctctaagg aagacacaca  86940
aatggccaat aagtatgtgt aaaatgctca gtatcactaa tcaccaggga gatatcaaaa  87000
ccacaatgag atgtgatctt actccagtta gaatgtctat tgtcaaaaag acaaaaataa  87060
gaaatgccgg tgaggatgca gagaaaaggt aactcataaa ctgtttgtga aaatgtaaat  87120
taatacagcc attgtggaaa acagtctgga gatccctcaa aaaactgaaa atagaattat  87180
catatgatct cacaattcca ctatggggta aatatttaaa gaaaataaaa taaatatgtc  87240
aaagagatat ctacattccc atgtttactg caacattatt cacaatagcc aagatatgga  87300
atcaagccaa gtatccacca gcagatgaat ggataaagaa aatgcacatt tacacaatgg  87360
aatactattc tgccaataaa aagagtgaaa ttggcgtggc acggtggctc acgcctgcaa  87420
tcccagcact ttgggaggct gaggtgggca gatcacgagg tcgagagatc aagaccatcc  87480
tggccatcct ggtggaaccc agtctctact aaaaatacaa aaaattagct gggcatggtg  87540
gcacacgcct gtagtcccag ctacttgggg ggctgaggca ggagaatcgc ttgaacccag  87600
gaggcagggg ttgcagtgag ctaagaccac gccactgcac tccagcctgg cgacagagcg  87660
agactccatc tcaaaaaaaa aaaaaggggg ggggtgaaat cctgtcattt gttacaaaac  87720
aacattgttg taactggagg acattatgtt acctgaaata ggccaggcat ggaaagataa  87780
ataccacatg ttctcactca tatattgaag ctaaaaaagt tgatctccta gaagtggaga  87840
gtacaatagt ggttactaga ggctgagatg ggtagaggaa agaggagaat agggagaggc  87900
tggttaacag atacaaaatt acaattcaat tggagcaata atttctagtg ttctatacca  87960
cagtaaggtg actgtagtta acaataattt attgtatatt ttcaaatagc tagaagagga  88020
gattctgaat gtccacaaaa caaagacatg ctaaatattc gaggtgaagg atatgctgat  88080
tatctcagtt tgatcaatac acattgcatt catgtatcaa aatatcctac tgtatcccat  88140
aaatatgtac cattattgtg tcaattaaca ttttttaaaa tgtctactgt aagaaaaaaa  88200
actaaactaa acaaagccca cttaccatat cagatagatt ttcataagca atagtcagcc  88260
cagttttctg gcctatagag ctaggaatct atttgtcatg aattacgaag gaagccctct  88320
gagagtttat gtcagcaggc aaacttgcct accatctcct gctatagtat tctaaggtgc  88380
tgaatggaaa aactgggcta atgatgtttt cgtttgtatt ttacatggaa aagctcaata  88440
gagatgactg atttcatgac atgagagggc tttttcagaa tgaaataatg aattgcattc  88500
ttaatattgt aaatgccctg cctagatttt ctctaaatca ttacaatgag aggcaattcc  88560
ccaatgtaga agggtgtgac tgtctccaga gaagtggaga gtcaatgcat cacccgtgta  88620
atttaggaaa accacccact ttatttcaag tgctttttca gatgatcatg ctttttggac  88680
ttaaattctc tggataattt ctccacttct cttccctgtt atgtgtacat caaagcataa  88740
cgacttggcc ttggacaact gaaaaattaa taaccgaagc aagagtttaa gaaatccata  88800
gtaatgacac aaatgagacc tatcaaatta gaaaatcaaa atgaaaacac actaaacact  88860
tcaaaattta attagaaaaa gttccaagtt cagaccacac tgaggccatt atgcaccaga  88920
agcactctat attgaaacct gaaaaggaga gtcattttgg tgaaatgtga ccttgggaag  88980
gaggtaagat cgctcactgc ttcttttact ttatctgctt tttaaggctc accccttaac  89040
gttttatgaa aggcagatcc aaggcaagca tctcttcaat ttaaccttca caagagacac  89100
aattcagtct tttatttttc ccaatgatac tgcaatcaac ttgagactgc tcaccatgaa  89160
ccatttgaaa atatttttca aattaataca caaattatga agcatacgtt ggctgctgat  89220
ccctgtgaac cattcccatt gactttttaag tccaatgctg tatatcaggt aaggatgatt  89280
```

-continued ttctcccttg caacttaatg ggatgagagg gaggcttgtg ggttatatat gtttagaatg 89340
aatcatcttt cttttctgcc gccctttca tacaaattgt atatcctcca aacattttat 89400
agacttctat aacataggag agtataaaga atatattaca agaggcagga gaatagacaa 89460
gcttccaatc ctatgtgaag tttatatggt acctatcttt aaaggcttta tatattttgc 89520
cttactacct cacatcttag aattaaaccc actttattat gcatttagtt ctcaagttat 89580
ctctgtttga tgagcagcat tgccaccaac cacattttta tcaataataa agctgagaca 89640
aactgaggtt cctacaaggt cacacaataa gtatagtgac taaagactag tactcaagtc 89700
tcatatgagc catttaagac aaccctgaag ttaagcactg ggtgactttg ggaggtgtgt 89760
gtgacagggt tgagttatta caaaacacag catactcaca ttccccccaa accaacttcg 89820
ttatttgtat agtttctgaa cagaaatata tatttgcaaa tagttataga aaaattttgg 89880
atgcatttct attaagaact gcatgtgtat ttccattaaa gtcagtgtgt atcctgaacc 89940
aagcctgctg cagccttgtg gccatctgtc atttagattc tcctttcttg actatccttg 90000
gaagcttctt tttcactttt tccttggctg atcaaaagct tttacctctc actactggtt 90060
gttagttctc attcctccat ttcataatat ccttcaaaag tttagtttgg taatagaccc 90120
tcatttcaat atccctcaga aaaagcatag gaatttttta aatactgctc attgtcttct 90180
tctttctttt cttttgaagc aactgacttg cttgacctag gtggttgtgt ttctttgatg 90240
tatgccagct ttcaatgtgt tgagaggtgg gagtccaagt accttattgc tgggctcctg 90300
tgctcatatt ttaccatcat agacaaggtg acaatttggg atgggagggc actgcttaag 90360
caggcatggg gagtggagtg agggccaaca tgggctgtct gaaaaaggtc aaagcactag 90420
gtctgtccat gaatctggga atacttgctc tgttcaggga aaaaaggctc ttctacaggg 90480
caagtgcagg tatcataatg tcaagaactg ccatttcatg aatagtgcca ggccctcttc 90540
tgagatataa taccaagaga aatattatct gtgccatttc cagataaaga acctcagctt 90600
cttttagaaa aatttacggt tatctgaagg agccagaatt ttccacaatt tcttccagga 90660
ttatgtgtat aagcaaacct ttatcactta catacaaaca cacactcata cacagttttc 90720
taagggaaag caaaatttg gtgacatgga tgtggctaat acatgagtag ataaaatact 90780
acacataact ctttatatat tattgagtag aaacaaatta cggtgtattt ttagtgagtt 90840
atttcaggca caaaaacatg cctcatggag aatacaacag ttgtagtagt gtattataat 90900
tcaatagtgg tttaaatgca aatgatccac aggtggaatg tccacttctt cccagcttag 90960
ctgtaagaca ctagcttttt atttatgtca taactcaaag aaaaagagaa agattggggt 91020
agctccagag agcccaatta ctaatatggc ttgaaggacc aatggaaggc accatttttt 91080
aaaacagttc accagcctgg ccagcatggt gaaaccccat ctctactaaa actacaaaaa 91140
tcagccaggc atgatggtac atgcctgtaa tcccagctac tcaggaggct gaggcatgag 91200
aatcacttga acctcggtgg cagaggttac agtgagtcga gaacacacca ctgcactcca 91260
gtctgggtga caggtggaga ctgtatctca gaaaaaacaa aaacagaaca gttcataacc 91320
ccagggctgg gcatgcattt tctctctgtg atcaacccct ctgtctgggt agtgaactga 91380
aactaaagtc ctcagaccag caaggatgct agttgtgcta ggctattatt gcattgctat 91440
aaagaaattc cggagcctag gtaatttata agaaatgagg ttcaactggc tcatggttct 91500
gcaggaagca cagcactggt atctgcttct gggggcagcc tcaggaggct tacaatcatg 91560
gtggaaggct aagtgggatc aggcacctca catggaaaaa gcagtagaga gaaagagagg 91620

-continued

```
gagacagaga gagagagaga gacagagaga gaaagtagca ggatgctaca cacttttaaa  91680
tgaccaggtc tcgtgagaat tccctatcat gaagatagca ctgagctatg aggatatacc  91740
ctcatgaccc aaacacctcc caccaggccc cacctccagc actagggatt acaattcaac  91800
atgagatttg agcagggaca aatatacaaa ctatatcact aggtatctct gagggcccct  91860
ctgatgctga ccagaagcca ggatgtgtgc tacaaagacc caggaaagcc agggggtggt  91920
gctgatagag ccaaatacct ctcaggataa caaggatagg gtttccagat ttgatataat  91980
acagaacaac ttcttccatt tccagctttt cctccaccaa atcaaaaggc atcaaattaa  92040
tgaagctgtg gcttgttgac attaaagttg attacaaaaa gacatgtttg agtgacaggt  92100
aaacaatagc aaaggaatga gtttccataa atacttattt atatatgaag agtatatggt  92160
ttgtagaata aataaacctg tagtcattgt ttcttatttg aagtttgtaa cctgtcatca  92220
taggttaaat aactgtcagg aaagctcata cttgtgatat tttaaatagg agctgaaatt  92280
ggtgtttccc taaggtaaat ggatgtttct aaacattgat agttctttct tttctacaaa  92340
aaggtatatg taaatataca aaatgagaag tcaaaatatg tattccatgc acagaaagag  92400
atcaagaggt ggaatggagt tggggtgtga acagaggaag gttgatttat gttatatggt  92460
tgctctcttt ttgtagctat ttttatatct tttcagcttc ctccagatta ctctagttta  92520
tttcctattg tttcttacta ttgactttta attgttccct gacaataaac tgttttattt  92580
aatccatctt tgaaaatttc acataaccat atttagggac aaggctttga gcatctttta  92640
tttcttccac taacatattg taccctaaat aagtttccct cccaggctca tttactacct  92700
ccatttgctt tgtatttttg ttgttgttgt ctccctatct tctttgtcct cttctgtaat  92760
ccattcctct ctctttcttt cttttttttt tttttaagat aagagtgttg ctctgtcacc  92820
caggctgagt gaagtggcac gatctcagct tactgcaacc tctgcctcct gagttcaagt  92880
gattctcctg cctcagcccc ctaagtagct aggactacag gcacataccg tcgcacccag  92940
ctaatttttg tatttttaat agagacaggg ttccattttg ttggccaggc tggtctcaaa  93000
ctcctgacct caggcgatcc atccgcctca gcctcccaaa gctctctatt tttataatag  93060
ttatgttgac ttgttcttct ggctgcagct gcagcttttt ccagttgtct cttcctgttg  93120
tcacaataaa aaaatctctt ctttatttcc tgtctatatg tgttttgttt tcattttttt  93180
gctttccaca tttatccttc ccattcctgt atcttcatga acttgtaaat tcttaggaaa  93240
gcaaaaaaaa tataaagctt gaaagtttca aagtcaaagg aaaagagaaa actcaagctt  93300
gcctcagaag agattgtgtc ccatttctgc agtagagttc atggaatttg tgcaaaaagt  93360
gagaagatat aagggaagct gtgctggctt gtgtgtcatt taaattagag agcttggatg  93420
ttgatattac accactgata aaggaaatga gacagtttcc acttttaatg aaaagaagtg  93480
cagtggcaaa gttgtctcac accacaagat aagcaagatt caaaggaagg ggacagtcat  93540
tctggtgtta tcattccaat tctatccagc ttatttacat aggcctgaaa atgagatgat  93600
cccaggatat ccatttgatg taaaaaaaaa aaaaaatctt aacagcccca aaaagggata  93660
atttagttgt gctacacaca tgggtgcgtg cacacacaca cacacacgca cacacacaca  93720
cacacgcatc ccaagaatga cacacctatt gatgagagtt gaaaacccat cagatatcca  93780
aatgagtatg tatctagagt tgtctatact atgcgttata tgactgaacc attttcagat  93840
ttttttctag ttttggaaga tatctgatgc cgtgtagata cagacactat cttgtgggaa  93900
acccatagtt tccagtctga acataaccaa ataaggatct catttctctc tgtctctgtc  93960
tgtctctcct tctttctctc tctgttgctc tctctctctc tctctctcat cttatagcag  94020
```

-continued

```
caatgcctaa agagaacatt tatacattct acccaaatcc cctttacaca ctggcatata  94080
tctttagtgt gcatatgtgt gtgtctgtgt gcatgtgcag ttgcacattt tgttaagcag  94140
aaaagctcta gtgaagtatc atcgccttta gaaggaaaga aggactaatt tgatttttct  94200
gattccaata catggtgcta tcaatgagtg gagatagcac tgagataata tagaacatga  94260
taaacagcca gtggaatggc agcattccat aataatgcca atgcttgctg tcccatcact  94320
cccattgctc cgtgggaagg atctcgtaac tgataaacca atagtagcag gcatttggga  94380
tgtttcctgg agaagcagag ggaagcctca ttggacatag tttcttgcat tttgctgtaa  94440
tttatggaac acgtggattt ttaaatctac aggtaattac gtaaataaaa tattgaataa  94500
gacacaaacc tctaggttcc cccaatctct gtcgcaagcc aaccagctgc ccttcccact  94560
ctacttcttc tccacacaaa gcacagaacc gaccaacact ggaaaagaac tgtgttatca  94620
cattttctca tagttggatg gccattctgt tactctgatt ttgagaaaat caaaagcatt  94680
acctttgagg aacaattaac atctatttcc agtccattat tccttttcag gacaaagggc  94740
tgtatttcac aggcttttaa acaggatatg aatatcccat caaatatcag tggtctgagc  94800
tacagctctg gcaccaggca cactgccaaa aatgtgacca agtttaaaat gattgatgct  94860
aaatcacatt cctcttaagc atagtctagg ccgagtgagg catacctact catacactca  94920
gtcctcctat ctgggaaatt catggttctc tcccaacatg agaattatgg ttttgttcac  94980
aatgtgtgga aactagaaag gcactgaaca tctgaggtaa aatggaaaca atttagttct  95040
gttgaatgtc accctctgtt gttgattcca cacatctgtg catcttttcc ttatccaaaa  95100
ctcatttaaa tgtgctagtt tctcctggag atgtggcaga taatgtcatg agccctcact  95160
gcattctttt ttttaataga tgagggatta aaatttgctg tacatagagt tacctcttgt  95220
ttgaaagtcc acgtacagtc agataacgtg tttatgcttt ccttgtaact aaaaaccaac  95280
tattttggct tggaaattcc ccactttcca aagaccattg cttctttgcc atggttaacc  95340
agaacctagc tcacacatcc actgggaaga aaataaaggc tctaatggct gaatgtagcc  95400
aatgcagcac agaagctcag acctcctagg gaagcctgaa aatggtgata cccttctcca  95460
tttgctgctt gctaatgagg ccaaggtgtg tccccctgta aatcctgaca acctaagagg  95520
ggtgtgcgat tcatctcagc tcccttccca gatgacaagc aagttgtaaa ttgtattcca  95580
ttccactctc cactgtttat ctgccctgac agtccactgc agctcttgtg tagctggaag  95640
cccacagggc atgtgtgact tttctcaagc tcttcccagc tgtcttaagt gtctctgtcc  95700
ttcttgtatt tttctatctg ttgcttcttt ttagaggtcc ctcttcctct ttccttgatt  95760
ttcagttttt ctcgctatat gcatctctct ctctctccct cagattgcct gtgtcttgca  95820
gttttgttac cttacaaact gctacttcgt tttatccctg actttctttt ctttgaaata  95880
catttttcat ctttctttta tagtttattt gtatttttttc tgtttggttt ttggcaaagg  95940
agctcagcaa ctgacccagt aagctaacac tttcagaaaa tgttgagtga tggaaaagca  96000
aatttttaaa aatctctatt actttcctat cttctttctt acttgctgct cattctagat  96060
gtcctcatgt ctatttcatc gtctgctttt atactaagct ttctcctctt aagcattgct  96120
ttccctacac ttatctgcta tttcagatct ttaaatatcc tacagtagtc agaatgggac  96180
tgagtactga cctgtgagat gcttaccacc agaaatattt tgcaagttca ggcttttgaa  96240
agaaacaaca gaactatata ttatgtttta tatgtccatt cgggaaactt aagacatatg  96300
ggggcttggc agaaacatca tcaacattgg agtagtgctc agtcatttcc acagagaaca  96360
```

-continued gtcttacaac ctatcaccgt cttctagtaa atgggtacca atgctgatgg aaaataaatg 96420
ggaacaagaa agatttagga aatgttccca agtcttttga ggaagactga attaataaaa 96480
actgtgagat tattggagta aggttgtcta ttcttgtgtt ctaatatacc attgaaccat 96540
gacctttcca atgcactacc tgtaaatata aaggtatatt taatagaaga aatttttctg 96600
atattcaggg cttaaaggct caaatttgcc tttaaaattt ttttctccca atactggcag 96660
gaacaacatt tttagatctc attctttacc ttaaaatatg attttcagcc cagaaagctt 96720
tactctaatc caaaataaaa tttctgtgct acagaacaca ggagcaaaga ttagattcaa 96780
ctcatctttg gcaatcaatt cagggagcta ttttgcactc cctccttttt ccatacctgc 96840
caacacactt cctatggatg ctttttcttct cttaactcta gagaaaaact ggaggtgaga 96900
aagtctgtat tcaatgaata tggtaggttt tattaatgta gtcacagaga tgttgcataa 96960
attaaaaaat agtacatagt tatctttgca ttattttttt ccttttaaga tgactttgtg 97020
tatttaccac ttaattttat aaaaccctaa agaacttttt aaaaatcgca tcagataaaa 97080
taaatattct tatctaaatg gagttttgga tcttctccac ttgccaataa ttattttaaa 97140
atgaatttat ggtctagaag tctcaaagac ctagttattc ttgaatttgt tgttattgac 97200
tagagtcaaa tgctagtagt taaatattta gcaaattctt atgaagctag aaaagccatg 97260
cataagcagt aaaaactgta agagatttcc ccttgggtta aagaataaga aagtaaaaag 97320
accagttcac ctgaatcaga accctgatgt ccaatggctc ttgctgacac tctacatgct 97380
gacggaagtt tcttgttcct ttttttccag ttctttttgt ctccctattt tttctctgta 97440
ttgaaaatga tgctcatttt gcttctaagt gatgaaggag aaagaaatgc ctgtttcaca 97500
gatcaaaagc aggcactgct ttagagcaac actggctgaa tgtcttacat cataactctc 97560
tctggcttta tccatcatcg ccaacatttt ctcttttgca gctttgaggg tgatggggat 97620
aggtcatata ttattagtgg aatacaaaga aacacaaggg tgtataagaa gccctggttt 97680
cagaacctca gtgtgccaat acccaaacta acccatagag actcgtagtc ttctaagagt 97740
atttatttac ttgcaagtac ttattgagtt tctattatct tacctctaga ttattgaaac 97800
agtctcctaa ttagtctctc agcttctgtt ctagcccttc ttcagtctat tctcaactca 97860
gcagtcagaa tgatcctgtt acaaactaag tcattcattc aatcctcttc tccaaggctc 97920
ctcagttcat gcagagtaaa agcataggtc ctcatacatt gccacacatg atcctccagc 97980
atctcttgaa cccatcctca tttagtctcc tctcacttgc tctactatac ctcaaagatt 98040
tcctccttat ttttcaaagc caccaggtaa gctcccacct cagagcctct gtggctgccc 98100
ttctctccac cggtttctcc cctccttccc ctaggcacag taagacctct cctggagtcc 98160
ctatctaaaa ttgcagcccc tccccctatg ttccctgtcc ccttttcttg ctttcttgtt 98220
ccccttagca cttaccaata tgtaccatac tatatatttt tcttatttgt ttattttttta 98280
tgtttccaac taaactgtaa cctccatgaa ggcagggatt gtttgtttgt ttgtttcatt 98340
cttatatcta atggtgccta ggaaagtgtc tggcattaag taaaccctaa attaatatac 98400
tctgggttaa tgaactggtg aaggaaatcc aatagttaat aagacagaca tggtcactgc 98460
ccacaaagct atcacaatca actgggaaag accatacgca tttaaagaaa taaacaatca 98520
ttttaaactt tggcaggtac tataaacaat gaacaagata ctgaggcaga ggatagcagg 98580
aaagccgatg tagcttagac tcaatggtca ggaaaggccc tcctctgggt aagatttgaa 98640
ggatgagata aaactgaaca tgagatggtg ttgggatggg ggcagtgagc aatcaaagaa 98700
ccgtcggaat agagggcaca gcaagtgaaa agaccttggt gtcctgagat agagaaaacc 98760

-continued

```
ttgctgtatt gaaagaatga aaaagacttg tgaggctgga tctaagttgt ccgaagagga  98820
ataacatcat tgttcacatg tatggggcta tactaagatg ccagacactg ttctgagagc  98880
tatttctaga tctgctcatt aactctcctg ataatcctat gcagtggata gtatcacatt  98940
atccatttta taggaggaaa cagggtacat ggcttgtaag tggtggggct ggagttccag  99000
aaatattcca tgcataagca cagagtgctt aaacacactt ccttggatcc ccgacacacc  99060
cacttaagtg tagaattgaa gcgtagaatg ggtgtgttga ggatccaagg aagtgtgttt  99120
aagcgctatg tgcttatgca taggatattt aaagatcagg caatatagtt gccagaattt  99180
atagtccata gtcctttcac ctgtgaaaaa aaaaaatgaa gtgaggagag caatatatta  99240
tcttgacctc acagggagga agattggcgg tacaactttt acacaattac agagacaaac  99300
aagtgcagtg caagaatgaa aacctatctt gccttagact ccacaggtta tctgccctgg  99360
atcaatcagg gatgcccctg cacactcaca ggccagggtc cgcatgctct ggatgcaggg  99420
ggctgtgtgc acacaggcac acacgtatct tattctcagc cacttccttg aaataaccag  99480
gaatacaatc caaaaggagt gctttgtgtt tctgagaacc ctcaaagaag ctttgaaaga  99540
cttgaagaga aatgatctta acaaaagaac aaaaaaaaaa aaaaaagaaa gaaacttgaa  99600
agtgaacaga agttctgaag tgtgtggggg tggaagaagc tttcttggag aggaacagta  99660
aggagatagc taactcaaag cgaccagaat agcttagcga gctgagaatt gagaattttg  99720
tgactcggtg gttctgctcc atagggacac tgccggctcc cggggagaat gcatcttact  99780
ctgcccccta ggcaggtcca gtttctggac ttccctggcc acacagctgg agatttccac  99840
atcatatatt ctgcttgtct tagaaaactg aaggactgat tttctgggcc ttctgactga  99900
ccagagagcg ttctttgtga gagacacaat agctatctat tcctttgtgc agtgtgcttt  99960
gccaagttcc atgagggcag cggtccctgc tatctttgtg taattctggg cagtctgagt 100020
cccacaaatt ggatttacac agcacctgcg agttctcaca caagcccccct tgttggtaat 100080
atcatttggc atatgtagca agcattcatt tttatcatag tgttaattgt tagccatggc 100140
agtaacaagc cagaaaaaag cacaggcaga aaaaaagcca cgtctgctca attaaaaggg 100200
gtaaatggct tggcggcacg gcagggtgct gcggacacaa agagcaggta aaggaagtga 100260
cctgtggtgt tgaagtttat ttgtttgaac agctgagaat tatctcctga cctaagtcac 100320
ctccataaca ggtggccctt tctgtctgag tcccacagca cttggcttga gagagtgtcc 100380
aatctcattc atgtggaaaa gatcaactct tttttccccc tgtaaggaaa aaaaaaaagg 100440
aatgtgactg gctgttcaat tgtaatcatt tctttgagtg cctctgtgtg gaaaggatgc 100500
tgcctcacct attcctcagt ttccacatct gtaaaatatg gaaactacta cttgctctat 100560
ttcccttcga gggctttttg ggaaatccat acagtaacaa aaaaaaaaaa aaaaaaaaaa 100620
aagacaacac attaccaatg ctaagtgcaa agtcacaaag tcatgttaca aatgtctaca 100680
ggagcaaaac tacagtcaag aacaatgtca taagatattt taaaattcat ggctgtggat 100740
tatttgttga gcacttgttt tgctgtagct cctggtgact gggggataca cactccttgt 100800
gaagggctct aggtgtggca tagacagata cctctgcttc catagcagcc ttcttctgaa 100860
ccccatgcta ttacctgctg gacagtcagc agtggggcac catcactgtg gcaggtgaag 100920
cactctaccc caaagagaga gaaaagctgc ctttcattgc aagcctcctc tccagacaca 100980
ctctggagtc acagcagttt ttgtctgtgt ggccttgtcc taaaattgct ggctgttctc 101040
ctcatcttcc tttctcttgg atcagagtta gcactgggag aaccctacag ggtgattgtc 101100
```

-continued

```
agaccacagg catgttctgg ctctgtggtc tgataggctg tctgtgggcc ttctctgtgt 101160
acccaagcca tctctgatta cacacagagt gccagagaaa aacaaaacac tttcagttta 101220
ggcaaagttg agaaacccat caaaataaac actgttgatg gtcacagatt taaaaaagaa 101280
tatgtagaga gataataggt aaaatgcatt gacagtcaca gacataggct gcgtggctgg 101340
ctgcccctac tgcttaaagc actgtgtgtc cggagatcta agtgtcatta gtggtattta 101400
cgaatccatc aaatgtgcag atttttactt tgcagatcaa gtaaaataag gagagaggac 101460
gagaggcatg ctgagactcc atgctgcttg aagagaaaaa ccctcatttg tattcctaag 101520
ccctttgcca tgaactgctg atgtccccaa acaaaaagaa agctcgtggt ttctgttctg 101580
gtaaattaaa aagcccttta gcttaacagc aaagcatctg tctaccttgt tatacatatg 101640
gcatctaatc agaatgcagg aggtcagggc agaggggagt aaagaaagtg aagatattgg 101700
ggtagaaagc taaggaaagt attaaaccta agatttgggg agtaaattag taaggaaatg 101760
aattttacaa aagaaagagg agaatagcaa atgagaatca gggaaggtaa caaaaagata 101820
acatccaaaa gaggagcaag aaagaataaa cgggaaaggt gtgtaaaact gaaatgaagt 101880
tggttgacga tgggaaaaag agaaggatcg tccagcagca gataaagagc agctggggag 101940
aacgtaacag attctgatcg atcgtgatgt ctggatgagc tcagtttcag ggctgtgata 102000
atctttacaa tggactgagc tttgctctcg gggtttatga tcctggaaga accacttgat 102060
tgactcatga ttctccaatt gatcacttca tatcagcaat ctttgcttct atgactcatc 102120
accactcaga acctctcaca aagaagctgt tgtgtcttga gaactttggt gatattaatt 102180
attttttaaa gagtatatta aaacttagat agcccctgtt gacattccac aaggagaaaa 102240
atgccctaaa taccaatagc tgcctgtgat atcctgtgat agaaaagtaa taaaacaaag 102300
taaaaattag gaggcatgct agactgtgct tctatttcct tgctgaacta agtcgcagct 102360
ttgttaagaa ttatatagca gttggcatgt ccagttgata tttacttgca aaatcatcat 102420
tggctcttat acagctcatt cttgactctg atacgccaac gttccaatct acataaaggt 102480
ctttggggta gtatgacatg cagtgattct gagtatgctt tagaagtctt taggcagtat 102540
agacctgact tcaatctagc tagaaaggtg gaagacaaaa ctctttttca gctgaggctc 102600
tttctcagaa cagaggcctt tcctcctctt cctacacaca aaaaaatact cagcctgggt 102660
aggaggagct ggctctagcc caatagagca gattatttac cagtttcaat tatctgcact 102720
aatgctcccc ttcattggtg agggtaattg agagttgaat gtatttacaa ggacagggct 102780
ataaagctga aacaatttta caaggtgtgg tgcagaaatg aaaaggtaga aaaagagctg 102840
gtctagacaa tgctttttga aaacatattt cacataactc tagcaagatt gctaggtcct 102900
gaggggagga tgggtatttc agaagagcta ttagaagtgc tattaggttt taggagattt 102960
ttgtggagtt attggacatt tcatatttta agttaggatg agggtattat ctctgaatcc 103020
aattcctttc tctcctttta tttccaaacc cactctggtc ttcatcctgc tgtggtgtgc 103080
ttgttcccag gagcaatcta gcatcccagt ggaaagtggc cgacctaaat gtggctctcc 103140
aaagacaaaa aatttattct gggtattgta tgatgaccca gatacagtat gatataaaat 103200
agaatatatt actgtgggtc tgataatgtc gatttcaagt ttcctaacct agtatctact 103260
tatagtatta ttatttttag gtccggcttc tccctttaca aggagtaatg actatgtgtg 103320
gccaacatat ttggctttat tactttaact ctcaatattc tgatttctct ttagatcata 103380
taaatctttt gcctttctca ttaactctca aaatgagaag ccaaaaagtt ttgttgctgt 103440
tatagtttga ttttttaaag tatacaaatg acatctgctt tcaaaaatat tgaaaccact 103500
```

gggtttataa cttcttgaaa taccagttag tttggtgata aaagttaaac gagacaagca 103560
tgaacttatc gaaattacaa ctccttattt gcagcaggat agtttttgat gataatgtcc 103620
actgataaca atgatgaaat aaactacatg catttcccct caaggcctct gcacatgctc 103680
tggggcctct cctctgtgtg tggctggctc ctctcatgct ctggatctca ccttgaagtc 103740
acctcttcag ggaagccttc tttgactctc ctgcctaaat gacattattc tctacctcag 103800
cactcagcct gtcctttata gtacttgcca ctgtttctag ttgttttatt tatttgctga 103860
tttaaaatga gtcgatctca tgactacact gtaaattacc taagttgagg agatcatgtt 103920
tctcacgttc actttttcat cctagtgcta gcaatgacct gacatgccac atagtagatg 103980
tacaactaac atctacttaa gtgaatgcac caatgaatga tgcctgggtt atcaatgtga 104040
tgtacacctc ttcattcact attacctgct ctgaatccca taagtaatta gaggttacta 104100
ggtttttatc agagaaaaga gaaaactctt aactttcata aacacttgaa atatttcttt 104160
tcctttggta ctactgctga taatacctat gactgctgag tggttggtgt tttccaggca 104220
acttgcttta tgagcattcc tctatttaat attcgcaaca aacctataac gggtactttt 104280
attatcccac tttacaggta aagacacaga gagttggcga ggttaatgaa tttgcccata 104340
taggctatta atcaaggaca gactgtaatt taaactcaag cctatctggt gccaaagctc 104400
actgtcttac ccattgctat ctatggtaaa ttaaaaattt agtgttgtaa ctatctaatt 104460
atatgtatca tacatattta ctactagata taaagtatta tcagaaaaaa agggcttatt 104520
ccttctcatt ttttatcttc ccattcctcc ccacattttt attaatctat taacatatgt 104580
atttaattct tatagaacct agtatagtaa tctgctatgt gaatgctcat caataaatgg 104640
ttctttgagt gagacctcca aagcagcata tgacatggta catgttaacc tttaggtgag 104700
gaaaaaagcc aaattcccta atttatcttg ctgctaacgg caaggttgaa caccaccaca 104760
gagtatgtat ataaagaggt gcagttagct gacgccctcc tctgttccca aaaatgttta 104820
ggtaagtttt tatccgggaa tagtaaaagc tccaaaaata agaaaaatca tcctggaaac 104880
tatatttatt atttatttat tttaaaatta agtaaaatta attaaatgtg aacccattca 104940
cggaccctaa ggaaaacaag ataacatttt tggggggcat taggttttca ctgggaattc 105000
ttctcaaggg ccctgtagct ctaaacagta tcgttaataa ctccattgga tctcatggca 105060
cactccctca caatttcatc tgccaaatac ataaaatttt tgacaagtta aagtatattt 105120
cctcacctag aatatagaaa ttgaaatatt tgctgaccat caagctctca gaaatttaac 105180
aagagtcctc atgtcctgga tttctttgta gtatgtctca tgcacagcac gcaataaggc 105240
tctgtacaca atcaggcaga ggaaatgttt gctgaatgga atttctgtaa ggagggattc 105300
atgtcatagc aggatttcca ctgcaagcct attttaagac agaaaatatt tatcctgtct 105360
aatcaaccaa aagatcaggg tctgaatgtt ttttaaatct acacctattt ctactaggag 105420
gcaccataga gcatttgtca aatcttcttt tactttgctt gggtttatta acacaagcaa 105480
aataaaagaa gatttgacaa atgctatatg gtgaaatcta accaaatagt ccaacagaat 105540
aatggggcct gaaaattctc ttttgcacaa tagtctaatt tttgcccaaa ttaccgattt 105600
ttgctctgaa tagtacacat taaatgacta gaagaaacag tttgaagaca tataactgtc 105660
ctactgttca aattaactgc tgatacagtc attgcaataa ttgctcccat tctgaaagtg 105720
tctctgcaaa cattcttacc acaaaaaaga cattttaaga aaaaaataca ctaaaatatt 105780
ctcaatacaa atatgtatgt gtgtacattc ttaaatatta cagaatggta ctgcattctt 105840

-continued acccaaatga tactattact tatctaagga acagggtgat ataatacata aggttaattg 105900
tgaaataatt atgattcata cagtgatctg gacagttcaa aacaatggct taatattttc 105960
ctgtgaagta acttttaaat aatgaagtta ttaatattta cttgatttct ggcctgcatt 106020
tgccaaaaaa aaatttaaaa cttaattttt aagaggagat gttgcaataa actgaaagat 106080
aaaatctttt caaagggaga agtgatcgtg tttcatagtt tttcaatagt ataagttaac 106140
aaactaacta aaacttaagc ttataaacag gatggcagtg agctaccaaa tataaaaatg 106200
tagttatcct gcactgaaag ggttatttct tatattactt aattgttttg agcttactgt 106260
ttcttaccta aaagttttgt ttatttatgt actcaatact gaatcagatc tccttccaca 106320
cttcagtgat caggccattt acaactgaaa tatttttatg catatggact cgaagaggca 106380
gttactgaaa acgcatactt tcctggcaag aaataatgca ataactgttg aaaataatgc 106440
tggcaactag tgttttcctt tgctgctaaa tggcatgacc agtgtcatag gagaagataa 106500
atagtgtgtg ctcattcact tgacattttt agcacctgct ctgatctaaa ctgggtgccc 106560
tatctgggga tttcattttg ctaatgtctg cattaatcaa cacagtctca cacacacagg 106620
cacacaggta caccacaaaa aaaaggaaga gagctctgga agtagagcta aaatgaatta 106680
tttggggaca aacatatttc taacttcaga aactctgtct ttctttttgaa atgtccaaag 106740
cgaatggtat attgattttt gcagcacact ctgcactttt cactgattgg tatcaggatt 106800
gtgaaggcat ccattaagtg agctcaaaat gctctcctag tataaacaaa atccacagtt 106860
ttaatcaaat ttaatgtact ctgacctata tgtgttttgt gaaagtcaga gtggactatg 106920
gcaacagaat tgaaagcata tattacaaag tccttcacct ttcagatctc ctgaaaggaa 106980
ggattgtcag aggtattgtc tatgtattct tttaagtcac ctctgaggag gcagcagggg 107040
catggggaat gagatttgca tttcagagct ggagccaacg tcaggttatg gagatatgat 107100
gaattaaaat acatctgcat ctgaaggaca atgagatcct gtggcccagg gcttcatttc 107160
ttagtgtaag aagagcaaga gtttcaggta ttcacatctc aaggtcccat ctcagaaggt 107220
tcccagcaat gaggtaaaat gctgcctgaa tactgataaa ttctccttgt ccaaaagtga 107280
ccaagatctt attcctaaca caaatattgt taatggcact caagcagtat tgcttgtttg 107340
tttctcaaat tcacggagtg ctaaggctct ggcagtttta ctgaacacac tttactagta 107400
aacttaatac tgttagagaa tgtttcagtg taattacttt tagttcattt atgaaaaata 107460
aatgtatttt agtacacaac cattaacttt ccctagaact tttactgata ataatgtcta 107520
ctgccataga caagaaaagg gtcaaatatt gtcaacagga ttacataggg agaatcagtg 107580
aaaagaatag taagtattca ggtaagagga aggaattttg gagttaattc aagaatgatg 107640
gggatatggc acaggatcag gggaaagaaa ctttttgttt tgttttttga gagagagtct 107700
cattcttgtt gcctaggctg gagtgcagtg gcacgatctt ggctcactgc acctccacct 107760
cctgtgttca aatgattctc ctgcctcagc ctcccaagta actgggatta caggcaccta 107820
ccaccatgtc tggctaattt ttgtattttt aggagggacg gggtttcacc atgttggcca 107880
agctgatctc gaactcctga cctcaggtga tctgcccact tcagcctccc aaagtgctgg 107940
gattacaggc gtgagccact gctcctggcc tatatattaa ccttttatgt aacccaaggc 108000
aacacatgca aactcacatt attctcagtt ttcttatcta ttaaacttgg atgattatat 108060
atctgttcaa cagttaccat gagaagtttg ttaataatta tttttatgat gatgtttcct 108120
gttatctata caaaatttta aggtactcaa aatattttct cttattagca ctatgctaac 108180
cctatgatct agtaaatact ggggagaata gtgttcccag aagacacccc tttcctctag 108240

-continued

```
aaactgttag acagtcatgc agtacttgtg aaggaacaga gtagacaacc aggtttggta 108300
tcctaaaatc acattggctt acagctattc atatgtcatg ataatctctt agttggagaa 108360
ggaaaataaa atgagaaaca gtttcttctt cctgtttcaa ggggaacaca atagtcttat 108420
ctttacattc agctaccttg ggtataagta tcagcttttc gtattttgcc tttacttttc 108480
cgcccatgca gattaatgtt gagatattct taacctaaca cacacatgca cgcacacaaa 108540
cacaccaaca cgcatattgc actcatccat acaaacgttt gggcttatca aggtcaattt 108600
aagttttttt aaaaatgtca taatatttat gttatctgta tttttatgtg tctgtctttc 108660
tccccctttg gaatgtaagc ttgacaaagg cattggtgag atctgaattt gtccattccc 108720
ttttatataa ctatttcatt tcatgtatat ttttattctc aattaacata cttggcttct 108780
tatagatatc tctatgaatg tccatctgac cctttcattt ttagattctt cagagcagag 108840
attatacctt tttcaattat tcaatctgaa aaccaagaac agtatcttat atataatgta 108900
cacataataa acatgtctat gattgaattc tatatattga atcactacat aataactgat 108960
tctttgcaca gtgatttgca tacacaataa ggatataatg attatattta cctgcctaga 109020
ctttacagta ccaaacttga ggtatagatg gcagtgctgg gcacacactg gttaaatgtg 109080
ttgatgagaa ccctagctca agaaagccat tgttcccttt atctttctgc ctggtcaaac 109140
aacttttgca aaatctggcc ctgagctctc cctggctttc atttagaggt aaaatcaaac 109200
actttgttca agattttcta ggataatttt catttttaag gtgaagatat tgagacacat 109260
tcgttctttc aagacaaagt tattgacaga cattcccagt gagaccaagc cgactagcag 109320
ggttgtaccc atacaaatcc tccttccttt atcctcctct ccttaagccc actttcatcc 109380
acagaccaca gatacaagga ctaagacgag ggaaggaaag ggctgataaa tcacagaaca 109440
aatggtatac aatgaatgga aataaaatgc tgatttccta atgagaaaca tatggttatg 109500
actacgtaat aaacatcaga aaatgctctt tcatggctcc caatagtcat aaagtttctg 109560
gaataaagag gaaggaaaga tgcaatttaa tcctataacc taaatgtctg aggatctacc 109620
tttctcaatg gggctgtctt gttaatgaac tagaccaggt ttctttgtgt agctttcacc 109680
tgattctacg taaggctttc tgccaattgc taaacatagg ccgctgaaag atgaataagg 109740
agggaatcat cagctgttcc accaggtcag aagcatgatc tttaactaaa gggccagatg 109800
gcttttataa attaagcaca aaaatctctc atttatgcct ttttaaagta aagaggttag 109860
gagttatgtc ttatacttct ttttaatttt taactctatt atatcccttg caccaatgat 109920
tgagagttat tcagttataa taaattatat acttatcttt agttaggcta tcagactctg 109980
tttatacagt agtgacaggt gttaaggtcc agagaaaaaa tttagggttc tggagcctag 110040
ggtttgccta cacattgggc tccttcttca ttggttcaca tatgctcctg tctacggctt 110100
attatttggt atgactctaa aactcattcc ttgtactcac ataccatgtt tactttacag 110160
aaaaaaatgt taggacttaa tacacatggg ccctatgaag atgaaaaagc tgcttttaaa 110220
tgtttgttgt tgtttctatg aaaactacca cgctgttatg ttctagttca catataaaga 110280
gttcattctg tttaaataag tggaacaact cacatttata ttccacactc aggacccata 110340
tgcttggcct tgtgctggta actaggaata taagataaca agacaattcc cttgctttca 110400
aggaaatcac actttataaa actttgaatt cttgaaatgg gtttcagagg ttccaaggtc 110460
aaattcaaga ataagagttt aagaagaaaa agactatgag aaaggaagtg ttgaccccat 110520
ttgcatttaa atagcaggaa tagtctcaat ctactcattg ggaaaaaatg tatgttgcat 110580
```

-continued

```
atttttgaga tattgcaact tgctctctct ctttgccacc ccaccctttg tcatgctctg 110640
tttttgtgtt gaattggcaa gaaaaatggc tggagggctg gaagaagttg gacccttctt 110700
ccttcttcct tcttccttct ttcttcttct tcttcttctt cttcttcttc ttcttcttct 110760
tcttcttctt cttcttcttc ttcttcttcc tcctcttcct cttcttcctc ttcctcttcc 110820
tcttcctctt cttcttcttt cttcgggggc attgggagct taggaggttt gggtggtaaa 110880
gaaagggtta aatcctgggg atgtgggtaa agggtgcact ggagctgcct tggggaaaaa 110940
tgtggtctcc cactttccat ggacactttg ttcatagaaa ggacaactgc taggaatgaa 111000
caaaaatgaa caattagatt cattgtacac cttctagtac atttgaggct ctgtgatccc 111060
agatgcttac atcatttaat cctcataatg accatatgat agatccattt tacaaatggg 111120
gaaattgaag tttatcctgg aaatttgttg agattaatct ctatttgatt acaaaattta 111180
tcttcttctt gcagttttgg tgacttggaa atcaccccat tatcttgaaa aataacccag 111240
atatttaacg tattctataa atccctggaa aatacaaaag agttgcccaa tgtagtgcat 111300
actctctggt atcatgagat actgacagtt caaacatggt aagctagcct aattaggaaa 111360
ctctccttaa ataggtgacc agggttttct tctaaaggaa gaacaccatg tcaacattaa 111420
ggagttcaat atttgctgat gaatgcagta atccaaagca acaaaaagtt cctgtggaag 111480
aaaaatatac agtttgaatg ggtctcaaaa atgtgaaaat ggaacactgg gatattttta 111540
aggaaatttt ctttcaacat agtgcaccca tgagagtgat tcattgtcat ctggaatcaa 111600
ggatgaacgc aaacttgccc tttcactgaa ttagtctgac atacatctac aaagagttca 111660
agccctcctc tgggttatgg tggagcagcc accctcagag gaaattctca aggctgtttg 111720
taattgcaaa ggtcctgctg tgggactgga aggataccac tgaaggcaag cctcagcagg 111780
gctttgggag gcattcttct gtggtatata caagctgctc tccagggtct atgagaaaca 111840
aagcccaggg attgaagctc taggagctga aagggagttc attctttgtg cagttacctt 111900
aggtaaaaac aatagttcct tctcttttcc actgttccca tgaagctgtt aagctaaatg 111960
tccacagagg gatacaagtt tgtatcctac tccgtgctct gtgtattcat aaatgattag 112020
atggcatcac caatgtcctt ccagctcatc agcctttcca aaatagtcct gaggagcata 112080
ggagaagaaa tagagacaaa aatttggatc ctcaggtcta caacctggct gggccaggat 112140
gtcttttcag ggatcattag ttagaataca cagttataca tttgcataat tctgagatga 112200
gaaagacttt cctcagaatg acaccaaggt cgaaaaataa gattagaaaa caagattagg 112260
aaaaatggaa aagaataaaa catttaaaac ataaatatgt aagctttcat aatagtaaaa 112320
tataaataac aaattgggaa aagcagtcat atgaacagac tttataagaa aaatatgtac 112380
tgctaaagca aattaaaagt aaaatataca aattggaata agttgactat ttttctcatt 112440
aaatcttaat gataaaagca aatgattttc cttatgttga taaaggtttt gccagaactg 112500
taaattggta caagtttcct gaggcagatg tggtaatact tatcaaaagt ttcaaaaata 112560
ggtgtaacat ttgggtgaag taatttctat ttctaaaaaa ttataataaa gaagcaatta 112620
agaatgttca caaagaatta gttgtgagaa tgttctttgt actgttgttt ataatgtagt 112680
gggggcagaa agtgaaccta aatgtcaaac aatagaattt gagtaaataa gttttgtttt 112740
gttctaagag atggagtctc actgaagtgc aatagcatga tcatagctca ctgcagcctt 112800
gaactcttga gctcaagtga tcctcccacc tgagtctccc cagtagctgg cattacaggt 112860
gcatgcctgg ttaaatacat ttttttcagg tccctgtaaa gtctgggatg attaaataca 112920
ttttacagac atctttacaa cagcatactc tggagctatt aaaagacagt gctgtagatg 112980
```

-continued

```
tatatctatt cacatacaat tgttatgtta attacataat attaaatgaa aaaacccatt 113040
tgcaaaattc tgtatatggc aatttagttt atgaatatgt actaaacatg aaaaaataca 113100
caccataatt ttcacactag ctgtctatgg ctcgtggaat cagagccatt atttttggga 113160
aggggagttc tctttttatt caaatgcatt tcctaatatt tctttaacat gtatatatta 113220
cttatttttt ttaaaatatt gaaagtaaaa ttctttagga tttagtctgg aaagaaaatc 113280
cacaacagtg aaattttttt ttcccctgct ggccttatag aagcataagt ctttatgtgc 113340
ttctgcagag gaaaaaaaaa cagaagcaaa gtctaacttc tagcagctct aattagaatg 113400
aataaaaccc tacagttgaa gcataaccag gtcacagatt tgacatctta taaagagcag 113460
gcactttaga gacataatgt cctgggtcta gcctctgtgc cttgcttata tgaaaacttg 113520
aaaaagtaac agaaattctc tgaggcttat tttctacaaa tgtgataaga agataataac 113580
gcttatggca cagggcagtg agaattaaat ggtaatgtgt taggaaacat ctgttatgta 113640
gtaggtgctc aaaacagttt tagcttcctt cccttttttcc cttgcagtct tgtttaaggt 113700
atcaaaatta gagcagaaca ttgccactgc catgtgggcg gggggagact gattcctcgt 113760
ggactgaggg aggttctact aaggagtggg gtgagtgctg tgaggcccag gacaaagatc 113820
tgtctcgctg caaccctccc ctcccccagc acaccaattc ctgtatcagc atttgctagg 113880
ttgctctaat tttccttttt atatgttctt ttctgtctga tgtccttgaa tgttgggaga 113940
cagaaattgc cctgggactt ctatgtaatg aaaagagagt aacagtgagg atgctgatgc 114000
tggatggagc ttgggatggc cataggctaa gaatcctaga agagcctaga caaagaatcc 114060
ttggaaattt cgtataatat gcaaggttca gggaagcacc agtaaatatt aacttccaat 114120
cctctctctc tctctctctt tctctctcag cttgttttcc tcttcttttt ctttatattt 114180
tcttccccct cccctttttc tcctttccct tctccttctt cctcttctcc ttctccttct 114240
tctccttctt catcctcttt tcctcttcct tctctctttc cctcttctct cccttctcct 114300
ctcctcctcc tcatgctcct tcatattctt cttcaatata gggggtaatt ttatttggat 114360
aaaagaaaat tatcagatta ttctatactt agggcctact gtcatcttcc caaactctgc 114420
taggcaacat tctctacaac aatcgcttgt ctcatacttc ttgctttact tagaaaacac 114480
attcatttcc caaaggctaa ttaaagaaat ataaaagtta gagttacagt ttgtatattc 114540
tcattagcaa atcaccaacc caggggacaa gaacaagtta ggagcatctc taccaaaaat 114600
ctaaggaatt gcaatccatg taaagacact acgttaagtg ttgcgtgtgt taccttcttt 114660
acaaattaga gtcctcactg ctggattgag gctggcctaa tgaagttgta aaatgaagat 114720
atattaattc tttacctggt gcttttatta aggaaagtta tctaaatcat ttaatgaaaa 114780
tcaactaaat gtattacctc ctacattagg aatacagtga cacagaagaa gaaaaacaac 114840
tcttggataa tgactctggg cagaaaaggg agatgagatt gcaaacaaaa tatcccaaaa 114900
taggtttgga gagaaaatga gaaagaaaga gtcttggtga ttgaagggaa ttagaaatga 114960
tagaagaagg ggagatacat agctctctct tggttgatta tcttgcactg aggaatttct 115020
atgagaacgg atctagggaa gtacaactta gtccaggtta gatgactttc agaggcaatt 115080
tctgcataga actagattcc tcagtattca gaagaagtat ggtagaagtt tgcccggatg 115140
gcacaaactg gaatgcctgt atgagctgat ttaccctgac tgacgttcag attgactgat 115200
cggtaggatt ttgctgttat tcacccacat ctccagtttg tactagccta gaaaccttct 115260
atttgatgac ttatttgtcc cattttgtct caaatacata gaaggggcga aaaacattat 115320
```

-continued

```
tctagtggga ggtttctgtc acttttgttc attctgaatt tgtacagaag gtaacacaca 115380
caacacttag gtggcatcta tatggttgtt atttcattag atttctagta gagatgcctc 115440
tgacctgttc ctgttccctg ccaaaccaat tctgagagcc tgattaaggc aacagggtct 115500
tgaggtcaag attccacaag ccaccgttga ctaattaaat atcacaacgt aacagctaaa 115560
cttcctcttt gtagcttcag agactccata gcacaaatct tccccctaaa tcatataaac 115620
ttgataaata aagcagcatg catataactg agcatatatt ttgaaatgct tctaaaaagt 115680
agaacatcaa tttaaagcat taaaaaaatg ttagacttct ttcttttttt tttttttttt 115740
tttgagatgg agtctcgctc tgttgccgag actggagtac agtggtgcaa tctcggctca 115800
ctgcaagctc tgcctcccgg gttcacgcca ttctcctgcc tcagcctccc tagtagctgg 115860
gactacaggt gcctgccacc acgccccgct aatttttgta tttttagtag agacggggtt 115920
tcaccttgtt agccaggatg gtctcgatct cctgacctcg tgatccgcct gcctcggcct 115980
cccaaagtgc tgggattata ggcgtgagcc accgcgccca gcctagactt cttaatacgt 116040
atgcctctga tagactgcca ctttctcctt taatgataag tttctatttg cctcaccccc 116100
cccaggagtt gtttgctctt gagtaggacc tatgcttaaa tttgtacctg ccactgctga 116160
cactactacc aaatcaattg ttcttactaa gttagtatct tatccgagaa agaggcactg 116220
ggttttcttc atcattcaat caatctctag aggcagcttt cagtgtctct caaattctat 116280
cagtaaattg aagtttctcc tgcctgaact gcaccctgac ctcacccctt ggtgagggtg 116340
ccccatatct catccatcca tgctcagaca aatgtcacag atctctaatt caactcttat 116400
tatgtcatcg taatggatga acaaatgaag tgaatttaca gacagcaatc ctgggcttcc 116460
cgtctttgac tctcgatgta tgggcccctc ctgctgcata tttacataca attagcaata 116520
aagtagggtt ctcacagtta ttttgtttct ttgtacataa ggcaatttta gtgcctttat 116580
atatctagta tgttcttaca ctctcattca ctcattcatt taaaaataat tttgctcaaa 116640
agctgaagat gcaatattta tgatcgagga gatttattag gacaggagaa aatatcagat 116700
gaaagttgga tgactggtac aaagtgctgc agaaattttg aagaaagaaa gaatataaca 116760
tacaactgag aaacaattta ggaaatgcta ctttcaagta cttaatttca ttatgggtgc 116820
ctgtctcttt tgctatcata agacaaatat agacccaaag cacaggacac aagcattagt 116880
gaacaacttg ggaaagcagc attttccaga gtgtgctcca cagaaatcct acaatgtatt 116940
tcatcgaaaa agattccatg gccactaaat ttgggaagtg ccacctaagc aaccctctct 117000
cttgtgggtc acagtaacca tcagtatatt aaagactctg aagttgtgca cttaaaacaa 117060
aataaaacac acacacactc acatacacac acaaccagaa aactgtttcc ttccttcctt 117120
ccttcttccc ttcctccctt cctccccctt cttcttccct tcccttccct ttctctttct 117180
ttttgacagt ctcaccctgt tgccaggctg gaatgcaatg gcacgatctc ggctcactgc 117240
aagctccaac tccctggttc aagtgattct cctgcctcag cctcccaagt agctggaaat 117300
acaggtatgc gccaccacac ccagctaatt tctgtatttt tagtagagac agggtttcac 117360
cctgttggcc aggatggtct caatctcctg accttgtgat ccacccgcct tggcctccca 117420
aaagtgctgg gattacagac gtgagccaac atgcttggcc aaaaaatttc ctatgtttaa 117480
ttttgatttt tcttcccttt tgaaacgaat gcatatagta ttactcttag gagtactatt 117540
tacttgttta attcatttat tgccatttct acatatcact gtgctggtga ctctgtgcat 117600
gtatatgcag ggcagaatat gcattaaaat cttggaagtg caagttggcg gaggatgaat 117660
agaatatgtg ctattggaat ccaccacagg atttttaacc ttcttcctgt accaacccat 117720
```

-continued tgtaaatgcc ttatacagag taatagcaga acactatggc aaggggagtg ctccaataaa 117780
tatctgacgg gaatgatctt ccttcacagt tagtattaat atttgtttca ttgtctttat 117840
tttaattatt ttccattacc tttctatgaa agataaagaa gagacatttg tatatctgta 117900
accttcacca aatgccacct gcctggtaaa tgtcagcagt ccccagggct ttgtcctggg 117960
tccctcctca tttgcatcct cactgaggaa catttgtctc cttccaagtc ttcatttagt 118020
acctcattct cttggcattc tatcacaagc cctacacacc agtggccagg aatagggcag 118080
ctcaaaccag cacacacaca catatttctg tgactttact catgtttcta catcatcaga 118140
gttgccctgg ttctcactca tcacctgtca aaataacttt catctttcaa ggtcgacaga 118200
gccgtattaa catagcggtc aagaacgtgt ccaacctaga ctgggttcaa atacagactc 118260
tagataataa ccttggaata atgttggtac ctagctcagg ttgaataaca tttaacacaa 118320
ataaaataaa acaaaagaaa atatacttcc aaaaaccttt ctctcataaa tttattagag 118380
ttattaggtt ggtgcaaaag tcattgcagt ttttgtcatt acttttaatg gaataaaaaa 118440
acgcaattac ttttgcacgg accaaattgt tcttctttgg caatccccta gcaaatcaat 118500
tcaacttctg ttattcactg acaacattgt tttttctact ggctgcagct tttcacaagt 118560
ctgtgccctc tcttcactgc tataaattgt gagcgcacca aggagaagac tgtcaagttt 118620 accttttttgc tcatattgaa agtatgtggc aataactggc ttccacaatc tgtgtgttga 118680
tttggaaaat gaagattgag gtacaagcaa aaaaaatcag tgaagcacca tttaatacag 118740
aggggaacag ggcatatttg gaagtgaaca tttatttctg aatccaacat cagtattatc 118800
tagttggcta actttttaaa ttttttattt aacaaatgta caacatattt aatattgtga 118860
tgtggacttg gccctgtcat ctagaaaggc cttagcacag gtagtttaat gaagtgtcag 118920
gtgagaagct gtcccatccc ctattaagca atgtattgtc taaatgagtt taattaccat 118980
gcaaattact aggagctcat atgcccaagg cctacaacat atcagatggc aggtctaaga 119040
gaaattcagt aggctgtgcc tctctttgta gtaatgcttt tacgtaatat agaaaaaatg 119100
tcaatgtaac aagaataaaa tgctatgatt cttggcaaat ttttaagtca gtgaaatcac 119160
tggtaaaaat tgtagtggac ttataagata gttgatataa gcaagtcact ttcaagaata 119220
gctattaact tatttgttct cctttctcta aaaacatact ggaagtgact aaatgtctga 119280
atcctgcttc tacacaacca tgaatatttt ggaaaaggct acaccactca tgtttatggg 119340
gaaggccttg gggtgtgggc atggactgga tctgaaaata aaaggtttat atcctgggtc 119400
agcttactaa atgtgatctt gaacaggtca ctcaacatct cagagtttcc attttctctt 119460
ctgtaataaa gactagtgat gccatcttta agatatagac taaatgattt aaagtatttt 119520
caaaactcat gcaaacatag gtattatgcc atagacaatt tttaaaagtg aaacaaaaga 119580
tatattcctg ttttcagcct ctatccatag acagagtttg ggtctgtcaa aatgttaacc 119640
gcagtataag accaatctga agtgctgtca gactaatggc atctttacct atcctgaact 119700
gcatggttct ttcacacaca caggcctgac acaaaacagt atatcttgta agtgctaaat 119760
aaatatgaac aagatgagac tgaagtttta ttactactac tcatttgaac atctttccaa 119820
atactgacca aattacaatg taatagaatg tgaccgtctg ttatctagga aaaaaaaaaa 119880
atcacctaat gctttaactt ttacaatatg tctaatctat tcagagccaa gaataacctg 119940
ggagataagc acatgaattc agattggatt tctaagagat ttttagcaaa gtcttcacca 120000
aatgtgccta gaataagtca tatcttctga gcaataccccc aaagagggat gattctacaa 120060

-continued gagtttccaa actttcttga ctgcaaccct cagcaataaa cactgattta taggtaatga 120120
gatggaaaca tggcttatta cttatataca taaataaaac aaaaatattt tactatttgc 120180
aatgcactct gatattttct atcctatcct acataacatt caaacaaaat gttatatttt 120240
agtttactta aaaagtatgt ggttgacaaa ctgttgatga attctacatc atcagggttg 120300
ccctggctct cactcatcac ctgtcaaaat agctttcatc tttcaaggtc gacagggctg 120360
tattaacata gtggtcaaga atgtgtccaa cctagactgg gttcaaatcc agactctaga 120420
taataacctt gtttgggaaa caccgtgttg tggatccagc actgtgtagg catataacta 120480
tttcatagtc catttgctta tttggagaga tgagaaaatc aggcctaggt gttcatgaaa 120540
tgcatccttc aaagactgag tgagagttgt cagtggtaaa atggcacttt gcagattaca 120600
aaatccagca tgaaccatga cttcaataaa gagtatttgt tgcattttgt aatagttgta 120660
tgcaaggtca aaaggactaa tattgtgctt gattttctcc tttgcctctg caataactga 120720
aaaacaggta tacacatggg taaaagaaat attaatatgg tgtttcaata acagctcaat 120780
aatttgattc agtacactgt attggattct tttctgttta gttggaacta atgggtgcaa 120840
cttaaagaca gttaaatata tatacttttt aatttgaagg aaaaactttt tctttttttat 120900 ttaaaggcat tgaactgagg aatgtgctgt cttatggcct agtgtttctt atctgcctgt 120960
gtcaaagcag tgcctgaaaa aggatttgca agagctttaa tggagaaggt tccagcactg 121020
ggtcatggag tagaagaaat atctaaacct gcactgattc cagttctgta gcaattagtc 121080
acatgtggct attgagcact tgaaatgtgg ctagtgtaac ctgaggaact aaattttcag 121140
gttttaattg tatgtaaatg taaacttaaa tagccatatg tgattagtcc ttaccacagt 121200
gtactataca gatctagagg aatcaatgta ttggctattt gctaagtaaa tgtgacaatt 121260
tttgatacct catattatca taatttataa tgcatcccac atactaaaaa gtgatctggg 121320
atccatgaaa agcagaaatt acaggattca tatatttaaa atagaactat tttgagacta 121380
gagacaaacg tattgccagc tttgggtttt agtttttaca tctctcaatg acaaataggt 121440
ttcttctgat tctccagaga gactgctgac tgcactgact cttattagtg gccttcaaga 121500
agtcctgctc caaatttcag ccactgcttg tatatacaat tttagacatt gaaaagaaaa 121560
ttctgctagt tccttgaaaa tggggctgtt tatccatttg gattgacaca agaaattaag 121620
acagggaatg tttttgtgaa gttggtcatg tagtatttgt atgatgggac tcttctaata 121680
agttcattta atcttaaaaa taatatgcaa taggctgggc atgatggctc atgcctgtag 121740
tcccagcatt ttgggaggct gaggtggtca gattgcttga gctaaggagt ttgagaccag 121800
tgtaggcaac atggcaaagc ccaatctcta caaaaaaaga aaaaaaaaat aagctgggca 121860
tggtggcatg tgcctgtaag tcccagctaa cttggaaggc tgaggtggga ggattgcctg 121920
agcccaggag tttcaggctg cagtgagttg tcatcctgcc actgcactac aacaagggtg 121980
acagagtgag gaccagtctc aaaaaaaaaa aaaaaaaaaa gataagataa aagaaaaaaa 122040
atgcaacaaa actaaaaaga ataatgatct aaaatttgtc aaacacagca aaacaactga 122100
ccttttaata ataatttggt tgcatccaat tttctccata ttccaagaaa ctcttgatta 122160
tatggcagtt ttattgactt acgagaaaaa cccactccgg atataataag caatttgtga 122220
tatgcacaga atagaggtga atgcacaagg ataaactgta tgctttagca attaaatcca 122280
gggcatttaa gggaacagct acactaaagt atagataatc aaattgaact aaggaatggg 122340
gtctttccat gatattccca gtgagcaaca gaacgtcatg gaaaactcca atcagtattt 122400
cagtacctct ttcttgcatg caaacaaatc actaaacggc aaatttgatg tcttttacat 122460

-continued cctggaactc caggctagag acacccctgt aaattccctg tgaggtggga aattttgcct 122520
gagttgcagt caactctggg gtttgagtat tcatgggaca ggctgttatt taataggttc 122580
aggagaagaa tttgagggaa ttccaagaat tatggatttt acaggcgcgg gaggcaccta 122640
aggataattg tgtagaattc actgaggact aggaaatgat gttgacctct gagaatcaaa 122700
gtaggtggat gcagagataa tgtgtgtcca acagccacct ctagaaaaaa gccaggttat 122760
gatatttata aaggtgagaa caaaaaggtt tgagaattct atataacttt catcaagatg 122820
aactaaggaa agcaatgcag cagtttgatt gaaatgtaat gaactggact ccaggcaatt 122880
attgtgtatc ctgtctagtg aaaaactgaa caaagtgaaa aagattagct tggactgtag 122940
aaaagggaaa ccaaagggcc agaatttggt agagtattga acactggctg agagaagata 123000
gtctctgtac caggaacttg cccaatttct gtgatagcta tgtatacatt atagcaaagt 123060
gtttaaaagc taggatctac tgccagatta ctaattcctt aaccttggag aacttatttt 123120
catctctgtg actcaatttc atcttctgta agtgattata atagcatcca tcattaggtt 123180
tattgtataa ataattgagt taatatgtac taaccatttg aaatagcact ctcaataaat 123240
gtttattatt atcaccccag agatagatac attagacatg ttaatatata tgcaactcat 123300
acaactaatt atctctattt taggttcaag gatgctaagt aattcttcga cccctgaaga 123360
ttggcctata aggagggatg caccagttag gcagatatca gcattgggat acttatatca 123420
ctctaaattt gcatcttggc attttggctc atagttcagt cttttgtgag ttttattatc 123480
attagtcagc ctcctaaatc caataactct agacactgat aagtgacatt tggaccattg 123540
aggctgagag ctagacccag aactggtaaa ttcactaaca gtatgctaaa ggtaaaatct 123600
gttggcaaat agctaaaaag ccatctgctg tagaccttga tctatcttct ttcaaatatc 123660
agtaattcac taccaagatt ttaccaaatg ccaagtagtt tcaaattccc cccaaaataa 123720
aaaggaatag attatcttag agatatttag agttacagaa gggttacact taaacaaaac 123780
atatcaatca ttaagatttg ccctgtcttg tctaatactt gagggttttg ccactacctg 123840
aagactaagt cctgaattga tacacacaaa acagtacaca aaggaatcag tgatttttag 123900
tccagtgata cctagctcgt gattcaagtc aacttatcag tgtgctaaag catactcacc 123960
tatcccagta accactatct ctccactatc tctatttatg aacagaaatg caacaatcta 124020
tatttttaga gtatgggcct aggaatttgt gatacagaat ttttttaaag aaagaaaaat 124080
atcatatata tacttccatt gcaggtctgg cagcagatag ctgttttgcc actttctgga 124140
aaaactaatg gcttttgata taccctccac tatgtagtat atttgtgaaa attccagagt 124200
ctcaaatgca atttccaaga ctgttctggg ccttatgcta ctaaccatgc aaatatccct 124260
cagctgaaaa attttaaaca catcctgggg ttgggtttat gttggagaag ctctcacagg 124320
actatcggcc caggattata ttgtagcccc taagtaggaa aggttttgtt tatgttgcct 124380
ctatttacat gggattttct ttttttgaat aactcaaacc caattataaa ggagcagaac 124440
tgagcctgtg agatatgacc aggctgccaa agaggaaatc gacaaagact ccacaaacta 124500
aggagacaag agcagctgtt attctggcaa ggagatgcaa cttgccaacc ttctgcccag 124560
cggtgccaca ccagtggtct gaacaataag ttgagtttac agcctcccct gtgactatgc 124620
cagtcacatt caagaacatc tgccacagcc ttaatgacag agcctatggg aacttaatga 124680
gtaccccata cacctgtgcg gttctacgag acagctgttt cccactccgc cacctccttt 124740
ctcagtcctt cccatcacgt gtgctcactg ccccatcttc cccataggat acagctgact 124800

-continued

```
ctcataccgg ggtctgtgct tttgtgagga tttcatttat ctccatttac atggcactta 124860
taggcagtag agataaaaag cataatatct ttcacactgc tcaagcttca cagtttgcta 124920
tgcaagaggg tgagtgctgg agactgagaa agtcaatcag aagaatcaat ggtctaagag 124980
ataaggggac aagaaggaag aagatgagaa gtgctgctac tttttctttg ccaacaactc 125040
tcagacacaa attagaaatt cacaaagcca tggaaacact tcacagttta cctctgtagg 125100
tatctatgaa attgctttgg tcaaagcatt ttctggttga gaaagctgcc tagtggaaga 125160
cctaacaaaa caaaaaacac aaaacaaaat gcaagacaaa acaacttact aaaaatactt 125220
ttaaaattct gagaattcta attacatgga aagtgcacaa tgttagtata gtgcatgata 125280
gaaagaatct caaaaactgt atgacctttg gcaagttatt taacacctct gagtttccat 125340
ttttttagtt tgttaaatta ggataattac ttagatttgg taaaaccaca ataaataaat 125400
tatatatgtt atataaagtg ttttacataa taactagcac aaccaagtgc ttgataaaca 125460
ttattattat tatcattatt attattgcca catcaagccc atttcttatg gctttactgt 125520
aaccactaaa aaatgtgttc ttgttccata ttttacagaa taaatcattc ttttaatgac 125580
aaaaaaggtg aaatatcccc tagagagaaa aacctaaaaa taatgatctc atttgttatg 125640
taaatcaaaa ggtatgagct tgaattttgt agatatatga ctaacagaat gtagaaattc 125700
ttcagtcatt catttcggac tgtttacata tcagaagcat tatatgttct atgataaagg 125760
ccacgtggca tggcaaaact atgacaatat tagtagttta tgttaaaaag aaatagtccc 125820
ccatatcact agactgcact gtccaatatg gtagccacta accgaatatg gtagccacta 125880
accgaatatg gtagccacta accgaatgtg tctattgaac atttgaaatg tatctgctcc 125940
aaattgatat gtgctgtaag tataaagtac acactagatt tctaagattt agcatgtaaa 126000
aaagaattta aaacaactta ttaacaattt tatatgaatt acatgttgaa atgataaatat 126060
tgggttaaat aaactatatt atggaaataa attttatcta tttcttgttt gttttaattt 126120
gtctactaga agatttaaaa ttaactgtct ttctcctatc atatttcttt tgggcagtgc 126180
tgctcgggac taatgattct caatggttct tatatatgca gtaatatttt gtttataaat 126240
gtcacacaag gagcttgaaa aaaatttaaa cccctggtct ttcagtgatt ctgactccaa 126300
tggccaagga atttgcattt tcaataagaa actggatatt tcaaatgcag atggtcactg 126360
gaccacattt tgagaaacac tgctatagac taaggtttct ttagttgaaa catgatgtta 126420
tgaaacacag atatgattgg ggggatgttt atggacagca tctagactaa tatgaaggca 126480
gaaaaagaga gggagaatca agatggtaga agatgcccat taacctgctt tcaggatctt 126540
ctccctaata agtagtaaat ataagtctgt tactttttcc catattctag tgccagtggg 126600
gatggaggag taaagtctgc actgggccag gtacggtggc tcacacctgt aatctcagca 126660
ctttgggagg ctgaggcagg aggattgctt gagcacagga gtttgagacg aacgtgggca 126720
atatagtgag accttatctc tctggaaaaa aaaagtctgc actgcgagga cctctcacca 126780
gtaaatttta agatttgaag gcaaggttta caaggctgtg gtgaataaaa gtgatgacat 126840
aattattttc agtggtaact aataacattc ttctcattta acactgtcac ttccattact 126900
actgcaaatc ggctggtggt gagaggtata agtggtatag atcaaatctg gagaaagaga 126960
aatattccat atagcctcca tgtcccactt ctttcatgat ataccttagc cactgtccac 127020
atagcaatta cattccaggc actgggcaac aaaatcacaa tcattcatgg ttgctgcaga 127080
gacacagagc ctctcctgcc atgtccagca taagaggctc tttcttggct gacacacaaa 127140
aaacctttca aatataaaga aggagagact ctgagggaaa caactcattc atcaaaccaa 127200
```

-continued cctcatccgc cattaacatc acaccttttt ttgagattct tctattacca atgccctttt 127260
atttccttcc taccaacttg atgtgtttgc ctcaacaagt actctttcct cacagtttgc 127320
tttgccgtta tgttattgta tcttttgatg cctttttttt ttcgtccagc ttacactaga 127380
tgcaaaactg ataaagttgt gctgattgga tggtgactgc ccaatcccag aaggacatcc 127440
ctcccacaat tgcctttcaa agttgtcacc ctcctatatg acgaaactat ggcagtagct 127500
gggaattttt ttttgcagtc aggtttaatc ttcattttgc tgaccaagcc accagggcaa 127560
gcacctctta cattgagggt ggtgtgctct tacagtgaga gcactactac agttatcagt 127620
gatgaaacag gaattcctga tgcagtaaat tgccttttgg aaataaatgg tagcatactt 127680
tcaggcttaa gttgacaatt taggtcattc ccccaaatct aaaacttcct atcacaaaaa 127740
cctgcaaaga aatcacacaa ttgttgaagt tagctgctat actgaggtca tttagtccaa 127800
tttttaatgc aaaatacctc ctaattggat gtcactcttc ctgaaatata aacagtaaca 127860
attgattaag tttcagatat tcttgctaga agtttttcttg acttaaccca cttaaccctc 127920
agtagaggta ttactagctc cctccctccc tttacaggtg ataaaacaga gatccagaga 127980
aactgagtca cttgcccaag attacaaatt aaaggtgtga gctggttttg aactccagtg 128040
atccatttct aattcctaag gaggactatg ccttaagaca attcatctgc attttctaga 128100
caccatggcc acagttttag gcaaataaga gttaggcctg ggactcttta ggaaatgact 128160
gagaaagaga agcccttcct tcctttacca ctggggtttc taaaaggcta gatagtaact 128220
gtggaatttt gcaaccatga tggcactgta agtggtgagc cagagatggc gtggtcctga 128280
gctctgatga tctggaattt actgctttct ctgaaatgtg agccaataga ttccttttct 128340
ttaagccagg ttgagttgtg ctgtcacttg aaaacagtta agtccttaag gagtgaacaa 128400
ctaagtaatt gacataaagc tccaagtttg taatgcttaa gccaatatct tgcacatatt 128460
agatattcaa taaatattag tttttattct tccacaatgt tcaggagcaa tgattacgct 128520
tctctatttt gcacagagcc taaaaagggc tgaaacataa aaaataaata cattgaatac 128580
atgtctgcag atcaacagac atgttgagaa ctatacccag gagagattag acagtcagac 128640
tgtacccact catcatttcc acttctggct ctaagtagga gccagggaag gaaagtgctc 128700
tcagcatggc tcacagggga gactttccca acaggattct acagattgga cttgactcat 128760
agtcataatg tgccagactc accccagtgc cacctggtta atcaaagggc cagaaggtat 128820
ctgtggaaga aagacttaag gaagccgggg aagtagatag cagttcactg aagttcctgg 128880
catttgcctg agggcacagc tggggacatt aataatcatt tttctcatca gactgctgaa 128940
aatgagagca aagtgagaaa gggaaaaaaa caagtgtttt gctgcctcct gtttgaatta 129000
atctcttctg acaactgctg atttgggttt gtgattcgat cttccatatg tctagctcca 129060
ttggtcaatt aagtgtcgag ggtgattggg ggaagcagtg acactcagcc tgattagagg 129120
aagaagcatc acaaggcatt tagaacatgc aaagcagccc actgagcctg gcttaaacag 129180
agccaagcag agcaagggtg gtgtctggta ctgccaggag ggtcagggaa gagtcgaacc 129240
tcagcactca gagcactaat caagtaagga ggacatcaaa gtcagtttcc tgtgagcagc 129300
gagtaagctc tggagagttt tggagggatc taaggctcat gcaaagttaa gcccccgtca 129360
acccattcaa atcttattct tctagactgt ccaactaatg aactactttc aacaaagtat 129420
cataaacttg agaacagaaa ataaagtcat gtctaacttg gagagttcaa tttatacatt 129480
tgaaggaatc ctctgaaatc aagaaatggg atagcagaac acttaagtta gacaaaaaca 129540

-continued

```
atgcagaagc agtagtgctc acacattact atgcagtaat aaaaacattg aggaactatg 129600
agttctagtc ctacctcagt taatggcttg ttggttactt tgcagcaaga tgcttctttt 129660
cttcattgtc acttccccat ttttttttt tctttgagaa agaatctcac tctgttgcta 129720
ggctggagtg cagtggtgca atctcggctc actgcaacct ctgccttctg agtgcaagtg 129780
attctcctgc ctcagcctcc tgagtagctg gcactacagg ctcacaccac catgcccagc 129840
taattttctc atttttagta aagacaaggt ttcaccatgt tggccaggat ggtcttgatc 129900
tcttgacctc atgatccact aaggctcagc ctcccaaagt gctgggatga caggcctgag 129960
ccaccatgcc cagcctactt ccccattttt aaggaggctg atggaggaag tgggggcact 130020
tgtacgctcc taaataaaac tgaaacttga tctaacagct gaagagaatg ttttgactgg 130080
agcaatggca gcctaaagtc ttttatgagt taaatgctaa agtacttcat gtgactgttt 130140
aaaagaatag ctaataaaaa cgattgtacg ctattttttt ataaagatcc atatcaatgc 130200
tcaacaatca tcatagaagg caacaggctc ctttaaaagt aacattatgt caaaaaagca 130260
cctatgattt cttggatgta gtcacagttt tgttgttcaa atttaatgaa aatagaacaa 130320
atgtggcagt tgttaaaaat aaatggaaaa actttggctg gattgcaaac tagttaagta 130380
tgatcttaat agaataacca tctaagcatg taaacatgtg gatttatatc actctgaagg 130440
aaaaactaat agcctagcaa agcctccatt caatgcttta tctcattcaa catatttatt 130500
gatgactgac atgggtaaaa tatacttaaa tagagagatt atcaacttac ttccccaaat 130560
ttaaggagaa aagctaaggc ataataaaag cagggtacaa aatgaactag atctgctcta 130620
ttccacagtt gtcattgtaa agatcaaata cagatcaatg ccacaacatt aaagatataa 130680
caaattttag gtcaagtgaa gaggacgtgt gatggtgaag aagacttggg cactgtcagt 130740
caaagaaaaa ttgaaggaaa tggatcaaga gagagcatgt ttgagggaaa caatggcaaa 130800
ataatcagtc tattttaaag gctttttaat ggggaaaaga tttagattta ttctgagtgg 130860
atccacaagc aaaatacttt agagagatag attttgacac aaatgaagag attttttaa 130920
ataagtaaaa tgactttcct aataaatagt gagttctctg atgggagatg gggctcaaaa 130980
gaaaccaggg aaagactctc ccggtaaaag agattcacat gtcaagtaag catctagact 131040
gcatgacttc tgagatactt gtagttctaa aactccttga ttctattacc atagaagaat 131100
tctacagcta tttattttac atatagaaaa agcatgttaa gtcttgagaa atatgtattt 131160
cttagttaac tgtcatgatg ggaaaataga acattaatag acttaaatat ctgaatatac 131220
gtgtccctcc aaaattccta tgttggaact tagtgaagtg atggtattga gaggtgggac 131280
ctttgggagg tgattaggcc tcagggtgga actagtgccc ttagaaagag ctctagagag 131340
caaatatgtt ccttgttgac ccctgctacc tgtgaggact cacagaaggt gctgtccatg 131400
agaaacacgc ccttaccaca cacacatctg ccagaacctt gaccttggcc ttcctagcct 131460
ccacaactat gataaaataa aattcttttt ttttaaatca atctaaggta ttttgttaca 131520
gcaccccaaa cagactaaga caaatgtaaa ttctgtaaat tcttaagcat acagtagaag 131580
gaataaaatc taacactaac aaatggtaga gtttttagag aatgaataat ctatgaaaga 131640
aggcatacat attgactact atgaaaagac cgcacgtgac agaattgtag ggagtgatgt 131700
ttaagagcac aagctctagg ttagctgttt tcattcaaat cctggctctg ccacttgcta 131760
gatgtataac cttggacatg ccacagtttc tgcatctgag acatgaacat aacaatatat 131820
ctatcatata aagtttttac aatttaaatg agtttaatat atataaagat tttgtaatag 131880
ttcttaaaac acagtaaaca ctatacgagt actcgttatt ttaccagctc tttaaaaatt 131940
```

-continued ttcagaaaaa caggactaga gatattcaag tgaaggtgga tgtgctttca acatccctct 132000
taataaaaat aggtaaatta gttaatagac aatagaggtc agctttttaa atttcattat 132060
tttatttatt tacttggtat tagccttctg gaatagctat atgtgaaaaa ttgattttca 132120
tcctgttgtc ttgccattac tgatgacgga atatatagca cagaaaattt taaaccactg 132180
atttttatct attacataac ttttgcaaaa gctgaaatat aacaacctgg ggtaagcatc 132240
tcccatgcct tttcctttc ttgtacccta aggaagtggt atcaatgaat ggccaaaaga 132300
tgaaaagtaa taaggcagcc catctaatta ttgaattgtg taaatagctc ctgaataaat 132360
gaaagttgat tgtatgtata aattacaggt tatctaaaaa tggataagtg tattttaaaa 132420
ataacaacat tcaacctagg tgatctgatg agatgaaaat aaactatgaa agtcaaaata 132480
tttaaacaaa caatgtcaat aacaacaaat attttgaaca tttagcatca atttattaac 132540
ttcctagtta atgtggcaaa aatggcagag tattttacac atcgttcata acgtgggaat 132600
tctaacagaa atgttttctt gattcagaac caagatgtct accctttttt gtctccttgg 132660
tctgtccaga ctgaagcaca atcaacggca aatgggagat atgagaaaag atgacatatt 132720
tgaataaatt ccatgggaaa aaattctcac atctttagat aatacatcta aactcttttt 132780
tttttctttg accttcagaa aaatcctaaa tgtcagcagc ctgatttaga aaaaaaaaat 132840
gtctttggca gatttctctt ccttttgttt tctttactgc ttttaatgaa atgctaatga 132900
taccatttta ttcagcaatt ctacttctag gaatttggaa gtagaagtgc ctatagctga 132960
gaatgtggcc ttagattcaa gttctagttc caatgttgtc tagctgcatg accttgagaa 133020
aatggattaa cctctctaaa cctcactatc gttatctgta aaacaaggac ataaagtctt 133080
tagcatacat acaggtattc taagttcctt ctttatatca aaataagtca gtcattggaa 133140
cattattagt tttagacaaa cataacttaa tccttctcaa atctaccagt ctatatttta 133200
atgatcttct ctgagagttt actgagggca aatataagaa gctcttaaat aaagcatttt 133260
tttatttgct ataacgctgt taaaggcatc atctttaaaa gtacccgctc tttaaaattc 133320
cataaagtaa attcatttca gcatgtacta tcacgaacac tatctttctt aaataattag 133380
tatgtgttct tctactcatt aatgaaaata taaataaact tctattttag atgccaggaa 133440
actcagagta aatttctcat tcatatttat ttcatccttt tttgtaaaat catttttttcc 133500
attataaata ttatattgta taaacatgtt aataagcaga ctcaaatatt tcataatgga 133560
acccagagaa ctgattactt ttataaagta taatgtgact acaatttagc ctgcatcaaa 133620
aaataattaa aacatgtttt atatttttat attaaatctg cattaaaatt acattagata 133680
atacattcaa aaaccataac caaaggatat ttctcactgc tgatgcaggt gtggagagaa 133740
agcatcttgg aatagttcct aatgatagtg aaaatgtcca tgaaaggctt ggtaaatctt 133800
tacaaatagc cataaaaatg tcaacataat tcaaaaaaat ttgcttctag aaatctatga 133860
tttctaagaa aataatcatg aataaggata aaaatgtatg tatgaatgta ttcattacag 133920
tactacactt gtaaaaatat tttatgaaaa aatcccaagc taaggaaatc atgaactaat 133980
gaaatacatg taatttcaac ttgttgtata tttaagtgaa ttattttact caaaagaatg 134040
atattaggta ggaaaaaagg ccaacaaaga gtagattctt ctcaaaatta tgttgaaaaa 134100
ttattactgt tcagatatta tttccaagac tagaagaaaa tacaacaaag tgttatattg 134160
cttaaatatt ggtaatagga tcaccaatgg tctttgtatt ttcttttgat tttcatgtgt 134220
tttcttgttt tctacaatga atatcacatt aatcagaaaa agtaaaaaca aaaataattt 134280

-continued gtgaaagaat ctaatatgaa aagggaaaat ataagacttt ttatattatt ctaataaggt 134340
agttttatta gaaaacatgt ctattctaaa ggaatgtact atttcacttt attataccat 134400
gaagtatgat tctgagctct gatataatgt atattgtcca aaatgtcctc aattccacaa 134460
agcactaaaa attatggaag taataattgg gagcgaactt gacaatcatg gttaaccata 134520
ttaattataa aactttcaaa gtgttggcac accgtgtctt ctgttgaatt gattattgca 134580
gcactctgca aggtaagcag atcatatatt aatgctttcc ttattcaaag gggttgaatg 134640
actcactcaa ggtcactcag agcttccata tacacaatct ggactctaat tcaagtcttt 134700
agatctaaat tccttggaat tttataggtc tagagacggg tttttgttt gtttgtttgt 134760
tttaatactc tctttctctg tctctctctc ccctactatt acttacttct atgcaaagca 134820
gttagactag tgcttgggac acattgcaca ggcatataag tattcattga ataaataaaa 134880
gtgggacttt tcatactggc ttgaaggaaa tatgcctttg gatcttcttt tggaagaagc 134940
tgtgttcatt ttccttgatg aaaaaaaaat gtaatctaat aattagtctc acttacaggt 135000
gaaaaacagg attattctac tcataatagt agaggctcac atgcccctca cttcattgct 135060
gttagtcatg ctgctgaaag ccaaacagaa gccaggtact gactggctgt gtacagggca 135120
cattctgcaa tcccatgtac tttgtgctag caccaccgca gcaggccttc aaaaattggc 135180
cctgtcactt taaatataat agacaataaa tcatccctct gagacagccc ctaaggaaaa 135240
caggggaaaa aaaatagaaa tagcatttaa aagccctttt ctattacaat gcctctaggg 135300
agcttttaaa attggaactc ttttgaagtg aattttatgc tttttggggc ttttaaaaat 135360
gcttctagaa ttaatcttgc aattctagga ccaaatcctc catgagatcc tttaatttgg 135420
gggtctttat tatgctagta ttatcatatt tgctcatctt ctctgtgctg ctttccctgg 135480
tattccataa ccaatcaacc ccttttctca tgctctttgt aatttcttta ttcctcgttc 135540
ctccctatcc atgtttctgc cagtatattt cttgcttggt ctttcttttc tttttttct 135600
ttttttcctt catcaaatct agttttagtt acttctcctc taagataccc tttgttcttt 135660
tgcaccttgg atgcagataa tcctaattag gctaccatgc agataatcca gaattttcta 135720
ctttcctcct cctatagcag aattttctta gacacagttg aaccacaact gcctctgttt 135780
cataagcctc cccttctctt gttcttgtga ctgttcctag ttgataagag aaaaacatca 135840
aaatagcaaa gaaagttaat ttagtttagt ctgaaaaaaa tcttagtcaa atcctgaaaa 135900
aaataaatgg taaggtgtga acatataaag cacagattat acaaagggtt agggtttaca 135960
ttaagaaaga gagattcaat atcagcctga ctctcatgta accagtactc agctatgatc 136020
atttaagtca tatagcatta tgtggcccaa taaaacagtt atggctcaat ggcctttatt 136080
attcttacaa attaaaaatc tatactgaac aaaacacagt tcatcttaat attgaaaaac 136140
atacacactc agtgtaaata acaggacaac agcaactgtt tcttgacact acattacatg 136200
tcttcttaga ccccctgatc tgtgaaggaa ggcaggagaa attcaacttg atattgagct 136260
ggtgtctttt gataaattgg gaggccaaag tatgaagcaa aaagcagtga gaagagatta 136320
ttctgacacc ttttagattt atagacttcc cagcctactt aatggccatt catctcatct 136380
ggcctgccat agtcactcca gccaccctct gggtgagtgc ttattaccaa caaggcagca 136440
atcaaattat tgcagggaat ttactgagtg agataaataa aagctgccta agtcagtgat 136500
tctcagtgct ttctctggaa cataagtctc ataagaagct ctaaaaatgt cccacagaca 136560
cataagtgtt gtcaacacta catacctaa cccctctgca gagtaatggg aagtatatta 136620
gcatagtaaa agcactgaca aaagaaagct gtctggcttt gtttaaccca gcatgtaccc 136680

-continued aaagcatggg acatgctgtt ttactttttt tttttttaag aaatggggat ctggctatgt 136740
tgcccaggct gcaatgcagt ggctattcac agatgcaatc atagtgtgtg cactacagcc 136800
ttgcattctt acttaagtaa aacttatgaa aattctttgg aaactttgga aaagcctaga 136860
ttaagtactt gcctaaaaga agatctggga caactatctt gaaggtaatg atgactgtta 136920
aatgaaatga ttagatgaag aaaaatagga agaaatactg aaggtttgta ttaatgatta 136980
ctatcaccaa aggagagaaa tgtaccagca gatcacagtc attaaaaatg acccatcagt 137040
ggacagcaaa ttacatactt gggaaccaat gctggagaaa aatcaaagag ggagaggtca 137100
tgttttattc cacttgtaga gcttttcaaa ttcagtccta accaaacctg attaaagtaa 137160
atcccttttt tacaggctgt ggagtctata agattatggt gttaatggaa gtgctattcg 137220
atccgtcagt aatggtgcat gtcgggaccc tggcgcctct gacaagtcca tttttaaga 137280 cgtatttatt gttttgtttt tttttctcc cttctgttct ctgcattgcg gggtttaatt 137340
gaacagttta aagtgattct tcttcaaggc ccattaattg attttatttg tgtattctcc 137400
agggtcaagg aaaaggggga aaaaaaaaac caataaaatt gcagctctgg ttttcactgt 137460
catattctcc ctggaaattc atagctctga attttgtttc ttttctctgc ctcaagaggc 137520
cattttatga tttttgcaag gtgcattttt ttttgtttta tattactgat ttattcaatt 137580
ccgataggga ttcgccatta agaaaatagt aaaatgtgcc caatctgacc aaccatgtag 137640
tatctagggg ttcctcatga taaacccaat taaagaggaa atacttcggt gaaacagtca 137700
tgaaactgta cattctcatg acaaagcatc catagcggtt tctttctatc ataatgggac 137760
aaagtctctt gaggtttgat gttgtgacat gcctacacat atataatcac agtgtgttca 137820
tatttattca tttaacccag cactgcccct gaatggtctt atgtctgtga agtaagaatg 137880
aagatgctac ctggattgca aaacagtata ttcaggggga ggaaactgta gagtgaaact 137940
gagattctgc caagggcaga agctatacat atgtgtgtac atacatattg gcatcacacc 138000
acaagaggct ctgtcctgtc atgtcatagt gccctatgat gtcacattat tatgtcacct 138060
aatataattt gtaccatttc ttaatgcttg tttctatcag gaagtagcta atcctcacac 138120
tgaacttatg aagcaggtat tactatcacc attgaatcgt caaagtctga aactcagatg 138180
tgaagtaatc ttccaaagat ataaataagg tttaaatatg catctgattt actccaatgc 138240
ctctactttt ctgttccttg gatatactgt tgccttggag acttagtttg caatggcttt 138300
tatttcacta aagatgaaaa tataataaag tcatttaaag gtggataact ttttttctac 138360
ctctgcttcc ccagagtagg ccccaaacaa atactagttg aataatggaa taagattcct 138420
gcccctttgc tatcacatca ttcctgcttt gagcttcact ctaagaccag tcctttatgg 138480
gcattgtaat aacaaggcca gggtaaaaga taagaaaggg acagggccat aaacaccaat 138540
ctggattcta tcatgtggac aagctaattc tagcctcttg gtttttttga catatccatc 138600
tcttcattca tttctttgtc ccttccttat tcaaattccc ttgatgaagt ccccaataac 138660
acataaagct taggtctttc attgaaatgc aggtcaaatt tgtcttttgc atacactagt 138720
aaaactatgc cactggcttc tggttcctga ttatcttccc ctgaatgttt taagagagat 138780
tgagagttta aagctaatac taagattgaa agaaaaagca gcaggggaag gggagggatc 138840
atatagaagg aagtattttt ttgcttgctt gatttactgt aatcaatagc tgagaggaga 138900
aagcgacaag ttcgaaattt acttccagcg gatgaacaga tcatcgtcaa ggacaagaca 138960
catatattta agaatgtgtc agtcaactga aaatctcaca aaggcaacct tctcgcggaa 139020

-continued

```
ggggtgcact ctctgcacgt tacggtcaca cagttcagag gaaattctat gctatcttgc 139080
atctgcacct ctatgtccat cttctctttc tcgacttaag aaaatcagct tcctggaccc 139140
cctttacctc cattcacctt tcacaacttt cactcgtttt gtgagacagt tcaattatca 139200
ctttcaggat tgtgtctgtt tcctgataga tttaatagta aaatccttcc aagggccaga 139260
aagaatgaat ggcgaggaga ggtgtcccag tctgaagcca ggtgtagtga ataggaatag 139320
ttagtaggag tgagtacaaa atcctcaact agtagtcgca ggtggtgacc actacaaagg 139380
aaatgaaaac acgttaactt tttggatatt actccaagaa aagagaatat gcctgcagac 139440
ctttctctaa gcaataagac acactggtgt acaaaaagac ccacactcct ccccatgctg 139500
agatacgtgt cctcctgtgg attcccagaa catgaaaatc actatatcaa aatatgtgtc 139560
acacactacc ctaagctttg gtttgcatgg atctcccctc gaaactgaat caagtcacgt 139620
tcatctctat ctctagtttc tccttcagta cctggcgtat aagagatgct caatacatat 139680
ttcctagcat aaatgaaaga atgaataaga aggaattttc ttgtaagtac taatataaaa 139740
ttgtgatgca attacaaatt ttggagatag tggggccaaa acaaagtggg gctaaataac 139800
tggtccagaa aaaaaagaca gggataaact ttgaattttg cattattaag gttaaaaaca 139860
gctcttatct ggccagaaag agaacagttt ttgtgtaaaa taattttttc aaatttcaga 139920
aaaaaatatg cttatgaaag aagctttaga atgcaacctg cactgttcat gaccaaacat 139980
gtatcagtat agagggcatg agagcagaaa taaacagaaa taaatattca cctccacagg 140040
gtagccctaa ggatcctatg cccagataac tagcttgtga gttattcact cctggaattg 140100
cctgttacca ttgttccctg cttaagacaa ccatgttgtg agtatatgtg tgtatagtga 140160
ggtacaggga aagataaaac agtgtcctca aaagcccatg gacaagatgg tcatatttta 140220
cttgggagga tgtgaatatg aactaataca ctcctcttgt taagatatta gtacagggta 140280
gcatgttaat gttcatcaga atgcttgtca ggtggttgca gtgtcaagga ttccttccaa 140340
tatgagggta tgtagaaaat gcagccctcc actttgaca ctgcttacaa actttgaatc 140400
agagaagaca gttgtaaagg gaggtggtgt tcttcttttc acaaactttt cacaaactgt 140460
ctttattttt attcttctaa ttttctcctg agatatcaac atcgaagtag catataacct 140520
tcctggaagc aatctaactc cagaaaaagc acatacaggc acagaaaaaa aataaccaaa 140580
ttcattttta cataagaata gcagttgcag gtggcattac tttggtctga ttttatgatt 140640
agtggaaact gatgccttct gtattgctac cagagtacat aacctcttag gcctaagtct 140700
ccattgacaa ataattggga taacaagcac ttttcactgc atttgtgagt aatctcagtg 140760
aacagtcttc tttctgtctt gtacttaata tccttcaatg atcaaatttg taagcaggtt 140820
gagcagctac acttattcct ccaaattaag gacttcccat cagctgctca ttaacatctg 140880
tatggatatt gcctaaattt gttttaaaac tctgtgtgag ggtacacttt gatctgctca 140940
actgacttca ttctagctat taaataattt caacacaacc ttgatctgtc taatccaaca 141000
aaaccaaagg caacttctta gtactttctg ccatgtaaaa atacatcata gtctttcaag 141060
ccaatatatt gttatgaatc atacatgcac aaactcagca aagttaaact tccttaataa 141120
tagagtgggt gctatagtac ctgtacacca ccttcaatcc actgctgtga gcgaaaatca 141180
ggcagcagca ctagtagtta actcaatatc agctgcatta ataagggtaa aatgaataag 141240
tgtgcctgga tttttctccc ttgatgactt taggtccaga tttatcttat tttagcttta 141300
gtcttgaatg attgtcaaag atgtgcaccg gcctctgaga tagccactgt caagctaaca 141360
tgtatggaac cagatcggaa gaaattgccc aacagatttg cagggcttgt caaggcctgg 141420
```

-continued

```
aaatggtgga agtcagatga ttatatttgc attgcataat tggcggagct tgtcacaaca 141480
ctgctggagc cagcagctgc tctctgctga gagctaattc cacctgatct atttaatatt 141540
ataatgaatt taatcctctc cacattcatc caggagccaa agagcacagt ttatggctaa 141600
acctgcattt gcagacagat gacaagggac ccctctggtg gtaggaatta atttggggaa 141660
gtatgctgac agaattgccc aatcatttgt ttcggttgag attttttttcc ttttccagag 141720
agcagtcttc agtatggtct gaattttccc ttctctcctt aagaagaact cttggaagtc 141780
agaaatgaac ttagatattg tttagagctg aaatgtgctc cccctcactc acccactcaa 141840
attcatatgt tgaagcctaa acccctagtt cctcagaatg tgactgtctt tagatatagg 141900
gctgtcaaag aggtgattaa attaaaatga ggctgttagg gtgggtccta attcaatctg 141960
actggtgtcc ttataataag agaatacaga gagagatatg aggatatgag taatgcatgc 142020
acagtgggag aaccatgtga ggaaccaatg gccatctgca agctggagag gcttcagagg 142080
aaaccaaacc tgccaacacc tttattttgg actttcagta tccagaactg tgagaaaaaa 142140
aaaattcaat ggcttaagcc acctagtctg agtggtattt tgttatggca gtcctaccaa 142200
attaatacag ctattatcta gtgtaactca atgtaagttt cttctctaca gaatatcata 142260
attttttttt ttccagagga acgggaagag gaacacctct cttatacaac gcaactgtta 142320
gcattaaaag aagatcattt tatcagaaac ttctgtgtac tgaggcggga tgttcctcct 142380
tatgactgcc accttactgt cccacttctg tactctggtt cggaaccaaa taagatgtct 142440
tacagggcag ccctttaatt agatgcaggc agccgttgta tgtccatgct cctttttttaa 142500
accttctctt tttagttaaa cctttcttga tgccttcaga tactccctat atgccactgt 142560
tctgagtgca ttctctcatg tttgttctgc tttgaaccct ttctactggg caattgtttc 142620
tattaaaatg agatatagct aaagtcacta actcagatgt tatccagcac tgcagtgtgc 142680
tttaggactc ttagccctct tgctttcact accatatttt agggtcctcc ccattaagaa 142740
agaataaaac aaaatgatct ttaagccctg gtatggaatg agtatgtggt aagctcttga 142800
gggtaccatg ataccttca tatgtgacac aggggaactg agacttactg atggattttc 142860
tatcagctga gtattttgga aaacattatt tttaaaagtt gttaagaaat gttcttagta 142920
ttacatttga ttttactgat atatatatat atatatataa tatatatgta tagatgtata 142980
atacacatcc agattcaagc agctttactt gtatctattc acataattat aaaaaataaa 143040
atatattagg catttttttc cctcaaatac ttagaaatcc taaaatgcaa aaaccaaaca 143100
cctgggtata ataattgtat ctccaggagg gaacaagttt ccatagcaca ctaaggatag 143160
agattactgt aaatatccat taaacttaaa tatgccactc aattgagtct gcaatttgca 143220
acttaggaga aaatggccag aaatgatgaa gccccctgggc atcagtacat gaacagttat 143280
aaaaatagaa gaaaatagtg tatatttttg gcttctattt gctgatgtat gtattgtaag 143340
gcaatagcta acttcaaagg ttttcatgct tgcccaatag ctattgaaaa caggacataa 143400
ttaaaagcct tttcccctaa acaccatgac tccttaaaat gtagaatgca agacctagcc 143460
gacatggaaa caggatacag gtatactgca gtctgtcata ttgactctct acagttttcc 143520
tattatatga acatatcaaa aatacctgga ggctgaggca ggactacaaa aatgttttgc 143580
acatgcgagg gaatttgaga gctagcctag gggcagagta aatatcagaa acattagtta 143640
tgtccgttac cggaaaagga gtgaccaatg ccttatcact ccatggcact tattttttcc 143700
ctctctactt taagaataat ctctctagag aattagctct ggtatagctg aacactttct 143760
```

-continued tagaaattaa gtaacaatat gataatatct ttcaaattcc atcctaaaga gagagatcta 143820
ttttttaat gactacagaa tgtcctcccc ttaaccctaa attactttgc atttagcatt 143880
ttagctgcca gaaggtactg tcaaaacaga cagaccgctt aatggaaaag aaaagttaat 143940
gaactaacaa gggaacaata aatattccac aaatcaagga aaagatggaa cgatttccaa 144000
gggggaagtg gatgtatcga aatatttttg ctagaaactc aaagcaatgt gttttaaaga 144060
ttgaaatttg gggtgaggga atgatgtaat ggttgattag tgcattacta ccaataatct 144120
caaaacaatt atataacatt gtttatccga gtagaggaga agcaacagga aaagaaagac 144180
aagaaggacc agttcctttt attaagtgaa tggcatttct gccatatggt attagataat 144240
gcaaagataa tgccagtgac tgggagacca tcatgtgggc tttttggaag gaagcatgta 144300
tgcctgacac ctgtcacata gctcaaatgt gatgctggca tatttgcaac taaattagaa 144360
taatttaacc ttcattaacc ccttcctgtg tttatgaaag tagagcgtaa ttgacaaaat 144420
tctgggggaa gggtggctcc ttgacttaga ttcggtggaa tttttgtgag tagacgcaaa 144480
tactgttgtg tcatacttct atgctatcag gctttctgcc caggattcca tttatttgga 144540
gactgtgaac ctgaagtcaa ggatatctca tgttccagtg ttttcagtag aaaaataagg 144600
cgaactgtca attgacagat ttttcatata tataaaaagg aacagtctag gatttacggg 144660
gcaaataaat attgtgccag aacagctggc aagcgtgagt aagagcacaa accgctggta 144720
tgttatctgc aacctcccac acacataccg tgagctgcaa ctcaataagt ggatgattac 144780
agaggttatg agaaaagtag aagtaaacac agtgaagttt aaagaacacc tggtatgaaa 144840
gataacttgg tttccaacag atacctcagt ttcatgggaa gcattttaga gtgatggtta 144900
agagggcagg ctctaaattg gtgtaatttc atatatacca attatgagct gtgggattgt 144960
accaagtcgc tacacttctt taagcctcag tttatttata taaaaggttt ataatgttgc 145020
ctgccttata gagttacaga gagagataaa taaatcactc cacctaaatc acttatcaca 145080
gttcttaaca catgatatgt gtttaataaa tgctagctat taccattaac aatgcccatg 145140
atctagcaca ttctaattta tgatgccact atttccacat ccaaaatatc acctatttca 145200
actgaaggaa gaatagcatc aggtacttaa gttggtgccc atgaggaacc attatagaat 145260
atagtatggt tcgagatgtt ttaacactct aaatgaaaat atttatttgc aaaaagataa 145320
tcatgttcat gaaatggttt aaatattgcc ttatttccag gaaaaaacaa ataagtagaa 145380
attatatata aaacatatac atgatatgac tattatgcat acaaaacacg acacgagcta 145440
atgtgttttt agtttcacta ggctttcttt atacgtggtt tcactagact catgctttgt 145500
cccaggtctg tgtgaaaatt gcatttctga cttaaacttt tggaaaagga gaaaaggtta 145560
tgttaggaaa ttgcaaatta aatcattaac ttaacaagtg ccctaaaaaa caattacata 145620
gattcatata cacattgatc aacttaataa agcatattaa gaaaaccaca tctagtgatc 145680
tagttgcatc agcagttgaa agtcccatga gttcagtgtc catgcttacc actaacgcct 145740
agcaaacagc ctggcacata gtgagatgga aaagttccct tgaccccctc ccaggacttg 145800
tgacagggat ggcttgttta catggcagct gtgctcaaag cccatgtggg agggggagca 145860
cgcaggtgag caggtgcagc aggtggggca agtgcctttg ggcaccaaca ggaagaaact 145920
ggcccgtggc agcaactagc ggttgcatgt gaccactgga gccccagagg gcatgtgtta 145980
caataagtgc tctttcagca tttgccatcc ttggaaggct aagtgttaaa cagctcagtg 146040
gacagtcagt gtgacagcct cttgcaccta cacccagatc cttgtctggt gctcaagagg 146100
aatgaggcca tacagactgg aaggatggtg aatgcaaagg ttgcactgag tggtggaagt 146160

-continued agctctcagt gggatgggaa gctggaaagg gaatagagtg gaaacatagt cttctgcgtg 146220
agtttgtctg tccctggctg aacacctctc tgaccataat ctcctatgtc cagctgcctc 146280
ttctcttgat gttcagttgc ttcttctcct ctctcctctg ctgcatcgct ctgctccttt 146340
gccagtgaag cctggggttt ttatgggcac aggataggag gcatggcaga ccaaaaggtg 146400
acattcaggt gtgaaaacag ggatgtgaac ttctcattta gggcttcagg tccaggcttg 146460
agggtggaac ccttgtcagg gaccccgccc atttctacct agtatttccc tgcctcctgt 146520
ccatatcaat agtaaatgat aaataattac tgataaatca cttatctctt tatttcctct 146580
ctgtatgtag gaaaaattta gttctcattt catcatactt aggatatgtt ctacacattt 146640
tagctctact ttaatgaaac accttatgct agaaacttta aaagaaccat ccttaatcta 146700
tttttacaga tgaagaaatt aaagctcaaa catgtaagag ttagttgaat acaaggctgc 146760
acagctagga agagctagaa ccaggtgtga atcttcatat gacaatctct attcactacc 146820
ccatgacact tttcattcat acttgagctc ctttgtgcct agatgtgtga tatgaggtaa 146880
cgtgagcatc atgatctctt ctacattttc tttatctctc tgagaattag ttatgcatca 146940
gggagcacta tttcctttat cctccctatc aaataaagat tcatgcaaga tgtagcaagg 147000
ataattctta accaaataag tctattatat tcaacaagtt gtaatgagta agtgtataat 147060
ttcatacaca tttggtttta acactcttca ctcagctgtg ttagcttcac taaaagagtt 147120
aaacattact attcactaac tctgttccaa catctgccct gaaaaccaag ggttttcagc 147180
tataaagtct ttgttttcat aatcttttat cacactaagg aataatatta ataaatcact 147240
atttctctct gttggaaaaa ggccagcatt ttttggatgt acataggtaa acatccttgg 147300
gtttaagatg taagtgagga gggctttacc taccctttta attatgagga aatgtggaat 147360
tcagtggtgc agaaagccca tctgcagtat tgcccaaagg ggattctttt aagtgacttt 147420
tttagacctg gatcagacag tagtatctcc attcattttt agtcacagag aggctaaatt 147480
gaagtccatt tttctgaaac tagtcacata gtcaaaattc tcacattaag agtaataaaa 147540
tcctgtgaag ccataacttt tctgaaagag tttttctcac cataaatatt taaaaagtag 147600
caaccagttt caatataaaa attagcgtat taatgatttc ccataagata aactagatat 147660
ccgaatgatt ggcttagttt aatgaatcag cacatatatt taagaaagga acttaccatt 147720
agtgaaaagt tgaaacaaaa agcataatat aaattcaaaa atagtaactg tacttattat 147780
atctttcatt tattggtagc tcactgtatg ctaaatccta tgctgagcta tttatgttta 147840
ttaactcatt tacctatact ttgaatctcc aaggcaaatg ctattcatat atagtatgaa 147900
attatgctat tgcagattaa gacagattag ggttagcaaa gtgaagcaac ttcactaagg 147960
ttgcagagtt agttggtgac acccatagta gtctgactcc agggttaaaa tacttaacct 148020
tcatgtatat taaacggcat aggccagtgg ttcagtttcc aaactcctgt cctagaacaa 148080
gtgctaattc ctaaactttt cagcagtctt ttgataaata ttctagttgc attttgtttt 148140
taaatatgtt tatttgggaa aattaaaata gtgtcaaaca aatataattg ttccatatta 148200
aaaataaaca ttttggaagt aaaagaagaa aaagattttc aagttatttc tgtgtactag 148260
ataaatctga gctgctattt acatgaggaa tcctttttt gggtgcttaa gggtgacagt 148320
gttgaagacc agaagaaggt aaccatttaa ataaataacc aaggatgtag gaaatattga 148380
ggtgaaaaga acaagtaaaa gctgttataa tcccaaatgg cttggacatt ttatagacaa 148440
agaaaactct gggggaggta atgctatttt atttgggaag atgatgggtt gcctgttaac 148500

-continued

```
ttacttctga acatgttgag tttgtggtga gggatttaag taggaaaata tctagcaagc 148560
aatataagga aaactgcagg tttcctgatc agacaaaaac taaattcttc aaggtaagca 148620
atgtgccagt gtgtcagtga gtctggtcag tctccaaggc atgttgaaag gagggggaag 148680
tggtcaatct ctcagccttg acactgcccc tgttggtcat cttttccttg aacacttgtc 148740
ataaatgaat attgtcacta ttgcactggc ttgagggtag aacccttgcc aggggcatcc 148800
ccactttaac actttaccat gaacctgaat gcacatgcct tcctttaatt ttccattcgg 148860
agttgacgcc aggctgtttc cgaaaggcta aagactcaga gcaacaaaag ggaaattagc 148920
acaaagtata taatgtgtaa ttagatcaat gactttaacc tcttttgggt agcactgaga 148980
atctgatgaa tctccccata tatacataca attttgcaca gcctctgaga gcctactcaa 149040
attccagacc cagggggaaa aaaaagagag acttaagcga tgcagcaagc aacttctctg 149100
gcttaaggtt tgttttcatc tgcagatgat tgacctggga aatatacatt ccctgcagtg 149160
atatttaacc tgcctctctt ctctgactaa ggggtcaagt cttagtttat gactcccaag 149220
ggtcaactac ataaaataaa catgagttta acccgggtac gagagataca catgtgtagc 149280
acgagatata attttattac agaaataacc ttcacaaaat agggcttagt gaacccccca 149340
gtcccaaaaa ccacattact taggacacat ccaatttaaa caccaatcca catatctatt 149400
tccagaccct tgactagtgc tgtagttctc tactgaaaat tttattgagg gagtatcaaa 149460
gaagggatta aacttcgaaa tacatacagc agagatttcc tgaaattatt ccattcccac 149520
atctctctcc tcaaagctcc acacatcaca gcatttgctc aaatctgttc aaactttagt 149580
ccctgcccat ttgtctttct cattctttaa tgtcttcttt ctttactcgt atttcctctt 149640
ccagtaccac tctttttctt ccctcagcag gtctccctaa gttcttttct gtgtagaact 149700
attttttccc tcagaaagac aactagctag cagagctaca cacaaaacta tttggaggag 149760
cagacagagg gctctttctt tattccagct gaattataca aaaacagaaa gtgtacatgt 149820
ttagttttca gtcatattct aaatgcctcc cacagtgcct gacaatactt tccaagtaaa 149880
tatttgttga ataaatgaat aaagaaatac tgattgaact tcagttagag tttaggatta 149940
aaaacattga cttggctggg cgcagtggct tacacctgta atcccagcac tttgggggct 150000
gaggtggaca gatcacaaag tcaggagatc gagaccaccc tggccaacat gatgaaaccc 150060
cgtctctact aaaaagacaa aaattagctg ggcgtggtgt tgcgtgcctg taatcccagc 150120
tacgtgggag gctgaggcag gagaatcact ggaaccaggg agtctgaggt tgcagtgagc 150180
caagatcatg cccttgcact ccagcctgtt gacagagcga gactccgtct caaaacaaaa 150240
caaacaaaac aacaacaaca acaaaaaacc acagtgactt gaagggagaa gaccacagaa 150300
tgtcagaatt ataaggacca catgcaatat aacaagtgaa gccttctctg atattgctaa 150360
aagttataac taacaaaaga gatcaggtat cccagaaata gatcttggag acaggaagtt 150420
aaaatgtacc gaagaagtag caattagaaa gataatttaa aagagagaga gaaagagaga 150480
cagactataa gaaaaaaaaa taatgtaaca tcatgagtct aggagaaaag ataattatca 150540
aataaatatt caaagtcgac aacatatcac tgaagagttc ccatatacta taattcttca 150600
gctcaccatt taatgaaatc aaaaaggaag aattttttat tggccttctt aaacaaacag 150660
tttctttatc cagtatgctt tgcaaagagg taaattagta cctgaaactt ctagttgatc 150720
aaagaaaaac aatgaaaaat aatctggcct tgcttatagc cctgaggaca aaatagaata 150780
ctcaattttt atttcagagg catgtataat tctaggccat ttttggaagt aatttatttc 150840
taggttagtc tggaagagtt aattttcaag aaagaaacaa actagaaata ttctaatttt 150900
```

-continued

```
gaattaattt ttaaatagag agtataggaa ataaatctta taaagataca atattcagtt 150960
tgttatgggc aaatctcatt actactaata attaacctat attatgaact aatcatctgt 151020
taaatttcaa ttaaacttcc aatttaaaat gtataaggaa atttcaacca aacaatgaac 151080
tttttttcat tatcccatat ctttaaatga ttatctattt accattttaa aaacctcccc 151140
ttatttctga agtactgctc aagtgaaaaa atacattagc tatttattac acttcacttt 151200
acaaaatgac gtggctgata tttcatctaa tgtcatgtgg aaagacaaag atacctatga 151260
gcatggaagg agacgtgaaa gatgaagtgt gtgtttgtgt atgtgaaagg agtggggaag 151320
tggttagtgg gaagcaggaa agaattcaag aagctctttt ctaccagatg ccaatagact 151380
aagaagtaga aatacatcct tttatttccc cttttcttct tttatcttga accaccttca 151440
gccacacctt taaaattagt agtcccctat ggtcattatc aatcacatta atttcttcag 151500
tggcatctaa ctagggtatt ctcaaacaaa tgttcacaat agtggttctc aggtgaccag 151560
atagctaaga accaagatct ttatctcagt tttctcttag tgatgagaaa gggtgaaatg 151620
gtttgattac tggttgaaca aactctaaaa tgtaaacgta ggggttcttc attcacttca 151680
gggaagattt agaaaaattt tcctaatctt gattattaca caatttttag accgcttgca 151740
aagcaggaca tgttagtttc acttctacct gaagtgaatg aaatctggtt agtatgtgat 151800
tgaccaatcc aaggggtttc ctcatcaggc tgcacaggga gtcagcttta ttttgtctta 151860
ttgccaaaag gtatatatat atatatatat atatatatat atacgtatat atatatatat 151920
atatatatat atatatacac gtatatatat atgtatatat atatacgtat atatatatat 151980
atacgtatat atatatatgt atatatatgt gtgtgtatat atatatatac acacacacat 152040
atatatacgt atatatatat atatatatac gtatatatat atactcttag cttgcattcc 152100
tgtaactttt caaggagact gcataagagt gtgtagatag ggcattgcaa tatagtatta 152160
cttgatagca gaaaaacaac tcaaacaata tgtgggttat caataacagg tcgctggaat 152220
cattttcttg taaaaataat gtactaaata gctataggct ttatgaggcc tagaagtctt 152280
gggcaaatgt ctttaaaact gctgtgtttt ttttttggga atatttaaac tttatatagt 152340
tagtagagaa ataagatcat ttttgttttc ttacagaaga aaaaatacca gaatcattaa 152400
aaataaaaat aagacaagag gcatcttgtc tcgctctgtc atctagactg gagggcaatg 152460
gcacaatctc agctcactgc aacctccgcc tcctgggtac aggcagttct cctgcctcag 152520
cctcccaagt agctgggatt acatgtgctc accaccacac caggctaatt tttgtatttt 152580
tagtagagac ggggttttgc cacattggcc aggctggtct cgaactcctg acctcaggtg 152640
atatgcccac ctcggccttc caaagtgctg ggattacaag tgtgagccat cacgcttggc 152700
ttaaaagtat tttaatataa gtacttttac taggaaaacc aattaccaga ggaattggtt 152760
tactcataaa gtatttgtca tctgccaaat gcctggtaag gttgagatct tgttccttct 152820
aactctacaa gcatttttttg aggcaatact aataccttac attttaaaag tcactgtttt 152880
ccaaaattgc ctaattgtga gtacctgatt cctcaggtct taaccagaga ttgggtttag 152940
attaatctcc agttgaacaa aaacatttgt cttttacaaa actgtctaaa attttatctt 153000
accatccagc aagttggaaa gcattttaag ggagataagt ggataaatct tcccaaagta 153060
ttttagattt ttgttgtgga tagcatggat tgatattcta cattcattca atgttctttc 153120
tagcacacac cttcatataa tgccaaagtt acaacactaa aaactatatt tgcaagacct 153180
ccttgttgct agattttcag acgtaattta gagtttgcta gtcagagcac tttggttaga 153240
```

-continued tttggaaagt ggaaatgagg agagatgtgg aggcatttgg ttgtttgaca gcactgtcag 153300
cagagggtcc agtgtccaat cactagcttc acgggtattg agaagcaggg tgaggaatca 153360
ttcctctgaa gcttcttcta tttgggacca tcttgttcag atgtaacacg gttttgaacc 153420
agtcagcagc aatggaaatt ttctgaatat tagagcttct agagccggtg gcctactcat 153480
catagaagag ggactgcctc ccttggtgtg atagtttaat ggtatgtcca aaacacatac 153540
tattaaactg aaaattcagt ctaaaatcta tttttttcaac ctacccatgt gattcataag 153600
cctgtatttt tctttgatag agcctttctc gcttaaatga tctagagtag atttcattct 153660
ctgcaacaaa aattggacaa atataataaa ggctaattaa aactattaat ctattctatt 153720
taacccttcc tctactgttt ccagcatctt gccctttggt gcagtggtgt cccttttttat 153780 tcaaaagtta gttgacctaa ttagagattc agtttggaat ggtcttctgg gactgaggga 153840
agaaatgtcc tgccactggt aatctgatta tttaatcaat gtagaaagtt ttcaaggtat 153900
gtagacttca gttttgtccc tcaattttaa tttttattta tttgttgaag agaggtcaaa 153960
gcacacgaaa gttaaaaaga gatgaaaggt gtagaagagt atttgatgag ctaagaaatc 154020
gttcttgata tattttttcc tttcaacagc aggcagcaaa aatatatgca gaaaggattc 154080
aatttttcta agacaacata tatatgtgtg cgtgtgtgtc tatgtgtgtg tgtgtgtgtg 154140
tgtgtatata tatatatata tatttgttta tttaaaaaga ctggaagatg cagccaaata 154200
ttattaacag tagttatcat taggtggtag gattgtaggt ggttttaatt ggagcatttt 154260
gccctagtaa taattctttt ttcttcttct ggagaatgct actagtgaaa ggtgatccaa 154320
tgctgtaggt tgtctttagt atagtataga tgtgtttaat ttattctata tgcaatataa 154380
aatgattcaa tgggagcatc ctgagctact gtcaccagta caatgtttaa tggtgttaac 154440
taggaagaga caaggcactg aaaaaaaaat gggggatttg ttttcagttc agacctaagc 154500
aggaagagtc tttccaccta aaggcttgaa aaattgtttt tcctaatatc agaacctgaa 154560
tacagaatgc tcttatcact gaaaacaaaa ataaaagcct cagcctccac agattagagg 154620
actgagctga agctttatat agcttttcta aatgaatgag cgtatatagt tcagtactaa 154680
agaatacatt ttgaaaaagt gaacaataaa aggtttaaac tttgttatgg agccttgaga 154740
gaaaacacag catcacagta cagaaatgga aggcctggaa tcttcacttt gaatgctaac 154800
acaaagatga gtctccagat gaagcatgag aaaactctca tgtctcaaag agtggccaat 154860
tattaatttg tttttgagag agagaaaatg agacagtgtc aggcttttct ttctctgatg 154920
tggtatatac aattctgagt aaaatgggtt tcaaattctt ctaacagtca ttcttcgcaa 154980
attatttaga catttccagg tagtcccaag atgagaatct gtcttagcat tttccatata 155040
aaaataacta gcataactta atccttttct attagagtca aaattctggt attcaaacta 155100
agaaaaatca ggcaaggaac atcctctcca aatgctgtta taagaagggt tattttcgtc 155160
tgggtgtgct atgtattaca aacgcattaa ttcaagaaca ttatgtctct tggtaatctg 155220
tgatcaattc aagtgtattt tgaggcattt ggccaagata aaacgaaggg gaaaacaaca 155280
ataggaatta atacacaatg gaattaaaat attgatccca aaattataag tttcacactc 155340
tgtttaacta agctagtcag atgtgatttt ctcacataaa gtggaggttg ccatatattt 155400
ttaaattgaa taatatagac tgaaaaggtc tgagaagtac aacaatattt catctcacct 155460
ttttggggat ctaacttttt ataagaaaag tgatgaagct tggtaagaaa tgcagaagct 155520
ttcaaaactt ttagggccta caactatatt gtatatgtgt tgcatgagga agaccttaaa 155580
acttggaagt ttggaatttc ctgagacttt agaggtttct cttcctagaa ttgcttttgc 155640

-continued ttagagatcc ctttggaccc cttagtattg aagagcccag atagatccca gaaagaaaac 155700
tagacgttgg ctgtccagaa aggaaattcc ttccttttcc atacaggtat atattaaagt 155760
ctgtgagagt taaaaacgaa gcagggattc aaagcagtct cttgcttaga aataaagaga 155820
gtgcatataa ctgaagtttt cttcaaatga tatttgacaa acaggcatag aaggttgaaa 155880
agtgaagctg cccaaatccc agttacaggc ctatgtgaag tgtcactatg caccattaaa 155940
caccaggtgg ctttctcctt ctggtgcctt atggtggttt caggatgtgg gcagtgcttc 156000
ctgatgtgat cctatgcacc ttctctgctt tctatgctct gggtaacatc tatctctcac 156060
gccccaactg gggttggatc aagccactgc caaaaacact gggcatggtg ccaatctgta 156120
agtttggttt taaaatgtaa atgacttaaa ttttcagaga aatattttat caccttacat 156180
taactgaaac tactgaaatt acaaataatg taaaatataa cactagaaga tggagacatc 156240
tacattcaga atgcttaaaa caataactac acaatgctag ataacttcta gaatagaaat 156300
gacaataata gcaaccacat tgaaaatagc aacaataact atattaatcc cctttagggt 156360
ctattctgct gcctactgtg gtagtatact gttctttttc tgaactacct cagaacattt 156420
aacccatttc acccactata taaaagcatt tactattttc aaattatcca ttcacgttgt 156480
tccttcaaaa ttcaatataa ttttccttga ttcctttgat attttctttg tatgctaatt 156540
caaaacactc taattttttt attaccaaca gaaattctga gaaacaaaaa gttcttcctc 156600
tagcactagt ggcctcacgg ccatgtcaac attgttttga tccccatagg aattttccag 156660
attacgcaac tcatagagca ctgatggagt gcaacatgtt aagttgtaaa atttggatat 156720
ctcattacct cccccccatc ttatttattt tatgattacg tctagcttcc cattattttt 156780
cctctattga ctatgttctg tagctttcat atttgtccgt tagtaacttt ctaatatatt 156840
cctctcatag ttagcttcta catccctacc ttgcagtaaa gcttctccag gttttttctt 156900
gacaattctt gcatctttcc ttgtattgtc atatctcttc ttctcctttg ctctcactca 156960
ctccttccag catattcatg ctttgctgct tcaatgtccc ccttctgttc atctccattt 157020
cctgcctgga ctcagcttca ctcacccccct gtgccagtga gctctctacg accttccaaa 157080
taaaactctt ctgaaaatga cttctgtttt agtcttgagt tatctgggga ctgcagagct 157140
aggtgggacc agttccagcc ttggaggtgg taagcccatc aagtattcca acaaggagca 157200
atgacaactg agactggttt tggtaggaac aggtaatgca aaggcagtaa gaatgcaata 157260
tgaacactac tgctcagatc acaagaagag aggcattaaa aggggataaa tagacaagac 157320
acgatgcagg gtgagcacga gagaggctgt catgcctgtg ttacctggtg gttcagatca 157380
ggaagaaaga caatgtgcat gccacaagtg tctgggagca ctaccaaata tagattcagg 157440
ctgtgaaaaa tgagtagagg ggaagaacaa ctgagcttaa ctggattctt tctcggggaa 157500
gaacacgtga gtaactgcag cttacctgaa gtagtgatca cttgccaacc actgtggtta 157560
gcactttatg tacgtcatct catttaatcc tcaaagcatc cccatgaggc agacactatt 157620
ttgtaactgc attgtacagc taaaacccaa aggtctaaag aggttgaata actacattaa 157680
caacttgtga gtggtagaga taaaacctga acgcaggctc tctgactcca gagggcatac 157740
tgctagccac tactatacta tacctggtgg tagtgagcac gataggtcag tttgagacaa 157800
aataaaagca gatgaggga gagcagtaca atctgaggac actgtcgcag ggtggttgg 157860 tcccgttttt ctctggcttt ctgataattg ttgagcattt gcttcagaaa atggccaacc 157920
ttcactgact aacagaaaag cacagtgaga aaaagaatat tcttctaata agttatagag 157980

-continued gagccagact gataatgtaa taaaattttt attgtccctt ttctcacata cctctgggat 158040
ccaaaaaatt gattgattgt gattttatta ctttcttaaa tgagatattg tatttttgta 158100
gcctttaatt acttcattaa gatgacttta aaaccatgct tgtatgattt tcaattacac 158160
tttctaatca caaaaaaaaa aaaaataaaa gaactggaac tggttcagat ttaaaagaaa 158220
agtcagaaca gcctacccag tgtggccttt cagctgccta tgtgcttggc attatcttca 158280
tggactataa ctgaatttgt caccgcgttt ccaaaactat cttaagtgtg aactatctcc 158340
tcgcctttct tctcctttca tttgcaaaga agataatgtg gtgcattagc ataggataaa 158400
aaaaaaactt gtccttatac caaaatggca agtagaacaa gtgtccagag gaagaatgat 158460
gtcaacatct ttggtttttt tcaagtgctg taagtctgat tttttttttt tttcttaatc 158520
ttttgaattt gctctgtcgc ttcgttggca aattcttgtt aacaaaactg cccaagtggg 158580
gaatagaatt aacaagaagg ggaattgatg ggtcttcttt aattatcatc agaaaaagaa 158640
gtatacacat aaagagtgca gaatctggag tgattctttt ctaaatcatt gtaaccataa 158700
tcagataatg tcttaacttt ctgacagaat aacatgcatt tagtcattca acatatatta 158760
actgtgcgac tcataagcac aaggtactac tataataata tgaagatgaa tatgttctag 158820
ttttcatgct aaaggagact ggagcctggt aggagagaga aagccaagat ggcacactta 158880
ctgggaatat aagtgaaatg tcaaccaggg tgagtggagg aggattacaa gaaactgcta 158940
ggagttcata agatggtatg acaatgcaat aatactttgg ctggagtggt atagtgtagt 159000
aatgcttcat ggaagaactc atttttgagc atggctttga agagtgggtt gaatttagac 159060
atgtgattat gtctaggtgt tgggaatagt gtaaaggaag acactgaggc aaggccttta 159120
acactgttga ggagcaacag ccatttagtt ttgcctgata ttccagtgtg taaggaggaa 159180
tgaaggcaga taagactgtt gaggtctgat ggggtgagtt catagcattt cttggaccta 159240
gaactaaaga aagatgatcc atcctctaac tcaggcaacc ccagtgctaa gacagttcac 159300
attacaatgc aagcgaaaac ttcccaatgc ttggattcct ctactctctg gctaggaaga 159360
cttcattaat ttaaacactt attcctaaaa ttttattttt caagagcatt ttctattgat 159420
gaaataatga ttatagaaat tatctttcag gttggtttgt acatacttcc acccaggccc 159480
tttgactgtt taatttcacc atcagcttca gtgtctttta ccctattagt agtgggatga 159540
ataagtccaa gattctaaga tacacaggaa gagttggcta ccaaatagga agtctgataa 159600
ctttatgaag cttatttcag aacatccaaa tggcaacctc tggtcactta gaaggcaaga 159660
aaaacctagc ttaaaatcaa aatatatggt tgatgactaa ggtttaatac tcataatcat 159720
aaggagtttg aaccagatgg gaccttaaag atagtcaagt cctgtggttc cagatcttta 159780
tagactccta ttttttcaaa agacctacta aggtagtgaa gaggatcata atctgtttct 159840
aatatttcaa agccctagta gaaattaagc ctctcatgga tcatgaaaat agcaaccata 159900
ttatcaaata aataactttt ttgttatctt ttctgctgtt tttgctcttt taatatatat 159960
tcaataaaaa cattcttaat gaataaaaat gaaaaaaata aattattgat tgattttcat 160020
aagccaaata tttctaaata aaatatatgg gaataagtaa taaaaagaac tccttgtgtt 160080
gaacatacca cagctacatt taattcaatt ttcaaattat atagatggag gaactgagat 160140
ctaaagaaac agagactatc catgtaacca aatgccgctt gttcctcaaa aactattgaa 160200
atagaaataa atttactgaa atttgtttta tggaccagaa tataatcaat cttgataaat 160260
gatccacgtg cacttggaaa taatatgtgt tctgttgttg ggtggagtgt tttataaatg 160320
tcaactaaat caagttgatg gttcaagtaa aaaataaata aataaataat aaataaataa 160380

-continued atacagacac ttgccaaaga tcatataatt aattagtgat tcgggtagga tgagaaccta 160440
gatcttataa atgccaaatc aacattcttt ctacaatagc atgctactag gtgaactgcc 160500
tcagaagatc ccagagtgga aggtaggaga gatttggtcc agggaccata gattgtaaga 160560
tataagatca tgtcagctat ttatttttgt gttgtagaga attttactca tcaaaaatgt 160620
aaaacaataa aataacatat ttggtttact gtttctctaa aacagtctcc aaagtagctg 160680
acatgtctga agagtctggt ttattgactt gtaataaatt agctaatata ctatttactg 160740
tttcaacata cccctaaaac acacatgaga aggactttta ctcattttat aaatattaga 160800
gccgaggtct ggaaaacagt gtttttccaa aaactgtcag cagtgaggct gggattaggc 160860
catagggctc ttgaacttta ttctcaatat atattccagt ttcttggaaa ccaatttcat 160920
cagtttgact gcaagccgtt cctggaaacg gcaacaagca gttgaaggaa gtcaggagat 160980
ataagggaag tacaaagcta tataaggatt tttaacatat tatacttttg ttttgaggtc 161040
ttccctccat caacttgaat aattgagacc tgtcagtgat atactctcta attcccagat 161100
gcattgtgat caatttatta gcagtcaaat gtgttggaaa ccataaggtg ccatatcagt 161160
gctgataaat attaagagag aaggataatg catatcccag acagtatagg ctccactgga 161220
actgacatca gaggcctgtg ccctttactc tgattgttat tctgatctga atgtcattaa 161280
ggagagtcta gttcaggtca atagatggcc aagagttcta actcctgtca attccaatga 161340
tggttttaga taggaaaaat actacttacc tctactgtaa taaaaataca gattttccct 161400
tcatattttc tagccatgtc aatcaatgtc tttctttaac ctttctgcat catcttatat 161460
acatccattt gtgcaacagg aggcatgcct gttacgggag actctaatat tgcgagttgg 161520
ggtgttaaag tctcccacta tttttgtgtg ggggtttata tcccttagaa ggtctccaag 161580
aacttgcttt atgcatctgg gtgctcctgt gttgggtgca tatatattta ggataattag 161640
ctttacttgt tgaattgaac ccttttccat tatgtaaagt ctttctttgt cttttttgat 161700
ctttattggt ttagcgactg ttttgtttga aactaggatt ggaacaccta cttttttctg 161760
ttttccattt gcttggtaga tttttctcca tccctttatt ttaagcctat atgtggactg 161820
acattctttg cagaactaga aaaatctatt taaaaattca tatggaacca aaaaagagcc 161880
agaataacca agacatatac aaaaattaac tcaagatgga ttaaagactt aaatgtaaaa 161940
cccaaaacta taaaaaccct ggaagacaac ttaggcaata ccattcagga cataggcaca 162000
ggcaaagatt tcatgacaaa gacaccaaaa ataattgcaa caaaaggaaa aattgacaaa 162060
tgggatctaa ttaaactaaa gagcttctgc acagaaaaag aaactatcaa cagagtaaac 162120
agacaaccta tagaatggga gaaatttttt gcaaactatg catctgacaa aggtctaaca 162180
cctagcatct ataaggaact taaacaaatt tacaagaaaa aaacaaaaaa gcctcagtaa 162240
aaagagggca aaggacatga acagacactt ttcaaaagaa gacatacctg cagccaacaa 162300
tcttgtgaaa aaaagcttaa catcactgat cattagagaa atgcaaatca aaacctcaat 162360
gagacaccgt ctcacactag tcagaatacc tatttttaaa aagtcaaaaa ataacagatg 162420
ctggcgaagt tgtggagaaa aaggaacact tacactgttg gtaggagtgt aaattaattc 162480
aaccattgtg gaagactggc aattgctcaa agacataaag acaaaactac catttgaccc 162540
agcaatccca ttattgggta tacacccaag ggaatataaa ctgttctatt agaaagacac 162600
atacacacat acattcattg gagcacaatt cacaatagca aagacatgga accaacacaa 162660
atgcccatca gtgatagact ggataaagaa aatgtggtgc atatacacca tggaattctt 162720

-continued ttaaatatta attagcaagt gacatgtatt tgggtcaatc aatgcttttc caaatgtgca 162780
tcaaatgcta taaaggcata ttttttgtct taatcacagt atcagaataa ataggtattc 162840
atcaacgtga gaatgtggta tctgttacta tggtgaacgc tcaggagtta ggaattttta 162900
agtgtggata actatgcaaa ttgcccatgc tgtactgata agacatattc attaaaataa 162960
catatgttta ataataacac ttatctatta ataagcaata gctatgtaag tgagaacaag 163020
gtgttatgca acatgaactt ccaggcaaaa gctgccatcc ttgctactaa gtgtatctca 163080
tagacatata gactgaagga catactgaat gtaatttttc atttaagaac tcaccaaact 163140
gctcccaaac atgttagggg gatagctatc agagtaaggg tattctatac tgcaactcta 163200
ctttcatatc tactcccctt taacaactgc tctttccaag gaaagttaag ctttattagt 163260
ctaatatgat ttttcttttt ctttcctttt tttttttttt ttttttaga tggaatcatg 163320
ctctgtcacc aggctggagt gcagtggcat gatctcggct cactgcaaca tctgcctccc 163380
acgttcaagt gattctccta cctcagcctc ctgagtagct gggactacag gtgtgcgcca 163440
ccatgcccag ataatttttt gcattttagt agagacgggg gtttcactat gttggcaagg 163500
acagtcttga tttcctcacc tcgtgatccc cccacctggg cctcccaaag tgctgggatt 163560
acaggtgtga gccaccacgc ccggccatga tttttcttta acatgacttt tcttctaagc 163620
aaaagcatca atagacccaa agtagatcca ttagtatact tgcactggca acaaagttct 163680
acttttaata tttagtattt atctcttaga ttgtaaaacc caactaaaac caaggataca 163740
aagtggcttc tttactgcta tctgtacaag tttaagtaaa ctgaaaataa atttaagtaa 163800
attgggtagt gtttccatga acaaaagtca agaaaatgta taaatgagaa tgggctttct 163860
tgaaaccaat aaaaatgtgt agcatgatga ataacatgag gtgatatgtc tactaatcct 163920
ttatcaaagt agagataaaa gtttgggcct tggagtcaga taacctgtgt tcaatcatat 163980
tttcactact tctaagctat gtgaccttga acaaattata tcacttctct aaccttcagt 164040
ttccatacct atgaagtggg aacaatggta agatctagct catagaattg ttgagaaaat 164100
tatatgtagc gatagtcata atgtactcag catagtgctt gacattgagt aagcactcct 164160
taaatattac attataagca atgtttatta gtttacatag aggtaatata gtctaaaaaa 164220
atcagtatat tcaatgttta attcccaact gtaagtgaga acaggcagta gttaggtttc 164280
tgttcctgtg ttagtttgct taggataatg gcctccagct gcatccatat tgcggcaaat 164340
gaaaccaatc tgttcttctt taatggttgc atagtattcc aaggtgtata ggtaatacca 164400
catagacact agggactgat tgaaggagga gggtggtggg agaggactgt gggttggaag 164460
gctacctatc aggtactacc ttcactacct gagtcatggg atcattcata caccaagcct 164520
cagtgatgta caattgactc atgttacaaa cctgcacatg tatccccaga acctaaaatc 164580
aaagcagaag aagaaaaaag taagaagtaa aaaaaaagaa gaaatgttta aaatactttt 164640
taagtttcta ggaatgttaa aatcatttag ataagatttt aattaccagc tcagacttaa 164700
aaacacacac acacaccaca cacgcgcaca cacaaaatta accataacat ccatacatga 164760
gaacatcaga ttatataaac tgtggtgcag ctattattgc aacctttagg taattttcct 164820
tgaaaacaca ttgttctctg tgtccagata gtgaggtggc ttctcttgca tatataaaca 164880
gtaaggccaa agtatccagg agattctggg catggttcag tatccaagaa ttttgccttc 164940
caacagatga tactaatgtg gttcccaaac tgaagagttg acactaaata tctggaacac 165000
atcccataaa aacataagaa ctcatgccca gaaaatcatt gcatgtaccc ataaatatgt 165060
tgcctttggc tataataact gccacttgga aacatattaa aacttttcat gggtagttat 165120

-continued ctaaaatgtc caaatatcat tatgctttgg ggagtttaac ttgaccaagg agaaacaata 165180
ctactaaaag gaatgttttg tgatgcctaa acaaatccaa gtaactggaa ggtaggggcc 165240
aaaaaaaagt agccttctgg attagtttct gcatatatgg tggtagctta aatcaaagag 165300
tagtaatttg ttgtagagag gcaattggca gaaagcactg gcagaatcat tcacaaaaaa 165360
caagcctttc ttccctctaa aataggaaag catgagcttc tcaacttgat gtttttgtga 165420
cagaactcag ggattatgct gtcttatgtt tgtgggggta ggaggggagg tgggtgggag 165480
gaatttctga aaagcatatc tgtgttcctt tgcagtaata gctcatgctc ttgaacaaaa 165540
tcaaatatct cccatcctgc tataaagtaa atactgacgt aagacaaaaa ggcagtatct 165600
ggagactcta aatgcctcat actttgatta aaaatgcttt tgtcaattac agattgattt 165660
tgtagctcat tacaatgatg gatgtcaggg ctggcggagg tggtatttta ccacttggcc 165720
tgagggcaca cacagttaga agaagatggt aaaattataa ttattttcca gcactcatcc 165780
atgtgcctac attgacccaa tgggtaccac tgggataatt tgaaagaata gcatcagatg 165840
gaatggccaa aaagaatagt acctcagccc ctctctagaa ggaaaacatg ttagacaaat 165900
atttctcaac aacctgctga gattcttgtc acctgataag tcacattaag ctacatcagc 165960
caggttttaa agtaagctag agtgcttagc agaggctgca gcaaagaata tgcaaatgtc 166020
tctgtgtgta ctactatgaa tattaaaagt ccctatattt atatatcata atgtaggcac 166080
attcttccac atacataaat acaaatgtac tttctccccc actttaacat tggaggttgt 166140
tagaagctgt ggggaaatca gaggatatag gtaaaagagc tgcaggggaa agaaattaat 166200
attccgtagc ggctgaaaaa aaaaaaagaa ggaaattcat gtcactttgc catacattca 166260
tatcatgctc tgaagtgacc tgtatttctg gagacactgt gtggtttcta aactctgata 166320
cccatggtta gttcacaaga cattctctaa tggtatccta tgaatgacta cattctctgt 166380
gatagctgca cggccaaaga agtaatatcc tccagacaca taacatgcaa atcttctatg 166440
tggtatacct agcacctgct gcaaaatgat ggtgactcag cattcaatta aaaatgtaag 166500
aaaatcgatg ccaagtatta tggaaaaaga tattacatga gactgatatc agcagtctta 166560
ggattaagaa aagaataaaa tcatttcaaa ttgaagatta ggaggcctgc ctacactatg 166620
actatagcaa tattggccat atatctacac aattgctttt tataatagtc caccatgaac 166680
acaaacctat ttatggccta ctttcatggt gatatatctt cgttctgcta gttgtttaga 166740
atcccaatac tgtgaaatgg aactgtggtg acaaaaaaag taatacttca tataatgaaa 166800
tgtcaagaaa tttaagttaa agtaaggtaa tgatacatag gttcagggca taaaacctga 166860
tctatgctta taatcaaagt gaaaatggac agtggaacat cattagaaca tctggatcat 166920
tttggaaact tattatgttt ggcatcaagg accaggatga aatctcattt ttcttacctt 166980
ttgtattata gtggtggtaa agaaagagaa ggaaaatgtg ttcataaagt ctggaaaaat 167040
ataagcgggg tacatatgct ttaaaaaaac agacaataga caatcaaaaa ccaactctgg 167100
gatatctaaa gcattaaaaa cttttagata tttaaaatta gctagaattc tagttgttaa 167160
aataatatgc ttgtagatgg cttatttctg tgccaaagtg tcaatactgg agtagaagtg 167220
tgctatacaa atagtcttca ccatgaacaa tcccatgaca agtcttgctg atagggtaaa 167280
atttgaaagg agaaacaaca ggcatggtgg ctcacacctg taatcccagc attttgggag 167340
gccgaagcgg gcagatcact tgaggtcagg agtttgagac cagcctggcc aacatggtga 167400
aaccccattt ctactaaaaa tacaaaaatt atctgggcat ggtggcagat gcctgtaatc 167460

-continued tcagctattc cggaggctga gacaagagaa tcgcttgaac ctgggaggtg gaggttgcag 167520
tgagctggga ttgcaccatt gcactccagc ctgggtgaca gagcaagact ctgtcagaaa 167580
aaaaaaaaaa agaaaaagaa aaagaaaaaa taaagaaaga taaagaaaaa gtgcttaggg 167640
aagcaacaat gacttctatt ttaatggtcc caggtctttg gctccaagtg ttgcatagtg 167700
tctattccac aggtaaagat gactttaagt actatctaaa ggcaaaaagt tactatcatt 167760
ttatcatttg ggtaaaaaaa taatactcat cctagtatta taaatttgga agggaaagac 167820
tctcagtttc tcaaatcgta agttgctaaa gccaatgatc ttatctactc ttcctgcaga 167880
gagggaaaga aacatgtaga aagtagtgat actgcgcaat atttgctctt ccatatactc 167940
tggagttggc agaccatttg atggtttcat tgccttctct ctcctctgct aatattgctg 168000
ttacaattcc actaaatttt tatactcttc actcccagtt ttcactttct agacaactga 168060
atgcagatgc tattaagtgc atcaatagga gttctaagag gaatacagga gaagtttcac 168120
tgctgatcta gacctcagac ttggttacag gtaaggttaa aggaccctat actctgcctt 168180
ttgtagcacg aaaactgtca gaccatacca aatagaaaaa tgggaaataa tttttttctt 168240
ctgtcatgat tacaacatca atagataatc taagacattt tgaattcatg gtcttagtat 168300
ccaacaacct ttctgctgct tggtcctgta agagcactta ccatgccata tttaatttct 168360
gtgtactggt ctctctctac ttcactacct gtgagctctg tggcaaatat tctatctttg 168420
tctctgtatg taagacctaa tatattattg gttcacggga agtgctcaat aaatgttaaa 168480
tgcataaact tatactcatt tgaatggcaa tttctaaggt tttttaaacc acctaagtac 168540
ccacataacc aattagacaa gggacttaaa tctcatattt agagtatttt tttaaatttc 168600
agattttcaa gacatcttaa aatatctcct gaaatacaaa atagaaacag aatttaaagt 168660
atatagaaat ggtattaatg tcattgatga tgatgatgat gatatcatga aaatagcagc 168720
tgaaatgata taaactgtta catggtagca cagatacaat ttgacagaaa ccaagtttat 168780
aatgaaaaat gacaattctt aaactcctgc atttccttta ctatacatga atttgagata 168840
attgttccag taccagattt atgcccccact aaactgagac tgtcacaaaa cctcctcagc 168900
aatagcccct ctaggtgcag taaaggttga ataagtaatg aaaagactca gactacagtt 168960
gaatacacct gtgaaattac tatataccag aagctccaac aaaccatttt cctccctcta 169020
tgtgtaccct aaagcctgat tcagaagaca agttgacaac tcttacaagt taatggcaaa 169080
tatctgccca ataaaatgac tgcttgttgg tatcactgaa gtatttgttg gggtagtttc 169140
aaactttaag accatctgac ctcatctgac agaagagctt gattatatga gcctgatgca 169200
gtgtatactg tactcaattt actatactaa tgagttggtg atacaaaata taagtccata 169260
aggaatttca ttaaatgatg taaaaaaaaa ataagaaaat cagttaaatc aaatgtgtaa 169320
acctataatt aatgtactac aatttgtaat ttagctttga aatatgcaca tcacttgaaa 169380
actatcaatt cagaaggaaa atggaaaata aggttaacct taactgaata tgttacaacc 169440
cagtgagtac actatatgtt tatgtagaca gcagaatgtg gcacttccaa gtggggtctg 169500
aaatcagatt gcttcctttc acaccttaca agatacaaga tgttgtgcca attaacattt 169560
tctacctgtg ttaccatctg taaaatacag acaatatccc ctttctcaca gaattagttg 169620
gcacctcaag aaatgtcagc cttgcccatg acgggccaag ggcaacatag tagcaggact 169680
ctcccgcagg ggctgagaat aagggggtta tttgcaaaga atttgaaaac aattgtaaaa 169740
tcaacaaaaa gttggtcaac tttttattat aaacatgtat tagttaattc aaaacagagc 169800
cagtgataaa ttactcttgt tctcagaggc agaaacttcc agccccccaac tcttagtata 169860

-continued taccactgaa gtctcatggt aaaactgagc taagaataat catgcattaa ataaaggaca 169920
tttatatcca ttttaattta tcagatcaac atagtttgaa ataaaagcat agacatgtgt 169980
agaagatgaa atagtctctt taggttcact attgatctcg tttaggaaag caccatcact 170040
tccatattaa ttatttcttg gccattatta aactgctatg cacccgtctt tgactctgtt 170100
ttctgtctgc caactctcat tgcaaaaatt ttctgtctag tttattgaga tgtaaagagg 170160
acagataatg ttacatttat aaattatttt caactgctaa gataaaatgt actgtataga 170220
gtacatttca agctacaaat aacaaatgca aaatagtgat tacattttct ccatgaaaat 170280
tttgacagaa ataagggcac tgtcatctat tctgtataat tctctcctct cccatctttg 170340
ccctgttaat tagtctcaag atcacttact tttacttgtt attttttaag ttgatgagat 170400
cattaaattt attagctacc caaatacatt tgaagtttat taagattctg tggtgccttt 170460
gaactggaaa tagagaagga atagaactca cttttaaaga aattaaagta ataaagcaaa 170520
atgggtacca cttcatttta agtacccatt aaccagacca taagagagaa agtcaaaatg 170580
gaaatctcag agaaataaac aggtgaaaca tatgccattc ttcccacgca agcattagtc 170640
cagcagtcag cccatccaga atacatgccg aaagcatttc acaggggaat acttaaaaag 170700
tgtattttac atttttagag atagagtttc attgaaatct caatttgtgt gcaggactca 170760
ttaagagatt gagataatgc tttcatttgt tgatgataaa cgttaattta ttttctctat 170820
taagccactg caagtctttg ggttcaggat gacataaaat actttatatg aaatgatctg 170880
gttcatgaca tttttattcc ctgtacattt ggcagacaca aattttctta aactgcaaat 170940
actattcttg gtgtcatgaa gaactgtcgt tgcttctaaa tcttcaaaat ttgtttcatt 171000
taaatgtatt ggccaattgc tgcagttaat gatgatgaat aggattaaga ttaaattttt 171060
aataaactgg attgactgta gccataggca gaaactagct atctaaatga tgtcatctct 171120
gttgctagaa gtttcctgca ttataaatat tttcctatta ggttttaagg tacctaaaac 171180
ttcgtttaaa attatttgtt taaaccattg gtatcataaa accacattaa gatactcatc 171240
agggagatgt tttgagatag cactttaaca ggtattatgt ttctcaaaat ttttacagtt 171300
tttaatttta ttttttaaat tcacatatgt ttcttatgaa attctcacac cacccagtgg 171360
ttttgtataa gccaagagat gttggaaaca cggagtacta cctgagcctt aagtgagagt 171420
ctcagagttg caacctagaa ccaaggataa aggttgtgta attacagaaa aatcagacct 171480
tgaggaggct ggacctactt ctaattccct tctgaggttg gcctagataa taaactatca 171540
aggaagaaat aaaataattt aataaataat tgccttttcc ttttttgact ttttcatttt 171600
tgctttattt gagatattga tagcatagtt gacctaaatg ggatgaaaat tcacttgcat 171660
aaaataaaaa atacttaaat tctgtcagaa atttggatag cacctaaggg acctgactga 171720
ggtcacaaga tcagaagtct ttatatttct gctaaaatta cattttaaat gtttaaatta 171780
tataaatgcc aaatcattta ataactgaaa gtttaagaca atagattgac ctaaaccttt 171840
gcaatttatg aaactgtatt attagttcat gtgtcttatg gacatttatt tgtttctact 171900
aggataatag ctaaatttta ataacaaaca taatagcaaa aaaatcagta tcaatataac 171960
tgaaggaaat ggaaactttc ttttcaacaa gacatcttca tgtatttata agatttcagg 172020
cctggatctg gaactatgat tctgatatag gccccagtgc ttctaaatga ctgccattta 172080
actaaaacat cataactgta tagttattca taattttatt tgttagtaat attaattttt 172140
tgagattatt acttcatgca aaaccagcca gccaatcaac acaatggata caccagagac 172200

-continued acaagtattc taattcttga agtgatctta attgtgggtt tttgcatata gagattatag 172260
atagatttag ggatcataga ctatttgcag gtttcttact taatcctcct tgagcattgg 172320
tggaaacctg tggaggcttg aatgaaggcc ttgtagcgag ggtatgcagc aaatcttgtt 172380
gggaagcagc ctctctgagc taaatgacaa gttagcatcc cctaagttag cacatctgag 172440
tgaagaaatc tgtggaaaat ttgttttcca aagatatttg atattctgcg acctatttaa 172500
aatttaaagt aactttgggg gccagtcatt aggagaaagt gtcaaatatt ctctctttga 172560
gtacacttat ttaacaaatt tagctaggca tttcttcagt ggtactctca gagacaggac 172620
actggtacgg agatatgtat gagaatttgg tagtgtagct gttttctccg tagtccttgc 172680
tctagttcta cataaagact ttggtcttca aactgcccaa cccagcctta tcccctaagt 172740
aaagagaact caataaatgt ggtcatgtaa aggaataatt tatgatgctt gggattaaaa 172800
acaaatacca aaccaaggct ggaattaggt caaaaccaag tttaatatat aacaggttat 172860
aggcatatga aatatgattg taaatgataa gcttatgtat atataactat gttaattata 172920
tttatgcaag gtattttttc ttttcaaacc aatgaactgt cttgattctt caaaagtaat 172980
gagaaaatag taattaaatc tgataattac atttttctta gtgaatatat tttaatagaa 173040
aagatgcaca tttgagggga tatgacctta ttttagatga gagaggtcaa aataatcaag 173100
gtttgatggc aagagacaat tggaatatat ttctattttt gcttcacaac atctattaga 173160
tgtataaact attttatcta acaagtctcc agacacatga aaaaggcaca tttaaaaact 173220
atattttatt tcttattttt ctgattccca gcagcatctg aagaaatttc tagggacctg 173280
actgaggcta caggatcaga aatctttata tttctactaa aattacattt taaatgtttt 173340
tattaaagca taatatacac aaaagtgcaa agatcataat tgtagcacct gatgaattcc 173400
cacaaatttg acatagctat ttgaattagc accagatatg gaaacagcac attacctcac 173460
tcagaagctc cctcatgttt ttttacagtc attatccttc tcttctgact tctagcagca 173520
tatattaatt ttgtctttta agccagaagt ggaagctggc ttattttgct caacattatg 173580
ttacacaatt aattcatatt attgcatgta gtcacagatt gttctcattg ttgcatagta 173640
caccattatg taaatataac ccaattttta aaaaatttct cgttaaaatt tcatatctgg 173700
aaaaaacagt cctaaaatat atctttatct atctatctat ctatctatct atctatctat 173760
ctatctagga tgctgtataa ctgaacagaa cacagataca taaatgtttc aaaagttaat 173820
aatcttattt ttaaatgcca gagggttagg gagaagccac aaaagaaata tcttccaatt 173880
aataccacat gttttaaaaa agagaaaaat tcaatatcaa catcaattaa gaagtcttaa 173940
tatctgtata tactctgaaa tcagttttaa atgtgaatga gccatatcaa gttctctttg 174000
gtaaacaaat gagcaatgac atggatatta gtgacattga taagtattaa ttgataatta 174060
agttgatgat aatggggaaa atgttaagaa tcatgaattt gacctcagga ggggaagctc 174120
atcaaaatca gatcgtatct aaatgagaca tgtccttaaa atgaaaggca gctctggtct 174180
ataagaactc atagtaattc aactagtgac tactaaagta ttttcaaatt acagatctta 174240
cttgaatttg gtttgttgta tagggaagcc tcatttataa ataggagttg aatttccatt 174300
ttatgaatac gttaaaatcc ttataaacca ttttttaaat aatttacaga agcttcccta 174360
ataatcttgt ttaaagtatt aattttctaa actaattttt ttttaatgtt ctggtcacaa 174420
acttgagttc tgaattaatg aaatgtgaga aatacctttg ccagacttca tatattttct 174480
ctaatgttta tatttggaaa attttatgaa agaaaacatt ttttgaccac gcagaggcac 174540
catatatgaa gcattttggt tcaacggaga gttctgtggc tatttctgca gaatctctat 174600

-continued

```
ccatctccca ctctttatct tgccacatct tgtacatatc ctgttacctt aattgtcctt 174660
gatatttcct gcatttattc tgtagcatat ctccataaaa ttgtccttcc tctattatat 174720
tttcacagag aaaatgaaaa atgagtctct gcccataatc atccacctca caactattag 174780
aacagaatca agagtctaaa gcatttccaa gagctgagtg tctttattat cacaaacaca 174840
caactggaac tataaattca gcaaatgcag agtttatatt gattcgatat tgcactgagg 174900
tttcatggca atagcattgt ctctcaaaag acagcaacaa atgtccaatt gcatgtaagc 174960
taatgaagaa ctcagtcaaa tggggcaact ttgtcatgtt agtaaggctt ctgtatccag 175020
gtaagcataa cagtgcaggg aaaagaaaag tagtttcatg cccagggtca ctagacttta 175080
tcaactggac agccaacact tggaggattt ttcaggagaa gtagatcttt tccatgaatg 175140
aaacaaacat tcaatccaat tactagaaat gtaccataca taaaatattg tgggcattcc 175200
aaaaaaacac aaaaaacaaa aaaagttaac ctcgttaact tattgtaagt tgcttacaat 175260
atggtaaggc ttatattttg atgtaaacta taaatcacca caaaagtttg atagagaagt 175320
acataacagt aagaaaaaca atttctaatt ctcaaagcat agtgtctttg aacttgaatc 175380
ttgagataca atcatgtctg atgggactaa tttctgcatt ttaattatgg catttactgg 175440
aagtgctcct tgagaagaga ggacaaggaa gctcaagtgt cttttgtaga agtgtgtcca 175500
gaacaaaaat tatattggca gcaacaatca cttaatgaag gaagagaaaa atgaaaaaaa 175560
gatttcaact tgaaagctat tttataatca caggaggctt tagataatgg cctggcaata 175620
aaatggtccg ggagtagccg ccaaggggag ttattgttgt tctttgttta gttttctttg 175680
tctgaagctc agtttatgta aaaagaaggc tttgctttgc gggtagggaa aaaagatacc 175740
ataatctcac ctctgcccgg gtttaaaata tttctaggag aggaacaatg actctagaat 175800
gcctttgcct cagcttgaag ctgccactaa tggcatagca aacacaaact acaaaaaacg 175860
tctgtgttgc cggacctggg actttggtaa cctcctgctt ccaattagaa gaacaagcgg 175920
agccacagta cagccaggca agcttaagtc aggtatttgg aaggagggag agtgacagag 175980
gaaagtcaaa gcagtagctg tatggtcctg aagaagtggt ctggtagctg gaggaaccct 176040
ggagatttag ccaaggggtc atcatgagcc gccttccctg ctgtagttca tgctcaaatg 176100
ccagaatgaa ctaaatttct cacctgggaa aactgcattt tctacctgaa ttcctgatcc 176160
catcccccac ttcctctgtc ctcgtctatc aataacttgc tctttcctgc atcttcattc 176220
tgtccggttt ccctagctac tttcttttgc cttcattttc tcaaaagata aaatataaat 176280
aattatttta acccccacct gactgaatga tcccactagc aggagtctaa ggcactggac 176340
aagggctgaa gtctttggtg cctggactag ttacaggtac tgaggtgtgg aattaagtga 176400
agcatggtgg atggacctaa tacaggatga ttattcctaa ttcgaaaatt ccaaatttga 176460
aatgctctaa aatcagaaac tttttgagaa ctgacatgtt caaaggaaat gctcactgga 176520
gtattttaga ttttggattc cttgattagg gaatgtttat gtgtagtgca gatattacac 176580
aatttgaaaa aatctaaaat ctgaaatatt tctgcttcca agcattttga ataaggaata 176640
ctcaacttgt aaacaggtag cacaaaatgg aacaaggtaa tttgagggat gaactgaacc 176700
acatgcagtc ccaccatggc ataaaaacac aaaaagagaa caggataaaa caaagataaa 176760
atcctctgga gcatggggta ggaggcaaag cttagagagt tctgatctcc tggcatttat 176820
tcatagtcac aatttttacg aagattggtg atccagctca ttcagggaac gtttgaactg 176880
tcatcacatt tgtgccattg cctttcacca ccaaactaga taaacatttt accaatggtt 176940
```

-continued

```
cttttttcca tttctggtca catcgcctgt aaacattcaa aaatggtgtc ttttcacttc 177000
tcctttgaga ttgcattctt caatgtcatc cgtaactcca tagtagccaa attcagtgat 177060
ccttttttaa cgttcatgct ccttaatttt ctgcaacatt caattgtaat tatattgcct 177120
cttttctcaa atctcaccca taccactttg gcttccatct ttctttctgt tctctaattg 177180
ataaccttca ccaaatgaca gaaagcagaa aagagagcac acatttatga acttgcatta 177240
tgacctaaaa tgattaattc atattcttat aagtttcatt gaatcactct ggctgctctg 177300
ttgagaataa ctataggaag ccaagaacct cgttaggaag acctcacatt actacagact 177360
agtgttcata gtagctctga taaaggttat agcaataaaa gtagagagag atggtcaaat 177420
tctggacata tactgaatgg agagccacaa gatgtggtgg gctccctcac atgtagggtg 177480
tgaggggaag agaggagcca ggccattctg agatgttagg gccagacaac tggaaggaga 177540
gacttgccac caactatgat gggaacacat aaggaacgag aaagtttagg gggaagatcg 177600
ggagttcagg ttttgatatt ttaagtttga agtatttagg aagataaccc aacagagtta 177660
ttaaggaggc agtgaaatat atgaatctgg atatcagaga gaagtctcgg ctggaaattg 177720
aaatttggga ttcattggca ttttagatgg acacatgagc cagacagcaa atgtcagcat 177780
agcaagatct tggaagaatt atttcagatt cagagtcaat gaatatttat taagcaccta 177840
ccatatgcca agctctgtgc taggcacctt caaatacatt tttttcaccc ctacacaaac 177900
ccatgatgaa gttttatata agaaaagaca taatgaagaa attaagcttt gaaaaagtct 177960
ataaattttt ctaaagtagc aaaattagca tgttatgaag caaagattca aactactgct 178020
tgcttcatta cctcattttt atcactctat gggtatgtac atttgctaat cctcataggg 178080
ctcataaatc ctggatatct gaccctcaga tacttgtgtc ataaaatggg aactaaattt 178140
atccttagtg acctcaggac ctcatagatg agttgaaaca cgaggtactc aaggtggcct 178200
gcctggcatt ttgctttcag tgggcctgag cacccagtgg catggatgtg ggtctgcatc 178260
ccatgtgatg tgaatgtcct gcctgttctc aagtgctgtg aagtgcactg taaaacacta 178320
atctctctca gctgcaccca ctcaggctta ttcagaactg cacaaggctc attgccttgg 178380
aatctttgta gagaggaaaa ctcaaggcag ctagctggac cttagtatcg gggcaaatgg 178440
aggttctgac aggtaaactg gaaacagtgc cttccaaagg gaaatctgcc attttgcttt 178500
cttttggtgc cttcattttc tgcttcactg ggaatttgtg attgtagata tagaatatga 178560
attttaaaac tctcccattt gggcttccat tttaatgtct ctgagttggc aatacacgga 178620
ccttttcttc tgaacttctg gacatctgct tcttcaagtc taaggtagcc ttcagactac 178680
ctcctatttc tcactctcct actccacatt cctaattccc tataatatct aaccgctggg 178740
cctagcataa tttcctaatt gtttctgta ttcacatctt tactagctcc taagttcttc 178800
aatgacaaca ctatcttaac tccttaactt cactgtgtcc ccagtaccta gcccaatacg 178860
aagcatttag tgtctcaatc atatctactg acttatttca acaacttttg caggtattga 178920
cataaccatg cactctggct cataaggtca acaatgtcct agtttctggg aacagactga 178980
ctagaaggct ccctctgcag ctatgagcaa aagcagcagc ctttctagct tactgcctaa 179040
atttaaaccc caagagctta ggtttcctac cgggattctt gctgcggtgc ttccctgacc 179100
acgatgctca gactcacctg cttcacacca tgacctctgt tgtttgcctg gtactgggag 179160
tagctgccta ctctgtatgc caccttttcc tggtgccgta tgtagattaa aaaaatgtgc 179220
ataacaaact cttctttaca gaagaggaaa ccgaggctca gaaaggttat gccattttct 179280
aagatcccac agagaacaag tggtacattg aaaaatagaa gccaagtttg gattctcctg 179340
```

-continued agccattcct ctcccctgaa tttgcactgc tttggttacc taatctgacc cagcaaaata 179400
caaaacaaac tccacttccc ttgcattcta gttttgtgat atgctctcct taactggctt 179460
caacgatcac actttttctg agtgtttata tttttgttta ctgttttaca tcatattccc 179520
tcctcttcct ctacctgctc ttgtggtgta tacaccagcg ttctggaagt ctttatctct 179580
ttttacctta cgagaagatc atctttagta atgccatttg ttaccagagt tgcaactctc 179640
acctacatac tgatgctgat gattttaaaa tttgtctctt tagtcctgac ttctctcatg 179700
aattctctac cttcttactg gacctcttac ttgggtgttt cacaaacatc tcaaactgca 179760
aatatccata gctaaaataa gtgtcttttc tctcttatta ttccatcctc cagtgtttta 179820
aatttctgtc aaaaagtcgt catcctacca gtcattctag ccaggaaatc tcgagaagtc 179880
gctccttgcc tgtctctctt ttactcacaa agccagtcac caggttctct ccaaactgct 179940
tctaaaatgg ctcttgcctt tcattctcca gtcttcatcc ccgctgccat tcctgtcttt 180000
agcttagatc cacaccatca ctacaaatta gtttctctgg tttcaatctc ttccctcatc 180060
tggtgcattc tccatatgcc atcagagtta tgtttctaaa aacaatctaa tatgacatct 180120
cacgtcttaa aaaattcatt gggtaccagc taacaggaca cagcaaggat gctcagaata 180180
tggccactta gtacttttcc actattctat gaatcctcta ccatacagtg cagacacagc 180240
actttttcat ttttttcttt ttcttttttta taatttttcc attccatgaa cgctctctac 180300
agtttttcttt tgagactttt gtgacttctg atctgcagtc tttctgcctg gaccgcactc 180360
ctctaactct tcactcttga aaaaatctta catctttcaa agcccagatc cagttcattt 180420
ctgtgaagct ttccctgacc catccaagga gaattaatta ctctatattt tttgcttcta 180480
tattttttc atccaaccat tatagcatgc atcacattct tccagagtta atttctgaga 180540
ggtctgattc actagctaga ttgctagctt cttgaaggca acagctgcag ctcattcatc 180600
tccaaagcct atacattaag cacagtactg ggcatataat aggccctcag aaaatgtttg 180660
ctgaattaaa cttaatttaa atgatacata atgggaaaaa taatatttca tatataggat 180720
tggcaaactc actttagaga caactgttta gagacatatc tattccgaaa atgagatgct 180780
tcaacaatca cagtgcaaaa ggaaataatt aggtctgcca tacacacaaa cttaacttct 180840
gtactttcaa aatgacttca aagagagata tttttcacgg aactattgat attgagcaag 180900
atgttgcttt cctttcagta agcatgacag aaaaaaaaat taagtctcta gagtgtttgt 180960
aatttgttct tgtggaggga ggtagctagt aattcctgca gcaactgttg ggtgggctac 181020
agatatcttg acataatcta gagcctataa gacatgtctg tcgccaggga tgtcattctg 181080
atccgaagct ctggagtgct gcttagaaat gtgtaaggga gactgactta gaggtttgca 181140
gggaatatct cgctaagtga ctaatgatct ataaagtcct gatacttgcc atatctgcct 181200
tttcctggga ccatggatta ttgtatctgc tagttttcag cctcaataaa agaactctgg 181260
ccaagcaggt gagaagcttt aaagtataac tttattttaa acaatgcctt ttaacaataa 181320
ctaccaaagc attaacaata atatatgtat aaaatgttat gtaaatgtta tacaaattat 181380
atatatatct aaatctatct acacatatat attatttata attctgcctt aaatttaatc 181440
tctattatag ctgcaaagtt tatatattca ttcttatatt atctcaaatg ctagcacgtc 181500
cttcattttt tgcttcgtat ctgtattttg gtttgaggct agcaatagta accagatccc 181560
ctaatcccaa atgagggggc tctctgcaaa gacttagtcc tgcccaattt cattaccatc 181620
tcagatataa tcacttacat tgcactaatc tttcctaaat cttgagcaga gggagaaaga 181680

-continued aacaaagcac tctttttcaa ggtcatgggt agagaaagca gaaaatcaag acacagaacc 181740
cagatctgtt cttgattggg ttctcaatct agtgctttca aatacactgt gaacaaccaa 181800
acaggagtaa aaagacatat atcaaagcca acaaaagatg aaacctcaaa gggtgtgtga 181860
gtgaagggaa tcagatgaga gttgaaaata cagagttgat gagaaaagca ataaaaacaa 181920
gccactcagg tggcattagc tgcaaagaac aatcttgctg gtcaatccac cagtggtatt 181980
tgaatgctgg tgaaaggtga ttaaaggaag ggagtttcag gtgtgcagag aacacaaatg 182040
gaagatatac tagattttaa atcttaaagt gattttgaaa tctgttttat tattattatg 182100
tttctgaagc acagagggaa tctgattgag cgaacatctt agcttgtagc ctagccaggg 182160
gttcacaagg ccctgagaaa accttctgcc tgactctcac caggcctttg aggatcccac 182220
acgctcagtg gctgacagga gaggcagctg aaatatgacg agtggtgcca aggctgtcag 182280
cactggccca tttagggaga cttgtgttca ttcactgtct cagcttaagg ggcctttgtg 182340
ggaaatggca attcacagtg tgaatttcaa tagaatcttt aagtctctca gagatttttc 182400
tctttgccaa gaaaatttcc cactgccaaa cacttgtaga ttgacagctc tgcaggtatc 182460
tctctaatat agctgttcct ttcttacttt ttactgtacc tagggccttg tttcctaaag 182520
gtttttgtgt gtgtgtatat atatttttaa tattattttg atggatcttt ctttttctaa 182580
ctggcatgag ccttaagtta aaatgaattg gatgctggca tcatatagaa atattgtttt 182640
tacaggtttc tcaaagtaag atgtattaaa gaagacatat caagtttcca gggcttgtgt 182700
tgccatagca accagtatag gcctagtttg gagaatggga actgggggct aacaagagac 182760
tactagacat gttttcctcg accataaaag ctctgaatga attagattcc cactgtcttt 182820
gtggttttaa gatgtagaac aagcagaaaa taggtaggtg ggcaaattta ggttataggt 182880
ataggtacag gcagagagta agttataaat gagcgcaaaa ctgccccgac gtgcttcatg 182940
gaatcatcaa atatcagagt ttggaacaca tgaggaagtt gaggctcaga gaggttaagt 183000
gacctagcca gcaagcaagg gcaggtctga tacaggaaat aaactatctt gcctctccac 183060
taaataatgc aattgtgtcc caaatgcata gggaggactg tctcctttca gcagccagaa 183120
gttctttgaa gagatattga cccaatggaa tgacaacccc catctagcat gaaaaagaca 183180
acaataacac acaaacataa tcttatttcg gcacagtaaa aaccctctaa cgtaggaagc 183240
agaaactgga ggtggaatta cttgctggac tttcctttca cctttgtgga gatgcccagt 183300
gcagtaggaa aggaacgagg ctcactttca tcctcttcga tgtagttcac tatgggcctg 183360
gagctggtga aagtgtgttt tcactaaatt aggtctgtat gataacagtg aggaaattta 183420
tttccacact accaccaagc tagaagcttg ccctaaccaa atccacaaca ggaatgttct 183480
gattctcttt aactccatca tttgcttatg acctttcatg gagttctatg cttagaactg 183540
catgtctagc ccaatactct ccaattggaa tataatgcaa gcaatgaatg agacggacat 183600
atgtaatttt taagacccta gtaaacacat ttttaaaaag taaaaataag caggtaagtt 183660
aattttcata agcctatttt acttagtgta tataaaatat tatttcaata tataattaat 183720
acaaaaacat taatgagata ttttacattt tcataccagt tgcagaaatg gtacgcattt 183780
tacagttaca gtacatctca gctggactaa tcacatttca agagcccatt agtcacatgt 183840
agcaagtgac tgtcatattg ggcagtgggc atctagagtg tggggacata atgtctgtgg 183900
gacttgagag gaagaggaag aaaagatgaa atgttctatt tttttttttc ttttgaaaca 183960
gggtctcact ctgtcgccca ggctggagtg cagtggtgcc atcttggctc actgcaacct 184020
ccgcctccca ggctcaagcg attctcctat ctcagcctcc caagtagctg ggattactgg 184080

-continued

```
cgcacaccac taccacccag ctaatttttt tgttattttt tttttaata gagacggggt 184140
ttcatcatgt tggccaagct ggtcttgaac tcctgacctc aactgatcca cccgccttgg 184200
cctcccaaag tgctgggact acaggcgtga gccaccatgc ccagccaaga cgaactgttg 184260
ttacacccta aaatttcccc accctactat aagattatct ctgccaactt tttacataaa 184320
taatcttcaa atcacagaga ataatttatc atctcattag tagttcttcc ttaccaaatt 184380
ttattgcttc taaactaagt gtatgaaata caaacccaaa attttaagtt taaaatacaa 184440
atgcgtatag atatatagat taatgtgtgt atgtatgcct atatatatat atatatatat 184500
atataaagct tagtttcata aaattttgat tatttacttt ttgcttttgc ttgcctaatc 184560
agataattac cttggttttt attctaaatc ttctgtagaa caaggtggac tgtaaataaa 184620
taataacttt atttatatat ctcattttcc ccctgtagtc atagcattca tgtaaaaact 184680
cttatctacc caataaaata tttcatcaga atgtgaatgc cttgttttat cagagggaat 184740
ttcttttagc caaaacacct tgtgaccttc tgttattgaa ccatatatta atcatatgaa 184800
aagttataaa gagaaaattt gaatcagtgg ataatgaatg tctttctttt tttttatttt 184860
ttatttttat tttttctttt ttttatcata ctttaagttt tagggtacac actagactca 184920
ggctcgcagt ctctctcact acccgaggca tgagtgtgag ggaggctgtt tgtattctat 184980
gctaatgctt ttttttcaat gctcaattcc cctccccccg cctttttttg ttttaactgt 185040
ctcacatttc aacatttcca tataaccagc taatctgata aacccatact tgacatacgg 185100
aaaaagtcaa gaaaagccta tttgtgggct atctttgtct ttctaggttc taagtgtcaa 185160
acgatattta agagtgtttg tttgtttgtt gtggagccat tttcgttgct tttgtgatat 185220
aatagaaaaa tgggaagtga gctaagcacc gtggctcacg cctgtaatcc cagcactttg 185280
tgagacctga gtggatagat catttgagcc caggagttca ataccaacct gggcaacatg 185340
gtgagaccct gtctctacaa aacatacaaa aattagctgg gcatggtggt gcgcacgtgt 185400
agttccagca ccgtgggagg ctgaggtgtg agaatcacct aagcctggga agtcagggga 185460
agtcagtgca gtaagccttg cgccactgca ctctggcctg ggaaacagag caagaggctg 185520
tctcaaaaaa aaggaaaaga aaaagaaaaa agggaagtgc ctctttctgg cttctggcct 185580
agaggctgtg cttccatgac tgtgagaatg gccaccctgc aggctgcaac cctttgtaag 185640
aaataaagct ctcctttcca aatttataaa cctcatcact cttcagttga tgtgattaaa 185700
aaaaaagtta tgctaaatga aaactttaca ttaagaacag agaaaagttg cattaagata 185760
ggcaataaat ggaaggattt aggacagtct tgtttgaaca cagggtgtgt gtatctgtgt 185820
gtctctgcat gcatgtgtgt atgtgtgttt gtgtatgttt atgtctagtt tgtgtatgtg 185880
tgtttgtgta tatgtcttgt gtatattatg tctgcatgca tgtgtgtatg tgtgtttgta 185940
tatgtttgtg tatgattatt tggttgtttc accaaatctc taccagaatg tcaaatgtga 186000
cttattttta cgtagaatat atataaactc tgaatcatta tatttagctt agttgctaag 186060
gcaagtgtaa tttatttcct gcttttatct tttacttata aatataaaat taaataaagg 186120
agaatgtttt gtaataatcc acaaataact ctcaatattt tataaaatag ttacaaatac 186180
catggaagtt gtttattgga atgtggcttt acagtccctc atagaagtaa ttttataaga 186240
gcatgattga taataatggt tactattcac taaatttcaa catatgtatg gcatatcatc 186300
tctttttgtc ataacagtac tgcagggaaa ttattattat ctccatttta tgaatgagaa 186360
aacttaacat tacatgactt tctttttttt ttttttcctt tgagacagaa tctcactcta 186420
```

-continued ttgcccaggc tggagtgcaa tggcgcaatc tcggctcacc gcaacctccg cctcccaggc 186480
tcaagcaatt ctcttgcctt tgcctcccaa gtagctggga ttacaggtac ctgccaccat 186540
gccaggttaa tttttgctaa aaatacgtga ctttcttaac gttgtataac caaacattga 186600
cagagtcagc atttaaaagg aagtctctca ggtttaacag gtgtttatac acacatgcat 186660
gcagacataa catacataag acaaaacaca ggtgtgtgtt ttgtccacca aaccagaggc 186720
ttccttgggg ttgcagttgt acccatacaa tctgatttat ctccctaata tcgtattact 186780
aagttataat atttataaaa taataagccc taaagccaag tgtatcgtat ttattcgata 186840
tcaaactcat tctcagttct agctacagtg acaggaacac atctaccctt gatgcaattc 186900
tggctacact taagtaacag agaagaaagg ggaaaaagga agggaagaaa ggggatagct 186960
gtggcaggga agaaagcaaa tgtgaaattc cagtagaatc aaaaatggta agagcatctt 187020
cagctatagt gaggaggaac caggccacca gggctgcagc tttatacact aaggggccgt 187080
tcttactaaa gagatctttg taagaaaatt ggcaattaat gagtcagaaa ccgcttatga 187140
tttcctactg tagaaatgca ccaaatgact tgccacaaac ttgaactcac aatacttgtt 187200
cattcagatc acttctctga ttcaataaaa attgtaattc aactttacaa agcattagct 187260
attcagccca ttttgctgcc agcatagaac ctttttcctt aggtctcagg aaggccagga 187320
accatctagg tcaatagtta tcaacctggt aagcatttcc aagttatata gccttccctt 187380
cttagtgata cttcacttgg ggaagaatac aagaatggat cacagagatt ccaggtggga 187440
gaaacaggca ttctacctaa tgttatagga tcctcagatg actaatatgc aagatctctt 187500
atgccattct caccagtttc cctgcttgtt gaaaacacta agctagtcat cccctgctgt 187560
ggccaaagac ctgaacctag actgtctaac atctaaccca gtaaacctct ctgtgctttc 187620
atttcctggc ttgtaaaata tgggtaatag aatatattca taacattata gagaggtaac 187680
taattaacat aaacaaagta cagatggcct gacttatgat ggtttgactt aggatttttc 187740
aacttggtta tagtgcaaaa gtgatatgca ttcagtaaaa ctgtactttg aattttgacc 187800
ttttcctaaa ctaccagtat gcagtacaat actgtcttgc catgctgtgc agcagcagtg 187860
agccacagct cccagctatg tgatctgagt atatttaagg taggcgaggc tcagatatga 187920
tgttcagtat gttaggtcta ttacatgcac ttgcaactta caacatgttg aacttacatc 187980
aggatgtaac accattgtaa gttgagaagc atctgtactt cgaacggcat ctgacacata 188040
gaaagtttgt tgttgttgtt gtcattatta ttttatagtg agaaactgag ggctggatag 188100
accaaatgac ttatcttact taactaaggg ttcagaatag aatgcagatt acctaagttg 188160
aaatctagtg ctttttcatg acaccagttg actctcaaac tgaagttaat acatgtgttt 188220
ctcattttct tagcctgttt gtatctaccc gaagttatgc atttaaaagg atcttcacca 188280
acattactgg gaggcagtaa ttatttaact aatttaagaa atttaaacca ttttagtttg 188340
tacctcataa tattttagga ttttttccct caacagaaca atcgagaaca ttaaaagaga 188400
gcaagctcca cgtcactcaa ctgatgctac cacccaggac agaaatcagc agtttctgtt 188460
tttctactga ccagctttgc attaaacact gcaaatggga gagctagtcc actgaactca 188520
tgcaagcatt catttattta tccacaaaaa gcaaaatatg gcaaggggaa tttgggagga 188580
gtgaaataag ggttgtcaga ctaacagtga caaatgggat gcaattgttc tccaaaagct 188640
tggagcagag aagtcttccc ttttcccctc cccttaatcc ccactgattc caccctgcct 188700
gcacacagag aaggtggtta acagaggaaa gccccgtgaa taagctatga cagccctaca 188760
ttcagaaact gatgtcattt ccctaaatac tgtttgtaaa atggtaatta tctgccaagc 188820

-continued aatgacagct ggcacttagc atagacacac agagagacag aaaaagagag aatgagaaaa 188880
aagggtccct gcataattta ccaaagggct gaaagagaga gggaaacata atcagaaaaa 188940
taaaatgatt accagtgtgt gatggggtga aaattgcttt gggcattttt tttttccttt 189000
agagagcaca ggattgaatt ggaagaatga agctggagct ccacgatgca cactggaaga 189060
gaggaggttg tgttaaggtg gcggtaaaag gagaaataca ccaatggtgc tgggctgtgg 189120
caaagcagca ggaaaactct gtgcacacct agcccctcaa acaggaacca ctcagcccag 189180
caatacttaa taatacaccc aagattgttt cctttagttc atttgggttc aagatataat 189240
atattaagta cctcttgccc ccttccttgt tatttatgtg atggtcggtt ttatgtgtta 189300
acttggctag gctgtagtga tcaactatcc aatgacacat tactctaggt gttgctgtaa 189360
aagtattttg taggtatgct tgatgtctac aatcagttgg ctttatgtaa aggagttgat 189420
cctggatgat ctgggtgagc ctgttctaat cagttcaaaa gtcttaagaa cagaactgat 189480
gtttccctga ggaagaaaaa atctcccctg tggattgtgg catcagctcc tgcccaagtc 189540
tttccaaatt gtccttctga tggcctaccc tgtggatttt ggacttgcct agttagccct 189600
cacaatcaca ttacgatccc ttgcaacaaa tcgaactctc ctgtctctct tcactcacac 189660
atgcgtgcat gcgcgcgcgc gcacacacac acacacacac acacacacac acacacacac 189720
cccaacttgt tcaatttctc tggtggtacc ctgactgtta aacttgtcaa gtacctgtgc 189780
agtgatttgc tcagctaagt gaatatgtta tgggttgatt tgtcataatc ccctcaaaat 189840
ccgtaagttg aatccttaac ctccagtacc tcagaatata accttatttg aaagtagtat 189900
cattataaat ataattaatt aagataaagt cattagaatg ggctcaaatc ctacatgatt 189960
ggtgtcctta taaaaaggga aggtttggag acacaaacac acaaaaggag aatgccatgt 190020
gaagatgaag gcagagatca cagcgatgtt ctacaagcca aggcacacac cagagatcgt 190080
tagcaaacca caggaagaaa aagagaggca tagaacagat tctccctccc agccctcaga 190140
aggaaccaag cgtgctgcca ccttgatctt gggcattgag cctctaaaac tgtgggagag 190200
taagtttcta ttgttttagc cactcagtct gtggtacttt gttacagcag ccctaaaaaa 190260
cgaatgcagc acattaccag gaaaatcgag acagttgaat tggggaaagt taagaaacat 190320
acaaagttac aaaatttttct gagtattaca gaaagctcca tttccttact gcttttgaaa 190380
tacaaactta ttccctttta tgcataacgg ttttactgcc aatagctacc caagaaaaga 190440
cctggatgat taaactgaca attacagaga tgtacaaatg ttccagaaat ttttcaaagt 190500
agttctttta aattcctgga atctggtctc tttttggata acagatgttg tagaaccttc 190560
tataactatt catctctcta tttgtgtcct cctggagtgt agctcttcag ttctgtctta 190620
caggaaaagc taacaatcac cacctggtgt cccttcccct cttctagcaa gtgaagctaa 190680
tagatattct gtaaaaggaa aaaacaacgg ccgagcatgg tggcgcattc ctgtagtccc 190740
agctactcgg gaggctgagt catgagaatt gcttgcacct gggaggtaga ggttgcactg 190800
agcctagatc gcgccagcct gggcaacaga acgagactct gtcttcatag atagatagat 190860
agatagatag atagatagat agatagatag atagatagat agatggatga tagatagata 190920
gatagataga tagatagata gatagataga tataaatgga aaagcaacag ttgtgcccaa 190980
tcttccacaa ataacttgca accaggcaga acatagaacc caggtctttt gatgccagtc 191040
acatccagct gtccttccaa gacattgttt ctatgcaggt gttgagtcag caggccagat 191100
aattcctccc aacgtttatc taaatacagg tgttttttct aaaatgcagg aatgtgaatt 191160

-continued tggatataac attcgtcttt gtgaggtgta agtttcttct tttaaaaaaa aatgcatctt 191220
tatttagtcc tgacatttca aaccaacaga atcagcatca gtatagtgaa aggttaaagt 191280
ccagctattg tcagtttcta catatgtcat attggccaat ttacttaact ttattatact 191340
tcatttcctc atttttaaaa tgagaaatgg agtgttatct ctttcactgg gtcattacag 191400
ggatgaaatg aaataacatg tggaaacatg ttataagctc taaagtggtg gaaagaagat 191460
aaaaataaag tagtaatgtc acatctgtga tcttacggtc tcctttccta tcccatattg 191520
tagaggataa gccacactga atgtccattc agtttacatc agacttgttt gggaaagtta 191580
cagtttgcgt gggtatatcc agatcattat gtttttacaa gcttcacagt ctgacctagc 191640
atgaaaatta agtacatgaa aagtatttca gagtcttgta gttaatggac aaacttagat 191700
atccctaata ggtgcttcta agcacttatc aaactttttc ttacctctta ctcatctggt 191760
tccttcacta cactgtaaac acttacgaag gcaaggttat attttcatca tccctatatt 191820
cacagcatca gtctttaaaa tgttttgaaa tttatttgtt taattgataa gcaaaaatgt 191880
atgtatttat aatgcatatg atgttttgaa atatgtatac taaagaatat ttgaataaat 191940
atggtcttat tcaattttac tttggccata atcattttca ataaaaagta taaaattttt 192000
taaaagttga cgatgtatta cttaattgta atacataatg tatgtttaaa actaatccat 192060
tactaaaaat aattgactat tataagtaaa aataccttaa gccgttgaaa gtttatttac 192120
tattgatcta ttaatttaca taattcttcc atgtctagca gagcccactg attataaagt 192180
aatttacaga tatcaacttt ctaggctgtg aaggcttctg aaattataag gaagagacag 192240
ttgtgccgaa attgtgtggt ataaagctgt caaaatttga aatatagtta tagatttcag 192300
aatataaatg gttgtcatca gaacaagatt acaagtttca tgggctctga aaaacttagc 192360
ttatttaaca ctgaatcaat gacttcacaa ccaaactgag ttaaaacact tcagattctg 192420
aaagaatgtg ctcattcaac ttacaaagca gaatttcaaa atatccagcg tgtttggcag 192480
gaggtgacac aacaggccat tttgaggaac attttgctta gcccagtttt tctcagattt 192540
aatatttttc atatttttgc cattttcaca cactgtctcc actaatattt tcctttaaat 192600
acattctttt taacatattt accataattg taaaattata ttactgttat atataaaaga 192660
taagcatcac ttattacaaa taaataggac aaaaactgca aaaacaaaat aatggtatca 192720
ttgtctgttt ggattcagtt gaaagctctg agccttagtc ctacactgca actgtttttt 192780
tttcttttta aagagaaatt taccaagtgt ttataaatgt gttaaagcct tattagcacc 192840
aaacttagac tcctcttggt ataatcagat ggttgaagag atgtgaaaag agaataactt 192900
tctcaccacg tgattcagtg ctatgtgata ccatgctgtg tcatgtccta tctccaatta 192960
tttcacgtag cacttgaagc aaaactggag ttgcatatta agtgtttgga attttataag 193020
ttcaagtaca tgtgcactta caatatttac ttgttatgtg gaatgtatag gatttaaact 193080
gaaaagacaa acatgcagat tttttacacc taaagacaaa agcaggttga taactagtat 193140
ggatgacttt agaagaagaa agtcatatca gagcagaaag aatcttagag gccatctgtt 193200
ctaaaggtgg gcaaactgag acacaaaagt gttttctttt ttttgagata cagtttcgct 193260
ctgtcgccca ggctggagtg cagtggcaca atctcggctc actgcaacct ccgcctcctg 193320
ggttcaagtg attctcctgc ctcagcctcc caagtagctg ggactatagg catgtgccac 193380
cacgcctttg ttgtattttt agtagagatg ggtttcact gggttagcca ggttggtctt 193440
gatctcctga cctcatgatc cacctgcctc agcctcccaa agtgctggga ttacaggcat 193500
gagccaacgt acccggtccc caaaatgttt ttttattgat ggtcatagaa ctaagaagtg 193560

-continued ccccaagcag aaatggaacc caattgttct tgatggtcca gttcacttca ccaagatgat 193620
cctgttccat ctgttcatgg tggaagcagt taatttcata tgattttata ctcttattat 193680
ttatatgaga gtaggaggtt ttttaaaaga taagtcctac tgaggaaaga aaatttcaaa 193740
tgaaccattg ataatggttt ggctgtgtgc ccacccagat ctcatcttga attgtagttc 193800
ccataatccc tatgtttcat aggagggacc aaatgggagg taattgaatc atgggggtgg 193860
ttcccctcat gtggttctca tgatagtgag tgagttctca caagatctga tggttttatg 193920
aggggctttt cccccttac tcagctcttc tccttccagc tgccctgtgg agaaggtgcc 193980
tctcttcccc tttaccttcc tccatgattt taagtttcct gaggccttcc tagccatgag 194040
gaactgcaag tcaattaaac ctcttttctt tgtaaattac ccagtcttgg gtatttttc 194100 aaagcagcat gagaatggaa taatacacct gtgaacttta aacacatttt attgtaactt 194160
attgtaacag atcttagtaa ttgtttaaga agacaatgct agttgattac cctagacaag 194220
agaaagatat aggtccctca ttattgtctt taaggattct cctgtgcttc ctgaaaactt 194280
ggacacaagt aagtaataac tttttggcca tctttggaag gatttctttt tgttttgttt 194340
tgttttgctt ttttagagat ggtgtctcac tctgttgcct agcctggagt accgtgttgc 194400
gatcgcagct cactgcagcc ttgacctccc aggctcaagt gatccaccca cctcagcctc 194460
ctgggtggct tgggactaca ggtgcacacc atcatgccca gctaattttt aaaaaaaaaa 194520
tttgtagaaa cacggtctcc ctatgttgct caggctggtc ttgaactcct gacctcaagg 194580
gatccttttg cctcagcctc ccaaagtgat aggattacag gcatgagcca ctgtgcccag 194640
ccagaaggat atctttttaa aagcattgtg tatcatctga ctttttgtac aaatatattc 194700
tccagccttt tttttggtga gagggatgtt gctacttgat tctatttttt cattaggtac 194760 ataccctttga tgggatattt gttctcattt gaattgcttt attctgtaac tgtttggctt 194820
ccatgctttt attttttaaa aaagcagtct cactttttgt ttttcttatt ccttctcctc 194880
ttattcttct ttgtcttctt catcaccacc accagagatc attgccttaa tgacgtttac 194940
tagggctttt catttccttc ccagtctcta aggtattttt ttggcaatgg gtgaaaagtc 195000
ctgacattct gattgctatt cgtattagtc cgttctcaca ctgctataaa gatattaccc 195060
aagcctgggt aatttataaa cgaaagaggt ttaattaact cacagttcca catggctggg 195120
gaggcctcag taaacttaca atcatggcag aacgcaaagg ggaagcaagc ttggaccttc 195180
tcacgtggct gctgcaggag agagaagaat gaggagcgaa ggggttctta ccttataaaa 195240
caatcagatc tcctgagagc tcactatcac aagaacagca cggggggaaac cacccccatg 195300 atccaatcgc ctcccaccag gtcgctccct agacacttgg ggattatggg gattacagtt 195360
caagatgaga tttaggtggg gacacagcca aaccatttca ggacttaaca gttctatgtt 195420
attgacacct gcccagcact gtgaccactc atgcctcatg cactgaggag agaactgagg 195480
actttcaagg tctcttatag acaaatagag ttgtaactgc ttgtaaagca ctttgctaat 195540
acagagtgtg aagaaatgat aaatacgaat gattattatt gacagtggtg attggccatc 195600
atcatctctt catttctggc tatttctcat gcaaacgcta ttttagctta aatttttcaa 195660
ccttgaatcc aatgaatcta atcagaatga aggaaacaga cctatttcta gcaatgttaa 195720
acaaatgatg acttttgtgt tcaattagtt ggtttataga gactcatcca tttttaataa 195780
attgattttg tttatttttt ctattttatt ttacatttga atgaagtggg tttactatat 195840
gactacaaat gcatttgtgt tctctcctac tcaagctagc ctcaatccta gaaagtatag 195900

-continued tcctagttct gctgcaaact atgatgtata aaaagagtat aaaatattaa atattatact 195960
ttttagccaa gttaccaatt ctatcattct tatagcagca tagtttatac acaataataa 196020
atttttaaaa aaaggatata aggcattgaa ctgtcttcat gccagatgag agataatggt 196080
ttaagtatga aaaaaacagt tgaatcactt tcactatgtt gctatgtgat ttgagagaat 196140
ttctcagcaa ctctttttcc tctgtttctt catttctaaa atgcagagaa tacttaagcc 196200
aactttttttg tatgtatgtg gaatacatgt aaaaaatact tgtacatgca aatataagct 196260
aatattccta ttactgttat tgttgggtgt gaaaatcacc actatacaat gccctgaatt 196320
acatgttgta tattccatca aatgcttacc gcaatccagg gctaagaaaa tgcacaatta 196380
tctatacaga gtgactagag tttaagactc caataagccc ttatcatgtt caaacaaaag 196440
tactgattta acattccagg ctttgatgtc agaagtaaat tacagagtag aatcatgctt 196500
ttttggtata agtaatggta tatttcagtc acaaaaatag tatttactct ttcacattga 196560
atgaggaata tgatatcaca gaggatcaat aaaaatactt tttatacttt ataagaagat 196620
aaaaattcta acataaatga ccacctcaag gcttagagga atttaggctg gatctaaaac 196680
caaactaaac tcttagcgta taaaaattcc agtaaaatcc atgattatgt tttataagat 196740
taatactaaa tttcacactt taaaaagtca tagtcaaaag aaatattatt caattattta 196800
ctaagtgcta gttaaatttc tgctatacac ttttatttgg aacttacgta agtcatatgt 196860
atgacatttt atttatttaa caaatactca ttatttacca cattttagtt ctcagatgct 196920
atatatgagt aaaacatgct tatatttacc gctacccata tcataccacc tcttaggcca 196980
agaattatct gaacatcttg ctggtcttgt tttttgcttg tttatactgc agatttctat 197040
ttagactgaa taatataaga ataagaagtg tttatgtatg aactggaaaa tgataagaaa 197100
acaaacagat aaagttattt gcaaatatat tttttccttt taagttttat aaacctttct 197160
aagtaataag gaccagaagc ttccacagca tcagttcatt attagcactg atatgaaatg 197220
gttttataac cttcagcaga atttaagggt ttctggtaag aatttcttct tactgcagaa 197280
caaattgcat ctcttatggt tactgtacat ttgcaattga tgagccatca gaaaaaatct 197340
tggaaaagtg atgcaaccgg taacttgtat tatttttttt ttaaatggag tgtttgaatt 197400
atttattgaa tctaggtcat gtgagtcact tccacttcac aaataagttg aaaaccctac 197460
agtgaagaaa taggtactta attagtgggt gaaggatttt tgaaataaga tgagacatcg 197520
agtttgtttc ttactcttaa tttgagccaa ttgtattaga gaaagactaa tgaaatcaaa 197580
aatgacaaag cccaatgtca aaaaaaaagt aaagaaagcc ttaatagcca attaatacta 197640
gttcaggcat accacacaga acagagacca agggcttggg tgtgaggata agaatttcag 197700
agattcattc agtcctctag acatatattt tatgtttcca tcaatagcca ggtactatgc 197760
aagacactta gaatgtaatg gtgcaactga aagacatacg cctcgttctt acagagttta 197820
caaactggtt gaagaggcag atgataaaga gataaaccaa tcaataaata tttaacttaa 197880
ttaaaaagag tactatgaag ggaggctctt tttttttttt tttttgagat ggagtctcgc 197940
tctgtcaccc aggctggagt ccagtggcgc gatctcggct cactgcaagc tccgcctccc 198000
gggttcacgc cattctcctg cctcagcctc ccgagtagct gggattacag gcgcccgcca 198060
ccacgccctg ctaatttttt gtattttttg tagagacggg gtttcgccgt gttagccagg 198120
atggtctcga tttcctgacc tcgtgatcca cccgcctcgg cctcccagag tgctgggatt 198180
acaggcgtga gccaccgcgc ccagccggga gacatgttta cgctgtgcta gagattaaga 198240
taaaaaacat acttgaaggt taaaagaaaa agaaggatac cttcagaaag taatgtctaa 198300

-continued

```
tctgagtctt aaatgataaa aaggagatag catgcaaagg ccagcagaaa gcattccaga 198360
tgaaaattaa aaagcgcatg gtctctggga agagcttggt gtgtttgagg aattgaagtt 198420
taggcaacat atgctgacct ttggcagcaa cgaggggagt ggttttcaat acatttgaat 198480
gtataggatc caaatgataa aggaatttta ggctacagta aggaatttcg aattgtttac 198540
agagaaatgt ggaataatta gggctacaga aggatagatt aataactctg gatgttttgc 198600
taaggactca atacagttgg gtgaagtgga agtagaacga ccagcaaata ggctattgcc 198660
atttgtccag gcagaaaggg atctattttt ccatctggtt ttaattattc cccttccctg 198720
tctcccctcc tgcttctcct atctccccta aagatgcttt tcctgtttta aagacataac 198780
cccagctctc caataactta actgacttct aggtgtttca atctaccctt cgaggtgagt 198840
aggactgacc ccatactatg ttatcagact gttcagggtc aggatacctt tcttagcagt 198900
cacagtgagt aggaaatgct ccttgtaaac acaggaaaca gagccactga ggcagtcagc 198960
taacatctgc tagaaaatga gatttgagtt acaagataaa gttcaaacac caattttacc 199020
taacagcgat gttggtacta aaatcttata aagcttacaa tctgaaatgc acctgtccca 199080
ctgatactct ttgtgatgtt cattaaaaaa actaggtgga atattgaagt taatatcttt 199140
aagtgaatgt gtataaacat tgtgatagaa aaaaataaaa atttataaat aacttctaaa 199200
ttttgtgtct aagcatcccc tgtgccacct gtatacataa ctccctgttt tcctgttgac 199260
cattgtttaa taacctgctc tctggatagt tttaggtttt tacagtttca catatggtcc 199320
catctgctgg caattcaact cctattcaac caagaagcaa tcgaactaag acctgaaagg 199380
aagaatacag ctggaggcct tgaatgcagc tccactggga ctgaatttat atagggtaca 199440
gagggctact actgagtttg tgcagagaag tgccatttaa gatactgtta aaggaaggca 199500
aacagaggga agatttgttt attaaatgcc tactctatac caggaactct acataaatag 199560
tctcatttat tcttattagt tctggtatta tcctcctttt atgaaaaaag gtaactgaat 199620
ctcagcttgc ttgtctaagt tgacataata aatggctgtg cttatttagt tctatggcag 199680
tcataaatag aatcaagatt aatataaaag gattgattgt cttgccttta aaagtccgtc 199740
gtctgcccct aatgaatact ttacctactt tagtttactg aacctgccaa accgggaagt 199800
tataaaatac aagcaagcct tgtcatacag tttttgagtc agaaaatata ttcatgtcac 199860
ctagtatcat tatagctttc tatcacttat gatggcaaaa ataagtatat ctgattctaa 199920
taagaatatg aagaatcaaa aaaatggaaa aatattgaag ggaaaaagac gtaattctac 199980
cagaaaaatc acgacaaaac atctaacaaa ataacatatt taaataataa agaacccctt 200040
ttttaaaaag cagattgatg atgattatat ctataattat gtcaggggag gcataaaata 200100
ggcatatttg tagagctgtg attagtataa acagggctgg gtatgagctg agtcatctcc 200160
ttgccactgt attaaaacta caaaataata attccaagtt taatacttta aaatgattta 200220
ttaactaggt ttcataatca ccaaaggtaa cttatttcca tgttaaacta ctctttattc 200280
agaaagttgt ctttaatatt taaactaagt tgtaactatt gtagttcaag cccaatccac 200340
tcagctccaa gtgtctagtg ggaatcacag ttcccttctc tcatttgtag tatctctttc 200400
ctaggtgtaa atagttactc tgcttctctg ttatctttcc ttctgtctga gcatgcctgg 200460
ttcccttaat gtttccttat agatctcatt ttccagggct tttatcattt ttgttgctct 200520
cttctgaact gatttaaact tatctatgat tctttttcaa ctgaggaaca aacactaaac 200580
acagttatcc aattgaggcc taaagtgtgc ttgtagaaca aaataattac ctctcatttt 200640
```

-continued

```
atccacgttc tccctattaa tataccccaa agcagtgtct gggattttat atgacaccat 200700
tgtattgttg acttattgtc aatttatctt tcattatagc ttatatctcc atccccgtgg 200760
aacaattgtt tgtgcggttt atatttgttt ttattgaatc ctattttatt gatttcagcc 200820
ccacattcta tttatcaaga tggttgtttg taatactaac ctctaatttg cctccaacag 200880
tacatgatcc ccaagttctt aactgtgtaa atgattagca tactttctgt tttatctcac 200940
caaatctctg agtacacagc tgaatgtggg gtttgttttt gtttcgtttt gtttttttga 201000
ctaacaaaaa aagttgtgat agaatttaaa atatttcccc ttactgctta tagtgctaac 201060
ctcaaaagct atgattttgg gtgcccatga tattgctgag actgtttgcc atcatattaa 201120
tcctttaaca atattcctga ggtctgatta acccaatctt acagagaaaa agactctaag 201180
ggccatagat gtccagtaac tttctcagca cgtaactagg aaggagagga gctggaactt 201240
gaacttggtc tgtttggtct taccaccaag tactttccag tacacctgta aataattcaa 201300
ttcaattcac aactaacagc ttgttatatt aataagtttc tcacccattc tgctattact 201360
ggacaggatt ttatgaaaac catgacagtg ttttcactcc agggagtctt cttttagaaa 201420
gatgttgtgg gtgctatgaa tgatgaggcc attgttcctg ggcacagaga tgattccagt 201480
gacaaaatta ctgtttacta tgtgaaagcc atggtatctg aaagcctaac aaatagagtt 201540
gatcataggt tgttcccgct ccttttgcta tattaaaaaa ccattccaac taaggcaata 201600
tgataattaa cttgacttct atttgtttct ttgtatcaaa gtgattgaat ccaaacacta 201660
tccatccaaa tcactggcct aagtcaatgg ttgctaaatg aggtgctaag actctgctga 201720
gtattttaaa agttcctaaa ggatgctgta gattttagta tactagaatg taaaaagtac 201780
aatgcatgtt taattaagac tttatgagct gactgtgtga cttgcccaca tcagcaactt 201840
agccctgatc tcttgaaatc caaagtgcat atatactcac ttagctggtg attgctgaat 201900
tcagctgctt catggattgc atacagcagg tctgttttgc aaaatgggct tgttcataag 201960
gttaatattt gcattagtcc attttcacgc tgctgataaa gacatacctg agactgggaa 202020
atttataaag aaaaagaggt ttaatggact cacagttcca cttggctggg gaggcctcac 202080
aatcatggca gaaggtgaaa ggcacatctt acatagtggc aggcaagaga gaatgacagc 202140
caagcaaaac aggaaatccc ttttcaagcc atcagatctg gtgagactta ttgtctacca 202200
ggagaacagt atgggggaaa ccacccccat gattcaatta tctcccatgg ggtccctccc 202260
acaacacgtg ggaattatgg gagctacata caattcaaga tgagatttgg gtggagaaac 202320
agccaaacca tatcaatatt aatatgccta tttcttaatg taaaacaaat tgtaagggac 202380
aagaacaaat aatggatgat gctaataaca tcttattaaa attggagagt ttaggtaatt 202440
taaaataatt atcaagaata catgggtttg ctgttctagg atagttgcct agtaatgagt 202500
ttcccttagt atctgcaagt attttatcct ttccttaaat gcattaaaat gtgtcaaaca 202560
gtttggtttt caatagacag aggagaaaat tatctactaa atttaactac tttctggcag 202620
atcaattaag aagatattaa gttctgagtt cagattttgt taaaagtgtg cattagttga 202680
tggtgaaata taaagacact gagttcaaga tcactaacaa ggagcttgag aagtagaaga 202740
aggctgaaga gtataatcat atatcatgca gatgttggct agcttagggg tactgtccag 202800
gaagaggaat tctctgctgg tactggagcc tcatcccttg attgcctagg tgcaaggttt 202860
gggcatatac atccttcgtg tctgagaaga tgttactcct caaagacttg ggagtagttt 202920
acacataaat gagaggatta aaaaaggcac aatagagggg aaataatttt cctcttattt 202980
attttctgaa tacctcccta cctatttcct tcttgttata tgaggtttat tctcttcagt 203040
```

-continued

```
aataaacaat ttaaaaaaaa acactcaaag cagatattgt aaattcacag tattaatgtt 203100
tttaatttat attaaaacat acaaaaatag gtttctaata ggtagactaa tattctttct 203160
ggcttaaaaa ttgttcctca tttaataatg tttgatcaca ctgagattat actttatttt 203220
tctgtttgca tcatctcttt cttagtttta tctttccttc atacctttct cttacatcag 203280
atttttcatc ttagtctttc aggaatttgt ttgtttattt gcagtttgta caagagaaca 203340
cattagaaaa cgtagggctc agaacccact acccgaaagt atgatacttt ggcatgctga 203400
gtattttaaa ctgaaggaga ctggaagacc tcagaagtga ggtctttctg atcttctcca 203460
atcatgtctc ctacctctct ctctccctgg aagtgaaaca tagaaatcag tatttctttt 203520
ctccaaggct ggttacagaa gctagaactc atcttcccca aagcatggca taaaacctag 203580
aaaggtaact ctctcccttt tcccttgaag accctcattg caggtggtca gtgcctcata 203640
cccagaagga agaagtgcta cagagaggcc agaaagaatc tgatcagacg ggcctagctg 203700
ggttcaccct cttagtttat taccattaga tatacccttt tatctaatca catttctaca 203760
tagctgtcca ttcttcatag aatctaagca taaatgtgga cagttttccc tggaatttgg 203820
gtcttcattt ctaaaggctc tagtgagaca taaaattttg attaataaat ttgttgtgct 203880
tttttgttgt taaactgtgt ttggtttatg agagtgttgg atgaggaaca ttcacccact 203940
tacgatgggt gagaaaaagt atcacacgtt tctgcccctg caggaccaaa gttgttacaa 204000
atatattttt aaatcttaaa aacggaatag attaatccag gaaatatcta ttgctaatgc 204060
caaaaatggt tcctttggca ccgtgcatgt aattgtgtgc cagaacctga tgaaagagaa 204120
gtgattgtta agagaaggaa gaaggactaa tcagaattga gttaaatact gggaaagata 204180
gaagtcaaga gatgctcgtc taataaaatg agcaaagcag ttgcatccag gtagccccag 204240
ttagagttat attttcatga gaagttagaa gagtcagact aaggatacag ttagacttgc 204300
ccacatttaa ggtctgtttg gttaatgagt tagatttgtt gactcctccc ttttcaattg 204360
ttttcaaaag aaagtggtta aaaatatata gtctgcaaaa atgaagtatt tgttccaact 204420
gaaaaaaact aaagcaaata attcagcttt ttgttctatg tatccacatg cacacaaaca 204480
cacacatatt aaacacacaa aaagtgagaa atttagtttt cagaattgca gaaatgccta 204540
ataggaataa cattctaagg accaggaagg cgcaggatct attaagttaa aaacactaac 204600
aataaaaaaa tatataaaaa ggaaacaaaa actaaaacac ctcagctact tcattttgag 204660
tcttatggag gaaaacaaca aacaaaatta atatttaaag ttaaaattaa aatttccaaa 204720
atacattctt tgggatgttt tcagcaaaca atgtaaaaaa ataagcttat ttccaaatac 204780
aaacttattt atcatctaat tctattcaat ggcaaattgg tgttactgtt ttattcggtt 204840
tcactgagat tttcaagcgt gtttagaatt gaaaagtgtt ttctgtctct taagtgtgat 204900
gacaaaacat taactgatca tttttattct gttgacaaga caatctactt catggattta 204960
taaattgctc caaggcaaag ataatcatgt aattttctta tcacagccaa tgttaataat 205020
ttattattaa cattattttt aatttgaata caagtggaag gcatcccaaa gaagggaata 205080
ttgtataata ttcagaaaaa aatcttaact tcataaaaag tgaaaagtca ctattctgtc 205140
tttggatttt tttttttttt tttttgagct aaagaaagat tcaacagagc atttgctagc 205200
tcatattcag ttcctttgct ttccatttca attaaagatt tattttctat ttgtcaagtt 205260
ttaagaaaaa ttaactggca gtatgttgat gaaatgtgtt tcactaatca tctactctca 205320
gaaacagtgg aaaattttct ttaataggtg atttattttg gtgataccaa ctttattcta 205380
```

-continued

```
atttgaagc taactggaca ctccacttat gtattgacat gtttaactaa ttacatcaaa 205440
tcacgctatg caagaaaatt aatacacatt ccattagtag gaatgaatac ttacttaaag 205500
atcaggcctg gccaccttac aactccaaaa gtttgggaag tacacaagat aaaattgata 205560
tcttttttt aaagaaagga atgtcaacag ataaaaacag atcaagtagg taccagaata 205620
tcatcaaaat gtcacttagc aaaaatctag tttcattggg aatattcaat attgtacaaa 205680
tcttcaaata aaagataatt gctaatcata cagtgactta tgaaaacatt tgttacagga 205740
ttcaatctaa acagatttta ttatatctat atctgacaga tatagtaatg ttaataagag 205800
ccaactgttg gaaattgtac tggatattac aatattgtta cacagaaatg gttattgaac 205860
aatattcgtt aaaatgggag tttatactag ttgcaattaa ctcccaccat tggaaatgca 205920
tatttatttt aaaatatccc aaaaatacac acacaaaaac cttaatgcat acataaataa 205980
atcttacttc ttagatattt gaatcatttt aattagcctt acttttgaga atatttcatt 206040
ttgaggccag agaattgaag tttgtcctta acattaatct aactgctact taagtgattc 206100
tcatttagac tgtagctctt tcaatacaaa ggcctaactc cttttaaagt tctttcctag 206160
atctccttcc ctgaataaca taaataatgt tgagtatttg ttgaattgta tctaacaaat 206220
atctggaatc acaccatctt ccatttataa tgagaagtta ggtctgtcag ataaaaaaca 206280
taattttatg ctaaaacagc aacaaaataa tgtattttga catttatttc agcatatacc 206340
agctgtgttt ttttgagaca catacaaatg tcctccaaaa tcgccattta taaatccagg 206400
tttttaaacg aaaatatttt ttcttatgaa aggcatttgt aaatctcaag gaaagataaa 206460
atgtactcta gtctttgaca acttggtttg ttgttattgg tagcctatgg ttagtttgta 206520
cttactagag tcccttaacg ttggatatca ggaacggata ctcttattca ggaggaattg 206580
tctggtacaa atggccaact gtgtatcttt agctgtcaac acaaaacact ggcaaagcat 206640
gtgatatagc aaagcatgaa tatcccagta gatatggtta tttatgtttc tagaaataac 206700
caaaaccaga caatgagcgc ctgcatttgt agacctaaat gggaatttgc ttccttatca 206760
ggcgtagtga taaaaaagtc ctgttgtttt gtgggtgtct tgaatactgc ctgagactgg 206820
aatttgatag tgggcacatt acacctctat aatcatttcc gacatccagc tatgcctctc 206880
tgtgaaataa accacaaaaa ttgggcactt ttctgaagac aataatagta gctgagtttt 206940
ctacaaaatc agaacatatt tagttttttc agtaaaaagc ataacagata taaggcttgc 207000
tttgaaaata aagcgttcca ccagtagaag aaatagatag ctatcttgtg cacccaaaat 207060
agaattctgt acaccttcct tggaacatag atgagactac tttaaagatg atggcccagt 207120
ggaacttagc agttgatagg ctaggaccaa ctgctgagtt ggtttaactg gcacaaacat 207180
tggcatagaa agagcacact actatgtatt aaatcaataa agcaaggtag caaagaaatc 207240
aggtccatcc ataaatgttc actctttgta gaatagtgtc atataagttc ctcggtggac 207300
ttgaggtgtt tgaggtctgg gaagcatccc taatccttct cctgcaatct ccaccctcca 207360
tgcagcacca aatcacaggt gaccctggag tctggcaact tctctccata tgacctgcca 207420
atatcttagt cgaagatact gtcatctctt gcctacgata gtcttctttt tggtctcctt 207480
ttgtctactg ggctcaatct aattcatctt gtccactaaa tcagaagata ttttaaatca 207540
caaacgaaat gattactcct tcatcctacc accaccacac ccttaaatca ttcaatggct 207600
ttccattagt cttatgataa agactaaaat ctttggagga gccttggtgg tactttatag 207660
tctgactctg cctctctctt cattcttatc ttaacccaca taccctctgg ctctcaggat 207720
ggcaggaatg ccaggcatct ttctgtgaca gaaatgtccc acattgtcca tgctgtttcc 207780
```

-continued cctgcttaga atgcttcctg cccacctcct ttccctagcg aagtcctgtt cattagcatt 207840
tgatcattca tttccttagg gaaatctttc ccaacctcca tattatgtac cgtgctatga 207900
attcttacag tactacattg ccctcttttt gaaagcatgt aactccattt gaaataatga 207960
attcattagt gtgattattt aattaatgtc tgctttcctc ttggactaca cttttcatga 208020
tagaaggaat gtggctattt ttgcccagta ctctgtcctt gggacaaggc agaaagtctg 208080
tcacctagca ctagctccag aaatacagtt gttggatgaa tggaagaatt aacgaatgag 208140
actctgggtc tctttcacag aagtgaggat gaacagtgag caaactatac acagattttt 208200
gcctatcttt ttagcctgta tcagtgtttt aagtagtttg ctggggttac ctatttaatt 208260
tgaatacatt aatatttatg aggtaaatat aataagtatc tctattaatc taaactgagt 208320
ataccgaact cttgattttt ttcctctcac tattaccttt tagaaggtca gctggtctaa 208380
ccaactaagc tcatttacta tagccgatat ctactatctt gagaaagatg tggatatttc 208440
taatgcacat ccaatcactt gctggtggta taatgatttt tgtgtttata tatctctcct 208500
aattccaaaa tgcctgtata tttattgtgt cattatctga aaatatccag tgtggtagat 208560
gtgtatgggt attatcccca ttttactgct ggagaaaagg taaaacattt tggagggcag 208620
cttgtcatat gatacactgt ttgtttttgt ggggttttttg tttgtttctc cctaccatgc 208680
aatccaacaa tgaactcaca aaggttgctg tacaacagaa catttgccta ggatatcatc 208740
acctagcttt ataggaatgt gaagaagttg aagaattaag gtaataggaa gcagaactat 208800
ctgcgctttt tggtagctta ggaaagtaac caaggagctg acttactgtt aaatgaaaga 208860
aagccaagct gtagcaatgt gagtcaaagt tctgagctag gggatcccag gaaatagagg 208920
ccagtattgg gaaaatatag taagggcaca tcaattgttg attctaagtg tttaaaattc 208980
attctgccat attactaagc tcttttttct ttcaaggaag agtcttatca gtagaaatat 209040
tagccatgcc ttcatagtcc ttatatctta ctaatgtgca tctatttgct atctactgtt 209100
gacaaaaaat gccaaacctg gtaaaacatt taaacaagtt tattctgagc ctcatatttg 209160
agtgaccatg gctcatgaca cagcctaggg aggtcctgag aacatgtgcc caggtggttg 209220
ggttacagct tggttttaca cattttagag agacacaagt tacaggcaaa gacataagtc 209280
aatatgtata tgtatatatt ggttcagccc agaatggcag aatacctaga agctgggggt 209340
ggtgggaagg agcttccagg tcataggtgg cttcaaagat ttcctgattg gcaattggta 209400
gaaagagtta tgctttgcag gaagagttga agtcatcata aagaaatgct tgagttaaaa 209460
tacgggtgat tgtgaaagcc aaggttcttg ttatatagaa gaagcctcta attaacaggc 209520
tttacagata atagatggta aatgtctctt acctgacctt aaaagatgtc agactctctg 209580
gaaaagacct accaaggaaa ggaaagttta ctatgtgtca ggatgtccta gttagtttat 209640
tttattgaat tctcattaac aacaacaaaa tgaagaagaa agcagaagtg aagcttttga 209700
agcttaagct gccaggtcct tgcttgtact gcctccttca caaccccaaa cccccacatt 209760
tccccaagag atggctttgc agggccattt caaaatctgt caaagaaaat atattttaag 209820
gtaaaatact ttgatttcct tcagggcctg ctttccgtca tgtgatgcta taccagagtc 209880
aggttagagc tgagtatctt atcactacaa agaatctgtt ttgtctctta tgatctctat 209940
tttaatgtta aatctggtca gttgtgccca aactccaaaa ggaggagaat agagtgaggc 210000
aggtccattg cccccccttca catcatggcc tgaaccagtt tttcatgttt ctttgggatc 210060
cccttggcca agatgggttc tttcagttga ctggggggta ttagaatctt atatttggtt 210120

-continued

```
cacactgcca tgcaatgtaa tggttaaaat cataatttct agggttacat gatcagggtc 210180
cagaacattt cttcatctgt tcctagttct tgttaacttg aattcaatgt ttcagtttct 210240
tcatctgtaa aacagggatt ctaagtatag tttcaggaat gaattcatgt tttatagagt 210300
ctgaagatta gattgcataa tagggaaggg tgtctcttta ttaaaaaata aaaataaata 210360
aaaaaataag catacataca gccaggcgtg gtggctcacg cctgtaatcc cagcactttg 210420
ggaggccgag gtgggtggat cacgaggtca ggagatcgag gccatcctgg ctaacacagt 210480
gaaaccccgt ctctactaaa aatacaaaaa attagccggg cgtggtggtg ggtgcctgta 210540
gtcccagcta ctcgggaggc tgaggcagaa gaacggcgtg aacccgggag gcagagcttg 210600
cagtgagctg aggtcgcgcc actgcactcc agcctgggca acagagagag actccgtcta 210660
aaaaaaaaaa aaaaaaaaag catacataca aagtgcccac aggcgcacag ctcagaaacc 210720
tctctttctg gggtttggaa ggaggctgtc caagcaagga cctggcagct taagcttcaa 210780
aagcttcact tttgctttct tcttcatttt gttgttgtta atgagaattc aataaaataa 210840
actatgcagc acatcctgac acacagtaaa cacttctaag tacgagtctt catcctcatt 210900
attactttta ctataacata caaatgctta aagagtaaat aatttctatt tttgattcat 210960
aaaattttaa ttttattctt ttgaggctac ctgctggaga gaactaaagt tattagtgaa 211020
agagtggtgc atgttaagga atgagcttct ttgttctttt gtttacagaa caaagtatat 211080
caagcagcta ctatgctcca ggcaaggaat agggagggga gggacataca aatgaaaaat 211140
tcaaaacaaa tttaaagatg cataataaca aatgtgtgtg agtgccatgg agctaataag 211200
aggatgctag tatagagaat aatggggaga gacactaatt ggcccagatg cagagagaca 211260
ctaattggct cagatagtaa agggagacct ggctggagga gataatcatt aagtgggaat 211320
ttgaatatta taacagatcc tgtaatcacc tgaccactgc acagacaaaa tcagttcact 211380
gagactgtgg tactgcagta aagaaagagt ttaattaatg cgaggcttgc catgtgagag 211440
aactggagtt atcactcaaa tcagtctccc caaaggctga gagcttaggg tttctcaaga 211500
gcagtgggct agagaatggg tgttgctgat tggttgggga tgaaatcata ggtgtgtgga 211560
aaacatccct catgcattga gtctgcctct ggatgagggg gcacaggacc agttgagtca 211620
tgagtcacaa gtcctgttgg catcagttgg ttgccagaaa gcctaaaaaa aaaaatctca 211680
aaaggctaat cttaggttcc ataataatga tattatctgt gggagcattt agggaagtca 211740
caaatcttgt gatctttggc cacatgactc caaagcagta aggtattatg cctacatctt 211800
agcagaattc aggcccctcc aattctccaa ttatcttaat ctcatggcct ttcattcgtt 211860
ttcagtccct gagcaaggag ggttttagtt ttagggagaa actattatta tccttgcttc 211920
catgttacac tatcaactaa attcctccca tagttagctt agcttatgcc taggaagaag 211980
caaagcccag ccagcctctg aggatggaag ccacatggag tctgctgtgt tcaattcctc 212040
tcactgctat tatctttgca aaagcagttt caatgccctg aagagacgct gggaatagca 212100
ttccagacca aaaaaaagtc atgtgtgaag gctctactag aaagaacatg acacattcta 212160
ggaatctagg caccataaat aggccacatg ttacaagaat gatatgagag ccagtgacta 212220
attgatcata aatgctttag tgagataaat tcctaaagga acaaataaca gattttgatg 212280
gagtcaaaca cctaaagctt ggatttgctg ctggaaaaac atcttcctct atattactat 212340
gagctcttag catagaattg ccttacttta cctcttctgc tggcttatgg aagcaagctt 212400
ggaaaagtcc agggcctagt gtgctaatct ctttctgtct cagacagaca tattaaaatg 212460
aactagatta agtaatacct aatgagcacc cttaagtgta aaataatagt tgctttaaaa 212520
```

-continued taatttttaa aaaataaact atattgtcaa cattaaatta agggcagaaa aatgtattaa 212580
agttctaaaa ctacagaatg aataattgaa atattctaac ctagaagagt aaaaaattgg 212640
tgaatgtcat taaaggtttc taacagaaga tccacttagg aagagaagtg ggatacaaat 212700
tgctagtaag aaaagggaga gggggaatag aatatacgta tgtttaaaac ttccaacatc 212760
cttttcctag cccctgatct atgcaaaatg aagtcttact aagtctcaaa acagtattct 212820
ttacatttca ttttctttct ttttcaatca ttgtttttga gaaaatccta aaccaaagca 212880
aaaaagagag aatctgccag tgaagcagct gaagtttcag gaaataacta aaccatccca 212940
tgctcacccc aaaaagtatt catttgactc tttttttttc tttttttttt ttttgtaaga 213000
caggtcttgc tctgtcacca aggctagagt ttggtggcaa gatcatactt cactgtaacc 213060
tggaacttct gggcccaggt gatactcctg cctcagcctc ctgagtacct aggactatag 213120
gctcatgcca ctgcaccagg aattttattt atttatttat ttttattttt ttagagatgt 213180
ggtcttccta tcttgctcac gctggtctca aactcctagc ctcaagcaat cctcccacct 213240
tggcctcagc ctcccaacat gttgggatta caggtgtgag ctataccact cctggcccct 213300
aggagctaat ttcatcttga tgtgaagagt aaagttgcta tgtatttttg tggaggcagc 213360
cagttaatgc ttgttaaaca aacaacaaca acaacaacaa aaaacaatat atacaaaggc 213420
acctacagaa aatctcattt cagacatccc tatcaatata aatagtatca ccatggcaag 213480
caagtgcatt gttcatgtgt gtcccagtgt tactttgatg atctattaaa tcatcaagta 213540
tatttttgtg ccatatgaaa aatacacatc tttcctgtta actcttgcat tcgatcaatt 213600
gtaagattta cccaaaaggg tctaactgtc cacaaaattg tccctgcctt ttatcatttt 213660
tgctttcttt cagggttcat tcttccaagt tgttaaaggg tgtcagttag attgcaacag 213720
aggttgcaac tctcattaat ccaggaatca cataaaagta ttctcaattt ctaccactgc 213780
ctccagttag aagcctttct gactattgat gcctgtaact atgtaaatgt gcgtgattta 213840
ggggaattgc taacctggcc atatctatca ggctgacttg agaaagggca ctggagctat 213900
ctcaataatg gcatggtctg gctttaagga ttaaggttac tatttttctg gggaagattt 213960
ctccctaatg atacaattca aagtgaaatt ctacttgttt cttcatttaa aatgagacta 214020
gagtctgtct tttcatctct catatagata tagatataga tatagatata tataaaacag 214080
ttcttcaata gatactgagt taaactacat acattcctat ctatcatcat tcctaggatg 214140
agaacaacag tgaaatggat acttatatct ctgcatgatc tgttttgacc atgaaaacat 214200
ggccacctac acaaaccatt tggttcttaa tgagccataa tatctgtact gggtaaatga 214260
acacaaaaat agtggtttag aaacaagcat ttcaaacagt tgtgtttgta ttgcctaaga 214320
gcctcacagg gcctgtagag tttattatga acatgtcata ggtcttacac tgggatgagg 214380
cttttgtgtt tttttttttt tttttttttt gttttttttt ttggtgcacg tttgaacaac 214440
aaatggcatc ttcacaagtc tcaaaagctt ttatgggcat ttcaggtcct aacattttca 214500
catacgttgg tttgactgct ggacagtaat gtcttatgct aaattagtaa gggacaaatt 214560
tcaatagata tttcatatta tttttctgaa aattgtaaat tcataaacat tattttctgg 214620
acttttcttt ttcctccctg tggtcatcac ctaccattta tctgattatg actcaaaagg 214680
aaacatgtgt gttgatttag actgcttcaa cattccagtt ccaatctgaa gctatctatc 214740
ttcccaaatg gaatgttatg cagacctctt gtcctccctc ctgcttgttg tggcagagat 214800
ttatacttgt aatttcccag aacatttgaa ttagagatgt gagccccgat gccaactgtc 214860

-continued

```
tacaggttga agttataaag gtaaaaactt ggtccagcaa atcttcctct cctttcactc 214920
caggattcac ttttcttagt gcccaagtaa tatttatgag gctcttgtta tttagctgtt 214980
gtattatatt tatgttaaat acatttctaa caaattctac tgcatttaca tttattattc 215040
aacaagacat cacaatatga tagcagataa tgatgaatct ccagataatt cttaccgcta 215100
agtcttcagt tgtctaaagt cacacacaca cacatacaca catacacata cacacatatg 215160
cacacacaca gagtcagagt ttggattacc aaatgagaaa taattcctta gtgtgtgcag 215220
tactttttgc tctcaaatgt ttcttttctt cacacatact tatttgaccc attcagctaa 215280
aagcaacatg catcttacta attctataaa tgtgtatact agagttctta cctttttgaa 215340
agattaatta atacagtcat ggctaattat ctgtaactgg ttatatgagc aaggccatta 215400
tacacagtga acattataaa gataatcatt tttctttagc ctctcagcac aggtcaggat 215460
aaaaccgtaa tatccttcat aaataggaac actggccatc actggagagt aaaatgacca 215520
ctggtccagt ctggtaaata ttcgttcatg gttatgctct taaaaagtgt ttaggaaata 215580
agagagaaaa aaataggaaa aaaattacaa aaaaaaaaaa acccaaacac atatagactt 215640
gaagagttgc tctcagatca aaatatcctg caataatctg aagtagaaaa gtatcattat 215700
gacctaagaa ggttcatgaa aatgtttctc atcatagtag ctcagaagga ctgatttaga 215760
atgttgccca tggatttctg tttgcttgcc tgtgtaaata aatacatgta tagatggggg 215820
agaaatttga ttttaacaca tagccttagt gttcaacttt aagttacata agatgggtct 215880
ggggacatta tcttaaattt ggatttctga aaaatatgta ggtctggctc tgaaatctga 215940
gttttaatcc atattctaaa aatttgcaaa ctaaagcttc ctcttttttc ttcacagagg 216000
cttaggcaca tcatgttgaa gggagcaatt tgggaaggta ggcaaagcta taatcaatca 216060
accaaggctg ctgaaagtcg gggtgaataa atactcaacg atcagtctat ctaatgtaca 216120
tcaaccctaa cttattataa aagatcgtta aacctttgaa aggtcaatgt atatactgct 216180
atctatcaca ggcgggcacc attcattatg tcctgtcagt ggctctccac tggccaaccc 216240
ttcaaggtgt caagccgaga cgctcagagg ccatgtggtc atgagggccc aagcttcctc 216300
cccaaatata gtttttattt tccatctcat tctattgcct tgcctttttt ctactttggt 216360
ttctcttcct gcttccctca atttggaagt ctctcatttc cccatgaacc acagacattc 216420
ttcattaacc aagttaaggg ccatgccttt tggggggtta ttctttagct attcatgcct 216480
ctgctttgtg aattccattt caaccaattt ttgttttcat ttttataaat ggtattgttg 216540
ttgttgtttt gtttcctctc cgctacgtcc tttcagccat gaaagatgca tcttctactt 216600
ttatattccc ctcaatatca tatatagcaa atgctttata aaaattataa taaagcatat 216660
tttaggtttt tttgtttgag gttgcttttt tttttttttt ttgacagagt ctcactgtgt 216720
tgcccaggct ggagtacaat gctgccatct cggttcactg caacctccat ctcccaggtt 216780
caagcaattc tcatgcccca gcctctggag tagatgggat tacaggcaca caccaccaag 216840
ttcagctaat ttttttgtat ttttagtaga gatagggttt caccatgttg ggcaggctgg 216900
tctcgaactc ctgacctcaa atgccttggc ctcctaaagt gccaggatta caggcctgag 216960
ccaccacacc tgaccataaa gcaggtttct taaacagcaa tctgtagacc agccttatag 217020
gaattatctg aagtgtgtgt gcagtatgca catttctggg ccacacccta gacttgctga 217080
acaagaaact atatttttaa gctagaaggg agacacatat atgccctgaa gtttgaaatc 217140
aattgaccta gaaacatagt ttccctaagc agtccaagca taagaatcat ttgaggcagc 217200
tgtaaaaact acacattcca gatctccgtc agatcttcag aaggaaaatc cctagagcag 217260
```

-continued taacatggga atgagccttt ttcaccccac tctggctcac tagatcattc taaccatgag 217320
gcaaggtgat gaaactttct ctaaactatt agtagtgctt ttccaaatgg ataaaagcac 217380
attttgcaga ataatgtaat ataattattt tctcaacatt ttgccttaat tataatcagt 217440
ttcataattt aaagcattca tagtttgaga aatgtaagcc aaagaataat gcatttgttt 217500
tctaaattat tatcccctga ttgagttagt agccttgtag ataaactgca atagcataaa 217560
aataacaaaa tttgcagctg ccaaaattta tcctaccttt gacatttatg gactggtggg 217620
tgtgagaaag ttatcaaatc cctaggaaat tcagtttcct ctttaaaaaa aaatggggac 217680
catgatacct aacttgcaag aaaatagatg tagcacacta caatgtgagc cacaatgctt 217740
tatttattca aaactctaaa attccagcaa actgagggaa agtgtgaaag gttcatgggg 217800
ctggccgtaa gagccttcgt gtacctcttg gttcctctgt gccagcaaac agaagacttc 217860
tcttcacaag accacttggt agcctatgtg gattgactct gcattacaga tctctgactt 217920
ccatactggt ttgtggctgc aatagaggac tcttcacgtc tttctaaccc tcctcaattg 217980
tagaaacatg gaacagcaac attcttaaat gctcatgtac ctttattaaa gtattatatt 218040
tgcagtgatc atttaataag tagataggct gaatatttta taatcttttc tgagccaatt 218100
gtttgtgtgt gttttgctga aaatgacctt tttaaaaaat agccataatg tttatagagc 218160
ataaaataat aaaagggaaa tgaaaaccac ccaatgaaaa tcactattgc tgctttcaaa 218220
tacatgtttc attttttcc tagaaatatg tatttttgtc ttttttaaa tggaaagata 218280 ttacatagtg atctttccct aatgttatat catgtgcatt tctacattca ttcaaatagt 218340
ctttgaaaaa tgatggctaa taaatactta acatttctta ctgtaacagt tgcgtgattt 218400
gtttaagtgc tcttctatta ttggacattt tgttttcttc tgttttacta ttataaggag 218460
ttttaaaatg ctctcccaac agaaaacctt gattgcatct ttaattacct tcttagaagt 218520
catttctaga agtgatatca ctaggtcaaa aggaggaatg tttcttaaag ctcatgatat 218580
atatctcgca attacttctc agaaatgttg ctaatttaaa ctctatcatt ttccctccta 218640
cccaagaagg aatttcatta tatccaatat caaagcatta ataaattttt aggttattgt 218700
ttaataaccc ctaaagaaaa tttcatgctt taatttgtat gtttttcatt aatattaagt 218760
ttgctctttt gtcatttact ttgtttctgt gttttctcct tgtccccttt ttataataaa 218820
aagccagtgt tttctcagtg atttgtaatc acactgttta tttggagagt aaatccctag 218880
ctatattagt tgaacatgtt tttcctaggc tgaaatttgc ctttaaattt atttagttaa 218940
aatattaata tttattttga tagacatatt ttttcttctt ctgaacatct tttaaacatt 219000
ttattataaa catttttaaa cattcataaa agttgcaaga attgtacagt gaacacctga 219060
tatttaggac ttctattctt taaaaaatat tttatcattt tctttataat atagctaatc 219120
atctactgga aatttttata cttgcttata gtcaattatt tttccttaat cccacttctc 219180
tgaatttaat caaaagaaat atttgctaaa gtataagttt cattccaagt aagttcttca 219240
tctgccttgc cttccgatgt accccactat ctggaacagg acctatcgca ttgtaacact 219300
cactaaataa ttgttgattg aatgactttt ctcaatgagg ggaaattttt cctgctctag 219360
gagaataaag atgactcttt aatatgttga ggcctcaaga ctttaaaatc tactcggtac 219420
aaagaagcat agcatactct agaaccagta agagataact ggcttttttta attagtatgc 219480 taagtttttc aaaatgtatg ccttaaaata tgagagacat caagtatctt ttatctacaa 219540
ataagcaaag aacttgtgga caaactgtca tagtttctgg gtaatggttt gcatctttta 219600

-continued atggcaatat cccatatctg ggagagaatt agaattcaaa acattttcaa ttccttcccg 219660
aaaatgatga gctaatgttg aaatgcctat gaagacagaa gaacaaaaga aaatgttgca 219720
ggctaaggta tctgacaaga atggagaaaa gtgtgtcaca gattgtaaaa tttagctcat 219780
tgagaaggga acagaaaaat gatgcatgat acttcaaaag gggaaaaaa gtctgtcatg 219840 aagcttctga gtccagattg tctggatgag cagaaatatt agaaacaagc taatcactgt 219900
ctgtctttta ctctcccagt taaaaacaaa agggaaaaag aagccactcg gtatttccta 219960
cgtgtactaa tgaaaaaaac ttttattgtt cctttctcag gagttgtgga gcaaaggtaa 220020
ctttatcatg tggttgcagt cataaccact tgtgaaactt aaaataatga tgcctagaca 220080
ctattgcaga ccaatgaaat caaaatctct aagggctggg tacggtggga gggttggagg 220140
cattgatata aaatttctgc aagtcatcct agtgtacagt tatgaaagca aaacattgga 220200
agaaatagtg cagcaaggaa ggcatggact agtcaacctt gcagagtgtt cagttctgtt 220260
ccagaatttt gttcgtatac aaccatcatt caaatgggag caaagagaag aaaacgcttt 220320
ccaaatattt ctgatttctg ctaattctca cccaaatgtc aggttcatgc atcatttttt 220380
gtggaaaagg gtaagggagg tgttcatgat gagtcaggtt tttcctttgt atgttaaaca 220440
ctgcataggt taagctgata cgagtttaag gaatacttta tttacatgaa acaaaataaa 220500
gcaaaaacag gaataaagca cctagaccag gctctagagc gttttggtcc ctaacttttc 220560
tgctgttgat gttctgcaat ataaatgaaa tcaagtattt ggagctgtcc tgaaagaaca 220620
gattctagtt aagggggcaa tgagggagag cattcttcta taaattgact ttctaaatat 220680
atcatgtttt tcataagcac ttcataaatc ttgacacatt tctttgaaag tatattatca 220740
ccactttata ggcaaggaaa ttgttttgga aagcagagct gggatttgaa ctagcattgc 220800
ctgatcctag tgccttatgc tcttataatt actgttttcc acatttactt aacctttttat 220860 caatttttga catttagagc atttctcatt tccaacaatt ataaaattgt tggatggttt 220920
catgtctgta ttttcttccc catgtttgga gttacttctt tggaacagaa tctcagaagt 220980
tattcgagac tgtgacaagg tttatgtttt ttttttttta catattgcca aattgcttgc 221040
aaaggagttg tacaaaatta caatgcatcc agaaaggtat gatagctagg tctcaagaat 221100
atttaattat tttcaattta ataggcaaaa atatatatat tttatctcat ttcttaattt 221160
tcatttggtt tatcggtgaa tcagggcatt tccgtgtggt aagttggttt gctttgtcca 221220
tttatctatt ggaatcttca tttatgatct ttgatatgac ttgatttgta gaattcttga 221280
cagttgtaat gtatgttttt tgtggcatta tgttcaatgc ctgtctctcc agatacacag 221340
taaggcacct gagaacagat cttgtacctg tttggtttat ttttgctttc tggtacctca 221400
tactgtgcct ggcacataat atgtgctaaa gctatacatg atcagaaaga catatttctt 221460
tccccatata tgggagaaca atacactgga tttttttata gtgttgattt tatggttgtt 221520
ttgagtggtt tagggcagta ccaaggctag tcagtaacct tcacaaagcc attcattcgt 221580
aaatgaaatt gtcactgagg agtcataaaa tttaaaaggc aatttgaatg aaatgggaat 221640
aatgtagaaa atcttcaggg aagaggtgag atctctttac tgataagacc ttttcaaatg 221700
aagaaaatag ttttgtggta tcttccctgt tgggggttct gctgataacc ttttatagga 221760
ccaagtggaa caacccatat taagtaggct gtagtggact cctaattagt ccaattaatg 221820
tgatggcttt aatttgtaag agatctaatg gtgtagaatc tgatttcttt gaaatcactc 221880
ctctctagaa tgtaaaacaa caatgaaagg cagctaaagc agtcctggag tggctaagta 221940
ctgcatttag ttattgtatt tcccacccct tccctcctta aagagaaaat aaaaggtatt 222000

-continued tcttcctcca tattattccc cctggcatgc tgcctttgtt aggacaacag cagccaagag 222060
cagatttgaa atgactcctc ggcattttct taagatgagt ccagtggagg ctcttcaatt 222120
agtagtggtc atgtgtgccg gggtcaatat tccagaatac ttaagttttt gctcttttct 222180
gcagaaataa acattattat tgttgttgtt attaaaatcc aaaaggaaac tataatgtct 222240
gaggcaaact gttcttgtca cagcctgcta ttcccatgag ccgagaagca tcacaataca 222300
ttgcctgctg tctcaaccca tggaaagtct gattagctct ctagcaatct gatctccaga 222360
aatcgccctt tccttactat ctcaacaccc tttcatggaa aacagtatgc gtgcttctct 222420
gttcagactc cactgtaaaa tttttaagcc aattcccatg ggattctgat ggtttttatg 222480
taagtaaagg aaccaaagat tttcaatgag aactattgag cccgacaaag gcttactgat 222540
ttatgtagtt accacctgaa gtaagaaagc cactttgata tttaaaaacc attctaggcc 222600
gggtgcagtg gttcacgcct gtaatcccag tattttgaga ggccgaggtg ggcggatcac 222660
gaggtcaaga gattgagact atcctggcca acatggtgaa accccgtctc tactaaaaat 222720
acaaaagtta gctggtcatg gtggcacgcg tctgtagtcc tagctacttg ggaggctgag 222780
gcaggagaat cgcatgaacc tgggaggcag aggctgcagt gagcccagat tgtgccactg 222840
cactccagcc tggcaacaag agcgagtctc tgtcacaaaa aaataaacaa ataaaaataa 222900
aagtaaacaa aaactattct aaattaagtg gctggccttc cttccttctt tcttttcttc 222960
cttccactgt ctttagcata tgttttggac aacttcatgt aaataaaatg gaagcacaat 223020
tgggagccac cataataacg tcagtaatct ggcaggaaat tttctacatt agtgattaat 223080
aaacaatgta tttttaatgc ccaaagttgc atttggcaca agtgtttgtt cagtgtttct 223140
aaaacaatta ttaaaactaa ttttaatcat ttagaacttt gctggttaat atagtagcta 223200
ctagtcacat gtggctatgt agcatttgtg actagcccaa actaagttgt gctgtcagta 223260
taaaatacac actggctctt gatgacttgt tattaaaaac atgtaaaata tctcattagt 223320
attcatgttt attgcatgtt gaaaggataa tagtttatat acataattaa aacatcttat 223380
gaaattcatt tcacccattt tgctgcttct ttaaaaatgt gacttctaga aaatttaaaa 223440
ttacatatgt gaaattgtat tatgtttata ttggatagca caagatagat atatttaggc 223500
tctagccctg ctggagttcc ccactaacag gatgatcaca attctctatc cagcagcaca 223560
atgtgagtgg aattatgcag gtaaacgtgt gctagtcagt tacagagcta gacctcaagg 223620
ggagcagatc atagcctaag gaagtagacc tctcaattcc cactgcctgc atgtcccaga 223680
cttagaacgt tatcatccct accatcgcaa acatggttgg gatgatctgg tcccagttga 223740
tctggtcata gtctgagcct caacccttca atctttaatc tgcactctgt gaccaataaa 223800
aattttagaa ttctcaagca agaacttgaa tactattttt ggcattttta aaacaaaaat 223860
ctgtaatggt tattaattga tgtaggcatg gttgaataga cagttttctt tgaaaacctt 223920
tgccattgag caaataaata cttaaaccaa atttcatcaa agtgcagtcc tgctgtagca 223980
gaatcaaatg caatagttgt ttaaaatgca gatttcagag ccccaccacc aataatgata 224040
atttagtagg tctagaccag ggaacagaat ctgagtttaa acagcatcat tctagttatt 224100
ctcatgcagt ctaaaatgtg ggaaccatca cttgaagcta tagttgtttt cctttaattg 224160
ttctatttta aataagtaca ttatatagca aatatactgt catatcatta tcctataaat 224220
ttagaggtta ggggtatcta cccaggaata tttggtttct ctattacttc attgtgagaa 224280
cctgaacaca atttactgtc acagtttccc aacaaatcta aaaatttact ggtgatatta 224340

-continued tttatacttc taaagttatt taataaaaaa tatttaatta acatcttatt ctattatttg 224400
attatattcc taaaatgtaa acttctatga tagttcatac agttacaaat atccagcttg 224460
taaagaacat attagaaaga ctcatttttg ttgatgggga gggaatccca agaatttgcc 224520
attccctgga aatatattca ccaggaattt cctagaattt atgaaattat accacataaa 224580
tttccaccca tgtctaccca ctggtaaact gaggagagag aaaaatcagt gattatttgt 224640
ggattaaaaa tgagatacat cagacagcaa catgtcctag gtatcaaaac aaatcagaga 224700
gtattaacct ggagtcgtgt catgtaacac agaggaaaaa acagtgcatc atgtttcaaa 224760
gcctggattc ttgtttggag tcatccacta acagtgatgt gggcatctgt ttcctcatct 224820
gaaatttaag actgtgagac aagatgatac agagacatcc tctcagttct gacagtctgt 224880
gtttttcatc cacacttgca gtgatataga cctatcagga gggacgactg gaatcctgac 224940
tagattgagt tagatttaga gcatctcaga gataagcctg cgtgtggtct ccttacagga 225000
tagcaaaaaa tattgcaggg cacgcacata ggcaggagtg tgaggtttct agaatgtcat 225060
ggctgctgca ggataaggtt gaattgtggg tcctggaaag aggtgaccag ggagctcagc 225120
tgtgactgag gatgaggtga ttaggggaca gtttctgagt caggctgcct gaggcagggg 225180
agagggcctg agggcagggt cacttcctgg agcattacca gtcctgagca tcaccactta 225240
aacatcagag agaaaggaag aaaggcgata ggtaagtgac acttcccgat atcgccttgg 225300
gagaatggct tttgctttat ttttcttttc ttttattatt ttcaaaagaa aacatcagga 225360
aagctagtca agccagctgc cttttgagta aacaaagaac cagagttcag ggagcaaggg 225420
tggcagtaaa gatggataag tcagagggta ggtgtttttc tctcaacatg aattgtgaga 225480
agtttctcaa aacttacatt ataaataaat gatagtacta acattttttt ctttttttctt 225540 tcttttctat tgactgacca tgacacttct gtctcacaat tcctcaccat tttgccatga 225600
ggttttctcc ttccccttgc ctaggttcag aataaaagat gcctatatat taggtcccgc 225660
cagaaaaaaa ggcaagaact cacgtgttag taaaacattt aataaacctc agcacacact 225720
tggccaaatt cctggaagat cagagctgca tccctgaaat ttctttttat cttgatccag 225780
ttaactgcct gtttagagta aatgatgtgc tcccacgttc tttatactgt cctccccata 225840
taagcatata cacgagagga ttatacctgc tctccggaag cttataattc agacgttatt 225900
accccttttg gaagtattct ctgggaagct cttttcacta atgttcaatt tcaacaatag 225960
tattactata atagctaagt ttcatttagt gcttagtgtg ttctaagcac tctcaaaagt 226020
gcttcatata tatttaatca ttaactctta ccataactct atgccctagg taatattatt 226080
gtccccattt tacaaataag aaaacaagca ccaagagatg ttaggtgaac ttgcctagag 226140
ttacacaaag aataagtgac tgagccactc attgaaatgc tgctcttgca agaaaacata 226200
aaattgtatg atggtgccac ataacacata cttgacacgg gctttgaagg cagagaagcc 226260
tgggttcaaa taaaattcag ccacatacta gctgcatgat tctaggacaa gttacagaac 226320
ctgaggccat cagttatcat ctgtcaaaat ggagtgaata cttataaagg ttacatgagg 226380
gtcaaaaata atgtataaaa ggagcctggt acatagttgt cattcaaaga gagctgctga 226440
tgttattaac attagttgac tatgtaatat tacttaaaac tcttacttcc tatttttctt 226500
cctactgcaa taaagtttct gccatttctt ctctctgtgt gaagtttttc ttcttcctcg 226560
gtctgtagct ggaatgtgcc tttctgtgcc aagcccactg actcatggtg atatagccca 226620
cagagcaggg tgcaagcaat agaagggcca taccaggcca caacatatgt ctcagattcc 226680
caggacaagc tttgttcacg gcatggaaga atggctggtt aacttaatcc cagggttgca 226740

-continued ttctccgtaa tgatacatct caggccatcg atccatggct ttattttcaa gcttgtttaa 226800
gcaggagcta taaaaaacag agcatcatgc acgtgcaata tggaattaag cctcacactc 226860
ttaccactct aattctctta gatacctatt tgtttgtctt gattttagaa agcagaattc 226920
agtaaagaaa caaattgggg aatatttttt agggttataa tcttccacgt aatgatataa 226980
acgattctgt gtagaattgc tatcttgctg gtgagttgtt ttctgaaata atgtgcccaa 227040
aacagaaatc agcattgttt ttttgaggca attcactgtg gcattgtggc tgctgtgaat 227100
gttctagaaa ttgtaaaata cgcttttgca aacgtagaga tggttttagt tttcttatat 227160
caataagcag taggattaaa tgtaacaggc ttacgagaaa tgagggaaat attcaatgca 227220
ttttgcgata aagagcaaag gaagctcaaa gctccttcag ccataacgac atccttgttt 227280
cttcttcctt ttcctttccc agtgtgtgta tgaaaaccag gaaacaaggg agaatcaagt 227340
gctgggttgg gtgaggttaa gagaatcggg ttctcttcac atttaccttg gacttttcag 227400
gaactttcct ataattcatt taagctcaat aagttctatt atcttctttg gtagagcttg 227460
ttggggggac tatagtaatc ctgccaagaa aatgttatct tgttcctcaa ataacaaaaa 227520
agtgatttgt ataaaagcaa ggttcataat gtaaaatcta agtatatttg aaagaaaaaa 227580
tttctaaaat atttgagtct cgagtaaatt ccttgagctt cacaccatac aacttagttc 227640
ttggtaaatt aaaagtaggg cttctagtga tttgcataaa aactctcaag aggaggacct 227700
cagatacatg gcttatcaaa ctggcacttc atagagtctg ggccatatca gatccttgaa 227760
tgcttgcttc ttaatagtaa ctcctatata gtttctaagg ggtttcggct gtctatatta 227820
tgaggagtgc atgtttttaa gagctttaca ggggtcagga gaattggctt ctctctcttc 227880
atttgcattt aacgttctaa aagttcttaa gctggaaatg atctgagaac tctctctggg 227940
aatctatttc ttagtttcta aataatcaaa cctatcatca gtcaatgcac tgttttatct 228000
tccttcaggc aagtttaaaa tatgtacata tatatgttat agaagctgtt ttttttttcaa 228060
acctcatttt atgagccaat atgtttgttt cccaaagaaa aaaaatgttt gttttcatga 228120
ttttggcaga aacaaatgtt ttctttgggg ctgttcaaat agtcatattt tcaagttttc 228180
ttgcttcttt ctattggggg gagcaccccc tggtggaata ccatgaaaat gtttgccacg 228240
tgttttgact ctaatattca acagacagat gtgttttgca aatattactt ttacacaaag 228300
cacactcaga accattttgc caatgttaat gtcttggaaa attccatgcc ttctttctaa 228360
ttatcaccac agtattcaga atgggctccc ttgttttagg tgttacacag ttgtggtcag 228420
agatgctgca gcagtctctg tgggtcagaa atgagtcggg aagggcactc tggcattatg 228480
ttcctacttg tgggaaaaaa gggacccttt tctcctttcc ctcagttctt ccttctttcc 228540
ttccatttct tcctgctact acaaacaaaa tggcatttgt tggagggtct gactgggtga 228600
gaaaacagtc ggccatgaca gtgcccagtt ataggtaaag cctaaggtac atctctttcc 228660
agagtaacgt ccctgtcact gcaagctggg ggagattaac agaaagggaa tttgctggga 228720
gatattctta atcccccata tccccccaaa tataaattta aattagtact aaaaacatat 228780
cagattaatc aataagcctg taatttctgt atcttataga gaaaaaagta tcatccccaa 228840
ggtaactgga aaggatgggg cactattgtt tatcattgct gttgtgtgct gaattgtgtc 228900
tcccctcctc ataattcata tgttgcagct ctaactttca gcaactcaga atgtgccttt 228960
atttggaaac agggttttgc agacgtaatt agttaagatg agggtatgct ggggtagggt 229020
gaccaatgtg actggtgtcc ttataaaaaa gggaaatttg gacacagaca aacacacaga 229080

-continued gaacagtatg tgaacatgaa ggcagagatt gcagtaatac atctacaaac cacatttcta 229140
agaagagacc aatcctacca agaccttgat tttgaacttg tagcctccag agttttcaga 229200
cgatacatta ctgttatgta agccactcag tttgtggtac ttggttacaa caatcctagc 229260
aaatgaacct tcctctgaac tcaagtggtg gtcccttccc acacataacc tttctgagta 229320
gagaccagtt tttgtagctg ctgttgtttt aaagtaagga ctgaaacagt ttactgcctc 229380
catcaactat tgcatcatgt tatgcagcct gtattttctt aagaatgaaa ataacgtttt 229440
ctttataaaa gcaagccaaa atggactata aattatatag atgtttcttg gctcacagag 229500
aactataatt catctggaac caagtaggaa tggatctcca tatttttaaa tttttatatt 229560
tttaaatttt gtgggtacat agtaggtgta tatatatata tgtggggtac atgagatatg 229620
ttgatacagg catacaatgt ataataatca catcagcata aatggagtct ctatcatgtt 229680
aagcatttat cctttctttg tgttacaaac aatccaatta tacatttagt tattgttcaa 229740
tgtacaataa attattattg actgtagtta ccccgttgtg ctatcaaata ctagatccta 229800
gtcatcctat ttaactatat tcttgtatac attaaccatc tctacttccc catcacctca 229860
ctacccttcc cagcctctag taaccatcct tctactctcc atctccagga gtttaattgt 229920
tttaacgttt agctcccaca gataaatgag aaaatacaaa gtttgtcttt ctgtgccttg 229980
ctcatttcac ttaacataat gacctccagt tccatccatg ttgctgcaaa tgacaggatc 230040
tcattctttt ttatggctga atagtactcc actgtgtata tgtaccacat ttttaaaaat 230100
ccattcatct gttgatgggc acttagattg cttcaaatta ttggttgttc tgcatagtgc 230160
tgtaataaac atgggattac agacagctct ttgattcact gattttcttt cttttggata 230220
tatacctagc catgggattg ctggacccta tggtagttct attgtaagtt ttctgaggaa 230280
actccaaact gttctccata gtggttgtac taatttacat tcccaccaac agtgtacaaa 230340
ggttcccttt tctccacatc attgccagca tttgttattg ctcatctttt gaataaaaca 230400
agttttaact tgttttattc aaaagaggta agatcatgtc tcattgtggt attgatttgc 230460
atttctctga tgatgaatga tatcgagcac cttttcatat acctgtttgg catttgtatg 230520
tcttcttttg agaaagtcta ttcagatctt ttgtctattt tttaattgga tttttagatt 230580
ttttcctagg gagttgcttg agccccttat tctagttatt aatcccttgt cagatgcata 230640
gtttgtaaat attttctccc attctgtgga ttgtctcttc actctgttga ttgtttcctt 230700
tgctatgcag aagcctttta acttcacgtg atcccatttg tctattttta ttttggttgc 230760
ctgtgcttat ggagtattac tcgagaaatt tttgcctggc ccaatatcct ggagagtttt 230820
cctaatattt tctttttgta gtttcatact ctgaggtctt agattttaat tccttaatct 230880
acattgtctt ggtttttgta tatggtgaga gatagggttc tggtttttac ttttctgcat 230940
agggatatcc agttttctca gcaccatttt attgaagaga atgtcctttc cccaatgtat 231000
gttcttgcca cacttgtcaa aaatgagttc actctagatg tatgaatttg tttttgggtt 231060
ctctattctg ttctgttggt ctatgtgtcc gtttttacaa cagtatcatg ctgttttggt 231120
tactatagct gagtagagac caatttgaat gatctctgtt actacagctg aatagaggca 231180
aatctgaatt gtctctactg agccacagta acttcccatg gtccccaggc catcccatgg 231240
tctcctggcc aactactttc aaaagcactt aagacaaaga tggaaggtag atagcaggtt 231300
ggatgctggg caatatatgg ccagtctccc aagtcccaag tgattcttcc ccaatacaaa 231360
gtcctaacaa taactttcac tgccactgcg cagaacctaa atgtaatggc aaaactgcta 231420
aagagctcag agtctctctc catgttctgt gttcccgata acctgagtgt ggttattcta 231480

-continued gcaggcaaac aaaatagaaa cagagatatg tgtcacctga aatacctgtg ttggttggag 231540
ttttcttcaa aactcttcta cctgtctttg atacagcagt tcattacagc gagtctcatc 231600
ctctactata caaggtcatg attctcttgc ccaagggact gtcctccatg ctgttcccca 231660
aatacagcaa aacctttcc ccatttgatc tgctcattgt acagtctgca tctcccaaag 231720
gcattctctg ttggacattt atggaaatcc acttcatctt tcagatccag cttgagtcca 231780
gcctttaca tgaagccttt cccagtcata caaaaccaca tctatgtctg aattcctgtg 231840
agacttgttg actatgcttt agcctctgtg aaattctctc ccactttaaa tagcaaagtc 231900
caataaaagc aatggtaact cattctattt caaaggtaca acttacagta tatttcaggc 231960
tgctggggat acagtgggta agcaatacag gcttacttgc taaaataaaa tgaataatac 232020
taattatttt gatggatatc tgtctccaag ttatatacat atatgtgaat aatgattttt 232080
aatttttat taatgagttt taatttgcac tatgtcatat aatccttaca gcaaccctga 232140
gagatagcta ttcttacaat agcattgatg gtttagaatt agctaaaagg tagtctaaaa 232200
cagcttcaga gtattaggat ttcaggcata tgatcctcac aaattggtat tttgtagaaa 232260
aactactcaa gaaaagaagg aaaactctac tcagagagga actttcagcc ttcagagttg 232320
tttttcccct cttcatcttt cttctccttt catttaaatt cctggttaat gaaaccccca 232380
cctcactatc atccttcaaa caactatgca gattgcactt tcatcacacg gtctgtctta 232440
aacagctctc caaaagaaat aaaaagaatt ctgtgctatt tactttttt ttaaacgatg 232500
aaacaaataa caaggagaaa gagccatcta acaaaccttc accctagcaa aatgctgagc 232560
tgcttgcagc taccagccag tttgattaag gtgtcatccc tcctcttcat ttatatttat 232620
tatttttgga agactttttt tccctttagt gtttgtttat cttttccaat tttttaaaag 232680
tcatgaatca tagtttgatt tacaaccttg ctcaggggag atcggcaact ctaatgaagg 232740
agccgtctgc aagtgtaatt aatacctgcc agacatttta ccacattagc gtgccagtat 232800
cctgggctgg ggaagaatga agccgggaga cacatgcacc gagctatgca gccactcaca 232860
cagtgcatca gcagagatta gtgatatgaa gtgggagggt gcagaggatc accaccccac 232920
tggtcaagct cagaagactg gaagaacagg caggtgagag gagcagagag tctgagagcc 232980
tggtgaggaa gatgagcaag gtgcatggag gggggatgtg gagacagaga cactgcatgt 233040
ggctgatgga tcactcccat ttagaacaca aaaataaggc agcttgccag agcagtttgg 233100
gccagtttca ttaaaactct tcattcatca tactgaaatg aggcagtatt tgttattgca 233160
cgggtgccgt tctagcacga aagctattcc aatactaagc agtaattcaa gaaaggcaga 233220
gtagcaggtg ggaaaggaga ctgaagaaag gaagaccagc atgcattggt gtttgcccca 233280
ttctctccct cagccctgca cccagcagta cataggcatg tggaaaaggc ccagaacctc 233340
catcatggtg aagagccagg aacccacatt ccactctaaa gccactccca tgggacaaaa 233400
taatcagaat gatcatcatc tggcttctca gtagggaagt tacggaggag cagctgcatt 233460
ttcatatgtt gccttaatgt gctcatggaa gaataagttt tcataaatgt acaaaaataa 233520
ttataagtgt gtgtgtgtgt gtgtgtgtgt gtgtgtgtgt gcgcgtgcag aaaggtgttc 233580
ctgcccatcc ttaaggtgaa atacaactat gaaaatggtt aaaatgatag caccctaaaa 233640
tttccccagt tatttttgtc ttcttcatca taaaactctt ttgtttgctt ttaaatacct 233700
taatggggaa gagaaaagac agaattagat tacaatgtaa aaggtctgca ctaataattg 233760
ggtctaacac tggtaccgat acttccttat acccgattac acagacgaag agaaaagaaa 233820

-continued aaaatagcta cacaagaaag gcctgaccat tgtttctcat gcatcagttg ctgcgtccct 233880
ggccatgcta cgccagtctt ttcttggtac aatactcacc ctgagatatt tctgacagtc 233940
agattatgaa agcttatgta gtaatgttgt aggtgttata aaatgaacaa actcgcccac 234000
agctgtaaag acatgactgg cagtgatgtt ccaagatgag gagtgaactg catatatcaa 234060
acttgtctcc agccttttga tcgattcttt gtttgctgcc tgatgatgcc aagactgcat 234120
ctggagccaa agcttcggta gtagctaacg gatagcatgc attgttaaat tacacacaga 234180
actgctgtgg aggattgcga ctatagtagt ttattttcca ggattgaggt tggcatctga 234240
ataacacaga atccattttt cagcttggaa tactgaccag aaatatggca tctcatatgt 234300
gatatgaaga attatttaaa ttgtgttcta attttgttcc ttaacattaa ttcatctctc 234360
atttatttac ttattcagca gcaagagtgt ttctaatgac tgtagggcaa gttgtaggca 234420
agggagatgc agagatgaat aagatacaat ttccctgcca aaggtgtgca tttgagttat 234480
gtttacaaat aagatatcca taataagtga cattagaatg ataaaaggat tctatgaagg 234540
agactaagtg ctgacaaaat atattctcac agacacacaa atatacacag tctgtcagct 234600
tatgggtgtt gcaactatga atttggcttt aaatactaac atcaagaata caatagtctg 234660
acctcatcca tgggggatac tttgtaagac cccccagtgg atgcttaaaa ccattgatag 234720
cagcaaccct tacatccact acgttttctc ctacgcatac ctatctatga taaagtttaa 234780
tttataaatc aggcacagta agaaattaac aacgataact aataataaag tagaacaatt 234840
ataacaacat gctgcaataa aagttatgtg aatgtagcct ttctctccaa aatatcttat 234900
tgtactgtat tgcaggtaac tgaaaccata gaaagcaaaa ctgtggaaaa ggggactcta 234960
ctgtactgca tattattttc aacattaaat taaaaaaaac ctccactgaa aacacaatct 235020
cactttagcc ctgcatttga ctttttttgct gtttgacctt ttcaaaccct gaagtccaac 235080
tatcttacat gagactcacc taagcttcct acctcctttc tgttctctag gataaagctg 235140
ttgatgaatg gccaaaaaag gacaagttaa ggggaaaaat tggaaccaaa gagcccaggt 235200
aattattaga ctgaataatt gccttctgca aaaatgagtg ttgattgtac atataaatta 235260
ctagttaaca aaaaatatta atatgtaggt ccagaatgaa aattataaca ttcaaaatag 235320
gtaatttggt gagatggaaa tatgccctat aagtcaaatg ttaaaaagca aggttatcat 235380
tcatttgatg tcaactgatt aattataaac tcactgtagc ctagaatagc tcactaatag 235440
gaaagcagtg gctccatcat tttccttatc actgtcaaaa aataactaaa ttaccataaa 235500
agagtggcgc ctccatgtga ggtcttcctg gcccattatc aagctgccca acaaaatata 235560
tctacttgtc ctgctagaca taacctcaac cattttttat ttattgtggt tggggagggt 235620
agagatggta taaataaatc tatagaaaaa aacccaagcc ttacattagc taatggttta 235680
accttcttag aatttccact gctgtcttta gagatgtgga ttttctatat atctgaaaaa 235740
gtaaaccaaa gaaaaatata ttaagcttcc tttcttgtca tgcataagta gcttccaagg 235800
aaatagctaa tgctcaatga aatggacaag agacacagta agcaaggtag gatagggctt 235860
agagaaacat gctgagttag cacatttcaa attattaaat tagattgcct tttggaggaa 235920
tctatctgct accttacatg aattaaagat tgactagtta taggacgtag aagataaaag 235980
agaactaaca tagtatgctt tcagcctctg tgatatgcca ggaactatgg acatgctacc 236040
tcattgattc ttttatgaca tattttaaaa ggtaggtata ttccatttaa taggcaagaa 236100
aattgaggct tagaaagttt tagtaattta atcaaatttt tgcagctaat aaatgatgaa 236160
gttaaaatga aacctctgtc ttacctactc cactccacag ttttcctccc tagaacacat 236220

-continued tattttaaca ttttaactgt ttgcctatat tggaagcagc agggaacact gaagacacct 236280
gtacagccct gaagaacaac tcagtttata cactgggtgc acacacacac acacacacac 236340
acacacacac aaattcacat aaacatgctc catcaaaatg caagctgcat agtcaaaaac 236400
acaatggatt gatttactat caatagagat gtgtcagact tgctttagaa aatccttgtt 236460
aagggggatt tttcatctca ttttgggcca cttttatttt gactggcaat cttatctcag 236520
cactttggag ttatttctca attcagtacg ctttacatca ttctgcagcg aacaatgaag 236580
acccatcttt taaataagat gaacagcagt atttcatgtt accataggtt caaatctcag 236640
tgctgctacc ttttatctca gtgaccttga aaaagttact gaaactctat gtcccaattt 236700
cctcattcat aaaataagaa taatattaac atgcttacca tgaatggtta atacacgtaa 236760
aatacttaaa agggtgcctg gtgcccattt actgtgatat aatattttgc ctttattata 236820
ctgataacat agataaagca tatagcccgg ggcctagaac tgaacagggg cttaacagtt 236880
cctattttcc tttcctcata tgaaaacaca tagtcacttt ccttcagaaa aaaactgtag 236940
ctgaattaag ttcattcact gttcaatgtc cttttatttc ttccactcct ctaactctcc 237000
agtatcccta ccttagattt ttactactct tgggaaacac gtatagtgtt atttacatat 237060
gccctcacat atcccgagag tctaattact gccattcatg ggctaaccct ggaactctga 237120
tgggttcatt ttatgataaa aataagaaaa tatatcagta taaacccctg cttaaatttc 237180
actgagtctg aattacagta aaaaataaaa agaagaagaa aaaggtaaaa tgacaatcgc 237240
tgagctggga attatcttaa atcttatcct ctccctttgg catctgatgt ttaataatta 237300
tgtgatggaa cagaacagac taggctctgt ttaaatattt acattctaag aattttttaa 237360
atgatgaaca tcatttaaat atatttcttt attttgagct gaaaatgtcc tctcttccat 237420
tcattggccc tggatttgcc ttccatggaa atagcaccca cggttgtttc tggtatttgt 237480
agtagatgct gtggtgattc tctagaccct cacctgtagg agaagaacat tcactccccc 237540
actactgagt ctctcactga gatatcaatt gagtcttcct tcaaagtcac aacctttctg 237600
ggacagcctt tgcctaatga caggtctgtg cggggccata aagtcctggc ccctagcccc 237660
atgagtcctc tgttataagt aaattgtgga tcagcaactc tctctgccca atcatgccgc 237720
cttcactctc ccacaggtgt taaactcaat atcactttga atgaactttg gtctttgtct 237780
cagagtacgc ttcctatgga acttaatgag taatagtgta tctaccactt taagtttaaa 237840
ttgcactatt tccaagacct aatacgttac tcatttggtt tttcacttat ttatctgttc 237900
attcattcat ccatttagtc attcatttct tcattcaaca aaaggatttt gaataaggtt 237960
agcatatatg tatatggtaa catgctgagt accacaggga cagagaatgt cctttcccaa 238020
cccttatcct gatacagctt actgtctacc aggtaggatt gggtaagtat aacagtacac 238080
caaccataat actagggaga aaatagtgcc aagacagaga gagagagaga gagacagaga 238140
aagagagaaa gaaagagaga agcaagcaaa ttaaattcaa taaataaata aaaccaaaac 238200
aaattaccat cgaacatcat cacaggtgat atggtttagc tgtgtcccta cccaaatctc 238260
atcctgagtt gtagctccca taatccctac gtgttgtggg agggacatgg cagaagataa 238320
ctgaatcatg gaggcgggtt tttcccatgc tgttcttgtg atagtgagta agtctcatga 238380
gatctgatta ttttataaag ggcagatccc ctgcacacac tttcttgcct gccaccatgt 238440
aagatgtgcc tttgctcctc tttcgccttc tgctatgact gcgaggcctg cccagccatg 238500
tggaagtgcg agtccattaa accttttttt ctatataaat gacccagtct caggtatttc 238560

-continued

```
tttgtagcag tatgaaaatg gaccgataca agaaggatgt atgtactcac atgagtgtga 238620
taacttctta aagatataac tttctattga atcttttcta ctaaatccta ttatttagag 238680
tagtgttttt tcctgcaccc atgccattac tttcctcccc acctgcagct ctttatggat 238740
accttttctg tatacaacct tagaccctta tctaccttcc taggccctta cgattttcaa 238800
gtgtttcaaa tttgatttta tgcctgaagg atattgacac ctttctttcc cttaagcttc 238860
ctactaatcc actttctccc tttggtactt ctttctatat catctgaagt ttgaagagaa 238920
atgatatctc taatgaaaat cccatgaggg agaaggtgat aacaagtcaa gccttaaatc 238980
tctgctcata tctgccagaa agttgtagta aaatattgta gtctttcatt gacagaagag 239040
tttaagatta aaatccaatg ctcataaaat ataccaattt tagtaaaacc aactaacatg 239100
acactaagtt atatctgttg aaaaaaattc attaatgcaa tgagttagaa gtataaattt 239160
taaaatgaat aaatgaataa aactaattca atagtccact ctaaacagat tttaaagtat 239220
gattagcagc attacagtta aaatataatg catttatgtt tgggctataa agtattacgt 239280
gtaaatcata gatgtcgatc aggcaaatgt catctatgtc cactgagcac aagatcccag 239340
gtttttttcct tgatagcaag agaatctaaa aaagaaaagt gtctagaaaa tgtccactgg 239400
caataatttt acaaatcccc cccccccaaa aaataaactt gcaaattcca ctgaactggt 239460
cacataagaa atataaacat ctgcataaac cttttaaaag tataggttat atgtttttcc 239520
ttttgttaga tttttcttgg taaataaaaa taaaaagttt ctaacatttg actgagacgc 239580
agtcatcttt gttctagtca atgatgaatc acaggtatct agaactgtgc caggtaccaa 239640
gtaggcactt gaattttgtg gaatgaatga ataaattcca tcttgacatc tgtaggcata 239700
tcctctgtca ctttaaatat attactcaac agagtagtat atttgaagta tatccttagt 239760
catttattca atatttaaca aatatctact gagtcatgac ttaatgaaag gtggtatctt 239820
ggatgttaaa ttcaggtttc actcaagggg agaaaggtat tcctagttaa gtataatatc 239880
cattaacaca atttgaaact ggaaggtaac actttaaatc tactactcaa agttcaaaat 239940
cattaaactt ttctcctgat tattcctaca caagccattt tattttttcc tcatattctc 240000
tgtggcaatg ctgcttccct gggattttcc ttatgctttc taattaggcg tccaattggg 240060
tgtctgaaaa caatctgaag taggtaacat gcattttaaa ttacttttat ctcaaaggag 240120
acaatatttt aacattccat tattacatta tcatcttgat tattgaagtg gctgttgtaa 240180
tagagttgtt ttatatttta tttgaccaaa tccaaattaa agaaacacaa agacataaaa 240240
tgatgagata tccttaaggg ataggggaga aaagatgaag tagagaataa aatataataa 240300
agtacatatt cttaaattaa ttaaataatt tgatacctat tattattctt gccacacgaa 240360
ataatggaat taactggata atagtgaaga ttccactgca aaaaaaaatt ctacttaaaa 240420
ttttgggttc ataagactag aggtaggttt tctttctaac aataattctt attctgaaat 240480
atcaacaaca tatgcaatgt aaaccagtat aaattttaat ttttttatgg aaaaaaaatt 240540
tatttttgaa tgtggcctct gatttcatat ctgcactgtt ttcttcttgc taccttccag 240600
tttcaaattg tgttaatgga tattacactt aattaggaat acctttctcc ccttgagtga 240660
aatctgaatt taacatccaa gatatcacct ttcattaagt catgactcag tagatatttg 240720
ttaaatattg aataaatgac taaggatcaa gtgcattgaa ttataacatt aaatatgggt 240780
gggttactac aaaaggaata aaagatattt tagttgatgt aatcaaaatt atagtactaa 240840
aataaagaac atgcatttgt aacagtttgt atgtctctca tatttcatac catagtttaa 240900
tagttacact ctagtagtaa atactaagct atttttactc ctacttacat atagctgtgt 240960
```

-continued cttctatgtg tttgcacatg cagtttgcct ggaatgtcct tcccatctca cccccggcat 241020
ctggctgcaa tttctggtcc tccttcagat ctcaagttag aagtcacacc ttgaaaagac 241080
ttagtagaca cacccaccct tttaggaggt tttccgataa ggcatcatac taccctactc 241140
atatccctac aaaaagactt gaacgacata aggaaataaa ctttaattat atgtctttct 241200
ctttccctta agattgtgag ttccttgaaa gaagaatctg tgtcttgtgc accattgttc 241260
ttccttacct gtaacagaaa ccctggcacc aggtaggcaa gtctttgata aatatttctg 241320
gattgattaa gttgtattta ttcattaaat gtatgccaat ttcctttgtt tttgctacta 241380
tcctagcatt gcatgttact tccatgaagc tgatctatga aagcaaaata ttaacatctt 241440
atggcaggta atttttgcct tgatagcctg tgatgagtta ctgactgctt gttagaaatg 241500
tcactgcctt gttcctgtta ggcttacagc tgacatgttg aaaaatttat tcaatgtata 241560
aaaaagctct acaaagatat tcattgtatc actgtttata attgggaatt gtttggatag 241620
tcgaatgagc tgtgttacat ccaaactatg aaacattatg caacaattac gaagaagaag 241680
gtagatctat gtcttataaa ataaattgat attctactta aaaaaaagca aatggctaaa 241740
agatactttc agtacaatac catatttaaa aactgcagtg tactttctgt ggttaccata 241800
gaggtatagt tataacagag gcatatggac atatggaaaa taaccataga actcatatta 241860
aactcactta tgtgatcagt ggctacatct agaaaggtag agaggggacc aagaataagg 241920
cttggaggtc aaaagcgact tctttgaaat gttttttttt ttatggataa tgttttagtt 241980
ttttaataaa gagttcttag ttataaaatt aatcttaaac atgttgatac ttgatacatt 242040
tgaaagataa aaatatataa cctatgaaca attatgtaaa aatataccgt ccatgtatca 242100
atttatataa aggtagaatg ctaaaaatga aaatttggcc tatagtaaac atctctaaat 242160
caaaacattt tctttcataa taaataaaag agaaggaatt agctatattc tattagctca 242220
taattgtgtg gatagtagga tgaaataaaa atgactacat aagtcagaaa cataaaaaca 242280
gccattgatt tagaatctgt tgacatgaag gccaccccgg ctccaccaca tcttgaacta 242340
gatgagtcat aaactccaga gtatccatta tgctaaccta taaagtcaag gtggaaacta 242400
gagtagtgat tctcaaacct acaagtcatg attctcttgg gggaacacac acaaaaaatat 242460 tatattgaag aatatgctgt tatatgctgc ttcataataa attactgtgc agataaatgg 242520
taatatgcag cacatttgtt tgtttcattt tgtgttttaa agctttctct tccagcagac 242580
tgatgtgaat ggaggcagag aacttgtttt agtcaatgta gtatcccttg cacttttcat 242640
actatgtagc acattataga tactcaataa cttgttttta atgaataaat ggcaaaatat 242700
cataggagaa aatttttaag atgattctgt ttattaaact atctcccagt acatgtagat 242760
aatcccacca ttattttatt atagaaaatc tacagtcgtt ccaacttcta aaatgcaatt 242820
aagaactcca gttatgataa tctttaagga tcattcttct ctaagataat atgtctctac 242880
agcttttact gcctttgaaa atcctctctg tcacatctcc tgaagaaaac agtttcttgt 242940
ccagatgaat tacagtgaaa aaggaaaagc atttatctga acattaaaat ccctttccat 243000
tacaaccctg aattctttag aataattctt gttcatttgg gtaatttccg attaccttaa 243060
accagtatac ttgttattct cataaagcgg atgtacaatt ctacctggtg taacatgaac 243120
tccggaacca ggttgcttgg gtttgaatcc taagtctacc aggtataagc tctataacct 243180
tgaacaagcc acttaatatt tccatgtctc aggttcctga tctccaaata agtaaaataa 243240
aaataattat atcaaaccct taatttaaag tttaactcag ttagtacatg tgaaatgcta 243300

-continued agaacatggt ttggccggta gtagctgaga aaatggacct gtagtaactg ctatgcaaat 243360
attctttgaa ataaaaacaa aacgaaataa atatgctaat ctttttacca gattgcatga 243420
ctattcagtc ttaacaaagt tggctaagat taggccaaca tcatccagaa aaatgtcctc 243480
agttataaac agtagggaaa tcttagaaag aatgattgaa gcacacaaag taaacaacac 243540
aggaaaatta gcgatatatg tgtctgcaga aaaatgagaa ccaagggttc ctgaggtaga 243600
tggttaggca tttcatgtgt gtaaaagatt ccaattataa atctggaaga caaggcactg 243660
gtagagtacc tgaccctaat aaataaatac tcattaaaat tttgcttaat ttagtataaa 243720
taaatttaat taattattca gttaactggt aaatgaaata gttgtttgac tataagccaa 243780
gtcacttgac atgtctaggt tctgtttcct caactgttaa ataaggaaaa ttatctagat 243840
cagcatttcc ttaattgtgt tcaactcaag actgggttct tagagttgtt aatcagctct 243900
tggaaacaaa tccatggttg aataatttta ggaaaaccca tatgctatct ttctcttgca 243960
tttacaaaca aactggtata gtagacattt taagatcttt tattgtaagg aaattttatt 244020
tatctgacaa tttcccaaac ttaattgacc attgactctt ttcctctggt ttctagccta 244080
ttggtatttc acagaattac tgctattctg aacaaaaatt ggaaataata ctactcaatg 244140
tttggtgtgt ggctcagtgt cagtctgcaa attatttacc agtctataac agaataagta 244200
caaaaactaa gagcaggcat ttaaaaactt ttatagcaat ttgacacagt aattttatgt 244260
ttattgaatc taataatgaa aatcagggat tgtattttgt aggttttccc ttcattgctt 244320
ttttccttat aaattaattt ttattagttg tttttttttt tttttttttt tttttttgag 244380
atggagtctt gctctttagc ccaggctgca gtgcggtggc atgatctggg ctcactgcaa 244440
gctccgcctc ccaggttcat gccattctcc tgcctcagcc tccagagtag ctgggactac 244500
aggcgcccac caccgtgcct ggctgatttt tttgtatttt tggtaaagac ggggtttcgc 244560
tgtgttagcc aggatggtct cgatctcctg acctcatgat cggcccacct cggcctccca 244620
aagtgctggg attacaggcg tgagccacag cgcctggcct tttattagat ttcacttagt 244680
ctcttgtaca ctgaaaattt tttctgaatg ttcacagcag ctttattcat aagagcaaaa 244740
aacaacaaaa aaattaaaat gggttcttta ccacagatag tttcagaaca ccaatgtcat 244800
ctccaaaaag attcacatta taaatccttc cactaattcc atgcagaagt ccatgaagat 244860
gaagtttcct gggttctact gcaaactttt atcagaatct ttagaatcat agggaatcta 244920
cattttcaca gcacccaagt aattctgact atattttgag cattacactg tggcaacctg 244980
atgggagaag ctgtattttt atttatcttt gttccatcag taacgaaccc acagtaaata 245040
aatatgtttg tagcatatgt aaatgagaaa aatcaagtaa cgatatggag tctctgaggt 245100
ctatgttcat ggatagttta gagttaaaca aaactggaaa caaattacta cccccaaaga 245160
atcaaatcct atacatcact tgtcaggaaa aaaaaaatgc cattctccag acacttccac 245220
ttacagccta cttcatgttt taattatctt gaagtgggtg ggatttttca gcatgatcct 245280
gcaaaactgt caatcatttc tcttcttatc caagcatagc accataacag aagttgatct 245340
actaaacagc tccttagtac tgcaatttaa tataaaaata cactctcagt ccatgtcata 245400
gccaacatta tattcactat gtggacacaa ataatttgaa cactttgtta aaatatactt 245460
ttactagtcc ttgcccagta aggcatcaat cagtttaatt ttactgtgga atttttgtac 245520
atgttttcat gttcatatct atagaaagct aaatgtttaa agtccagctt gacatgtttc 245580
tcatattttt actctgctaa taagtcaaaa tatgtgtgtg agacatgaat accttaggat 245640
attgtgtgtc tgtttgttga gatgacccta aactctgacc ctaaacagtg gtcctccact 245700

-continued tggaccacac tttggaattg tctgaagtac tgagaaatac agtgcttact ttggcagcac 245760
atgtactaaa attggaacaa tacagagaag attagcgtgc cccctgagca aagatgatat 245820
gcagactcat gaagcattcc atgtttttga gaaaaagaaa tgcttttaca ttgttggtgg 245880
ggatgaaaat tagttcaacg attgtggaag acagtgtgac aattcctcaa agatctagaa 245940
gcaaaaaata ccatttgacc cagcaatccc attactaggt atatactcaa aggaatataa 246000
atcattctat tataaagata catgcatgtg tatgctcatt gcagcactat tcacaacagc 246060
caagacatgg aatcaaccca cgtgcccatc agtgacagac tggataaaaa aagtggtata 246120
tataaaccat ggaataccat gcagccatta aaagtaacaa gatcatgtcc tttgcaggga 246180
catggatgga gctggaaatt gttatcctca gcaaactaac acaggaacag aaaaccaaac 246240
accgcatgtt ctcacttaca agtgggaggc gaatgatgag aacacatgga acaacataca 246300
ctgtggcctc tatgggggtt gggggaaggg agagcatcag gaagaatagc taatggatgc 246360
tgggttagat acctaagtga tgggttaatc tgtgcagcaa accaccacag cacacatcta 246420
gagtttctga ttgaattcat tattggagtg gtctgaaagt cagaattttt aaggcttctt 246480
aaataattct aatatatatc ctgagttgag aaccataaat aaaatcaggt gcagttctta 246540
tcaaaaaaaa aaaactgcag taattatgag agatcccata tccaaggtaa atgggtggat 246600
ttgtatttga attgaattag agaagggtca gctgtgaacc caccatgaaa gggtttcttt 246660
tcacttactg agaattaaga agactgatga tgttcagtct taggagagaa acgtacatcc 246720
ttctctacac tcctcacccg tttcctctgc acaccttcag caatcattat ttgctcatca 246780
gactaaggtt gtttatgggg aaaaaaaaaa agttaagaga cagataataa gggaccgaaa 246840
aagatgagag agacagagta agacagagtg agagagaatg tcttcattaa attactaaaa 246900
caaaacaaaa catttatcac tctttcagct tcaggccctc atctctaata cgctcctgaa 246960
ctactggggt cctgaaggca taaaattctt ttctcaggct cagatccttt cacctctaga 247020
tacagccaga agtcctggag agaggaaggg aaaggagtaa ggaagaaaga aaggaaaagc 247080
attactttgg gggcaagaga gatttgcctc ttccctttcc ttcctgcatg tatggagggg 247140
caaggaaaga cttacttgac cttcagccag ataacggctt gtggctttct cttacacacc 247200
cagaggccac attccttgat tcaatctact ttcagctgca caagctctgt gccttcattt 247260
cattagaagg gtagtttcta ccacaaacaa gtcttcgttc ctggtactag ggttaggcct 247320
ggtaacgctt caaaatctta agaaaaaatt taaaaccccg attttatatg tagagaacca 247380
tctcttttga ttaagaatat tttacatcat aatgaaatgc agtcaaagct gaggggcaat 247440
ttgtcctctg ggtatcact tctctgagtt caaaaaaata ttcctgtttg ttctaaatca 247500
cctctaaatt tactttgatt tgcaaattca atgtactttg tataaacaaa cactgacaat 247560
gaattaacaa tactatatga ccccttcac tgaatgaata tagattttca tgctcagatg 247620
atatttgtgt ccctgtcaca tattttactt cagatcttaa tgagtaacct tgagtcttaa 247680
taacttttcc tttaagccaa gctctcttat ttttctttga tattttcatc aactacacac 247740
catcccctgt aataaatgag aaaaggagag ggtgcccagt cacagtggta ttctgtccag 247800
ataggagcac gtttctatcc tgtctacttc ctactggcaa aagcaatgca tgataatttg 247860
ctgccagtat tactcaacct taccatatag acaaattatg ttatctacga aatccactct 247920
aagggaaatt attgttctgt ttcaatcgat ttcttcattc ctcactatca ccaaaccata 247980
ttctccttca gttgatttgt atttagtatt cactcaacaa accttaattg agaactacca 248040

-continued tgtgccaggc atcattgtgt atttaggaaa tagtttagac tcttggtatc aactctcaaa 248100
gaactggaca gctcacttgg gtagaagaaa taagaaaacc aaagattaca aaaaaggaaa 248160
tagacaggaa gacttattta cttatttgac agacagccat agtctttcca taggcctgca 248220
gagaaaggtt agagcagcta atgcattttg gcttgggaga gaatagtaag aaatagtcta 248280
gaaagacttt agaaaccaga cagagaatag aacaggcgta aaaactgatc ccagagtaac 248340
tccacgttta aggaatacaa cagaataaca gtatgaactg tgattggtgt ggggatattt 248400
ttgaaacaat gtaaagagaa tttgagtata attataatca gaaagtaagg gaccaatgtc 248460
tttaaaaatg tatgtaaaaa taaggcaaga actgatgaac caaggtctca gaagaggtag 248520
aacatgggac tgtctcctac tctacagggt caccacaagg gcaggttcca ggcatggatt 248580
acatcataac acttatacca ctaatctctg tttagaagtg aaatcccata gctgatagca 248640
gccattaaaa ggcatgggtg acatatgatg acagtagaga atatagagac agtgtgtgca 248700
ggtgtgcagg aagactagat ttggacattg gctgtaaatg acttaatgga ttcaaccaaa 248760
atgtaatgag cacttgtaca gaggccacgg atgtgtgtca ttcagatgcc gtttctggag 248820
aacctgaccg tttggagaga agaagtgaca gagagccctg gttgctgccc ctttgggtca 248880
actgcacagt cttgtcaagg ccaccctcct gccaagcttt tctcagtcaa tgcctggtcc 248940
cagcagtgct accgattctg acccattcct attggatttc tgtaacaggt cacttttgct 249000
tttccatcag tctggctgag atctttctaa gaactgtgcc gcagtctatg actctcccta 249060
caaaatcctt tctcccttct ctcctttcag cattgcagtc tgaagccttt ccctgcctat 249120
acctcctttc cccccattta tccaacactg gcagttctta ccataaatct cttgtactta 249180
taattctgtc ttggcatctg tttctgagat agcccaaact aactcatggg attagtttaa 249240
gggctaagga ttttaaaaaa ctgacaaaaa agacaaagtt tctaccacca aaggtatgag 249300
aattcattgt tttaaaatat agaacattag tgggtatatc ttgcttctgt tttcagtttc 249360
tgtaaagaga gtgatccctt tcttttttttt cttttgtttt gctttaattc attgctttag 249420
tattggtata ctctaggata cctagggctg cttttcatat ctctcaattt gagtttatac 249480
tgtttccctt acatctctgc cagtatcaga gtatcatttt tccttacctt tatgagcaat 249540
ctcatcattt ataatttgtc tctcacagct gccccttggc actgtagcag aaagtgagtc 249600
atcctacatc tatgaaatct aagatgattc tgagataatt tagtaaagat taactatctc 249660
acatctttcc ccctcactct gtttttcatt ctggctccct gcccctggct gacaacatgt 249720
gcacgtaact ttactcattc tgaactgcac aggctagaat gtctctacac tcacatgcct 249780
ttcatcaaaa tcctacattg atttaaaatg catgagtcac tttattcata tcttgggttt 249840
tgtttgggaa aatgctgatg ctagaaaatg ggagtctcat ttcttccccc tcctttattt 249900
tcaatgttcc tccatagcct atgtagcaat tctggttcac gcttggtatg gcccatggct 249960
tgcaatgctc cttagtcaca aaggcccaat gattcacagg tttggcagga ttgctacttg 250020
atctggtatg ctgacccttt ccctaaaggt cttaaggccc tccttctttg tggaaggaaa 250080
aattgttctt ctggtatatg tgtatggaaa ggagtggaaa gggaagagga tttagggtga 250140
gattgagagg acagaggcat ctcaccatgg aagtatgata actcactgcc tctcatggat 250200
gatatgatcc atctcatttt ctgcttttct gctttacctg gtataaagcc ttataaacca 250260
ttcaaaacaa tccattttgc aataaaatgc tgttgcattc cagtatgact gtctgtagct 250320
caagttaaac tcgaccccac atcaaaagtg agtgaaacga gtcagctgct aagtctcagt 250380
ggatgctcgt aggttgtctt cagggcttga aaaatgttga aggaaaccac attttaaaac 250440

-continued aaagtacatt gtatatcagt ggacatgctt caatagatgg gagtgttgct gcaggactcc 250500
ttagaatgca agcactaaag ctctgtaggt tggtgcacag gagaatctag tcttcttata 250560
ttaataaatt tttaaattca agtagaaaca aaaatatgaa aagatgtgaa ggagttagga 250620
acaagcgtta gggataatga acctcagtgg atttaagggc ataatctgaa atcaggagca 250680
ctgggtaagc ttccttacct ccttggagcc cttatggcag tgatggcaaa acagtgagat 250740
aagatgctat ggggtaaaat gcctggctga acaatactgc tctcctactt tgggaggatg 250800
aattggctct gatctcactg tgtctctcac tgtcttctaa aattatattc aaagttcatt 250860
ttttgggaaa cattccagac taatcctatt agtcaggtat gtttgcatag gtgtattaaa 250920
ttaataaaca tgcacagaga tatagatgta agggtagaca tatagcttct tccatgtgtg 250980
ccagttaagc tactttcttc ctagtgcatg gataatagag gctttttgt atgtttgttc 251040
tgccctctgc attaagtggc taactcttat agggcaagga tcatagctac acaatccgtt 251100
gtctctagac acccatctga gaaaggcaga ttattctttt gtacgaatgg tgaactttac 251160
ggtcagaaaa tcatggatct acttttatac aaatttagtc agataataat ctctaggtac 251220
ctcagactcc cctgctgtaa atcaggatca gaaataattt ctttgtgggg gtggtctgag 251280
aattctgata atggagggca agggaatgta caaggcaaag gtggtgtgga atttcacagt 251340
gctgtttttt cactactcta gtcttccagt ttgcgaagag attccatttt aatccattgg 251400
ctgtttattg aggacacttt atttctccat aagagctaac tctgcccccct tgtgctgagt 251460
aaaataattt ttctatttta ttcggtttaa ttttatttgc atttaagtgt ttatacctat 251520
ttgaaaaatc atatccagct actcttttca ataagtcaag ttatataagt gtattttctt 251580
taataggttc cctggagtaa tttttccttt ttttcatatt tttttccttt cttcaattca 251640
tctgcaacct tttatgttta aagtgcaatt cttcacaagg tctccctgat gctattcatt 251700
acaggctttt ctctgttgag tactgtcaca attagtttta ctgtccaatc tttaccatgt 251760
cataaggaat aactaagact taagggtcaa aagaccgaaa tgagatagca agagctgagg 251820
gcagcgttga aactttttga agagtgtaac aaatggatcc atcaattcaa aaagtgtact 251880
tgggagtttc acaaggattg cctcttttttc tgattgaaga cgtgttttca ttgttctgat 251940
caataagtga tataggtcct tttttaaaga gttcaggcat aaatgaataa aaacattcta 252000
ctagattcca tgggaaacaa ctcgtcctgc agagctaaaa gtctaattgc ttagttaaat 252060
aacaatacaa aaaaacagga tacaattaag aattaccaat ctaattgacc aaaaaaatga 252120
gtacttttga acttctgagg atatgtatat tcaagtggtc tgaaaaaagt aggtgatgaa 252180
acttaaagta ggccttgaag gataagatat ggtgatgtat taaaaataaa ttcagtagtt 252240
cacagaatta atgacagaac tggagaacaa ggctcaaggt tacgggaaaa gaaaatgccc 252300
caaaccacct tagaattggt tctgagcagg aaaaaaaaaa agtctgcttc cagagagaga 252360
acttgtacca cttgcttctc aaagtgtctt aagcatagcc agtggccctg gggtattttc 252420
ttcccaaaat gtaggtctca aaatgtagct tatgccacag ctgaaggggga agctgagaaa 252480
gtcagtttcc tctccagtag tggaagtaat ctcttcactg agacatcaaa tgtggttaga 252540
aggggaatgg aaatctccaa acgtacacat ggatgggcag atatcaggcg gccactgtga 252600
atgacaaaca cttgctatca gcagcctctt ttcagtcagc atcagctcat gagacttcaa 252660
aagatttcac aggaagagtg tatccatgtt ctcaaactct caacatttca gagctagcag 252720
ggacattaaa actccttcag cccaatcttt ttaataagta aaccaagtct cagagacatg 252780

-continued agaagctata tccagggtca cacagctgat tactggtgca gccatgatta atgctctggt 252840
cttctaatcc ctacccggtg tagtgcttgc gaatctgttc tatgggcaat tataagagaa 252900
atgcgcaatt ataagagaaa tgcttacttc ttggaagaat gaaagcagca tcatatcttc 252960
tctacacttg agaaaggctt ccttttctgc ctgtcagatg caaagtttta gaaaagtcag 253020
gactgctctg caggccttga aacaaacccc tatgggatta ttctcttcca ccagccccag 253080
gtcatgctcc ttgtgcccca agactccacc actggtttac attgtgtttg actacgactg 253140
tcgcccaggc tggagtgcag tggtgcgatc tcggctcact gcaagctccg cctcccggat 253200
tcacgccatt ctcctgcctc agcctccaga gtagctggga ctacaggcgc ccgccaccgt 253260
gccacgctaa tttttgtat ttttagtaga aacagggttt caccgtgtta gccaggatgg 253320
tctcgatctc ctgaccttgt gatcgcctgc ctcggcctcc caaagtgctg ggattacagg 253380
cgtgagccac ggcgcccagc catattttat tctcttttat aaatctgagc acttcctttg 253440
ggatagactc agtggcaatg aattactgta ttaaagaaaa gctctgtcct tcactgacat 253500
gtgaatttgt acatttcact tctcctttct gagacttact ttcctgatct gtaatatcaa 253560
ggtatatatc tgtcagtttt ttagttttgt tttgtttgtg tttgtttctt ttaggatcca 253620
aagagaccac caatgcacta aataggtaca taataaacgt tcactgaatg aatgaacagt 253680
gcatgtttca aaatatgtat ttatttgtag atataagaaa atcaagcttc tctctcacat 253740
cctcattctc agtcatacgc tctctctctc tctctctctg tctctttagc tcgcattctc 253800
ttttcttttc tcctttcctc actctgttct tttggcccgc tttctattct ctctctctct 253860
ttctccccca atgtctccat agtgcataca taaataatat acagacatct acaatagata 253920
tgtatgttga tcaaaaaagt aggtactact tctacccctt tatccataaa catgttatta 253980
aggaacataa actttgcaag tctctaccaa gaagccacag ctgtttatcc tctttatcat 254040
ccagtgtttg gcctctgctt ccagttttga tgtcaggata atgttaccat tctcaccatt 254100
tctttggttt agtagtctcc cacacaacaa agtcctaacc atgtttgtga attgggtacc 254160
cacctgtggc ctattgagca ctggtcttag cacacttaca caatatgcat tttgccttta 254220
ttctacagga gatattaatc ttcctttcat ttcttttacc acataccctt ttaaaaaatt 254280
tatgttttcc acatacactg gcttgaattt taattttgtg tttttgggtc tatgatccta 254340
aacactttat gtctatgatc ctttctgctt ttctcaagct ttaatgtgct tgaaacacct 254400
tctttcttag tgttctccaa ataaatatgc catcgatgtt atttatttag tttccagatt 254460
tctaatacag actttaatct ctgcccacca cttgtcactg aaataacttc ccaagtaagt 254520
atgtagatgg accagttctt agtagagaaa tttccatctg tgtgtaagta gtcacatatt 254580
ttatcctgat tgttttgcta tcagattgta attcctaata ttctaaaagt gttgacctat 254640
aaaagtttca attgtacata gttaaatcca ctgtatctac tgtgaaaaga gtacaagact 254700
tgaagtcagg agccatgagc taatttctgc cactgagtga ttgtaggcat ttacttttct 254760
ttacctctct aggcttcagt tcccacaact ttaggatgaa gctttaaatt aaatgatttc 254820
tcactttccc tctagccttt aaaaaatcca tatacacctg tcttgaagct tgtttaaacc 254880
tatctttaaa aaaactttta aaacattttt taaagtgttc agagacagaa catataaaat 254940
accttggaaa atagttctgg aagattttgc atcagaggct atttgtagaa atttggagat 255000
aaactctgtc tgccacagaa gttaagaaaa aaaattgttt tcacctcaag taacacctac 255060
ctatcagctc attgggaatg cctgcatgtt tatgataccc aacgtgtagg ataggccaaa 255120
gtgaaccaat tgtctcttac agctttgcta tgagaacttt actacaacta acaactcatt 255180

-continued actcagagtc ataggctctg agtcatcctt gacttctgct ctttgctttc tccattcaat 255240
cagctgccac atttctaccc actttcagtt cctcactaat tctgtactcc acacctatca 255300
cccaaattca ggccccatga accgttaact agattatttt aatcatccaa caactaccat 255360
tcctgcttcc aagatctacc cattttttag aatttatttt tttaatttta tttttcactc 255420
aaagcaaaaa tggtcaatat ccatttttaa tttaacctac ataagtctat cagttaaaat 255480
tccttaacta taactctgat cacattaatc tcaaacacag ccattagctt actaatgtct 255540
aacaaagttt aaaatccttt ggtctattaa aaattattct gagatttaat cccaaccatc 255600
tcccttatct tgtattctgc tgggtcaaat taatgttatt caagctccaa agttaatctt 255660
ttcttaaaac accccttagc tgttacaata aatcttctga tccctcaaat taactccctc 255720
aaagaactca tgactttgta gcagaaatca taatttcttg tgtacccatt agatcacttt 255780
ttattgaagg aaaataggga gtatattttc tttcaatatt acagcctcca ttatcacttg 255840
gagagagatt attatatgag tatagcataa acagatgact ttcctctttc ctatggtaaa 255900
aaagaaattt actttctttt aggtaaaagt agggatgaaa ttattttgat accttatatt 255960
ttaaatacaa aattaaaatt aaaaggtata tcacatttat atatcttctt ttaaaacatc 256020
atacaagttt cataagccat ttctttagag agaaagatat tatctttatt tatttaataa 256080
agacatttca gtttcagaaa atgtgtttta cttatttatt taatacatgt gtttcagcat 256140
ttcgctaagt agtgatattc tccaagttca attccaatca tgactcattg gcttagccat 256200
caaagtttat ctttcctttt gaactatgca caagataatg cctatcctat ccatcagtaa 256260
aagtcatgtg agtttctcta cttttcaagt aagtatactt tccaatccat caggttgaag 256320
agcaggatta aatacatatc aggaataaat aactccagta gtcaaaaaaa tagactcatc 256380
aatcagcttc ggaggtcaaa catttgacag gtgccaatga gcttgtttca atatcacctt 256440
tcagaaataa agacattaaa gaagttaatc aaggtatagt caaggagact accaacctaa 256500
ctgagacaaa agacactagt tggttccact caaggttcag gacaagctca gaaccagaat 256560
gtactttatg atattgttag ttgacccaaa taactaaaat tggtgaaata tttaacattt 256620
tcataaaaag tggtattaaa ggttgttcta agatatcaga gcagtatata tatttactat 256680
tattatcaat ctagtcagga tatccattgc ctctttaaaa acaactacaa caggcaaccc 256740
acaaaatggg agaaaatttt tgcaacctac tcatctgaca aagggctaat atccagaatc 256800
tacaatgaac tcaaacaaat ttacaagaaa aaaaacaaac aaccccatca aaaagtgggc 256860
gaaggacatg aacagacact tctcaaaaga agacatttat gcagccaaaa aacacatgaa 256920
aaaatgctca ccatcactgg ccatcagaga aatgcaaatc aaaaccacaa tgagatatca 256980
tctcacacca gttagaatgg caatcattga aaagtcagga aacaacaggt gccagagagg 257040
atgtggagaa ataggaacac ttttacactg ttggtgggac tgtaaactag ttcaaccatt 257100
gtagaaatca gtgtggtgat tcctcgggga tctagaacta gaaataccat ttgacccagc 257160
catcccatta ctgggtatat acccaaagga ctataaatca tgctgctata aagacacatg 257220
cacacatatg ttcattgcgg cactattcac aatagcaaag acttgggacc aagccaaatg 257280
tccaacaatg atagactgga ttaagaaaat gtggcacata tacaccatgg aatactatgc 257340
agccataaaa aatgatgagt tcatgtcctt tgtagggaca tggatgaaac tggaaatcat 257400
cattctcagt aaactatcac aagaacaaaa aaccaaacac cgcatattct cactcatagg 257460
tgggaactga acaatgagaa cacatggaca caggaagggg aacatcacac tctggggact 257520

-continued gttgtggggt ggggggagag gggagggata gcattgggag atatacctaa tgctagatga 257580
caagttagtg ggtgcagcgc acccgcatgg cacatgtata catatgtaac taacctgcac 257640
attgtgcaca tgtaccctaa aacttaaagt ataataataa aaaaaaaaga aagttgaaaa 257700
atcttagcac tcaaaaaaaa aaaaactaca acatataagc agaaaattgg actttttga 257760 tatatttgag gaacactttg agtcacattt attgaaaatg ctcatagaaa caaatagatt 257820
tttagctgac tatccttgac aacacctctt ttcatataac ccctggtatt atgaaaaaag 257880
aaaaaatatt ttatttgctt tatttgaaac acatgaaaat cacatagtca aaatgaggta 257940
ttatgtatct gaaaacccag atacctctct ctctgccgtc tgcttgagac agtcctcact 258000
actcactgct cttgccaata aactggaagc caaggtcggg agtttgacat tcttattatg 258060
ttctgactac aggatagacc cttaattcag gcaacttaat ggcaaatacc tacaaaaaga 258120
cttgatatgg tttgtatctg tgtccacatc caaatctcat gttgaattac aatccccaat 258180
gttggaggtg gggcctagtg gaaggtgatt ggatcatggg ggcagtttac aaaggattag 258240
caccaaccta ctagtgctga acttatgaca gagttctcac gagatctggc tgtttagaaa 258300
tgtgtagctc ctccccttc tctcccttcc tcctggtctg gccatgtaaa tgtgcctgct 258360
tccgcttcac cttgtgctat gattgaaagt ttcctgacac acctccagaa gccatcatgc 258420
ttcctgtaca gcctgtggaa gagtgagcca attaaatttg ttttctttat aaattgccca 258480
gtcttcttta tagcagtgag agagtggact aatacaagac accaaagaac cacagggtat 258540
cactgaaacc ttttcaaaca agtggaaaaa aaaaacactt aaagtttatg cccaacacaa 258600
gtctttcaca aaacttccag gtgatgaaaa ttaatcttgt ttgtttcttg tatttatcat 258660
cttcttgagg accagattta atttccacag aatgaaatct ggggaaatta actccccaga 258720
tttttgcccc ctcattagac atacttagct gagtcagcac tccactcata tataaatagc 258780
aaaaacaaca catgacagat agcacatttc tttctctcag gctcttcttg ccttctacag 258840
aaaatctttc actgtccact acactatcag aaaataataa aggagggact atctccccac 258900
taggatcctc ctcccaacct ctacttcatc aggtaaggat cttattttcc aactcaaggg 258960
agcatattcc actggccaca tttcaaacct gggtgctaat attaggaaac tgaacattta 259020
gagcactgct tgtgttactt ttatagggtc aacctatatt cttaataagc aatatattgt 259080
tgtctgtctc aaaggataga gcactgggaa taaagagcaa gcatcagtga atgaactcag 259140
cagccacaaa caaattacca gagatgtgta ccttcctgag aagcagagaa ttatagaggc 259200
aatgttgcat gatgggatat gtaaatacag ccttggaaga tcatgtgtgg atggaaacca 259260
attaagtaaa gcacttagga aaattgcttt ctactgtctg aataagaatt tatcatgaga 259320
cacagttttt taagtgaaaa acgtatatgt aaacctggac taagtgtttt gtccaaggtg 259380
acacaataag gcaggcaata gagataaaaa tagaatgctt gaaaccagcc tcctgatcta 259440
atcaccaaac actttgcaag tttatctctg aagaggacct aatgcaaagt agaacctttta 259500 gagtgagagg tcagcataag gattgcagca gccaactggg cagcaataga aatggaattg 259560
attgcttccc taaaaaatga tgaaatgtta tcaataacta cacagcaaaa gaaaaaaatg 259620
cagcgatatg catcatgaag gagaaagcat tttctccact aaaatagctt ttgttaatca 259680
ttaccagtca ttaaagaaca caaggtttca gatcttcctt aatccaggca ttctgcttga 259740
agttataaac aaataatttc attatgtctt tgtctattta aaaaaacata ttttggtatg 259800
atttctctca ctcattcaaa gttttacaga gcatctgcta aatatcaagt cctgtgaagg 259860
gtatataaaa atggaggggg catatttcca cctttcaagg aactcaggtt ctgttgtaca 259920

-continued tggatgctta gataatattt gtggacacaa agtggtaagt gctctaaaag aaataaggtt 259980
aaagtcctgt gggaatacaa caggggcaga aagaaagcga gattaagaaa gaaagatata 260040
gaagttccgc aatggtggag ttaaatcaag ccacgggagt tgatgacttt gcaggtggat 260100
acaggggaat atcatagaag agaatagaat tctgggcaaa agaaataatt taagcaaaag 260160
ctctgctact ttatttagca gatttccctt ttcagacatt tatttctcac ctcaacccaa 260220
gctttattcc ccattggctg ttttaagttt cttaatcttg atgattttca gtttcctgtc 260280
ttataggatg gtgatttcta atattgttgt cctgaggatt aaatgagata ttcctttcaa 260340
ggacttcaat agaaataaaa caaacattag atggattagg taatgattcc ctgagaagga 260400
tgcattcaat tagttagtca ttgcaaaaca agaaatgagt aaaccagctt taactagcaa 260460
gagctgcaaa gtggcagacc ccaaggagat gggaagcaag tagatatatt ttgatgtgaa 260520
gaaaaatcgg cagtgtcaca gtggagaata cttgaggggc aacagaatat cagatgagca 260580
aaatactcag aaaaaaatca cctacaacat agttctgact ggtggaacac cccaagagac 260640
tgtaattagg gtatcatcta ttggcttaga aggaatgctt caaaagtcca tcacataatc 260700
aatatggaca ggatggttag ggctacaggg atgatgataa gacatgaact atttcttcct 260760
gggaatattc cccctcaccc ccactaccta aaggtaccca gagaaactta taaacaattt 260820
atgaataaga tggtggaagg gggaatacaa attaaaaatc acccgccagg tgcagtggct 260880
caagcctgta atcccagcac tttgggaggc tgaggcaggc ggatcatgag gtcaggagat 260940
agagaccatc ctggctaaca cggtgaaaca ccgtctctac taaaaataca aaaaattagc 261000
cgggcttggt ggcagcgcct gtagtcccag ctactcggga ggctgaggca ggagaatggc 261060
gtgaacccgg gaggcagagc ttgcagtgag ccgagatagc gccactacac tccggcctgg 261120
gcgaaagagc aagactccgt ctcaaaaaaa aaaaaaaaaa aaaaaatcac cacacactta 261180
ggtgttatta aaaattcatt ttactggaaa aggcattttg ttgttgttgt ttttaagaca 261240
gagtctcact ctgtcatcca cactggagtg cagtggcatg atctcggctc actgcaacct 261300
ctgcctcatg ggttcaagct actgtctttc ctcaacctct cgaatgactg ggattacagg 261360
cgcatgccac aatgcccagc taattttttg tattttttag tagagatggg tttcaccatg 261420
ttggctaggc tggtcttgaa ctactgacct caaattatcc atccacctca gcctcccaaa 261480
gtgctgggat tgcaggcgtg aacccggcct ggaaaaggca ttttacgttg tgagcaggta 261540
ctcttcctaa gaattactgt gagtgtaagt gtgtttgtgg tgaggagggg ttgcacagga 261600
tgcatataag aagtatctaa atgtaacctg tatttgttac ttcagactca atgatatagt 261660
atgaagaata attatgacgg aatcacccat tgaaaagtga cacagatgcc catgctgtct 261720
tgggaaggaa gagaaagtgg gaacaaaaat gatttcttac tacatgaatt gctttataaa 261780
gaggagcct 261789

<210> SEQ ID NO 2
<211> LENGTH: 19
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is g or t

<400> SEQUENCE: 2
tgcgcgtgtn tggtgtgtg 19

-continued

<210> SEQ ID NO 3
<211> LENGTH: 23
<212> TYPE: DNA
<213> ORGANISM: Homo sapiens
<220> FEATURE:
<221> NAME/KEY: misc_feature
<222> LOCATION: (13)..(13)
<223> OTHER INFORMATION: n is g or a

<400> SEQUENCE: 3
aaataaatta acntttatca tca 23

<210> SEQ ID NO 4
<211> LENGTH: 17
<212> TYPE: DNA
<213> ORGANISM: Homo sapiens
<220> FEATURE:
<221> NAME/KEY: misc_feature
<222> LOCATION: (8)..(8)
<223> OTHER INFORMATION: n is g or a

<400> SEQUENCE: 4
atttctcntt aaaattt 17

<210> SEQ ID NO 5
<211> LENGTH: 21
<212> TYPE: DNA
<213> ORGANISM: Homo sapiens
<220> FEATURE:
<221> NAME/KEY: misc_feature
<222> LOCATION: (12)..(12)
<223> OTHER INFORMATION: a is absent or present

<400> SEQUENCE: 5
atttcatatc taggaaaaaa c 21

<210> SEQ ID NO 6
<211> LENGTH: 23
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is t or c

<400> SEQUENCE: 6
ccacctagnt tttttaatga aca 23

<210> SEQ ID NO 7
<211> LENGTH: 23
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is c or a

<400> SEQUENCE: 7
atcttgattn tatttatgac tgc 23

<210> SEQ ID NO 8
<211> LENGTH: 21
<212> TYPE: DNA
<213> ORGANISM: Homo sapiens
<220> FEATURE:
<221> NAME/KEY: misc_feature
<222> LOCATION: (11)..(11)
<223> OTHER INFORMATION: n is t or a

<400> SEQUENCE: 8
gcttagttgg ntagaccagc t 21

<210> SEQ ID NO 9
<211> LENGTH: 21
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is a or c

<400> SEQUENCE: 9
cctcactctn ttctcctcct t 21

<210> SEQ ID NO 10
<211> LENGTH: 18
<212> TYPE: DNA
<213> ORGANISM: Homo sapiens
<220> FEATURE:
<221> NAME/KEY: misc_feature
<222> LOCATION: (8)..(8)
<223> OTHER INFORMATION: n is t or a

<400> SEQUENCE: 10
ggtgcagngg catgagcc 18

<210> SEQ ID NO 11
<211> LENGTH: 30
<212> TYPE: DNA
<213> ORGANISM: Homo sapiens
<220> FEATURE:
<221> NAME/KEY: misc_feature
<222> LOCATION: (17)..(17)
<223> OTHER INFORMATION: n is a or g

<400> SEQUENCE: 11
aaccctcctc aattgtngaa acatggaaca 30

<210> SEQ ID NO 12
<211> LENGTH: 32
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a or g

<400> SEQUENCE: 12
ggaacagcaa cattcttana tgctcatgta cc 32

<210> SEQ ID NO 13
<211> LENGTH: 34
<212> TYPE: DNA
<213> ORGANISM: Homo sapiens
<220> FEATURE:
<221> NAME/KEY: misc_feature
<222> LOCATION: (20)..(20)
<223> OTHER INFORMATION: n is c or a

<400> SEQUENCE: 13
attcttaaat gctcatgtan ctttattaaa gtat 34

<210> SEQ ID NO 14
<211> LENGTH: 34
<212> TYPE: DNA

-continued

<213> ORGANISM: Homo sapiens
<220> FEATURE:
<221> NAME/KEY: misc_feature
<222> LOCATION: (16)..(16)
<223> OTHER INFORMATION: n is t or a

<400> SEQUENCE: 14
atgtgcattt ctacantcat tcaaatagtc tttg 34

<210> SEQ ID NO 15
<211> LENGTH: 22
<212> TYPE: DNA
<213> ORGANISM: Homo sapiens
<220> FEATURE:
<221> NAME/KEY: misc_feature
<222> LOCATION: (12)..(12)
<223> OTHER INFORMATION: a is present or absent

<400> SEQUENCE: 15
aatgataaaa tattttttaa ag 22

<210> SEQ ID NO 16
<211> LENGTH: 19
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is t or g

<400> SEQUENCE: 16
tcccaccgna cccagccct 19

<210> SEQ ID NO 17
<211> LENGTH: 19
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is t or g

<400> SEQUENCE: 17
ttatatcaan gcctccaac 19

<210> SEQ ID NO 18
<211> LENGTH: 20
<212> TYPE: DNA
<213> ORGANISM: Homo sapiens
<220> FEATURE:
<221> NAME/KEY: misc_feature
<222> LOCATION: (11)..(11)
<223> OTHER INFORMATION: n is a or g

<400> SEQUENCE: 18
acttgcagaa nttttatatc 20

<210> SEQ ID NO 19
<211> LENGTH: 20
<212> TYPE: DNA
<213> ORGANISM: Homo sapiens
<220> FEATURE:
<221> NAME/KEY: misc_feature
<222> LOCATION: (11)..(11)
<223> OTHER INFORMATION: n is t or a

<400> SEQUENCE: 19
ggttgactag nccatgcctt 20

<210> SEQ ID NO 20
<211> LENGTH: 18
<212> TYPE: DNA
<213> ORGANISM: Homo sapiens
<220> FEATURE:
<221> NAME/KEY: misc_feature
<222> LOCATION: (12)..(12)
<223> OTHER INFORMATION: n is a or g

<400> SEQUENCE: 20
aacagaactk ancactct 18

<210> SEQ ID NO 21
<211> LENGTH: 21
<212> TYPE: DNA
<213> ORGANISM: Homo sapiens
<220> FEATURE:
<221> NAME/KEY: misc_feature
<222> LOCATION: (11)..(11)
<223> OTHER INFORMATION: n is t or c

<400> SEQUENCE: 21
gtccaaaaca natgctaaag a 21

<210> SEQ ID NO 22
<211> LENGTH: 18
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is a or g

<400> SEQUENCE: 22
ttatttacnt gaagttgt 18

<210> SEQ ID NO 23
<211> LENGTH: 15
<212> TYPE: DNA
<213> ORGANISM: Homo sapiens
<220> FEATURE:
<221> NAME/KEY: misc_feature
<222> LOCATION: (8)..(8)
<223> OTHER INFORMATION: n is a or g

<400> SEQUENCE: 23
acatcttntg aaatt 15

<210> SEQ ID NO 24
<211> LENGTH: 23
<212> TYPE: DNA
<213> ORGANISM: Homo sapiens
<220> FEATURE:
<221> NAME/KEY: misc_feature
<222> LOCATION: (11)..(11)
<223> OTHER INFORMATION: n is g or a

<400> SEQUENCE: 24
ttgttggggg nactatagta atc 23

<210> SEQ ID NO 25
<211> LENGTH: 22
<212> TYPE: DNA
<213> ORGANISM: Homo sapiens
<220> FEATURE:
<221> NAME/KEY: misc_feature
<222> LOCATION: (15)..(15)

-continued

<223> OTHER INFORMATION: n is t or g

<400> SEQUENCE: 25
gaccctccaa caaangccat tt 22

<210> SEQ ID NO 26
<211> LENGTH: 17
<212> TYPE: DNA
<213> ORGANISM: Homo sapiens
<220> FEATURE:
<221> NAME/KEY: misc_feature
<222> LOCATION: (9)..(9)
<223> OTHER INFORMATION: n is g or a

<400> SEQUENCE: 26
agtttggant ttcctca 17

<210> SEQ ID NO 27
<211> LENGTH: 19
<212> TYPE: DNA
<213> ORGANISM: Homo sapiens
<220> FEATURE:
<221> NAME/KEY: misc_feature
<222> LOCATION: (12)..(12)
<223> OTHER INFORMATION: n is c or a

<400> SEQUENCE: 27
tcagagaaat gnaaatcaa 19

<210> SEQ ID NO 28
<211> LENGTH: 100
<212> TYPE: DNA
<213> ORGANISM: Homo sapiens
<220> FEATURE:
<221> NAME/KEY: misc_feature
<222> LOCATION: (50)..(76)
<223> OTHER INFORMATION: 27 basepair sequence may be absent or present

<400> SEQUENCE: 28
ctggaggaga taatcattaa gtgggaattt gaatattata acagatcctg ggaatttgaa 60
tattataaca gatcctgtaa tcacctgacc actgcacaga 100

<210> SEQ ID NO 29
<211> LENGTH: 33
<212> TYPE: DNA
<213> ORGANISM: Homo sapiens
<220> FEATURE:
<221> NAME/KEY: misc_feature
<222> LOCATION: (18)..(20)
<223> OTHER INFORMATION: caa may be absent or present

<400> SEQUENCE: 29
ataagcaagt ataaaaacaa tttccagtag atg 33

<210> SEQ ID NO 30
<211> LENGTH: 22
<212> TYPE: DNA
<213> ORGANISM: Artificial
<220> FEATURE:
<223> OTHER INFORMATION: PCR primer

<400> SEQUENCE: 30
gggcctagtg tgctaatctc tt 22

<210> SEQ ID NO 31
<211> LENGTH: 24

-continued

<212> TYPE: DNA
<213> ORGANISM: Artificial
<220> FEATURE:
<223> OTHER INFORMATION: PCR primer

<400> SEQUENCE: 31
ttattttaca cttaagggtg ctca 24

<210> SEQ ID NO 32
<211> LENGTH: 22
<212> TYPE: DNA
<213> ORGANISM: Artificial
<220> FEATURE:
<223> OTHER INFORMATION: PCR primer

<400> SEQUENCE: 32
ccagtttttg tagctgctgt tg 22

<210> SEQ ID NO 33
<211> LENGTH: 24
<212> TYPE: DNA
<213> ORGANISM: Artificial
<220> FEATURE:
<223> OTHER INFORMATION: PCR primer

<400> SEQUENCE: 33
tttatagtcc attttggctt gctt 24

<210> SEQ ID NO 34
<211> LENGTH: 20
<212> TYPE: DNA
<213> ORGANISM: Artificial
<220> FEATURE:
<223> OTHER INFORMATION: PCR primer

<400> SEQUENCE: 34
cttgcacctg ggaggtagag 20

<210> SEQ ID NO 35
<211> LENGTH: 20
<212> TYPE: DNA
<213> ORGANISM: Artificial
<220> FEATURE:
<223> OTHER INFORMATION: PCR primer

<400> SEQUENCE: 35
cacaactgtt gcttttccat 20

<210> SEQ ID NO 36
<211> LENGTH: 22
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' FAM modification
<220> FEATURE:
<221> NAME/KEY: misc_feature
<222> LOCATION: (22)..(22)
<223> OTHER INFORMATION: 3' MGB modification

<400> SEQUENCE: 36
aggtattact taatctagtt ca 22

-continued

```
<210> SEQ ID NO 37
<211> LENGTH: 22
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' TET modification
<220> FEATURE:
<221> NAME/KEY: misc_feature
<222> LOCATION: (22)..(22)
<223> OTHER INFORMATION: 3' MGB modification

<400> SEQUENCE: 37

aggtattact caatctagtt ca                                              22


<210> SEQ ID NO 38
<211> LENGTH: 17
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' TET modification
<220> FEATURE:
<221> NAME/KEY: misc_feature
<222> LOCATION: (17)..(17)
<223> OTHER INFORMATION: 3' MGB modification

<400> SEQUENCE: 38

ccatcaacaa ttgcatc                                                    17


<210> SEQ ID NO 39
<211> LENGTH: 18
<212> TYPE: DNA
<213> ORGANISM: Artificial
<220> FEATURE:
<223> OTHER INFORMATION: Oligonucleotide probe
<220> FEATURE:
<221> NAME/KEY: misc_feature
<222> LOCATION: (1)..(1)
<223> OTHER INFORMATION: 5' FAM modification
<220> FEATURE:
<221> NAME/KEY: misc_feature
<222> LOCATION: (18)..(18)
<223> OTHER INFORMATION: 3' MGB modification

<400> SEQUENCE: 39

tccatcaact attgcatc                                                   18
```

METHODS FOR IDENTIFYING AN INDIVIDUAL AT INCREASED RISK OF DEVELOPING CORONARY ARTERY DISEASE

CROSS REFERENCE TO RELATED APPLICATION

This application claims the benefit of U.S. Provisional Application Ser. No. 60/622,447, filed Oct. 27, 2004, the contents of which are herein incorporated by reference in its entirety.

GOVERNMENT SUPPORT

The present invention was made, in part, with the support of grant numbers HL073389 and HL073042 from the National Institutes of Health/National Heart, Lung and Blood Institute. The United States Government has certain rights to this invention.

FIELD OF THE INVENTION

The present invention provides methods and compositions directed to identification of genetic markers in chromosome 3 and their correlation with cardiovascular disease.

BACKGROUND OF THE INVENTION

It is estimated that more than 13 million Americans are afflicted with clinically significant coronary artery disease (CAD) (American Heart Association 2004) and the care of these patients costs greater than $133 billion annually. Of those afflicted, 10% are less than 54 years old. Although a minority of the patient base, this group provides a valuable source for the investigation of the genetics underlying cardiac disease risk, because family history is known to be a robust predictor of cardiovascular disease, even after adjustment for known risk factors, which may be shared within families (Shea et al. 1984). Furthermore, these diseases inflict a high economic impact on this group of patients with early onset CAD. The identification of novel markers correlated with CAD is important in order to understand the pathophysiological mechanisms of this disease state and develop effective prevention and treatment regimens.

Cardiovascular disease is the leading killer in America today. Over 50 million Americans have heart and cardiovascular related problems. By the time that cardiovascular heart problems are usually detected, the disease is usually quite advanced, having progressed for decades, and often too advanced to allow successful prevention of major permanent disability.

Circulatory disease is caused by the normal flow of blood through the body being restricted or blocked as a result of arterial plaque. This may cause damage to the heart, brain, kidneys or other organs and tissues. Plaque build-up is a slow and progressive progress that is dependent on our environmental and genetic environment.

Cardiovascular disease refers to all disease, which involves the heart and/or blood vessels, arteries, and occasionally veins. These problems are most commonly due to consequences of arterial disease, atherosclerosis, atheroma, but also can be related to infection, valvular and clotting problems.

In humans, $\beta_1$-adrenergic receptors ($\beta_1$-ARs) are polymorphic at amino acid residue 389 (Arg/Gly). Mialet-Perez et al. (2003) *Nat. Med.* 9:1260-1262, catecholamines stimulate cardiac contractility through reported that the human Arg389 variant predisposes to heart failure by instigating hyperactive signaling programs leading to depressed receptor coupling and ventricular dysfunction, and influences the therapeutic response to β-receptor blockade.

The present invention overcomes previous shortcomings in the art by providing methods and compositions for correlating genetic markers in a subject with various aspects of cardiovascular disease and its treatment.

SUMMARY OF THE INVENTION

The inventors have carried out a genome wide screening in 420 families with early-onset CAD disease (GENECARD study) and found significant linkage evidence (multipoint lod score=3.5) in chromosome 3q13 spanning over 60 mega bases. Systematic association analysis using single nucleotide polymorphism (SNP) was performed in case-control sets from the CATHGEN study. Subjects were selected based on their CAD index ($CAD_i$), a validated angiographical measure of the extent of CAD. CATHGEN included 301 young affected (YA: age≦55, $CAD_i$>32), 168 older affected (OA: age>55, $CAD_i$>74), and 204 controls (ON: age>60, $CAD_i$<23). A two-stage approach was taken: a preliminary screening in pooled DNA followed by individual genotyping around significant markers at higher density to define the boundaries of the linkage disequilibrium (LD) block. Initial screening of 16 SNPs by DNA pooling revealed that the frequency of the G allele of rs1875518 is significantly higher in OA than ON (OA-ON=12.2%, p=0.001), which is confirmed by individual genotyping (OA=57.2%; ON=45.5%). Additional genotyping around rs1875518 defined an LD block extending~100 kb that is highly associated with OA in Caucasians. Moreover, preliminary evidence supports the association of this block in the GENECARD probands versus Cathgen ON. Finally, a novel microsatellite marker (3M0238) within the block was identified, which breaks the LD and formed a significant risk haplotype (P<0.005) with rs1875518: rs1875518_G-3M0238_253 is twice as prevalent in OA (21.39%) as in ON (11.39%). In sum, the inventors have identified a 100 kb region in 3q13.31 containing genetic susceptibility for CAD. In particular, these data indicate that carriers of rs1875518_G-3M0238_253 are at higher risk of developing CAD.

The present invention provides a method of identifying a subject having an increased or decreased risk of developing cardiovascular disease, comprising detecting in the subject one or more genetic markers in chromosome 3q13.31 correlated with an increased or decreased risk of developing cardiovascular disease.

Further provided is a method of identifying a subject having an increased or decreased risk of developing cardiovascular disease, comprising: a) correlating the presence of one or more genetic markers in chromosome 3q13.31 with an increased or decreased risk of developing cardiovascular disease; and b) detecting the one or more genetic markers of step (a) in the subject, thereby identifying the subject as having an increased or decreased risk of developing cardiovascular disease.

In further embodiments, the present invention provides a method of correlating a genetic marker in chromosome 3q13.31 with an increased risk of developing cardiovascular disease, comprising: a) detecting in a subject with cardiovascular disease the presence of one or more genetic markers in chromosome 3q13.31; and b) correlating the presence of the one or more genetic markers of step (a) with cardiovascular disease in the subject.

Also provided is a method of correlating a genetic marker in chromosome 3q13.31 with a decreased risk of developing cardiovascular disease, comprising: a) detecting in a subject without cardiovascular disease the presence of one or more genetic markers in chromosome 3q13.31; and b) correlating the presence of the one or more genetic markers of step (a) with the absence of cardiovascular disease in the subject.

Additionally provided herein is a method of diagnosing cardiovascular disease in a subject, comprising detecting in the subject one or more genetic markers correlated with a diagnosis of cardiovascular disease, as well as a method of diagnosing cardiovascular disease in a subject, comprising: a) correlating the presence of one or more genetic markers in chromosome 3q13.31 with a diagnosis of cardiovascular disease; and b) detecting the one or more genetic markers of step (a) in the subject, thereby diagnosing cardiovascular disease in the subject.

A method is also provided of correlating a genetic marker in chromosome 3q13.31 with a diagnosis of cardiovascular disease, comprising: a) detecting in a subject diagnosed with cardiovascular disease the presence of one or genetic markers in chromosome 3q13.31; and b) correlating the presence of the one or more genetic markers of step (a) with a diagnosis of cardiovascular disease in a subject.

In yet further embodiments, the present invention provides a method of identifying a subject with cardiovascular disease as having a good or a poor prognosis, comprising detecting in the subject one or more markers genetic markers in chromosome 3q13.31 correlated with a good or a poor prognosis for cardiovascular disease.

Furthermore, the present invention provides a method of identifying a subject with cardiovascular disease as having a good or a poor prognosis, comprising: a) correlating the presence of one or more genetic markers in chromosome 3q13.31 with a good or a poor prognosis for cardiovascular disease; and b) detecting the one or more markers of step (a) in the subject, thereby identifying the subject as having a good or a poor prognosis.

In addition, the present invention provides a method of correlating a genetic marker in chromosome 3q13.31 with a good or a poor prognosis for cardiovascular disease, comprising: a) detecting in a subject with cardiovascular disease and having a good or a poor prognosis, the presence of one or more genetic markers in chromosome 3q13.31; and b) correlating the presence of the one or more genetic markers of step (a) with a good or a poor prognosis for cardiovascular disease.

Additionally provided herein is a method of identifying an effective treatment regimen for a subject with cardiovascular disease, comprising detecting one or more genetic markers in chromosome 3q13.31 in the subject correlated with an effective treatment regimen for cardiovascular disease.

Also provided is a method of identifying an effective treatment regimen for a subject with cardiovascular disease, comprising: a) correlating the presence of one or more genetic markers in chromosome 3q13.31 in a test subject with cardiovascular disease for whom an effective treatment regimen has been identified; and b) detecting the one or more markers of step (a) in the subject, thereby identifying an effective treatment regimen for the subject.

Further provided is a method of correlating a genetic marker of chromosome 3q13.31 with an effective treatment regimen for cardiovascular disease, comprising: a) detecting in a subject with cardiovascular disease and for whom an effective treatment regimen has been identified, the presence of one or more genetic markers in chromosome 3q13.31; and b) correlating the presence of the one or more genetic markers of step (a) with a an effective treatment regimen for cardiovascular disease.

BRIEF DESCRIPTION OF THE DRAWINGS

FIG. 4 depicts the quantitative trait loci (QTL) map for HDL cholesterol on chromosome 3.

FIG. 5 depicts chromosome 3 lod score curves using OSA that corroborate, strengthen and narrow the linkage peaks previously observed on chromosome 3q.

FIG. 6 depicts the genotypes of normal versus affected individuals with respect to three polymorphisms.

FIG. 7 depicts differences in allele frequency between affected versus control (normal) cases with exemplary SNPs within the region of human chromosome 3q13.31.

FIG. 8 depicts the frequency of genetic markers within the region of human chromosome 3q13.31 correlated with affected and control (normal cases) and the significance of the correlation of the G allele of rs1875518 and the 253 allele of 3M0238 with CAD.

FIG. 9 depicts additional SNPs associated with the risk for CAD on chromosome 3.

DETAILED DESCRIPTION OF THE INVENTION

Figure 1:
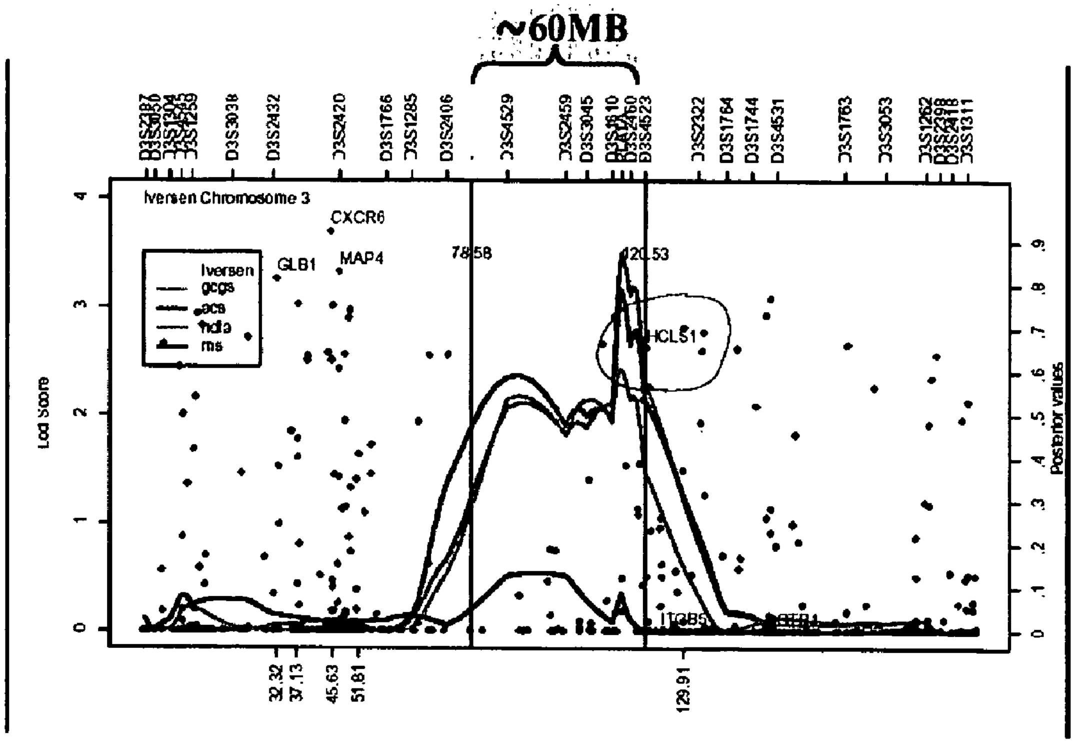
FIG. 1 depicts linkage evidence of the susceptibility for CAD (multipoint lod score=3.5) in chromosome 3q13 spanning over 120 megabases (Mb).

As used herein, “a,” “an” or “the” can mean one or more than one. For example, “a” cell can mean a single cell or a multiplicity of cells.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Definitions

As used herein, the term “cardiovascular disease” includes any disease, disorder or pathological state or condition that involves the heart and/or blood vessels, arteries and veins. Examples of such diseases and disorders include, but are not limited to, arterial disease, atheroma, atherosclerosis, arteriosclerosis, coronary artery disease, arrhythmia, angina pectoris, congestive heart disease, myocardial infarction, stroke, transient ischemic attack (TIA), aortic aneurysm, cardiopericarditis, infection and/or inflammation of these tissues and/or organs, as well as valvular, vascular and clotting problems, insufficiencies and/or disorders, etc.

Also as used herein, “linked” describes a region of a chromosome that is shared more frequently in family members affected by a particular disease or disorder, than would be expected or observed by chance, thereby indicating that the gene or genes or other identified marker(s) within the linked chromosome region contain or are associated with an allele that is correlated with the presence of, or increased or decreased risk of the disease or disorder. Once linkage is established, association studies (linkage disequilibrium) can be used to narrow the region of interest or to identify the marker correlated with the disease or disorder.

The term "genetic marker" as used herein refers to a region of a nucleotide sequence (e.g., in a chromosome) that is subject to variability (i.e., the region can be polymorphic for a variety of alleles). For example, a single nucleotide polymorphism (SNP) in a nucleotide sequence is a genetic marker that is polymorphic for two alleles. Other examples of genetic markers of this invention can include but are not limited to microsatellites, restriction fragment length polymorphisms (RFLPs), repeats (i.e., duplications), insertions, deletions, etc.

A subject of this invention is any animal that is susceptible to cardiovascular disease as defined herein and can include mammals, birds and reptiles. Examples of subjects of this invention can include, but are not limited to, humans, non-human primates, dogs, cats, horses, cows, goats, guinea pigs, mice, rats and rabbits, as well as any other domestic or commercially valuable animal including animal models of cardiovascular disease.

As used herein, "nucleic acids" encompass both RNA and DNA, including cDNA, genomic DNA, mRNA, synthetic (e.g., chemically synthesized) DNA and chimeras of RNA and DNA. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An "isolated nucleic acid" is a DNA or RNA that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence.

The term "isolated" can refer to a nucleic acid or polypeptide that is substantially free of cellular material, viral material, or culture medium (when produced by recombinant DNA techniques), or chemical precursors or other chemicals (when chemically synthesized). Moreover, an "isolated fragment" is a fragment of a nucleic acid or polypeptide that is not naturally occurring as a fragment and would not be found in the natural state.

The term "oligonucleotide" refers to a nucleic acid sequence of at least about six nucleotides to about 100 nucleotides, for example, about 15 to 30 nucleotides, or about 20 to 25 nucleotides, which can be used, for example, as a primer in a PCR amplification or as a probe in a hybridization assay or in a microarray. Oligonucleotides can be natural or synthetic, e.g., DNA, RNA, modified backbones, etc.

The present invention further provides fragments or oligonucleotides of the nucleic acids of this invention, which can be used as primers or probes. Thus, in some embodiments, a fragment or oligonucleotide of this invention is a nucleotide sequence that is at least 10, 15, 20, 25, 30, 35, 40, 45, 50, 55, 60, 65, 70, 75, 80, 85, 90, 100, 125, 150, 175, 200, 250, 300, 350, 400, 450, 500, 550, 600, 650, 700, 750, 800, 850, 900, 1000, 1500, 2000, 2500 or 3000 contiguous nucleotides of the nucleotide sequence set forth in SEQ ID NO:1, or the nucleotide sequence set forth from nucleotides 118500001 to 118761789 of the NCBI Build 35 sequence of human chromosome 3 (SEQ ID NO:1). Such fragments or oligonucleotides can be detectably labeled or modified, for example, to include and/or incorporate a restriction enzyme cleavage site when employed as a primer in an amplification (e.g., PCR) assay.

The present invention is based on the inventors' discovery of a correlation between genetic markers in chromosome 3q13.31 and various aspects of cardiovascular disease. Thus, in one aspect, the present invention provides a method of identifying a subject having either an increased or decreased risk of developing cardiovascular disease, comprising detecting in the subject one or more genetic markers in chromosome 3q13.31 correlated with an increased or decreased risk of developing cardiovascular disease.

Further provided is a method of identifying a subject having either an increased or decreased risk of developing cardiovascular disease, comprising: a) correlating the presence of one or more genetic markers in chromosome 3q13.31 with an increased or decreased risk of developing cardiovascular disease; and b) detecting the one or more genetic markers of step (a) in the subject, thereby identifying the subject as having an increased or decreased risk of developing cardiovascular disease.

In further embodiments, the present invention provides a method of correlating a genetic marker in chromosome 3q13.31 with an increased risk of developing cardiovascular disease, comprising: a) detecting in a subject with cardiovascular disease the presence of one or more genetic markers in chromosome 3q13.31; and b) correlating the presence of the one or more genetic markers of step (a) with cardiovascular disease in the subject.

Also provided is a method of correlating a genetic marker in chromosome 3q13.31 with a decreased risk of developing cardiovascular disease, comprising: a) detecting in a subject without cardiovascular disease the presence of one or more genetic markers in chromosome 3q13.31; and b) correlating the presence of the one or more genetic markers of step (a) with the absence of cardiovascular disease in the subject.

Additionally provided herein is a method of diagnosing cardiovascular disease in a subject, comprising detecting in the subject one or more genetic markers correlated with a diagnosis of cardiovascular disease, as well as a method of diagnosing cardiovascular disease in a subject, comprising: a) correlating the presence of one or more genetic markers in chromosome 3q13.31 with a diagnosis of cardiovascular disease; and b) detecting the one or more genetic markers of step (a) in the subject, thereby diagnosing cardiovascular disease in the subject.

A method is also provided of correlating a genetic marker in chromosome 3q13.31 with a diagnosis of cardiovascular disease, comprising: a) detecting in a subject diagnosed with cardiovascular disease the presence of one or genetic markers in chromosome 3q13.31; and b) correlating the presence of the one or more genetic markers of step (a) with a diagnosis of cardiovascular disease in a subject.

In the methods described herein, the detection of a genetic marker in a subject can be carried out according to methods well known in the art. For example DNA is obtained from any suitable sample from the subject that will contain DNA and the DNA is then prepared and analyzed according to well-established protocols for the presence of genetic markers according to the methods of this invention. In some embodiments, analysis of the DNA can be carried by amplification of the region of interest according to amplification protocols well known in the art (e.g., polymerase chain reaction, ligase chain reaction, strand displacement amplification, transcription-based amplification, self-sustained sequence replication (3SR), Qβ replicase protocols, nucleic acid sequence-based amplification (NASBA), repair chain reaction (RCR) and boomerang DNA amplification (BDA)). The amplification product can then be visualized directly in a gel by staining or the product can be detected by hybridization with a detectable probe. When amplification conditions allow for amplification of all allelic types of a genetic marker, the types can be distinguished by a variety of well-known methods, such as hybridization with an allele-specific probe, secondary amplification with allele-specific primers, by restriction endonuclease digestion, or by electrophoresis. Thus, the present invention further provides oligonucleotides for use as primers and/or probes for detecting and/or identifying genetic markers according to the methods of this invention.

The genetic markers of this invention are correlated with various aspects of cardiovascular disease as described herein according to methods well known in the art and as disclosed in the Examples provided herein for correlating genetic markers with various phenotypic traits, including disease states and pathological conditions and levels of risk associated with developing a disease or pathological condition. In general, identifying such correlation involves conducting analyses that establish a statistically significant association and/or a statistically significant correlation between the presence of a genetic marker or a combination of markers and the phenotypic trait in the subject. An analysis that identifies a statistical association (e.g., a significant association) between the marker or combination of markers and the phenotype establishes a correlation between the presence of the marker or combination of markers in a subject and the particular phenotype being analyzed.

The correlation can involve one or more than one genetic marker of this invention (e.g., two, three, four, five, or more) in any combination. In some embodiments of this invention, the genetic markers are located on chromosome 3 and can be localized to the region 3q13.31. However, in other embodiments, the methods of this invention can include correlations between genetic markers on chromosome 3 (e.g., at 3q13.31) in combination with genetic markers on other chromosomes (e.g., chromosome 1) and various aspects of cardiovascular disease as described herein. For example, the genetic markers of this invention can be combined with genetic markers in the ApoE gene on chromosome 19, genetic markers in the MEF21 gene on chromosome 15, genetic markers in the matrix metalloproteinase 3 gene on chromosome 11 and/or genetic markers in the $\beta_1$-adrenergic receptor gene in chromosome 10 (e.g., the allele producing the Arg389 variant Perez et al., *Nature Medicine* 9:1300-1305 (2003); Bengtsson et al. *Circulation* 104:187-190 (2001)) in the methods of this invention and in establishing correlations between genetic markers and various aspects of cardiovascular disease as described herein.

Non-limiting examples of genetic markers of this invention are set forth in Tables 9, 10 and 11, which are located in the region from nucleotides 118500001 to 118761789 of human chromosome 3, NCBI Build 35 (SEQ ID NO:1).

In some embodiments, the genetic marker is a single nucleotide polymorphism (SNP). Exemplary single nucleotide polymorphisms include but are not limited to T for G, T for A, C for A, C for T, A for G, A for C, A for T, G for A and G for T substitutions. Other examples of genetic markers include insertions, deletions and duplications, including but not limited to an adenine deletion, a CAA insertion, and a 27-base pair duplication on human chromosome 3. Further examples of genetic markers of this invention include but are not limited to microsatellite markers such as 3M0238, which has a variety of alleles, such as alleles 245, 249, 250, 253 and 256, wherein each allele is defined by the length of the PCR product (245, 249, 250, 253 basepairs, etc.) produced using the 3M0238 primers (SEQ ID NOS:34 and 35) shown in Table 4. In a representative embodiment of the invention, the microsatellite marker is a tetranucleotide repeat, optionally, the tetranucleotide repeat sequence is GATA.

In the methods of this invention, particular alleles of the genetic markers are identified as being correlated with various aspects of cardiovascular disease. Thus, for example, an allele correlated with an increased risk of cardiovascular disease in a subject or with a diagnosis of cardiovascular disease in a subject can be a G allele at single nucleotide polymorphism rs1875518 (rs1875518_G), a T allele at single nucleotide polymorphism rs2937666 (rs2937666_T), a 253 allele at microsatellite marker 3M0238 (tetranucleotide GATA repeat, 253 basepair PCR product, 3M0238__253), a C allele at single nucleotide polymorphism hcv1602689 (hcv1602689_C), an A allele at single nucleotide polymorphism rs2272486 (rs2272486_A), an A allele at single nucleotide polymorphism rs1676232 (rs1676232_A), an A allele at single nucleotide polymorphism rs4404477 (rs4404477_A), as well as any combination thereof. In some embodiments, a combination of genetic markers is provided that defines a haplotype that is correlated with an aspect of cardiovascular disease as described herein. Thus, for example, haplotypes correlated with increased risk of cardiovascular disease or with a diagnosis of cardiovascular disease include: rs1875518_G and G3M0238__253; rs1875518_G with G3M0238__253 and the A allele for rs2937666 (rs2937666_A); and/or the A allele for rs1875518 (rs1875518_A) with a non 253 allele of 3M0238 (3M0238_non253) and rs2937666_T. Other examples of haplotypes correlated with cardiovascular disease are: the adenine deletion allele of the single nucleotide polymorphism of SEQ ID NO:15; the 27 basepair duplication allele of the polymorphism of SEQ ID NO:28; the CAA insertion allele of the polymorphism of SEQ ID NO:29, and any combination thereof (Table 10). Still further examples of haplotypes correlated with cardiovascular disease are the A alleles for single nucleotide polymorphism rs1676232 or rs4404477 (rs1676232_A, rs4404477_A), or a combination thereof. Furthermore, rs4404477 appears to have an interaction with rs1676232 such that when both SNPs are homozygous for the A allele, the risk for CAD is significantly increased over that which is observed for a single SNP that is homozygous for the A allele, each of which is also associated with enhanced risk for CAD.

An example of a haplotype correlated with decreased risk of cardiovascular disease is rs1875518_A with G3M0238_non253 and rs2937666_A.

Other genetic markers associated with cardiovascular disease are set forth in Tables 9, 10 and 11 and the Examples. The genetic markers of the invention can be used individually or in any combination.

In yet further embodiments, the present invention provides a method of identifying a subject with cardiovascular disease as having a good or a poor prognosis, comprising detecting in the subject one or more genetic markers in chromosome 3q13.31 correlated with a good or a poor prognosis for cardiovascular disease.

Furthermore, the present invention provides a method of identifying a subject with cardiovascular disease as having a good or a poor prognosis, comprising: a) correlating the presence of one or more genetic markers in chromosome 3q13.31 with a good or a poor prognosis for cardiovascular disease; and b) detecting the one or more markers of step (a) in the subject, thereby identifying the subject as having a good or a poor prognosis.

In addition, the present invention provides a method of correlating a genetic marker in chromosome 3q13.31 with a good or a poor prognosis for cardiovascular disease, comprising: a) detecting in a subject with cardiovascular disease and having a good or a poor prognosis, the presence of one or more genetic markers in chromosome 3q13.31; and b) correlating the present of the one or more genetic markers of step (a) with a good or a poor prognosis for cardiovascular disease.

A subject is identified as having cardiovascular disease according to diagnostic parameters well known in the art and can have a good or poor prognosis according to diagnostic and/or clinical parameters that are also known in the art. A correlation can be made between good and poor prognosis and a subject's genetic markers according to the methods of this invention, which can allow a clinician to determine the most effective treatment regimen for the subject.

The present invention further provides a method of identifying an effective treatment regimen for a subject with cardiovascular disease, comprising detecting one or more genetic markers in chromosome 3q13.31 in the subject correlated with an effective treatment regimen for cardiovascular disease.

Also provided is a method of identifying an effective treatment regimen for a subject with cardiovascular disease, comprising: a) correlating the presence of one or more genetic markers in chromosome 3q13.31 in a test subject with cardiovascular disease for whom an effective treatment regimen has been identified; and b) detecting the one or more markers of step (a) in the subject, thereby identifying an effective treatment regimen for the subject.

Further provided is a method of correlating a genetic marker of chromosome 3q13.31 with an effective treatment regimen for cardiovascular disease, comprising: a) detecting in a subject with cardiovascular disease and for whom an effective treatment regimen has been identified, the presence of one or more genetic markers in chromosome 3q13.31; and b) correlating the presence of the one or more genetic markers of step (a) with an effective treatment regimen for cardiovascular disease. Examples of treatment regimens for cardiovascular disease are well known in the art.

Patients who respond well to particular treatment protocols can be analyzed for specific genetic markers and a correlation can be established according to the methods provided herein. Alternatively, patients who respond poorly to a particular treatment regimen can also be analyzed for particular genetic markers correlated with the poor response. Then, a subject who is a candidate for treatment for cardiovascular disease can be assessed for the presence of the appropriate genetic markers and the most appropriate treatment regimen can be provided.

In some embodiments, the methods of correlating genetic markers with treatment regimens can be carried out using a computer database. Thus the present invention provides a computer-assisted method of identifying a proposed treatment for cardiovascular disease. The method involves the steps of (a) storing a database of biological data for a plurality of patients, the biological data that is being stored including for each of said plurality of patients (i) a treatment type, (ii) at least one genetic marker associated with cardiovascular disease and (iii) at least one disease progression measure for cardiovascular disease from which treatment efficacy can be determined; and then (b) querying the database to determine the dependence on said genetic marker of the effectiveness of a treatment type in treating cardiovascular disease, to thereby identify a proposed treatment as an effective treatment for a subject carrying a genetic marker correlated with cardiovascular disease.

In one embodiment, treatment information for a patient is entered into the database (through any suitable means such as a window or text interface), genetic marker information for that patient is entered into the database, and disease progression information is entered into the database. These steps are then repeated until the desired number of patients has been entered into the database. The database can then queried to determine whether a particular treatment is effective for patients carrying a particular marker, not effective for patients carrying a particular marker, etc. Such querying can be carried out prospectively or retrospectively on the database by any suitable means, but is generally done by statistical analysis in accordance with known techniques, as described herein.

The present invention is more particularly described in the following examples that are intended as illustrative only since numerous modifications and variations therein will be apparent to those skilled in the art.

EXAMPLES

Example 1

Overall summary: Using linkage analysis and association studies in families and isolated patients with cardiovascular disease (CAD), a 400 kb region in 3q13.31 was identified, containing a DNA region that affects susceptibility for CAD. A specific DNA haplotype was identified that is highly associated with CAD ($p=0.0001$) in Caucasians. This haplotype is defined by three markers: the single nucleotide polymorphism (SNP) marker rs1875518; a previously unidentified tetranucleotide GATA repeat, named 3M0238, and a third SNP, rs2937666. The actual alleles that are associated with susceptibility are shown in Tables 2 and 3. Both young onset and old onset CAD are affected by these haplotypes.

A genome wide screening in 420 families (GENECARD study Table 1) found the most significant linkage evidence (multipoint lod score=3.5) in chromosome 3q13 spanning over 120 megabases (Mb). This is shown in FIG. 1. Within this region is a genetic entity that influences the susceptibility for CAD. The present study was carried out to narrow the critical region and identify genetic variants conferring susceptibility to CAD in 3q13.

METHODS: Systematic association analysis using SNPs was performed in the 60 mB centered around the peak area of FIG. 1. A modified DNA pooling method was used to screen 16 SNPs, 100 kb apart, to look for association with CAD. To do this, another data set was used, different from the GEN- ECARD data set, the CATHGEN samples, from a study of the Duke Catheterization Laboratory Database. Subjects were selected according to their CAD index ($CAD_i$), a validated angiographical measure of the extent of CAD. CATHGEN included 301 young affected (YA: age≦55, $CAD_i$>32), 168 older affected (OA: age>55, $CAD_i$>74), and 204 controls (ON: age>60, $CAD_i$<23). Association analysis was performed separately by ethnicity and adjusting for gender.

Figure 2:
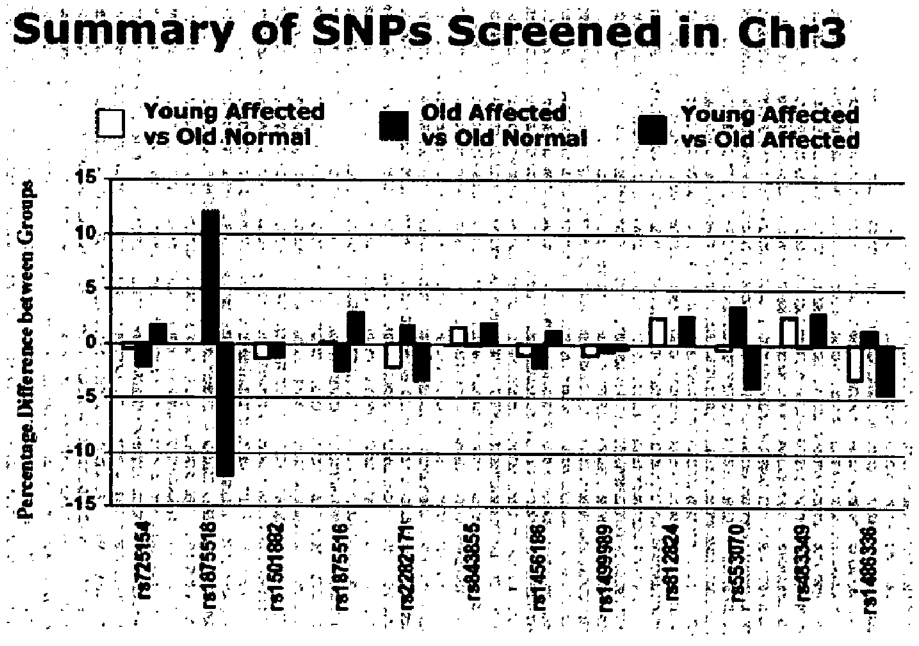
FIG. 2 depicts the screening of 16 SNPs for linkage to the susceptibility for CAD.
Figure 3:
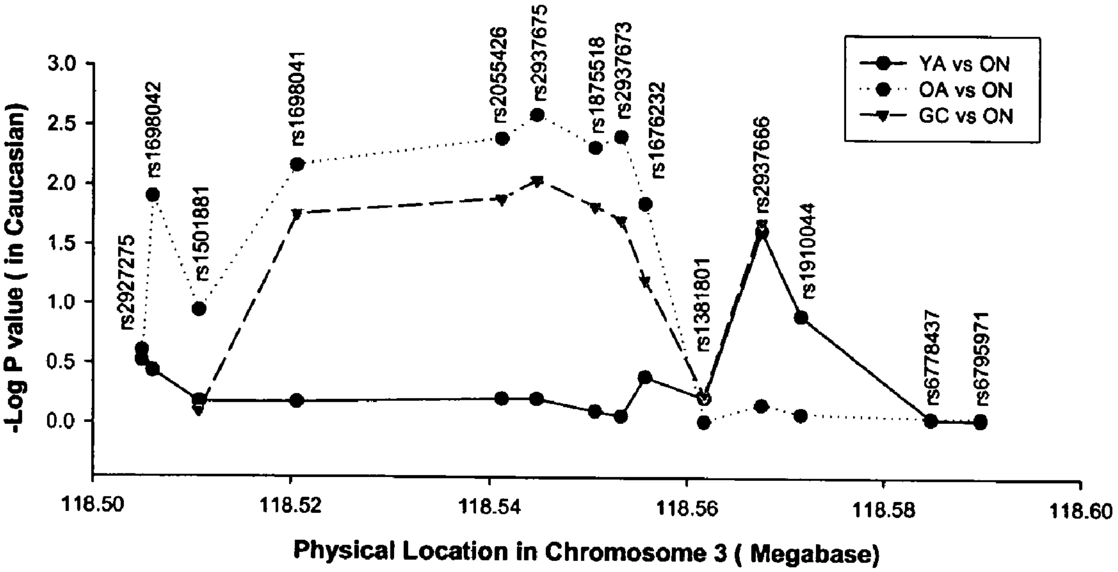
FIG. 3 depicts association analysis of SNPs around rs1875518 with risk for CAD.

Initial screening of 16 SNPs revealed that the frequency of the G allele of rs1875518 (A/G) is significantly higher in OA than ON (OA-ON=12.2%, p=0.001) in Caucasians (FIG. 2), which is confirmed by individual genotyping (OA=57.2%; ON=45.5%). Additional genotyping flanking rs1875518 defined a linkage disequilibrium (LD) block extending~60 kb that is highly associated with OA in Caucasians. Moreover, evidence supports the association of this block in the GENECARD probands versus Cathgen ON (FIG. 3). Finally, a novel microsatellite marker (3M0238) was identified within the block, which broke the LD and formed a significant risk haplotype (P<0.005) with rs1875518: rs1875518_G-3M0238__253 is twice as prevalent in OA (21.39%) as in ON (11.39%).

Additional markers surrounding this region were genotyped and a further haplotype was obtained that defines the risks and protection, as seen in Tables 2 and 3. Multiple risk haplotypes exist, which could represent different alleles of the actual causal change. Primers and probes used in the analysis are shown in Table 4.

Example 2

Coronary artery disease (CAD) is the leading cause of death in the United States and approximately 8% of CAD occurs in Americans under 50 years of age (AHA website). It is well established that CAD and death from CAD have a hereditary component (Marenberg, Zradkovic). The strong genetic predisposition of CAD may be partially explained by the heritability of disease related intermediate traits such as dyslipidemia. Dyslipidemia is a well-recognized risk factor for CAD, and abnormalities in serum lipids have been shown to have a genetic component (Breslow). Further, there is an increased incidence of familial lipoprotein abnormalities in family members of patients with premature CAD (Genest). Twin and adoption studies suggest that at least 50% of the observed variation in low-density lipoprotein (LDL) cholesterol is genetically determined (Austin, Rice) and segregation analysis has shown evidence for a major gene for high-density lipoprotein (HDL) cholesterol (Mahaney 1995). The Family Heart Study has found evidence for a common major gene accounting for mild elevations of LDL cholesterol (Coon, 1999), although the exact gene has yet to be identified. Familial combined hyperlipidemia (FCH) has been mapped to chromosome 1q (Pajukanta Nat Gen 1998), with subsequent identification of the USF1 gene (Pajukanta 2004). Linkage of HDL cholesterol to chromosomes 5 and 13 has been reported (Peacock 2000), and recently, a pooled analysis of patients with FCH has revealed a susceptibility locus for low HDL on chromosome 16q (Pajukanta 2003).

Many candidate genes have been implicated in the development of coronary heart disease (CHD) and dyslipidemia, but none have been shown to account for even a modest fraction of the burden of CHD in the general population. One reason is that CHD is likely an oligogenic disease with multiple genetic loci conferring susceptibility to the disease, with the phenotype determined by complex gene-gene and gene-environment interactions. One approach to unraveling these complex relationships is to examine intermediate traits. Methods to map genes for complex traits that explicitly take into account the presence of such heterogeneity are likely to have greater power to identify subtle changes. Two such methods for incorporation of covariates into linkage mapping include examination of the extremes of the covariate distribution to find genes that cause gross perturbations (ordered subset analysis (OSA)), or examination of the entire covariate distribution to find genes for trait variability (quantitative trait loci (QTL) analysis).

The Genetics of Early Onset Cardiovascular Disease (GENECARD) linkage study was designed to conduct affected sibling pair (ASP) analysis for the identification of genes contributing to early onset CAD. Linkage studies employ an unbiased, genome-wide approach to identify genetic regions shared in excess between affected relative pairs. This strategy for gene mapping has been widely used and has led to the discovery of many disease susceptibility genes. Strong evidence has been provided for linkage to early onset CAD in GENECARD families to chromosome 3q13 in the overall population (lod 3.50), and in stratified analyses by families presenting with acute coronary syndrome (ACS; lod 3.16) and non-diabetic (NDIA) families (lod 2.42; Hauser 2004). Chromosome 1q25 was significant in ACS families (lod 2.17); other regions showing evidence for linkage included 5q13, 7p14 and 19p13. Previous studies have also implicated regions on chromosome 3q26-27 in CAD (over 60 cM distal to the peak in the GENECARD analysis) (Francke 2001, Broeckel 2002, Harrap 2002), metabolic syndrome (Kissebah 2000), and type II diabetes mellitus (DM) (Vionett 2000, Mori 2002). There is also evidence of QTL for triglyceride-HDL cholesterol ratio (Shearman 2000), HDL cholesterol (Imperatore 2000, Coon 2001) and fractionated low-density lipoprotein (LDL) particles (Rainwater 1999) in the region of the GENECARD 3q peak. These results suggest potential interactions between CAD genes and intermediate lipid traits.

To incorporate disease-related risk factors, lipid phenotypes in the GENECARD study were examined. Incorporation of lipid phenotypes increases the power to map CAD susceptibility genes; uncovers additional regions of linkage, narrows linkage peaks, and identifies phenotypic subsets for further study. Since it is well known that lipid phenotypes themselves have a high heritability, QTL analysis was performed to identify chromosomal regions linked to variability in lipid values within high-risk CAD families. OSA was also performed using subclassification by lipid phenotypes to reduce etiologic heterogeneity.

Clinical data collection. The GENECARD study enrolled 900 families with early onset CAD to perform an ASP genetic linkage study for identification of genetic variants. The study design has been previously reported. Briefly, families with at least two siblings having early onset CAD were recruited from multiple sites. Individuals were recruited if they met the diagnosis of CAD and if the qualifying event occurred before the age of 51 years for men and 56 years for women. For the diagnosis of CAD, a sentinel event or diagnostic study was required that was verified by primary medical documents. Subjects were required to have myocardial infarction (MI) or unstable angina, significant CAD on coronary angiography, coronary revascularization procedure, or a functional test documenting reversible ischemia with imaging. Medical history was confirmed by inspection of medical records. A system of periodic review was implemented to establish quality control and to ensure consistency among all clinical sites in diagnostic criteria. A genome-wide linkage analysis for early onset CAD was undertaken on the first 420 families enrolled in GENECARD, and these families form the basis for the analyses presented in this study Laboratory methods. Blood samples were obtained by study staff primarily at the medical center or clinic, or by field trip to participants' homes. DNA was extracted using the Puregene system (Gentra Systems, Minneapolis, Minn.). Quality control (QC) samples were incorporated into specified slots in the genotyping lists. Laboratory technicians were blinded to the identity of the QC samples, and to affection status and family composition of all samples. Genotyping was performed using the gel-based FAAST method (Vance and Ben Othmane 1998). Quality control checks were implemented to maximize data quality during genotyping (Hauser 2004). A total of 395 (98.3%) markers out of 402 attempted passed the QC tests and were included in these analyses. The mean genotyping efficiency (proportion of non-zero genotypes) over the 395 markers was 97.6%. Using data from several large studies performed in the Duke Center for Human Genetics, we estimated an error rate in sample processing and allocation in 0.14% and we estimated the genotyping error rate to be approximately 0.8%. Given that GENECARD families were collected from six sites in the US and Europe, it is possible that they represent genetically distinct subpopulations. To test for population substructure Structure (Pritchard 2000) and Arlequin (Arlequin) were employed, using an indicator for each site. There was no evidence from either analysis that the sites could be distinguished on the basis of allele frequencies at the 395 markers in the genome scan. Based on these results, estimated allele frequencies were estimated from the family members in the entire sample (Broman 2001).

Serum lipoprotein measurements were done in the fasting state for 229 of the 420 families (54.5%) using a centralized core laboratory. Levels of plasma total cholesterol (TC) and triglycerides were measured as reported previously (Vega). Briefly, plasma lipids were measured enzymatically using the Boehringer Mannheim cholesterol enzymatic kit (Roche Diagnostics, Indianapolis, Ind.) and the Sigma-Aldrich kit for triglycerides (St. Louis, Mo.). HDL cholesterol was measured after precipitation of non-HDL cholesterol with dextran sulfate (Sigma-Aldrich, St. Louis, Mo.) (Warnick). The coefficients of inter- and intra-assay variation were ≦3%. The remaining 191 families, consisting mostly of United States participants, had lipoprotein measurements abstracted from the medical records. Adjustment for treatment with medications for dyslipidemia was done when creating the polygenic model used for quantitative trait loci analyses. 27 families were excluded for missing values. Reported results include all 393 families for the lipid parameters of TC, LDL, HDL cholesterol, and HDL/TC ratio, which has been shown to be an independent risk factor for CAD (Jeppesen). Reported results for triglycerides are restricted to the 229 families with measured lipid parameters, since serum triglyceride levels are highly affected by the non-fasting state. There were fewer than 10 families who would potentially meet broad diagnostic criteria for FCH; the family-specific lod scores did not identify specific FCH loci nor did these families appear to contribute an excess amount to the overall CAD genome scan, and therefore these families were included in all further analyses.

Analytic methods. Descriptive analysis for lipid values and for all covariates were performed using SAS software (SAS, Cary N.C.).

Quantitative trait loci (QTL). To identify genetic loci associated with lipid phenotypes, QTL linkage analysis was performed using a genome wide scan of 395 microsatellite markers. All lipoprotein subgroups had an approximately normal distribution, except serum triglycerides, which were log-transformed to approximate a normal distribution. QTL analysis was performed using the variance components approach as implemented in the Sequential Oligogenic Linkage Analysis Routines (SOLAR) software package, which uses maximum likelihood methods to estimate the genetic variance components (Almasy). The SOLAR package utilizes multipoint identical-by-descent (IBD) methods where the proportion of alleles shared IBD at genotyped loci are used to estimate IBD sharing at arbitrary points along a chromosome for each relative pair (Almasy, 1998). IBD and multipoint IBD matrices were constructed using the observed family pedigrees. An initial polygenic model was constructed adjusting for sex, age at exam, and treatment with dyslipidemia medications for each quantitative trait and used as the foundation for two-point and multipoint linkage analyses. Use of dyslipidemia medications was a binary, self-reported variable coded yes/no. A lod adjustment was calculated (lod-adj=0.61) and used for analysis of TC because of a high residual kurtosis of 1.6. Although the GENECARD probands were not ascertained on lipid values, the relationship between CAD and lipid values does not reflect normal population values, implying an ascertainment bias. As a result, analyses were done with and without adjustment for proband lipid values and the results did not differ appreciably. Therefore, only results with proband ascertainment are presented. Empirical p-values were calculated using models with 10000 simulations in each of which a fully-informative marker, unlinked to the trait, is simulated and trait linkage is then tested at that marker (SOLAR). QTL mapping results that achieved a multipoint lod score of greater than 1.2 (corresponding to an empirical p-value of 0.007-0.03 depending on the covariate analyzed) were flagged for further study.

Ordered subset analysis (OSA). OSA examines evidence for linkage in a more homogeneous subset of families defined by a trait-related covariate. The average lipid values in the affected individuals from each family were chosen as trait-related covariates. In addition to the family-specific covariate values, a matrix of linkage statistics Zi(d,y) is required as input, where d represents the disease location parameter and y represents the genetic model, and the maximum ordered subset statistic for each family is calculated at a set of values for d and y. OSA begins by ordering N number of families by the covariate value xi, both in an ascending and a descending order, where $Z_{(j)}(d,y)$ is the linkage statistic matrix for ordered family j. The maximum lod score is calculated for the $j^{th}$ family, as well as the estimates of $d_{(j)}$ and $y_{(j)}$ at which the maximum occurs. Then, element-wise addition is used to add the matrix for the next ordered family $Z_{(j+1)}(d,y)$ to the matrix for family 1 through j. In summary, the $j^{th}$ partial sum is created by adding each element of the linkage statistic matrix for each family up to and including ordered family j. The maximum subset lod score (the highest lod score using subsets of families with the highest or lowest mean covariate) represents the linkage evidence in a subset of families defined by that covariate. OSA also provides an estimate of the disease location on the specified chromosome. A permutation procedure, randomly ordering families and recalculating the OSA test statistic, provides an empirical p-value to assess the significance of the increase in the maximum lod score using the ordered subset of families compared to the overall lod score using all families. Significance was defined as a p-value <0.05 for an increase in the maximum subset lod when compared to the overall lod score. To further characterize subsets of families with significant results, the family-specific means of each covariate comparing families comprising the maximum subset lod score and the remainder of the GENECARD families. Mean family values for quantitative traits were compared using a univariate t-test (SAS).

Table 5 outlines baseline characteristics in the 420 GENECARD families, overall and by affection status, comprising a total of 1129 individuals, 952 affected with early onset CAD and 177 unaffected family members. Consistent with other studies, there was a high prevalence of cardiovascular risk factors among affected individuals, including hypertension (55.2%), diabetes (21.0%), tobacco use (32.9% currently smoking), dyslipidemia (82.3%) and metabolic syndrome (46.8%). As expected, these risk factors were more prevalent in affected individuals than in unaffected individuals. However, the mean values of total cholesterol, LDL and systolic blood pressure were higher in the unaffected group, consistent with the 14-year increase in the mean age of the unaffected family members and increased use of medications for dyslipidemia in the affected group. Heritability estimates revealed strong heritability of all lipid subgroups (Table 6), consistent with previous reports.

QTL results. The overall results of the QTL analysis are shown in Table 6. The largest lod score for a QTL was for HDL cholesterol on chromosome 3p (FIG. 4), with weaker evidence on chromosomes 7 and 15. QTLs for TC were found on chromosome 18p and 5p, and for LDL cholesterol on chromosomes 6 and 16. There was evidence for QTL for triglycerides on chromosome 13,14, and 18, and there was evidence for loci for HDL/TC ratio on chromosome 3q, 7q and 8q. Three regions showing evidence for linkage in the overall genome scan (3q, 7p and 19p) also showed evidence for lipid QTLs (HDL/TC ratio, triglycerides and LDL cholesterol, respectively).

OSA results. Significant OSA results are shown in Table 7. FIG. 5 shows chromosome 3 lod score curves using OSA that corroborate, strengthen and narrow the linkage peaks previously observed on chromosome 3q. The increase in the lod score is intriguing because it occurs on top of already strong linkage evidence in this region. The 167 families in the OSA subset represent 39.7% of the GENECARD families. These families appear to have a different phenotypic profile with significantly fewer CAD risk factors than the remainder of the families (Table 8). FIG. 5 also shows a lod score curve using OSA showing a strong linkage peak on chromosome 5q, but more distal to the linkage peak observed on the overall genome scan. This set of 54 (12.8%) families represents a high-risk lipid phenotype with elevated TC, high LDL and triglycerides and having a significantly lower average age of onset. However, these families cannot be distinguished on the basis of other CAD risk factors such as BMI, gender, or smoking. The chromosome 5 subset of families is a distinct set of CAD families from the chromosome 3 subset, with the two subsets of families representing the two tails of the lipid distributions among these CAD families. OSA also revealed significant LOD scores in subsets of families on chromosomal regions not previously found to be significant in this sample, including peaks on 9p, 10q, 12q, 14p, 17q, and 22p. The subsets identified in these regions are smaller, ranging from 22 to 80 families (5.2% to 19.0%).

These results reveal evidence for several QTL for lipid subgroups in families with early onset CAD. OSA results corroborated and strengthened areas of strong linkage in the overall population on chromosome 3q and 5q, helped narrow the linkage peaks, identified new regions for further analysis, and defined phenotypic subsets comprising the peaks.

Specifically, QTL mapping of lipid phenotypes in the GENECARD population revealed multiple chromosomal areas with significant lod scores for lipid subtypes, with the strongest lod score for HDL cholesterol on chromosome 3p (lod 2.43). Evidence was also found for linkage for HDL cholesterol to chromosome 7q (156 cM), a region also found to link to HDL/TC ratio (143 cM). This area has previously been linked to TG and TG/HDL ratio (Shearman 2000), and is proximal to another reported peak for TG (186 cM) (Duggirala). This locus contains several candidate genes, including ABC28 (ATP-binding cassette subfamily F, member 2, similar to ABC1 which causes Tangier's disease, characterized by HDL deficiency and premature atherosclerosis). A QTL for LDL cholesterol was identified on chromosome 6q, which contains the gene for apolipoprotein (a) (Lp(a)), a well recognized cardiovascular risk factor (Murai), and has previously been linked to small LDL particles in the San Antonio Family Heart Study (Imperatore). There was evidence for linkage to triglycerides on chromosome 18 (near QTL for total cholesterol at 55 cM); though not as strongly linked, this region is interesting because it contains the gene for Niemann-Pick disease type C1 (NPC1), an autosomal recessive lipid storage disorder. These results did not corroborate previous results on chromosomes 4 (TG, LDL) (Arnett 2001), 15 (HDL, TG) (Almasy, Duggirala, Arnett), and 2 (TG HDL) (Pajukanata, Imperatore, Almasy).

To understand the impact of heterogeneity, it is useful to compare these results to the OSA analysis. At least two phenotypically distinct sets of families with early-onset CAD were identified that contributed to linkage evidence. On chromosome 3q, evidence was found for linkage to early onset CAD in families with lower TC and triglycerides, higher HDL cholesterol and overall lesser prevalence of metabolic syndrome, when compared to families not included in the OSA peak. These results were corroborated by the finding of a QTL for HDL/TC ratio in the same region. Therefore, it appears that the previously reported strong linkage peak on chromosome 3q is comprised of families without a preponderance of traditional cardiovascular risk factors. A recent meta-analysis of four genome-wide scans for CAD revealed strongest evidence for linkage on chromosome 3q26-27 (Chiodini), and this region has shown linkage to metabolic syndrome (Kissebah 2000) and type II diabetes mellitus (Vionett 2000, Mori 2002, Hegele 1999). However, in each of these genome scans the evidence for linkage to CAD is over 60 cM distal to the peak in the GENECARD analyses. In QTL analysis of plasma lipids, there is evidence of linkage with triglyceride-high density lipoprotein (HDL) cholesterol ratio in the peak 3q13 region (Shearman et al. 2000). There is also evidence for linkage to HDL cholesterol itself (Imperatore et al. 2000; Coon et al. 2001) and fractionated low-density lipoprotein (LDL) particles (Rainwater et al. 1999) in this region. A genome scan of lipid traits in Pima Indians found a locus on chromosome 3, but more distal to this peak (182 cM) (Imperatore 2000). The 3q26-qter region harbors several candidate genes involved in glucose homeostasis and lipid metabolism. The 3q13 region, however, is an area of relative paucity of genes. This area may harbor a previously undiscovered gene, represent a genetic area exerting a downstream influence, or may be in linkage disequilibrium with more distal candidate genes.

A linkage peak for early onset CAD was again observed on chromosome 5q using OSA, but more distal on the chromosome than seen in the overall genome scan, and is comprised of a subset of families who are younger with higher total cholesterol values. This area contains many genes, including HNRPAB (apolipoprotein B mRNA-editing enzyme) and F12 (factor XII deficiency), though none have been previously implicated in the pathogenesis of dyslipidemia or CAD.

OSA and QTL mapping are alternate methods for incorporating phenotypic data in linkage studies. Overall it was found that OSA and QTL results did not overlap, except on chromosome 3q. This is most likely related to the fact that QTL and OSA analyses model different aspects of lipid phenotypes and address different issues. The lod score for the OSA analysis is still linkage to CAD and the phenotype data are used as a measure of similarity to help identify homogeneous subsets. QTL mapping models the quantitative traits of lipid phenotypes specifically, in attempts to identify chromosomal regions that may harbor genes for normal variation in lipid phenotypes. OSA was used to identify and narrow chromosomal regions harboring candidate genes for the phenotype of early onset CAD, using lipid subtypes to create more etiologic homogeneity and potentially concentrate the genetic effect.

The study population consists of those who remain alive despite early onset CAD, a so-called "survivor effect." Therefore, inferences drawn about genetic effects will be confined to familial early onset CAD, and may not be applicable to premature sudden cardiac death. Because the GENECARD families were ascertained on the basis of early onset CAD, their lipid values may not represent the normal distribution of lipid values. The phenotypic differences in the GENECARD sample compared to samples of unselected families, or families ascertained on the basis of hypertension or metabolic syndrome, may explain why QTL analysis did not identify the regions identified in other studies. Although genome-wide linkage studies may be superior in determining significant genetic loci, affected sibling pair studies only provide a general view of the true gene location. The permutation test employed by OSA analyses controls for the inflation in the false positive rate induced by examining multiple family subsets for a given covariate, and appears to give the proper type I error rate in previously done simulations (Hauser). However, these analyses do not control for OSA over multiple trait-related covariates, but the strong correlation between the lipid parameters makes it difficult to appropriately correct for multiple comparisons.

Regardless, the GENECARD cohort is an ideal population for genetic studies. Setting an age criteria for CAD selects for patients with a strong genetic predisposition and enriches the sample for CAD caused by genetic etiologies. It is also an ideal population for primary prevention, an eventual goal of the utilization of genetics in clinical cardiology. Furthermore, GENECARD represents a model database for evaluation of genotype-phenotype interactions in the pathogenesis of CAD, by virtue of its sibling pair approach; international population allowing for ethnic heterogeneity; relatively large sample size; and genome-wide methodology. The combined approach of using QTL and OSA analysis for incorporation of disease-related lipid phenotypes in a genome scan of CAD is unique. Such modeling of genotype-phenotype interactions in a multi-analytic approach will enhance discovery of genetic loci and aid in the eventual goal in creation of a comprehensive cardiovascular risk assessment model.

These results show strong evidence of linkage to chromosomal region 3q13 in families with early onset CAD but with more favorable lipid profiles, possibly due to a concentrated non-lipid-related genetic effect on CAD, and to chromosome 5q in families with early onset CAD but with higher total and LDL cholesterol values, possibly representing a hereditary lipid phenotype predisposing to early onset CAD. QTL mapping identified multiple loci for lipid phenotypes and overall corroborated results from the initial genome scan. These results suggest presence of etiologic heterogeneity in families with early onset CAD, potentially due to differential lipid phenotypes.

Example 3

Sequences of exemplary polymorphisms within the region of human chromosome 3q13.31 are depicted in Table 10. Of particular note are: the single nucleotide polymorphism as set forth by an adenine deletion in SEQ ID NO:15; the polymorphism as set forth by a 27 basepair duplication in SEQ ID NO:28; and the polymorphism as set forth by a CAA insertion in SEQ ID NO:29. FIG. 6 depicts the genotypes of normal versus affected individuals with respect to these three variations.

FIG. 7 depicts differences in allele frequency between affected versus control (normal) cases with exemplary SNPs within the region of human chromosome 3q13.31.

FIG. 8 depicts the frequency of genetic markers within the region of human chromosome 3q13.31 correlated with affected and control (normal cases) and the significance of the correlation of the G allele of rs1875518 and the 253 allele of 3M0238 with CAD.

Example 4

Association analysis of additional SNPs with risk for CAD is depicted in FIG. 9. Of particular note are the SNPs rs2272486 and hcv1602689 in Huntington-associated protein-interacting protein (HAPIP) and myosin light chain kinase (MLCK), respectively. The locations of these SNPs on human chromosome 3 are listed in Table 11. Particularly, the C allele for hcv1602689 (SNP is C/G) and/or the A allele for rs2272486 (SNP is A/G) is associated with increased risk for CAD.

Additional SNPs associated with risk for CAD are the A alleles for rs1676232 and rs4404477 found in the gene for the limbic system-associated membrane protein (LSAMP; both SNPs are A/G). Furthermore, rs4404477 appears to have an interaction with rs1676232 so that when both SNPs are homozygous for the A allele, the risk for CAD is significantly increased over that which is observed for a single SNP that is homozygous for the A allele.

The foregoing is illustrative of the present invention, and is not to be construed as limiting thereof. The invention is defined by the following claims, with equivalents of the claims to be included therein.

All publications, patent applications, patents, patent publications, sequences identified by Genbank and/or SNP accession numbers, NCBI Build 35 of human chromosome 3 and other references cited herein are incorporated by reference in their entireties for the teachings relevant to the sentence and/or paragraph in which the reference is presented.

REFERENCES

Hauser et al. "A genomewide scan for early-onset coronary artery disease in 438 families: the GENECARD study" *Am. J Hum. Genet* 75:436-447 (2004)

Marenberg M, Risch N, Berkman L F, Floderus B, de Faire U. Genetic susceptibility to death from coronary heart disease in a study of twins. New Engl J Med 1994;330:1041-46.

Zdravkovic S, Wienke A, Pedersen N L, Marenberg M E, Yashin A I, de Faire U. Heritability of death from coronary heart disease: a 36-year follow-up of 20 966 Swedish twins. J Int Med 2002;252:247-254.

Sorensen T I, Nielsen G G, Anderson P K, Teasdale T W. Genetic and environmental influences on premature death in adult adoptees. New Engl J Med 1988;318:727-32.

Shearman A M. Ordovas J M. Cupples L A. Schaefer E J. Harmon M D. Shao Y. Keen J D. DeStefano A L. Joost O. Wilson P W. Housman D E. Myers R H. Evidence for a gene influencing the TG/HDL-C ratio on chromosome 7q32.3-qter: a genome-wide scan in the Framingham study. Hum Mol Genet. 9(9):1315-20, 2000 May 22.

Mahaney M C, Blangero J, Rainwater D L, Comuzzie A G, VandeBerg J L, Stern M P, MacCluer J W, Hixson J E. A major locus influencing plasma high-density lipoprotein cholesterol levels in the San Antonio Family Heart Study: segregation and linkage analyses. Arterioscler Thromb Vasc Biol 1995; 15:1730-1739.

Peacock J M, Arnett D K, Atwood L D, Myers R H, Coon H, Rich S S, Province M A, Heiss G. Genome scan for quantitative trait loci linked to high-density lipoprotein cholesterol: the NHLBI Family Heart Study. Arterioscler Thromb Vasc Biol 2001;21:1823-1828.

Imperatore G, Knowler W C, Pettitt D J, Kobes S, Fuller J H, Bennett P H, Hanson R L. A locus influencing total serum cholesterol on chromosome 19p: results from an autosomal genomic scan of serum lipid concentrations in Pima Indians. Arterioscler Thromb Vasc Biol 2000;12:2651-2656.

Duggirala R, Blangero J, Almasy L, Dyer T D, Williams K L, Leach R J, O'Connell P, Stern M. A major susceptibility locus influencing plasma triglyceride concentration is located on chromosome 15q in Mexican Americans. Am J Hum Genet 2000;66:1237-1245.

Almasy L, Hixson J E, Rainwater D L, Cole S, Williams J T, Mahaney M C, VandeBerg J L, Stern M P, MacCluer J W, Blangero J. Human pedigree-based quantitative-trait-locus mapping: localization of two genes influencing HDL-cholesterol metabolism. Am J Hum Genet 1999;64:1686-1693.

Pajukanata P, Terwilliger D, Perola M, Hiekkalinna T, Nuotio I, Ellonen P, Parkkonen M, Hartiala J, Ylitalo K, Pihlajamaki J. et al. Genomewide scan for familial combined hyperlipidemia genes in Finnish families, suggesting multiple susceptibility loci influencing triglyceride, cholesterol, and apolipoprotein B levels. Am J Hum Genet 1999; 64:1453-1463.

Arnett 2001

J. J. Genest, Jr, S. S. Martin-Munley, J. R. McNamara et al., Familial lipoprotein disorders in patients with premature coronary heart disease. *Circulation* 85 (1992), pp. 2025-2033.

Pajukanta P. Allayee H. Krass K L. Kuraishy A. Soro A. Lilja H E. Mar R. Taskinen M R. Nuotio I. Laakso M. Rotter J I. de Bruin T W. Cantor R M. Lusis A J. Peltonen L. Combined analysis of genome scans of dutch and finnish families reveals a susceptibility locus for high-density lipoprotein cholesterol on chromosome 16q. [Journal Article] *American Journal of Human Genetics.* 72(4):903-17, 2003 Apr.

Pajukanta P. Nuotio I. Terwilliger J D. Porkka K V. Ylitalo K. Pihlajamaki J. Suomalainen A J. Syvanen A C. Lehtimaki T. Viikari J S. Laakso M. Taskinen M R. Ehnholm C. Peltonen L. Linkage of familial combined hyperlipidaemia to chromosome 1 q21-q23. Nat Genet 1998; 18:369-373.

Pritchard J K, Stephens M, Rosenberg N A, et al. Association mapping in structured populations. Am J Hum Genet 2000; 67:170-181.

Arlquin ver. 2.000: a software for population genetics data analysis. Genetics and Biometry Laboratory, University of Geneva, Switzerland: 2000.

Broman K W. Estimation of allele frequencies with data on sibships. Genet Epidemiol. 2001;20:307-315.

Chiodini B D, Lewis C M. Meta-analysis of 4 coronary heart disease genome-wide linkage studies confirms a susceptibility locus on chromosome 3q. Arterioscler Thromb Vasc Biol. 2003;23:1863-1868.

Vionnet N, Hani E, Dupont S, Gallina S, Francke S, Dotte S, De Matos F, Durand E, Lepretre F, Lecoeur C, Gallina P, Zekiri L, Dina C, Froguel P. Genome-wide search for type 2 diabetes-susceptibility genes in French whites: evidence for a novel susceptibility locus for early-onset diabetes on chromosome 3q27-qter and independent replication of a type 2-diabetes locus on chromosome 1q21-q24. Am J Hum Genet 2000;67:1470-1480.

Mori Y, Otabe S, Dina C, Yasuda K, Populaire C, Lecoeur C, Vatin V, Durand E, Hara K, Okada T, To be K, Boutin P, Kadowaki T, Froguel P. Genome-wide search for type 2 diabetes in Japanese affected sib-pairs confirms susceptibility genes on 3q, 15q, and 20q and identifies two new candidate loci on 7p and 11p. Diabetes. 2002;51:1247-1255.

Hegele R A, Sun F, Harris S B, Anderson C, Hanley A J G, Zinman B. Genome-wide scanning for type 2 diabetes susceptibility in Canadian Oji-Cree, using 190 microsatellite markers. J Hum Genet. 1999;44:10-14.

Kissebah A H, Sonnenberg G E, Myklebust J, Goldstein M, Broman K, James R G, marks J A, Krakower G R, Jacob H J, Weber A, Martin L, Blangero J, Comuzzie A G. Quantitative trait loci on chromosomes 3 and 17 influence phenotypes of the metabolic syndrome. Proc Natl Acad Sci USA 2000;97:14478-144783.

Schellenberg G D, Bird T D, Wijsman E M, et al. Genetic linkage evidence for a familial Alzheimer's disease locus on chromosome 14. Science. 1992;258:668-671.

Horikawa Y. Oda N. Cox N J. Li X. Orho-Melander M. Hara M. Hinokio Y. Lindner T H. Mashima H. Schwarz P E. del Bosque-Plata L. Horikawa Y. Oda Y. Yoshiuchi I. Colilla S. Polonsky K S. Wei S. Concannon P. Iwasaki N. Schulze J. Baier L J. Bogardus C. Groop L. Boerwinkle E. Hanis C L. Bell G I. Genetic variation in the gene encoding calpain-10 is associated with type 2 diabetes mellitus. Nat Genetics. 26(2):163-75, 2000 October.

Breslow J L. Genetics of lipoprotein disorders. Circulation. 1993;87(suppl III):III-III-21.

Austin M A. King M C. Bawol R D. Hulley S B. Friedman G D. Risk factors for coronary heart disease in adult female twins. Genetic heritability and shared environmental influences. American Journal of Epidemiology. 125(2):308-18, 1987 Feb.

Rice T. Vogler G P. Perry T S. Laskarzewski P M. Rao D C. Familial aggregation of lipids and lipoproteins in families ascertained through random and nonrandom probands in the Iowa Lipid Research Clinics family study. Human Heredity. 41(2):107-21, 1991.

Murai A, Miyahara T, Fujimoto N, Matsuda M, Kameyama M. Lp(a) lipoprotein as a risk factor for coronary heart disease and cerebral infarction. Atherosclerosis 1986; 59 (2): 199-204.

Jeppesen J. Hein H O. Suadicani P. Gyntelberg F. Relation of high TG-low HDL cholesterol and LDL cholesterol to the incidence of ischemic heart disease. An 8-year follow-up in the Copenhagen Male Study. [Journal Article] Arteriosclerosis, Thrombosis & Vascular Biology. 17(6):1114-20, 1997 June.

TABLE 1

| GENECARD Study | |
|---|---|
| Families ascertained | 438 |
| Sampled individuals | 1174 |
| Number of affected individuals | 976 |
| Total affected sib pairs | 491 |
| Number of microsatellite markers | 395 |
| Distance between markers | ~10 cM |

TABLE 2

| Haplotypes for maximum hap scores (from Table 3) | | | | |
|---|---|---|---|---|
| Comparison | Effect | 3M0238 | RS1875518 | RS2937666 |
| YA vs ON | Protective | NON 253 | A | A |
| | RISK | NON 253 | A | T |
| OA vs ON | Protective | NON 253 | A | A |
| | RISK | 253 | G | A |

TABLE 2-continued

| Haplotypes for maximum hap scores (from Table 3) | | | | |
|---|---|---|---|---|
| Comparison | Effect | 3M0238 | RS1875518 | RS2937666 |
| All Affected vs Control | Protective | NON 253 | A | A |
| | RISK 1 | NON 253 | A | T |
| | RISK 2 | 253 | G | A |

TABLE 3

Haplotype table showing protective and risk effects for all age groups.
Negative hap score is protective, positive hapscore is risk
CAUCASIANS

| hap# | Hap. Score | p. val | sim. p. val | Hap. Freq | CONTROL | CASE | 3M0238 | RS1875518 | RS2937666 |
|---|---|---|---|---|---|---|---|---|---|
| CATHGEN Young Affecteds vs. CATHGEN Old Normals | | | | | | | | | |
| Protective | −3.038 | 0.00238 | 0.0022 | 0.2296 | 0.30747 | 0.17375 | NON 253 | A | A |
| 2 | −0.55983 | 0.57559 | 0.5787 | 0.22209 | 0.22007 | 0.22444 | NON 253 | G | A |
| 3 | −0.2186 | 0.82696 | 0.8293 | 0.0595 | 0.05444 | 0.06302 | 253 | G | A |
| 4 | −0.07475 | 0.94042 | 0.9414 | 0.01434 | 0.01889 | 0.01105 | 253 | A | T |
| 5 | 0.46021 | 0.64537 | 0.6533 | 0.02893 | 0.01689 | 0.03616 | 253 | A | A |
| 6 | 0.55006 | 0.58228 | 0.582 | 0.06217 | 0.0628 | 0.06363 | 253 | G | T |
| 7 | 0.7818 | 0.43433 | 0.4331 | 0.16742 | 0.1594 | 0.17108 | NON 253 | G | T |
| RISK | 2.67549 | 0.00746 | 0.0066 | 0.21595 | 0.16004 | 0.25688 | NON 253 | A | T |
| CATHGEN Old Affecteds vs. CATHGEN Old Normals | | | | | | | | | |
| Protective | −3.34905 | 0.00081 | 0.0011 | 0.25059 | 0.30747 | 0.18609 | NON 253 | A | A |
| 2 | −0.35638 | 0.72155 | 0.733 | 0.01108 | 0.01689 | 0.00742 | 253 | A | A |
| 3 | −0.13402 | 0.89339 | 0.8899 | 0.16355 | 0.16004 | 0.16955 | NON 253 | A | T |
| 4 | 0.2043 | 0.83812 | 0.8432 | 0.01813 | 0.01889 | 0.01702 | 253 | A | T |
| 5 | 0.4506 | 0.65227 | 0.6599 | 0.21883 | 0.22007 | 0.22307 | NON 253 | G | A |
| 6 | 0.48243 | 0.6295 | 0.62 | 0.16897 | 0.1594 | 0.17521 | NON 253 | G | T |
| 7 | 1.59332 | 0.11109 | 0.1092 | 0.06765 | 0.0628 | 0.07454 | 253 | G | T |
| RISK | 2.55689 | 0.01056 | 0.0098 | 0.1012 | 0.05444 | 0.1471 | 253 | G | A |
| CATHGEN Young Affecteds, Old Affecteds and GENECARD-DNC Affected probands vs. CATHGEN Old Normals | | | | | | | | | |
| Protective | −3.87691 | 0.00011 | 0.0003 | 0.2123 | 0.30747 | 0.17659 | NON 253 | A | A |
| 2 | 0.14011 | 0.88858 | 0.8886 | 0.02028 | 0.01689 | 0.02209 | 253 | A | A |
| 3 | 0.15602 | 0.87602 | 0.8759 | 0.22737 | 0.22007 | 0.232 | NON 253 | G | A |
| 4 | 0.18761 | 0.85118 | 0.8515 | 0.01902 | 0.01889 | 0.01876 | 253 | A | T |
| 5 | 1.0031 | 0.31581 | 0.3225 | 0.06158 | 0.0628 | 0.06134 | 253 | G | T1 |
| 6 | 1.09965 | 0.27149 | 0.2792 | 0.08415 | 0.05444 | 0.09424 | 253 | G | A |
| 7 | 1.27078 | 0.20381 | 0.206 | 0.17844 | 0.1594 | 0.18358 | NON 253 | G | T |
| RISK | 1.29849 | 0.19412 | 0.1927 | 0.19687 | 0.16004 | 0.2114 | NON 253 | A | T |

TABLE 4

| Primer and probe information of genetic markers | | |
|---|---|---|
| Marker | PCR Primers | Probe* |
| rs1875518 | Forward: GGGCCTAGTGTGCTAATCTCTT (SEQ ID NQ:30) | A allele = FAM-AGGTATTACT**t**AATCTAGTTCA-MGB (SEQ ID NO:36) |
| | Reverse: TTATTTTACACTTAAGGGTGCTCA (SEQ ID NQ:31) | G allele = TET-AGGTATTACT**c**AATCTAGTTCA-MGB (SEQ ID NO:37) |
| rs2937666 | Forward: CCAGTTTTTGTAGCTGCTGTTG (SEQ ID NQ:32) | A allele = TET-CCATCAAC**a**ATTGCATC-MGB (SEQ ID NO:38) |
| | Reverse: TTTATAGTCCATTTTGGCTTGCTT (SEQ ID NO:33) | T allele = FAM-TCCATCAAC**t**ATTGCATC-MGB (SEQ ID NO:39) |
| 3M0238 | Forward: CTTGCACCTGGGAGGTAGAG (SEQ ID NO:34) | N/A |
| | Reverse: CACAACTGTTGCTTTTCCAT (SEQ ID NO:35) | N/A |

*The polymorphic site is in lower letter bold case.

TABLE 5

Baseline characteristics of GENECARD individuals (420 families).

| Variable | Affected (N = 952) | Unaffected (N = 177) | All (N = 1129) |
|---|---|---|---|
| Mean age (SD) | 51.4 (7.1) | 65.3 (11.3) | 53.6 (9.4) |
| Mean age of onset (SD) | 43.7 (5.8) | — | — |
| Sex (%) | | | |
| Male | 71.4% | 36.0% | 65.8% |
| Female | 28.6% | 64.0% | 34.2% |
| Dyslipidemia | 82.3% | 57.1% | 78.4% |
| Meds for dyslipidemia | 84.7% | 60.6% | 81.9% |
| Lipids (mean, SD) | | | |
| TC | 205.7 (57.3) | 220.6 (50.3) | 206.9 (56.9) |
| TG | 222.1 (167.1) | 213.8 (142.9) | 221.5 (165.2) |
| HDL | 39.1 (19.0) | 48.1 (34.9) | 39.9 (20.9) |
| LDL | 117.7 (49.5) | 124.7 (40.0) | 118.3 (48.8) |
| Hypertension | 55.2% | 49.1% | 54.2% |
| Blood pressure (mean, SD) | | | |
| Systolic | 141.1 (22.7) | 151.8 (26.3) | 146.1 (24.7) |
| Diastolic | 81.2 (12.2) | 81.4 (9.8) | 81.3 (11.0) |
| Diabetes mellitus (DM) | 21.0% | 15.4% | 20.1% |
| Waist circumference (SD) | 99.0 (14.2) | 96.4 (16.4) | 98.6 (14.6) |
| Obesity | | | |
| BMI < 25 | 19.6% | 35.0% | 22.1% |
| BMI 25-29 | 38.3% | 37.3% | 38.2% |
| BMI ≧ 30 | 42.0% | 27.7% | 39.8% |
| Metabolic syndrome*** | 46.8% | 30.3% | 44.2% |
| Pack-years smoked | 34.8 (23.4) | 42.7 (36.7) | 35.7 (25.3) |
| Currently smoking | 32.9% | 28.3% | 32.4% |
| Post-menopausal | 55.8% | 82.1% | 63.4% |
| History of MI | 62.9% | — | 59.8% |
| Multiple vessel CAD | 66.0% | — | 66.0% |

TC = total cholesterol, TG = triglycerides, HDL = high density lipoprotein, MI = myocardial infarction.

***Presence of 3 out of 5 of the following: history of DM; HTN or BP >130/85; HDL <40 in men and <50 in women; waist circumference >88 in women, >102 in men; TG ≧ 150.

TABLE 6

Quantitative trait loci mapping results, lipid phenotypes.

| Quantitative Trait | Heritability (SD) | Chrom | Locus (cM)* | Multipoint LOD | Empirical p-value** |
|---|---|---|---|---|---|
| Total cholesterol (TC) | 71.1% (8.9%)*** | 5 | 98 | 1.28 | 0.03 |
| | | 6 | 10 | 1.28 | 0.03 |
| | | 13 | 15 | 1.19 | 0.03 |
| | | 18 | 55 | 1.32 | 0.02 |
| Low density lipoprotein (LDL) cholesterol | 67.3% (9.7%)*** | 6 | 164 | 1.65 | <0.01 |
| | | 16 | 0 | 1.41 | |
| | | 19 | 52 | 1.25 | |
| | | 21 | 16 | 1.39 | |
| High density lipoprotein (HDL) cholesterol | 67.7% (11.9%)*** | 3 | 87 | 2.43 | 0.002 |
| | | 7 | 156 | 1.73 | <0.01 |
| | | 15 | 103 | 1.79 | 0.004 |
| Triglycerides | 63.7% (12.5%)*** | 4 | 119 | 1.30 | |
| | | 7 | 80 | 1.35 | |
| | | 13 | 18 | 1.55 | <0.01 |
| | | 14 | 76 | 1.22 | |
| | | 18 | 94 | 2.09 | 0.002 |
| HDL/TC ratio | 64.6% (9.8%)*** | 3 | 153 | 1.44 | <0.01 |
| | | 7 | 143 | 1.44 | <0.01 |
| | | 8 | 148 | 1.68 | |

*Kosambi map locus;
cM: centimorgans;
**using 10000 simulated repetitions;
***p-value < 0.00001

TABLE 7

| Ordered subset analysis (OSA) results. | | | | | | | | |
|---|---|---|---|---|---|---|---|---|
| Chromosome | Pos cM | Covariate | Mean covariate value (SD) in subset | Mean covariate value (SD) in others* | Max OSA LOD | Overall LOD | p-value | No. fams in subset |
| 3 | 146.9 | Low TG | 161.1 (49.3) | 372.7 (137.9) | 4.14 | 2.64 | 0.04 | 167 |
| 5 | 171.7 | High TC | 302.4 (78.9) | 192.8 (30.1) | 4.42 | 0.36 | 0.001 | 54 |
| 9 | 23.5 | Low TG | 99.3 (21.8) | 248.9 (121.0) | 2.51 | 0.12 | 0.03 | 49 |
| 10 | 127.7 | Low HDL | 24.8 (4.5) | 39.8 (8.2) | 2.49 | 0.00 | 0.007 | 44 |
| 12 | 61.0 | High HDL | 50.6 (8.2) | 34.3 (5.6) | 2.43 | 0.35 | 0.03 | 80 |
| 14 | 0.0 | High LDL | 225.5 (36.1) | 113.0 (32.0) | 2.63 | 0.66 | 0.03 | 22 |
| 17 | 120.6 | High TG | 340.9 (133.8) | 152.1 (44.0) | 2.10 | 0.19 | 0.04 | 77 |
| 22 | 0.0 | High LDL | 225.5 (36.1) | 113.0 (32.0) | 2.52 | 0.001 | 0.02 | 22 |

*mean value of OSA covariate in families not included in the subset;

TABLE 8

| Phenotypic characteristics of families in OSA subsets. | | | |
|---|---|---|---|
| Chromosome | No. families in subset | Phenotypic characteristics of subset* | Lipid phenotypes of subset* |
| 3 | 167 | Older at time of exam, older age of onset<br>Less metabolic syndrome, diabetes<br>Lower BMI<br>Lower waist circumference and weight | Lower TC<br>Lower LDL<br>Higher HDL |
| 5 | 54 | Younger age of onset | Higher LDL<br>Higher TG |
| 9 | 49 | Less diabetes<br>Lower weight, waist circumference, BMI<br>Less metabolic syndrome<br>Fewer pack-years smoked | Lower TC<br>Higher HDL |
| 10 | 44 | More metabolic syndrome<br>More pack-years smoked<br>More diabetes<br>More male<br>Higher height, weight, waist circumference | Higher TG |
| 12 | 80 | Lower waist, weight, BMI<br>Older at time of exam, older age of onset<br>Less metabolic syndrome<br>More female | Higher TC<br>Lower TG |
| 14 | 22 | Younger at time of exam, younger age of onset | Higher TC |
| 17 | 77 | More metabolic syndrome | Lower LDL<br>Lower HDL |
| 22 | 22 | Younger at time of exam, younger age of onset | Higher TC |

*when compared to family means of affected individuals in families not within the OSA subset; all comparisons statistically significant at $p < 0.05$. BMI: body-mass index

TABLE 9

| Genetic Markers in Chromosome 3* | | | |
|---|---|---|---|
| Chr | SNP/Polymorphism id | Basepair location on Ch 3 | Basepair location on SEQ ID NO: 1 |
| 3 | rs2927275 | 118666759 | 166759 |
| 3 | rs1698042 | 118667838 | 167838 |
| 3 | rs1501881 | 118672530 | 172530 |
| 3 | rs1698041 | 118682441 | 182441 |
| 3 | 3M0238 | 118690772 to 118690975 | 190772 to 190975 |

TABLE 9-continued

| Genetic Markers in Chromosome 3* | | | |
|---|---|---|---|
| Chr | SNP/Polymorphism id | Basepair location on Ch 3 | Basepair location on SEQ ID NO: 1 |
| 3 | rs2055426 | 118703034 | 203034 |
| 3 | rs2937675 | 118706580 | 206580 |
| 3 | 27 bp Insertion | 118711341 to 118711342 | 211341 to 211342 |
| 3 | rs1875518 | 118712470 | 212470 |
| 3 | rs2937673 | 118715077 | 215077 |
| 3 | rs1676232 | 118717529 | 217529 |
| 3 | 3I0320 | 118719088 | 219088 |
| 3 | 3I0311 | 118719132 to 118719133 | 219132 to 219133 |
| 3 | rs1381801 | 118723585 | 223585 |
| 3 | rs2937666 | 118729388 | 229388 |
| 3 | rs1910044 | 118733409 | 233409 |
| 3 | rs6778437 | 118726628 | 226628 |
| 3 | rs6795971 | 118751683 | 251683 |
| 3 | rs1466416 | 118753496 | 253496 |
| 3 | rs6795971 | 118751683 | 251683 |
| 3 | rs2937673 | 118715077 | 215077 |
| 3 | rs1698041 | 118682441 | 182441 |
| 3 | rs4356827 | 118661434 | 161434 |
| 3 | rs6790819 | 118659480 | 159480 |
| 3 | rs7427839 | 118648013 | 148013 |
| 3 | rs725154 | 117992940 | |
| 3 | rs1875516 | 118805109 | |
| 3 | rs1501882 | 118774319 | 274319 |
| 3 | rs1401951 | 119708716 | |
| 3 | rs1968010 | 119551910 | |
| 3 | rs1486336 | 119386693 | |
| 3 | rs843855 | 119239225 | |
| 3 | rs1456186 | 119110095 | |
| 3 | rs553070 | 119637627 | |
| 3 | rs1499989 | 119483894 | |
| 3 | rs39688 | 120225538 | |
| 3 | rs812824 | 120037336 | |
| 3 | rs705233 | 119952613 | |
| 3 | rs483349 | 120827383 | |
| 3 | rs2282171 | 120665288 | |
| 3 | rs834855 | 82731159 | |
| 3 | rs4404477 | 118857458 | |

*SNP basepair location on Ch 3 is based on the NCBI build 35 sequence of human chromosome 3.

TABLE 10

Additional Nucleotide Polymorphisms*

| SEQ ID NO: | Flanking Sequence (polymorphism in brackets) | Polymorphism basepair position on Ch 3** | Polymorphism basepair position on SEQ ID NO:1 |
|---|---|---|---|
| 2 | TGCGCGTGT[**G/T**]TGGTGTGTG | 118664719 | 164719 |
| 3 | AAATAAATTAAC[**G/A**]TTTATCATCA | 118670801 | 170801 |
| 4 | ATTTCTC[**G/A**]TTAAAATTT | 118673682 | 173682 |
| 5 | ATTTCATATCT[**-/A**]GGAAAAAAC | 118673698 to 118673699 | 173698 to 173699 |
| 6 | CCACCTAG[**T/C**]TTTTTTAATGAACA | 118699111 | 199111 |
| 7 | ATCTTGATT[**C/A**]TATTTATGACTGC | 118699690 | 199690 |
| 8 | GCTTAGTTGG[**T/A**]TAGACCAGCT | 118708380 | 208380 |
| 9 | CCTCACTCT[**A/C**]TTCTCCTCCTT | 118708990 | 208990 |
| 10 | GGTGCAG[**T/A**]GGCATGAGCC | 118713130 | 213130 |
| 11 | AACCCTCCTCAATTGT[**A/G**]GAAACATGGAACA | 118717982 | 217982 |
| 12 | GGAACAGCAACATTCTTA[**A/G**]ATGCTCATGTACC | 118718008 | 218008 |
| 13 | ATTCTTAAATGCTCATGTA[**C/A**]CTTTATTAAAGTAT | 118718020 | 218020 |
| 14 | ATGTGCATTTCTACA[**T/A**]TCATTCAAATAGTCTTTG | 118718327 | 218327 |
| 15 | AATGATAAAAT[**A/-**]TTTTTTAAAG (310320) | 118719088 | 219088 |
| 16 | TCCCACCG[**T/G**]ACCCAGCCCT | 118720122 | 220122 |
| 17 | TTATATCAA[**T/G**]GCCTCCAAC | 118720142 | 220142 |
| 18 | ACTTGCAGAA[**A/G**]TTTTATATC | 118720154 | 220154 |
| 19 | GGTTGACTAG[**T/A**]CCATGCCTT | 118720228 | 220228 |
| 20*** | AACAGAACTKA[**A/G**]CACTCT | 118720249 | 220249 |
| 21 | GTCCAAAACA[**T/C**]ATGCTAAAGA | 118722980 | 222980 |
| 22 | TTATTTAC[**A/G**]TGAAGTTGT | 118722998 | 222998 |
| 23 | ACATCTT[**A/G**]TGAAATT | 118723379 | 223379 |
| 24 | TTGTTGGGGG[**G/A**]ACTATAGTAATC | 118727468 | 227468 |
| 25 | GACCCTCCAACAAA[**T/G**]GCCATTT | 118728575 | 228575 |
| 26 | AGTTTGGA[**G/A**]TTTCCTCA | 118730282 | 230282 |
| 27 | TCAGAGAAATG[**C/A**]AAATCAA | 118730459 | 230459 |
| 28 | CTGGAGGAGATAATCATTAAGT**GGGAATTTGAATA TTATAACAGATCCT**[-------------------- /**GGGAATTTGAATATTATAACAGATCCT**]GTAATCA CCTGACCACTGCACAGA (27 bp duplication) | 118711341 to 118711342 | 211341 to 211342 |
| 29 | ATAAGCAAGTATAAAAA[---/**CAA**]TTTCCAGTAGATG (310311) | 118719132 to 118719133 | 219132 to 219133 |

*The polymorphism is indicated in bold text. The first nucleotide/sequence listed of the polymorphism is the nucleotide/sequence present in the NCBI build 35 sequence of human chromosome 3, the second nucleotide/sequence listed is the variant.

**SNP basepair position on Ch 3 is based on the NCBI build 35 sequence of human chromosome 3.

***K in SEQ ID NO:20 represents a G/T polymorphism.

TABLE 11

| SNPs in HAPIP and MLCK* | | | |
|---|---|---|---|
| Ch | SNP id | Gene | SNP basepair location |
| 3 | rs2272486 | HAPIP | 125470729 |
| 3 | HCV1602689 | MLCK | 125024094 |

*SNP basepair location is based on the NCBI build 35 sequence of human chromosome 3.

That which is claimed is:

1. A method of identifying a human subject older than 55 years of age as having an increased risk of developing coronary artery disease, comprising detecting in a nucleic acid sample of the subject a G allele at single nucleotide polymorphism rs1875518, wherein the detection of said allele identifies the subject as having an increased risk of developing coronary artery disease and wherein said increased risk is relative to a human subject older than 55 years of age that does not have a G allele at single nucleotide polymorphism rs1875518.

2. A method of identifying a human subject older than 55 years of age as having a decreased risk of developing coronary artery disease, comprising detecting in a nucleic acid sample of the subject an A allele at single nucleotide polymorphism rs1875518, wherein the detection of said allele identifies the subject as having a decreased risk of developing coronary artery disease and wherein said decreased risk is relative to a human subject older than 55 years of age that does not have an A allele at single nucleotide polymorphism rs1875518.

3. The method of claim 1, wherein detecting is carried out by a hybridization reaction.

4. The method of claim 3, wherein the hybridization reaction is carried out with hybridization probes in a microarray.

5. The method of claim 1, wherein detecting is carried out by electrophoresis.

6. The method of claim 1, wherein detecting is carried out by restriction endonuclease digestion analysis.

7. The method of claim 1, wherein detecting is carried out by an amplification reaction.

8. The method of claim 7, wherein the amplification reaction is a polymerase chain reaction.

9. The method of claim 2, wherein detecting is carried out by a hybridization reaction.

10. The method of claim 9, wherein the hybridization reaction is carried out with hybridization probes in a microarray.

11. The method of claim 2, wherein detecting is carried out by electrophoresis.

12. The method of claim 2, wherein detecting is carried out by restriction endonuclease digestion analysis.

13. The method of claim 2, wherein detecting is carried out by an amplification reaction.

14. The method of claim 13, wherein the amplification reaction is a polymerase chain reaction.

* * * * *

UNITED STATES PATENT AND TRADEMARK OFFICE
CERTIFICATE OF CORRECTION

PATENT NO. : 7,807,465 B2
APPLICATION NO. : 11/260842
DATED : October 5, 2010
INVENTOR(S) : Vance et al.

It is certified that error appears in the above-identified patent and that said Letters Patent is hereby corrected as shown below:

On Title Page:

Item (75) Inventors: For Jeffrey M. Vance please correct "Chapel Hill, NC" to read -- Coral Gables, FL --
For Pascal J. Goldschmidt please correct "Chapel Hill, NC" to read -- Miami, FL --
For Simon S. Gregory please correct "Simon S. Gregory" to read -- Simon G. Gregory --

In the Specification:

Column 27, Table 10, Table Column "Flanking Sequence", Item #28:
Please replace the listed sequence to read:
-- CTGGAGGAGATAATCATTAAGTGGGAATTTGAATA TTATAACAGATCCT[--------------------------- /GGGAATTTGAATATTATAACAGATCCT]GTAATCA CCTGACCACTGCACAGA (27 bp duplication) --

Signed and Sealed this
Fifteenth Day of March, 2011

David J. Kappos
*Director of the United States Patent and Trademark Office*